United States Patent
Mita et al.

(10) Patent No.: US 6,492,370 B1
(45) Date of Patent: Dec. 10, 2002

(54) UREA DERIVATIVES AND PHARMACEUTICAL COMPOSITIONS THEREOF

(75) Inventors: Shiro Mita, Osaka (JP); Masato Horiuchi, Osaka (JP); Masakazu Ban, Osaka (JP); Hiroshi Suhara, Osaka (JP)

(73) Assignee: Santen Pharmaceutical Co., Ltd., Osaka (JP)

( * ) Notice: Subject to any disclaimer, the term of this patent is extended or adjusted under 35 U.S.C. 154(b) by 0 days.

(21) Appl. No.: 09/623,779

(22) PCT Filed: Mar. 25, 1999

(86) PCT No.: PCT/JP99/01554

§ 371 (c)(1),
(2), (4) Date: Sep. 8, 2000

(87) PCT Pub. No.: WO99/50238

PCT Pub. Date: Oct. 7, 1999

(30) Foreign Application Priority Data

Mar. 26, 1998 (JP) .............................................. 10/79154

(51) Int. Cl.$^7$ ..................... C07C 323/44; C07C 327/22; C07D 213/40; A61K 31/17; A61K 31/415
(52) U.S. Cl. ........................... 514/252.13; 514/255.01; 514/583; 514/595; 544/374; 544/391; 564/47; 564/59
(58) Field of Search ................................. 544/374, 391; 564/47, 59; 514/252.13, 255.01, 595, 583

(56) References Cited

U.S. PATENT DOCUMENTS

| | | | |
|---|---|---|---|
| 5,312,831 A | 5/1994 | Ayral-Kaloustian et al. | 514/478 |
| 5,861,436 A | 1/1999 | Beckett et al. | 514/575 |

FOREIGN PATENT DOCUMENTS

| | | |
|---|---|---|
| EP | 0 849 256 A1 | 6/1998 |
| JP | 7-179414 | 7/1995 |
| JP | 9-118658 | 5/1997 |
| JP | 9-508115 | 8/1997 |

OTHER PUBLICATIONS

Clinical Immunology, 26, 1270, 1995 and an English language abstract.
Immunology Today, 18, 487, 1997.

*Primary Examiner*—Deepak R. Rao
(74) *Attorney, Agent, or Firm*—Frishauf, Holtz, Goodman & Chick, P.C.

(57) ABSTRACT

Objects of the present invention are to create compounds having urea structure as basic structure and having a sulfur atom and an amide bond in side chains and to find pharmacological effects thereof, particularly TNF-α production inhibitory effects.

The present invention provides compounds represented by the following formula [I] wherein $R^1$ is H, alkyl, aromatic, $R^A$—CO—, $R^C$—S—or the formula [II]; $R^2$, $R^3$ and $R^4$ are H, alkyl, alkenyl, cycloalkyl, cycloalkenyl or aromatic; $R^5$ and $R^6$ are H, alkyl, alkenyl, cycloalkyl, cycloalkenyl or aromatic; $R^5$ and $R^6$ can together form a nonaromatic heterocyclic ring; R7 is H, alkyl, cycloalkyl, hydroxy, mercapto, phenyl, $R^B$—O—, $R^C$—S—, $R^D$—COS—, $R^E$—OCO—, $R^F$—N($R^G$)— or —CONHOH; and $A^1$ and $A^2$ are alkylene.

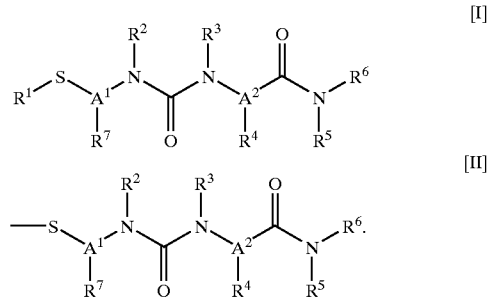

13 Claims, No Drawings

UREA DERIVATIVES AND PHARMACEUTICAL COMPOSITIONS THEREOF

This application is a 371 of PCT/JP99/01554 filed Mar. 25, 1999.

TECHNICAL FIELD

The present invention relates to novel urea derivatives which have TNF-α production inhibitory effects and are useful as therapeutic agents for various diseases, particularly as therapeutic agents for autoimmune diseases such as rheumatoid arthritis, and to novel compounds which are useful as synthetic intermediates thereof.

BACKGROUND ART

TNF-α (tumor necrosis factor-α) was found as a factor which induces hemorrhagic necrosis at tumor sites, and it is now recognized as a cytokine which widely participates in biophylaxis-immune mechanism through inflammation. However, prolonged and excessive production of TNF-α causes tissue disorders and is a factor which brings about causes and exacerbation of various diseases. Accordingly, it is reported that it is important to suppress the excessive production of TNF-α in morbidity where TNF-α is excessively produced (Yamazaki, Clinical Immunology, 27, 1270, 1995). The above-mentioned literature recites many pathema such as arthrorheumatism, systemic lupus erythematosus (SLE), cachexia, acute infectious disease, allergy, pyrexia, anemia and diabetes as examples of pathema in which TNF-α participates.

It is reported that TNF-α plays an important role in crises of rheumatoid arthritis and Crohn's disease, which are autoimmune diseases (Andreas Eigler et al., Immunology Today, 18, 487, 1997).

TNF-α is known to participate in various diseases as well as autoimmune diseases such as rheumatoid arthritis, Crohn's disease and systemic lupus erythematosus as reported in the above-mentioned literatures and the like. Compounds which inhibit its production or suppress its effect are expected to be useful for treatment of various diseases, and many studies have been done. Outlines of these studies of drugs are introduced in the above-mentioned literatures (Yamazaki, Clinical Immunology, 27, 1270, 1995, Andreas Eigler et al., Immunology Today, 18, 487, 1997). Recently, it was found that a proteolytic enzyme participating in secretion of TNF-α is metalloprotease, and a study of TNF-α production inhibitory effects of metalloprotease inhibitors is also reported. (Published Japanese Translation of PCT No. 508115/1997).

Various drugs having the TNF-α production inhibitory effects have been studied as mentioned above. Focusing attention on chemical structure of the drugs, however, no drug having a chemical structural feature of compounds of the present invention is known at all. The chemical structural feature of the compounds of the present invention is that the compounds have urea structure as basic structure and have a sulfur atom and an amide bond in side chains. Few studies of such drugs having the urea structure as basic skeleton have been reported. Moreover, no drug having a sulfur atom in a side chain has hitherto practically been reported.

Since the compounds having the urea structure as the basic structure and having a sulfur atom and the amide bond in the side chains have not practically been reported as mentioned above, a study of synthesis of such compounds and a study of pharmacological actions, particularly the TNF-α production inhibitory effects of the compounds were very interesting subjects.

DISCLOSURE OF THE INVENTION

The present inventors focused attention on urea structure of which application to drugs had hardly been studied, made studies on synthesis of novel urea derivatives wherein sulfur is introduced into one side chain thereof and an amide bond is introduced into the other side chain thereof, and succeeded in preparing many novel compounds. The present inventors further studied pharmacological actions of the compounds and found that these novel compounds have excellent TNF-α production inhibitory effects. In a process of the study on preparing the above-mentioned novel urea derivatives, the present inventors succeeded also in preparing novel compounds which are useful as synthetic intermediates of the derivatives.

The present invention relates to compounds represented by the following general formula [I] and salts thereof (hereinafter referred to as "the present compound" as far as there is no proviso), medicinal compositions containing it as an active ingredient, and compounds which are represented by the general formula [III] and are useful as synthetic intermediates of the present compounds and salts thereof (hereinafter referred to as "the present synthetic intermediate" as far as there is no proviso).

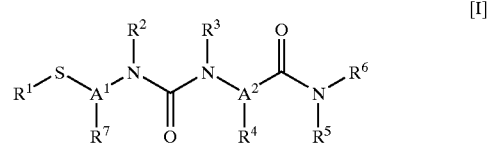

wherein

R$^1$ is hydrogen, lower alkyl, an aromatic group, R$^A$—CO—, R$^C$—S— or a group of the following formula [II].

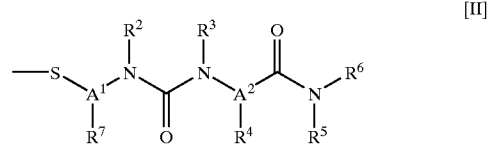

R$^2$, R$^3$ and R$^4$, being the same or different, are hydrogen, lower alkyl, lower alkenyl, cycloalkyl, cycloalkenyl or an aromatic group. When R$^4$ is lower alkyl, terminal carbon of the lower alkyl can join with carbon to which the alkyl is bonded to form a cycloalkyl ring.

R$^5$ and R$^6$, being the same or different, are hydrogen, lower alkyl, lower alkenyl, cycloalkyl, cycloalkenyl or an aromatic group. When both R$^5$ and R$^6$ are lower alkyl, they can join each other to form a nonaromatic heterocyclic ring having nitrogen and/or oxygen in the ring, and the heterocyclic ring can be substituted by lower alkyl, lower alkenyl, cycloalkyl, cycloalkenyl, an aromatic group or R$^A$—CO—.

R$^7$ is hydrogen, lower alkyl, cycloalkyl, hydroxy, mercapto, phenyl, R$^B$—O—, R$^C$—S—, R$^D$—COS—, R$^E$—OCO—, R$^F$—N(R$^G$)— or —CONHOH. R$^7$ can join with sulfur adjacent to A$^1$ to form a nonaromatic heterocyclic ring containing sulfur in the ring, and the ring can further have carbonyl in the ring.

A$^1$ is lower alkylene.

A$^2$ is lower alkylene.

Each lower alkyl defined above can be substituted by hydroxy, a nonaromatic heterocyclic ring having nitrogen and/or oxygen in the ring, cycloalkyl, cycloalkenyl, adamantyl, an aromatic group, phthalimido, guanidino which can be substituted by lower alkylsulfonyl or aromatic sulfonyl, $R^A$—CO—, $R^B$—O—, $R^C$—S—, $R^D$—COS—, $R^E$—OCO—, $R^F$—N($R^G$)—, $R^H$—N($R^J$)CO—, $R^K$—CONH— or —CONHOH.

Each lower alkenyl defined above can be substituted by hydroxy, lower alkyl, lower alkoxy, cycloalkyl, cycloalkenyl or an aromatic group.

Each cycloalkyl defined above can be substituted by lower alkyl, hydroxy, oxo or $R^E$—OCO—.

Each aromatic group defined above can be substituted by lower alkyl, hydroxy, lower alkoxy, lower alkanoyloxy, halogen, nitro, an aromatic group, lower alkylsulfonyl, aromatic sulfonyl, $R^E$—OCO—, $R^F$—N($R^G$)— or $R^K$—CONH—.

The nonaromatic heterocyclic ring having nitrogen and/or oxygen in the ring defined above can be substituted by lower alkyl, cycloalkyl, an aromatic group or $R^A$—CO—, and the lower alkyl can be substituted by hydroxy, cycloalkyl, cycloalkenyl, an aromatic group, $R^A$—CO—, $R^B$—O—, $R^E$—OCO— or $R^F$—N($R^G$)—.

$R^A$ is lower alkyl, halogeno-lower alkyl, an aromatic group, lower alkoxy, aromatic-lower alkoxy or $R^F$—N($R^G$)—. $R^B$ is lower alkyl or an aromatic group. $R^C$ is hydrogen, lower alkyl or an aromatic group. $R^D$ is lower alkyl or an aromatic group. $R^E$ is hydrogen, lower alkyl or an aromatic group. $R^F$ and $R^G$, being the same or different, are hydrogen, lower alkyl, cycloalkyl or an aromatic group. $R^H$ and $R^J$, being the same or different, are hydrogen, lower alkyl, cycloalkyl or an aromatic group. $R^K$ is lower alkyl, lower alkoxy or an aromatic group. The same definitions are applied hereinafter.]

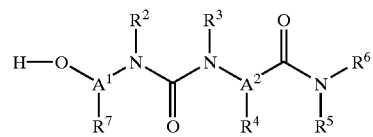

[III]

[The same definitions are applied except for a case where $R^7$ joins with sulfur adjacent to $A^1$ to form a nonaromatic heterocyclic ring containing sulfur in the ring. Hereinafter, a definition of $R^7$ to be used for the synthetic intermediates is the same as that mentioned above.]

The groups defined above are hereinafter described in detail.

The lower alkyl is straight-chain or branched alkyl having one to eight carbon atoms such as methyl, ethyl, propyl, butyl, hexyl, isopropyl, isobutyl, isopentyl, isohexyl, t-butyl or 3,3-dimethylbutyl.

The lower alkenyl is straight-chain or branched alkenyl having two to eight carbon atoms such as vinyl, allyl, 3-butenyl, 5-hexenyl or isopropenyl.

The cycloalkyl is cycloalkyl having three to eight carbon atoms such as cyclopropyl, cyclobutyl, cyclopentyl, cyclohexyl or cycloheptyl.

The cycloalkenyl is cycloalkenyl having three to eight carbon atoms such as cyclopropenyl, cyclobutenyl, cyclopentenyl, cyclohexenyl or cycloheptenyl.

The lower alkoxy is straight-chain or branched alkoxy having one to eight carbon atoms such as methoxy, ethoxy, propoxy, butoxy, hexyloxy, isopropoxy or t-butoxy.

The halogen is fluorine, chlorine, bromine or iodine.

The lower alkylene is straight-chain or branched alkylene having one to eight carbon atoms such as methylene, ethylene, trimethylene, tetramethylene, pentamethylene, hexamethylene, methylmethylene, propylene, ethylethylene, dimethylethylene, propylethylene, isopropylethylene or methyltrimethylene.

The aromatic group is a monocyclic or condensed polycyclic hydrocarbon aromatic group such as phenyl or naphthyl, or a heterocyclic aromatic group such as pyridyl, thienyl or imidazolyl.

The nonaromatic heterocyclic ring having nitrogen and/or oxygen in the ring is a nonaromatic heterocyclic ring having one or two nitrogen atoms in the ring such as piperidine, piperazine, pyrroline or homopiperazine, or a nonaromatic heterocyclic ring having nitrogen and oxygen in the ring such as morpholine.

The nonaromatic heterocyclic ring containing sulfur in the ring is a nonaromatic heterocyclic ring containing one or two sulfur atoms in the ring such as dithiolane, or a nonaromatic heterocyclic ring further having ketone in the ring such as thiolactone.

Salts in the present invention refer to any pharmaceutically acceptable salts, and examples thereof are salts with an inorganic acid such as hydrochloric acid, nitric acid or sulfuric acid, salts with an organic acid such as acetic acid, fumaric acid, maleic acid, citric acid, tartaric acid, diacyltartaric acid, benzoic acid or a substituted benzoic acid, salts with an alkali metal or an alkaline-earth metal such as sodium, potassium or calcium, and the like. When geometrical isomers or optical isomers are present in the present compounds or the present intermediates, these isomers are also included in the scope of the present invention. The present compounds or the present intermediates can be in the form of addition salts such as hydrates and organic solvates.

Preferred examples of the present compound are the following.

Compounds and salts thereof wherein the group(s) in the general formula [I] is defined by anyone selected from the following 1) to 8) or any combinations consisting of 1) to 8).

1) $R^1$ is selected from hydrogen, lower alkyl, phenyl, $R^A$—CO—, $R^C$—S— and a group of the following formula [II],

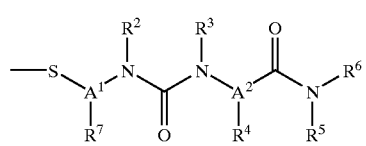

[II]

$R^A$ is selected from lower alkyl, lower alkoxy, phenyl, pyridyl, phenyl-lower alkoxy and $R^F$—N($R^G$)—, $R^C$ is selected from lower alkyl and phenyl, $R^F$ and $R^G$, being the same or different, are selected from hydrogen, lower alkyl and phenyl, each lower alkyl can be substituted by phenyl or lower alkoxycarbonyl, and each phenyl can be substituted by a group selected from lower alkyl, hydroxy, lower alkoxy, halogen and nitro;

2) $R^2$ $R^3$ and $R^4$, being the same or different, are selected from hydrogen, lower alkyl, lower alkenyl, cycloalkyl, cycloalkenyl, phenyl and naphthyl, the lower alkyl can be substituted by a group selected from hydroxy, cycloalkyl, cycloalkenyl, adamantyl, phenyl, naphthyl, pyridyl, thienyl, imidazolyl, guanidino which can be substituted by lower alkylsulfonyl or phenylsulfonyl, $R^B$—O—, $R^C$—S—, $R^D$—COS—, $R^E$—OCO—, $R^F$—N($R^G$)— and $R^K$—CONH—, the lower alkenyl can be substituted by lower alkyl, phenyl or naphthyl, $R^B$ is selected from lower alkyl and phenyl, $R^C$ is selected from hydrogen, lower alkyl and phenyl, $R^D$ is selected from lower alkyl and phenyl, $R^E$ is selected from hydrogen, lower alkyl and phenyl, $R^F$ and $R^G$, being the same or different, are selected from hydrogen, lower alkyl, cycloalkyl and phenyl, $R^K$ is selected from lower alkyl, lower alkoxy and phenyl, each phenyl can be substituted by a group selected from lower alkyl, hydroxy, lower alkoxy, lower alkanoyloxy, halogen, nitro, amino, lower alkylamino, lower alkanoylamino, lower alkylsulfonyl, phenylsulfonyl, phenyl and $R^E$—OCO—, and each cycloalkyl can be substituted by lower alkyl, hydroxy, oxo or $R^E$—OCO—;

3) $R^5$ and $R^6$, being the same or different, are selected from hydrogen, lower alkyl, lower alkenyl, cycloalkyl, cycloalkenyl, phenyl, naphthyl and pyridyl, the lower alkyl can be substituted by a group selected from hydroxy, lower alkoxy, cycloalkyl, cycloalkenyl, phenyl, naphthyl, pyridyl, thienyl, imidazolyl, phthalimido, piperidyl, piperazinyl, morpholinyl, $R^E$—OCO—, $R^F$—N($R^G$)—, $R^H$—N($R^J$)CO—, $R^K$—CONH— and —CONHOH, the piperidyl, piperazinyl or morpholinyl can be substituted by lower alkyl, phenyl or naphthyl, $R^E$ is selected from hydrogen, lower alkyl and phenyl, $R^F$ and $R^G$, being the same or different, are selected from hydrogen, lower alkyl, cycloalkyl and phenyl, $R^H$ and $R^J$, being the same or different, are selected from hydrogen, lower alkyl, cycloalkyl and phenyl, $R^K$ is selected from lower alkyl, lower alkoxy and phenyl, each phenyl can be substituted by a group selected from lower alkyl, hydroxy, lower alkoxy, lower alkanoyloxy, halogen, nitro, amino, lower alkylamino, lower alkanoylamino, lower alkylsulfonyl, phenylsulfonyl, phenyl and $R^E$—OCO—, and each cycloalkyl can be substituted by a group selected from lower alkyl, hydroxy, oxo and $R^E$—OCO—;

4) $R^5$ and $R^6$ join each other to form a nonaromatic heterocyclic ring selected from a morpholine ring, a piperidine ring, a piperazine ring, a pyrroline ring and a homopiperazine ring, the nonaromatic heterocyclic ring can be substituted by lower alkyl, lower alkenyl, cycloalkyl, cycloalkenyl, phenyl, naphthyl or $R^A$—CO—, the lower alkyl can be substituted by hydroxy, phenyl, naphthyl, $R^B$—O—, $R^E$—OCO—, $R^F$—N($R^G$)— or —CONHOH, $R^A$ is lower alkyl, halogeno-lower alkyl, lower alkoxy or phenyl, $R^1$ is lower alkyl or phenyl, $R^E$ is hydrogen, lower alkyl or phenyl, $R^F$ and $R^G$, being the same or different, are hydrogen, lower alkyl, cycloalkyl or phenyl, each phenyl can be substituted by a group selected from lower alkyl, hydroxy, lower alkoxy, lower alkanoyloxy, halogen, nitro, amino, lower alkylamino, lower alkanoylamino, lower alkylsulfonyl, phenylsulfonyl, phenyl and $R^E$—OCO—, and each cycloalkyl can be substituted by a group selected from lower alkyl, hydroxy, oxo and $R^E$—OCO—;

5) $R^7$ is selected from hydrogen, lower alkyl, cycloalkyl, hydroxy, carboxy, mercapto, phenyl, $R^B$—O—, $R^C$—S—, $R^D$—COS—, $R^E$—OCO—, $R^F$—N($R^G$)— and —CONHOH, the lower alkyl can be substituted by a group selected from cycloalkyl, hydroxy, carboxy, mercapto, phenyl, $R^B$—O—, $R^C$—S—, $R^D$—COS—, $R^E$—OCO—, $R^F$—N($R^G$)— and —CONHOH, $R^B$ is lower alkyl or phenyl, $R^C$ is lower alkyl or phenyl, $R^D$ is lower alkyl or phenyl, $R^E$ is lower alkyl or phenyl, $R^F$ and $R^G$, being the same or different, are hydrogen, lower alkyl, cycloalkyl or phenyl, each phenyl can be substituted by a group selected from lower alkyl, hydroxy, lower alkoxy, lower alkanoyloxy, halogen, nitro, amino, lower alkylamino, lower alkanoylamino, lower alkylsulfonyl, phenylsulfonyl, phenyl and $R^E$—OCO—, and each cycloalkyl can be substituted by lower alkyl, hydroxy, oxo or $R^E$—OCO—;

6) $R^7$ joins with sulfur adjacent to $A^1$ to form a nonaromatic heterocyclic ring selected from a thiolactone ring and a dithiolane ring;

7) $A^1$ is lower alkylene; and

8) $A^2$ is lower alkylene.

More preferred examples of the present compound are the following.

Compounds and salts thereof wherein the group(s) in the general formula [I] is defined by anyone selected from the following 1) to 11) or any combinations consisting of 1) to 11).

1) $R^1$ is selected from hydrogen, lower alkyl, phenyl, $R^A$—CO—, $R^C$—S— and a group of the following formula [III], and the lower alkyl can be substituted by phenyl or lower alkoxycarbonyl;

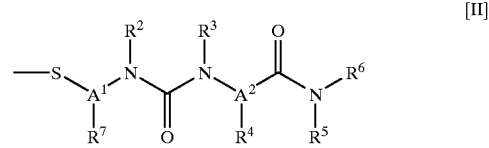

[II]

$R^A$ is selected from lower alkyl, lower alkoxy, phenyl, pyridyl, phenyl-lower alkoxy and $R^F$—N($R^G$)—, $R^C$ is phenyl, $R^F$ is lower alkyl, and $R^G$ is hydrogen;

2) $R^2$ is selected from hydrogen, lower alkyl, lower alkenyl and phenyl, the lower alkyl can be substituted by a group selected from lower alkoxy, cycloalkyl, cycloalkenyl, adamantyl, phenyl, naphthyl, pyridyl and $R^B$—O—, the phenyl can be substituted by a group selected from lower alkyl, hydroxy, lower alkoxy, lower alkanoyloxy, halogen, nitro and phenyl, the lower alkenyl can be substituted by phenyl, and $R^B$ is phenyl;

3) $R^3$ is selected from hydrogen and lower alkyl, and the lower alkyl can be substituted by phenyl;

4) $R^4$ is selected from hydrogen, lower alkyl and phenyl, the lower alkyl can be substituted by a group selected from hydroxy, cycloalkyl, phenyl, naphthyl, pyridyl, thienyl, imidazolyl, toluenesulfonylguanidino, $R^C$—S—, $R^D$—COS—, $R^F$—N($R^G$)— and $R^K$—CONH—, each phenyl can be substituted by a group selected from hydroxy, lower alkoxy, halogen, nitro, lower alkanoylamino, phenylsulfonyl and phenyl, $R^C$ is selected from hydrogen, lower alkyl and phenyl, $R^D$ is selected from lower alkyl and phenyl, $R^F$ and $R^G$ are hydrogen, and $R^K$ is lower alkoxy. When $R^4$ is lower alkyl, terminal carbon of the lower alkyl can join with carbon to which the alkyl is bonded to form a cycloalkyl ring;

5) $R^5$ is selected from hydrogen and lower alkyl;

6) $R^6$ is selected from lower alkyl and pyridyl, the lower alkyl can be substituted by a group selected from pyridyl, imidazolyl, phthalimido, piperidyl, piperazinyl, morpholinyl, $R^E$—OCO—, $R^F$—N($R^G$)—, $R^H$—N($R^J$)CO— and $R^K$—CONH—, $R^E$ is selected from hydrogen and lower alkyl, $R^F$ and $R^G$, being the same or different, are selected from hydrogen, lower alkyl, cycloalkyl and phenyl, $R^H$ and $R^J$, being the same or different, are selected from hydrogen and lower alkyl, $R^K$ is lower alkoxy, and the piperazinyl can be substituted by lower alkyl;

7) $R^5$ and $R^1$ join each other to form a nonaromatic heterocyclic ring selected from a morpholine ring, a piperidine ring, a piperazine ring, a pyrroline ring and a homopiperazine ring, the piperazine ring or the homopiperazine ring can be substituted by lower alkyl, cycloalkyl, phenyl or $R^A$—CO—, the lower alkyl can be substituted by hydroxy, phenyl or $R^E$—OCO—, $R^A$ is lower alkyl, lower alkoxy or halogeno-lower alkyl, and $R^E$ is hydrogen or lower alkyl;

8) $R^7$ is selected from hydrogen, lower alkyl, hydroxy, mercapto, phenyl, $R^B$—O—, $R^C$—S—, $R^D$—COS—, $R^E$—OCO—, —CONHOH and $R^F$—N($R^G$)—, the lower alkyl can be substituted by a group selected from hydroxy, mercapto, phenyl, $R^B$—O—, $R^C$—S—, $R^D$—COS—, $R^E$—OCO—, —CONHOH and $R^F$—N($R^G$)—, $R^B$ is phenyl, $R^C$ is phenyl, $R^D$ is lower alkyl or phenyl, $R^E$ is hydrogen or lower alkyl, and $R^F$ and $R^G$ are lower alkyl;

9) $R^7$ joins with sulfur adjacent to $A^1$ to form a nonaromatic heterocyclic ring selected from a thiolactone ring and a dithiolane ring;

10) $A^1$ is lower alkylene; and

11) $A^2$ is lower alkylene.

Further preferred examples of the present compound are the following.

Compounds and salts thereof wherein the group(s) in the general formula [I] is defined by anyone selected from the following 1) to 10) or any combinations consisting of 1) to 10).

1) $R^1$ is selected from hydrogen, $R^A$—CO— and a group of the following formula

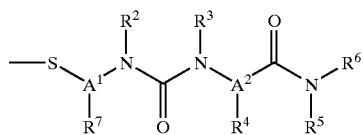

[II]

$R^A$ is selected from lower alkyl, phenyl and pyridyl;

2) $R^2$ is lower alkyl or phenyl, the lower alkyl can be substituted by a group selected from cycloalkyl, cycloalkenyl, adamantyl, phenyl and phenoxy, and the phenyl can be substituted by halogen;

3) $R^3$ is hydrogen;

4) $R^4$ is hydrogen or lower alkyl, the lower alkyl can be substituted by a group selected from phenyl, naphthyl, lower alkylthio and $R^D$—COS—, $R^D$ is lower alkyl, and the phenyl can be substituted by a group selected from hydroxy, lower alkoxy, halogen, nitro and phenyl;

5) $R^1$ is hydrogen;

6) $R^1$ is lower alkyl, the lower alkyl can be substituted by a group selected from pyridyl, piperidyl, piperazinyl and $R^F$—N($R^G$)—, $R^F$ and $R^G$, being the same or different, are selected from hydrogen, lower alkyl and cycloalkyl, and the piperazinyl can be substituted by lower alkyl;

7) $R^5$ and $R^6$ join each other to form a nonaromatic heterocyclic ring selected from a piperidine ring, a morpholine ring and a piperazine ring, the piperazine ring can be substituted by lower alkyl;

8) $R^7$ is hydrogen;

9) $A^1$ is lower alkylene; and

10) $A^2$ is lower alkylene.

The most preferred examples of the present compound are the following.

Compounds and salts thereof wherein the group(s) in the general formula [I] is defined by anyone selected from the following 1) to 10) or any combinations consisting of 1) to 10).

1) $R^1$ is selected from acetyl, benzoyl and a group of the following formula [II];

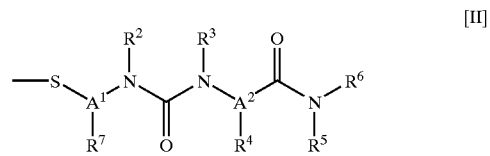

2) $R^2$ is selected from 2-cyclohexylethyl, 2-cyclopentylethyl, 2-(1-adamantyl)ethyl, 2-(cyclohexen-1-yl)ethyl, phenethyl and 3-(4-fluorophenyl)propyl;

3) $R^3$ is hydrogen;

4) $R^4$ is selected from methyl, acetylthiomethyl, benzyl, 2-naphthylmethyl, 4-fluorobenzyl, 4-chlorobenzyl, 4-biphenylylmethyl, 4-nitrobenzyl, 3-nitro-4-biphenylylmethyl, 4-methoxybenzyl and 4-isopropoxybenzyl;

5) $R^5$ is hydrogen;

6) $R^6$ is selected from 2-(dimethylamino)ethyl, 2-(diethylamino)ethyl, 2-(diisopropylamino)ethyl, N-methyl-2-(cyclohexylamino)ethyl, 2-(2-pyridyl)ethyl, 2-(1-piperidyl)ethyl and 2-(4-methylpiperazinyl)ethyl;

7) $R^5$ and $R^6$ join each other to form a group selected from 1-piperidyl, 4-morpholinyl and 4-methyl-1-piperazinyl;

8) $R^7$ is hydrogen;

9) $A^1$ is ethylene;

10) $A^1$ is methylene.

The most preferred practical examples of the present compound are the following compounds and salts thereof.

1) (2S)-2-[3-[2-(Acetylthio)ethyl]-3-phenethylureido]-N-[2-(dimethylamino)ethyl]-3-(2-naphthyl)propionamide

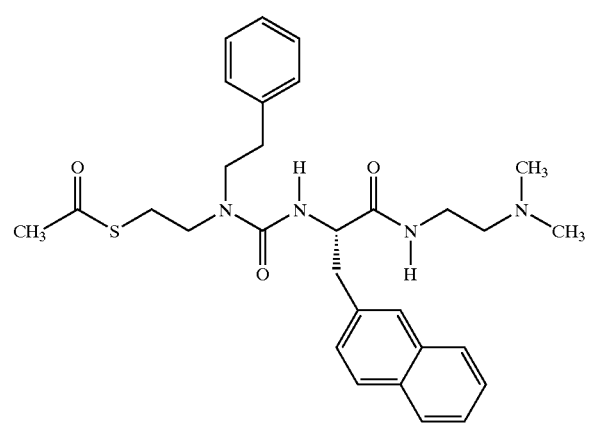

2) (2S)-2-[3-[2-(Acetylthio)ethyl]-3-phenethylureido]-N-[2-(N-methylcyclohexylamino)ethyl]-3-(4-nitrophenyl)propionamide

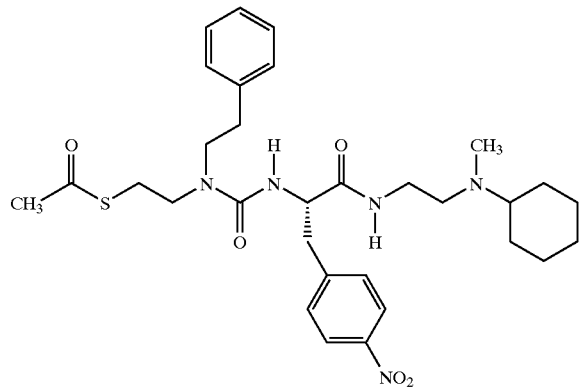

3) (2S)-2-[3-[2-(Acetylthio)ethyl]-3-phenethylureido]-N-[2-(diethylamino)ethyl]-3-(4-nitrophenyl)propionamide

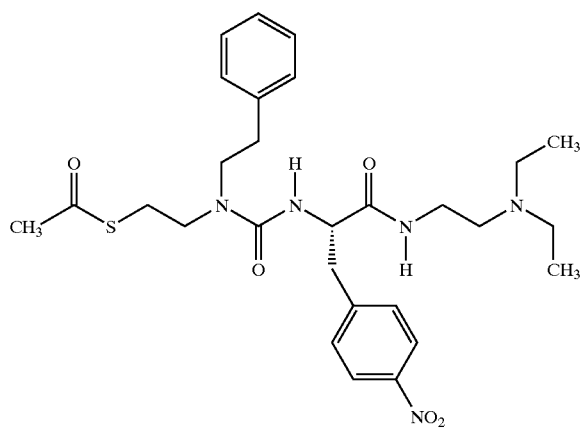

4) (2S)-2-[3-[2-(Benzoylthio)ethyl]-3-phenethylureido]-N-[2-(dimethylamino)ethyl]3-(4-nitrophenyl)propionamide

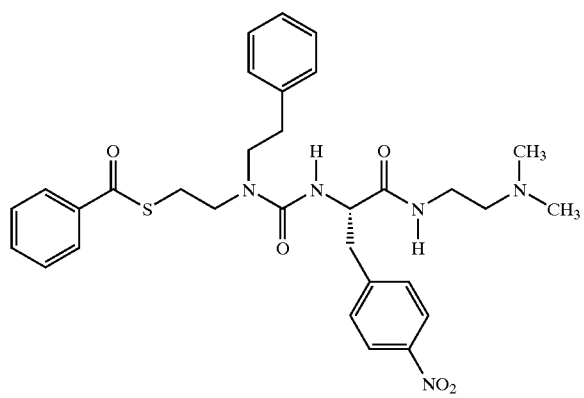

5) (2S)-2-[3-[2-(Acetylthio)ethyl]-3-phenethylureido]-3-(4-biphenylyl)-N-[2-(dimethylamino)ethyl]propionamide

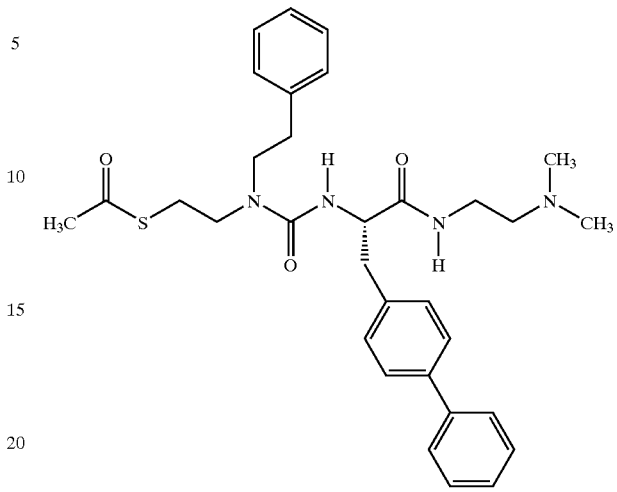

6) (2S)-2-[3-[2-(Acetylthio)ethyl]-3-phenethylureido]-N-[2-(diisopropylamino)ethyl]-3-(4-nitrophenyl)propionamide

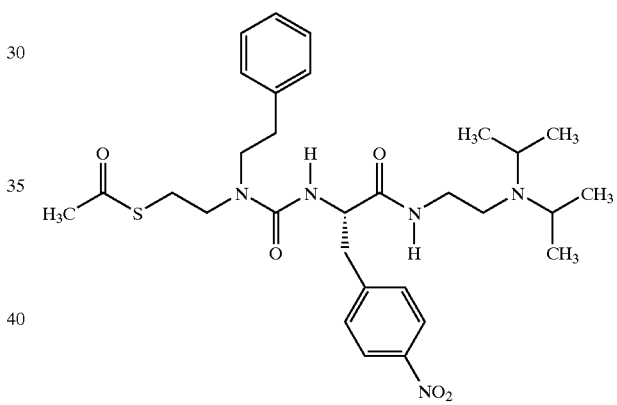

7) (2S)-2-[3-[2-(Acetylthio)ethyl]-3-phenethylureido]-N-[2-(dimethylamino)ethyl]-3-(4-methoxyphenyl)propioamide

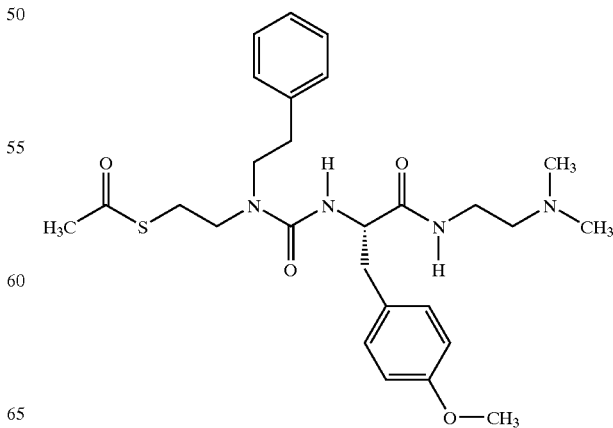

8) (2S)-2-[3-[2-(Acetylthio)ethyl]-3-phenethylureido]-N-[2-(dimethylamino)ethyl]-3-(4-nitrophenyl)propionamide

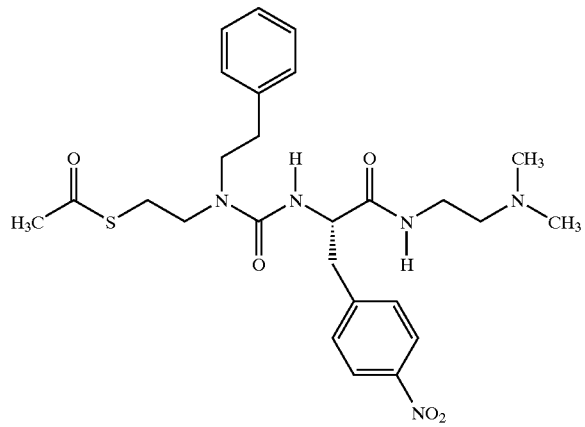

9) (2S)-2-[3-[2-(Acetylthio)ethyl]-3-phenethylureido]-N-[2-(dimethylamino)ethyl]-3-(2-nitro-4-biphenylyl)propionamide

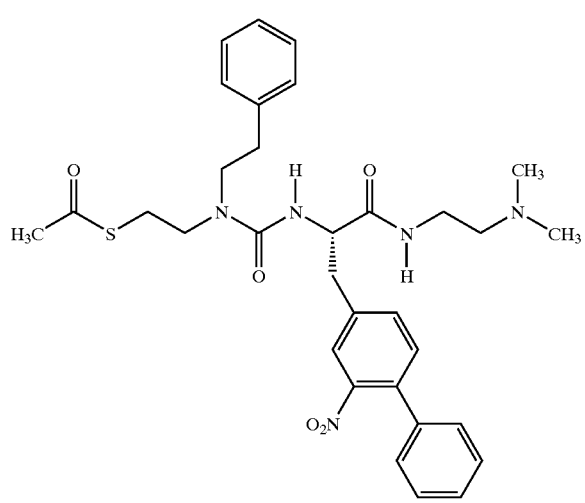

10) (2S)-2-[3-[2-(Acetylthio)ethyl]-3-phenethylureido]-3-(4-chlorophenyl)-N-[2-(dimethylamino)ethyl]propionamide

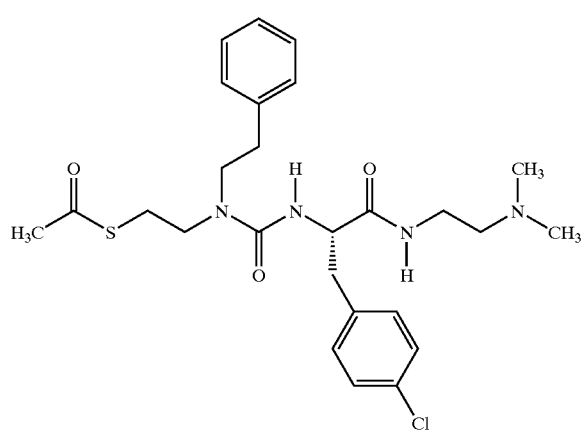

11) (2S)-2-[3-[2-(Acetylthio)ethyl]-3-phenethylureido]-3-(4-nitrophenyl)-N-[2-(2-pyridyl)ethyl]propionamide

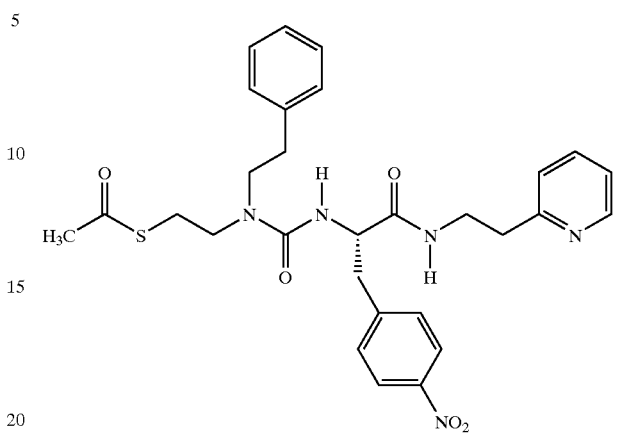

12) (2S)-2-[3-[2-(Acetylthio)ethyl]-3-phenethylureido]-N-[3-(1-imidazolyl)propyl]-3-(4-nitrophenyl)propionamide

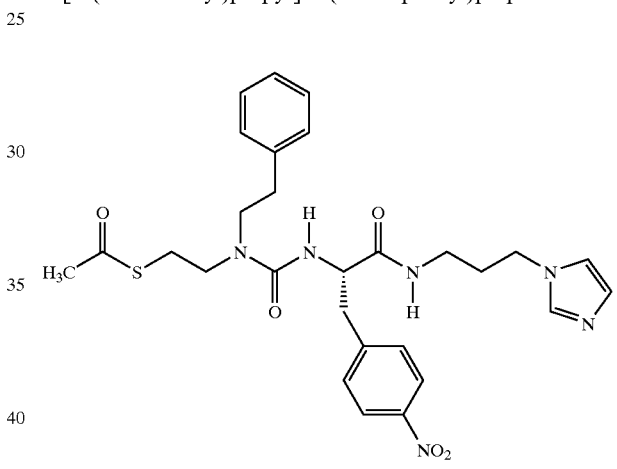

13) (2S)-2-[3-[2-(Acetylthio)ethyl]-3-phenethylureido]-N-[2-(dimethylamino)ethyl]-3-(4-fluorophenyl)propionamide

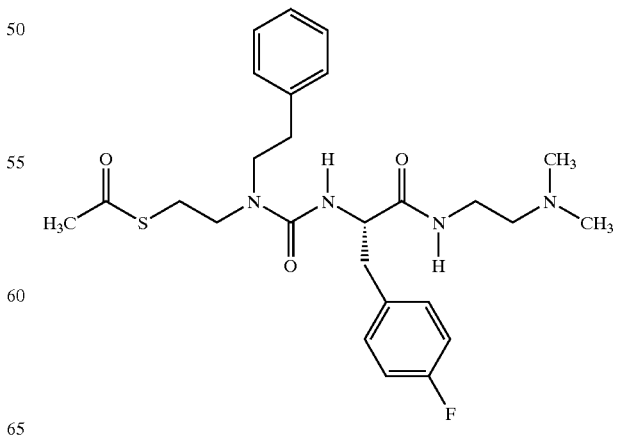

14) (2S)-2-[3-[2-(Acetylthio)ethyl]-3-phenethylureido]-3-(4-nitrophenyl)-N-[2-(piperidino)ethyl]propionamide

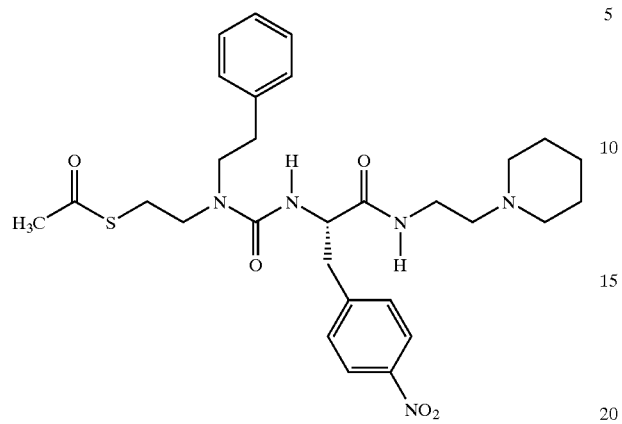

15) (2S)-2-[3-[2-(Acetylthio)ethyl]-3-phenethylureido]-N-[2-(dimethylamino)ethyl]-3-(4-isopropoxyphenyl)propionamide

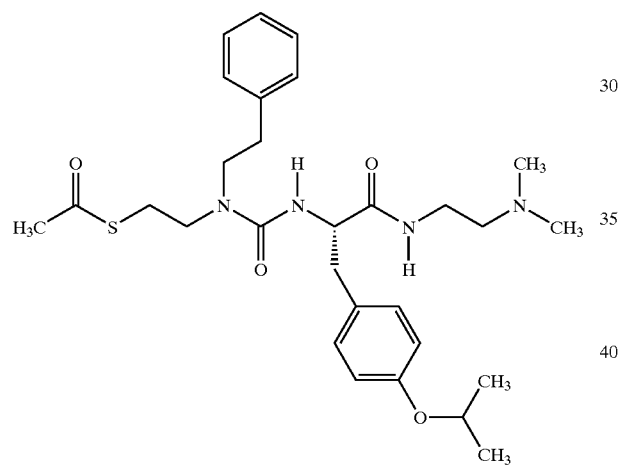

16) (2S)-2-[3-[2-(Acetylthio)ethyl]-3-phenethylureido]-N-[2-(4-methylpiperazin-1-yl)ethyl]-3-(4-nitrophenyl)propionamide

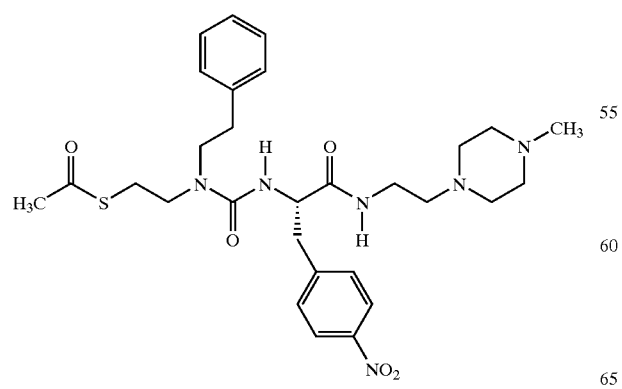

17) 1-[(2S)-2-[3-[2-(Acetylthio)ethyl]-3-(2-cyclohexylethyl)ureido]propionyl]-4-methylpiperazine

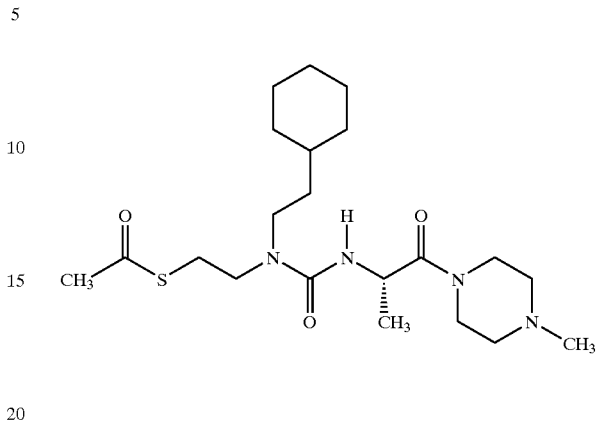

18) 1-[(2S)-2-[3-[2-(Acethylthio)ethyl]-3-(2-cyclopenthylethyl)ureido]propionyl]-4-methylpiperazine

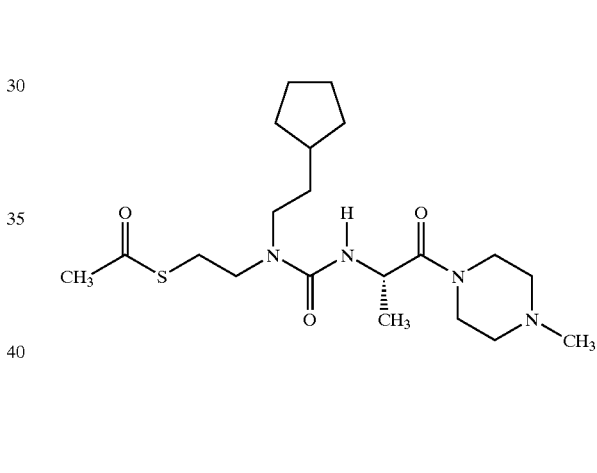

19) 1-[(2S)-2-[3-[2-(Acetylthio)ethyl]-3-[2-(cyclohexen-1-yl)ethyl]ureido]propionyl]-4-methylpiperazine

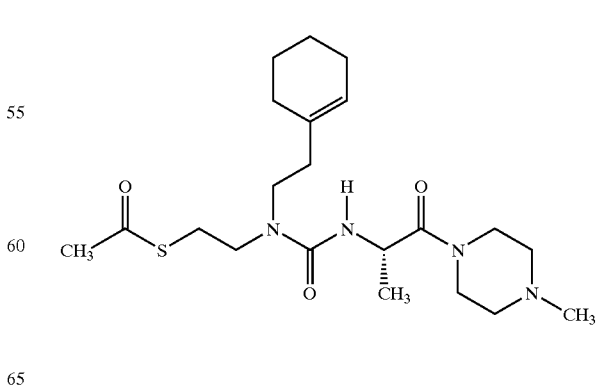

20) 1-[(2S)-2-[3-[2-(Acetylthio)ethyl]-3-[3-(4-fluorophenyl)propyl]ureido]propionyl]-4-methylpiperazine

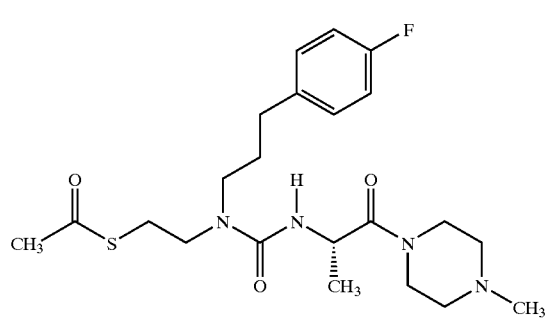

21) 1-[(2R)-3-(Acetylthio)-2-[3-[2-(Acetylthio)ethyl]-3-phenethylureido]propionyl]-4-methylpiperazine

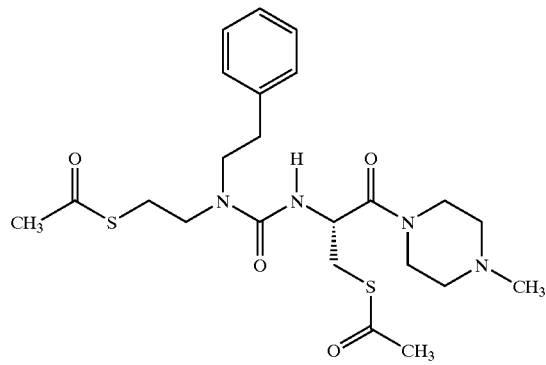

22) 4-[(2S)-2-[3-[2-(Acetylthio)ethyl]-3-henethylureido]propionyl]morpholine

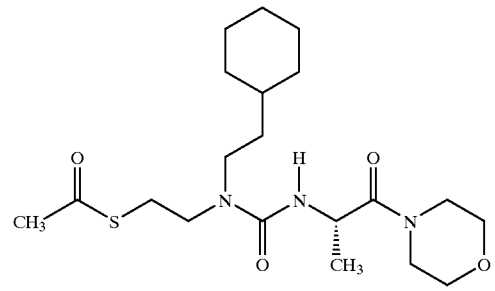

23) 1-[(2S)-2-[3-[2-(Acetylthio)ethyl]-3-(2-cyclohexylethyl)ureido]propionyl]piperidine

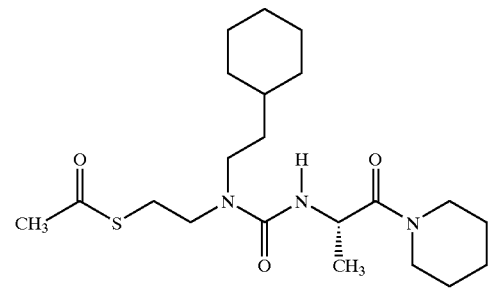

24) 1,1'-Dimethyl-4,4'-[2S,2S')-2,2'-[3,3'-diphenethyl-3,3'-(2,2'-dithiodiethyl)diureido]-3,3'-diphenyldipropionyl]dipiperazine

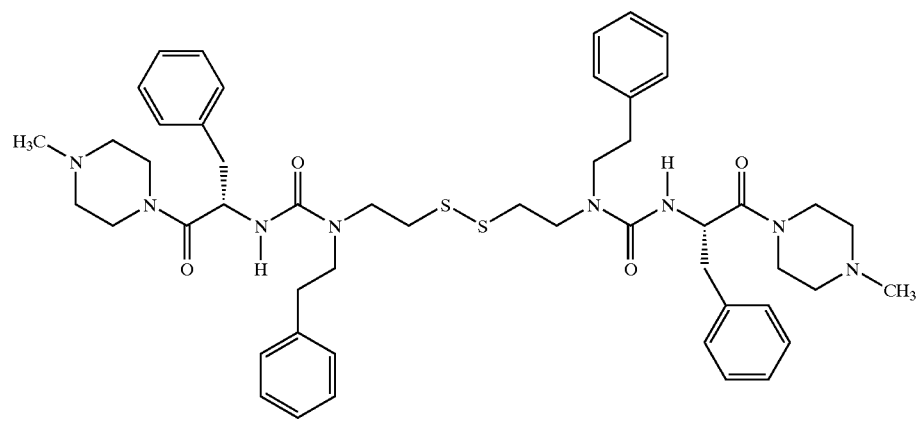

25) 1-[(2S)-2-[3-[2-(Acetylthio)ethyl]-3-[2-(1-adamantyl) ethyl]ureido]propionyl]-4-methylpiperazine
26) 4-(2S)-2-[3-[2-(Acetylthio)ethyl]3-[2-(1-adamatyl) ethyl]ureido]propionyl]morpholine
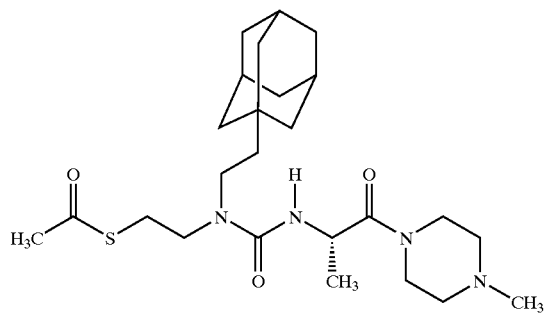
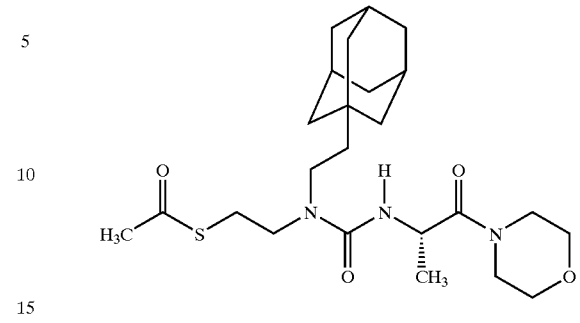
27) 1,1'-Dimethyl-4,4'-[(2S,2'S)-2,2'-[3,3'-diphenethyl-3,3'-[2,2'-(dithio)diethyl]diureido]dipropionyl]dipiperazine
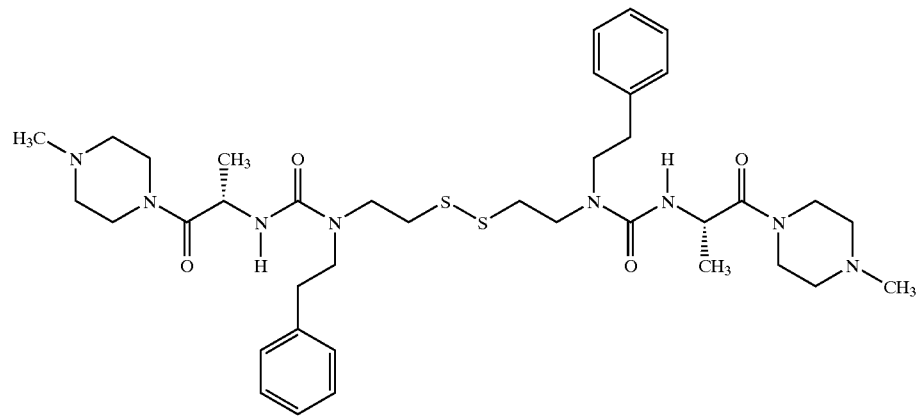
28) 1,1'-[(2S,2'S)-2,2'-[3,3'-Bis(2-cyclohexylethyl)-3,3'-[2,2'-(dithio)diethyl]diureido]dipropionyl]-4,4'-dimethyldipiperazine
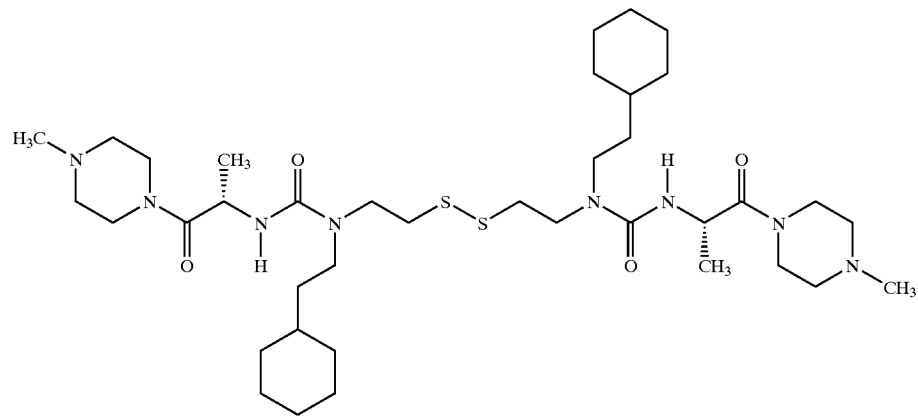

29) 1,1'-[(2S,2'S)-2,2'-[3,3'-Bis[2-(1-adamantyl)ethyl]-3,3'-[2,2'-(dithio)diethyl]diureido]dipropionyl]-4,4'-dimethyldipiperazine compound, preferred examples of the present synthetic intermediate are also selected corresponding to the preferred examples of the present compound.

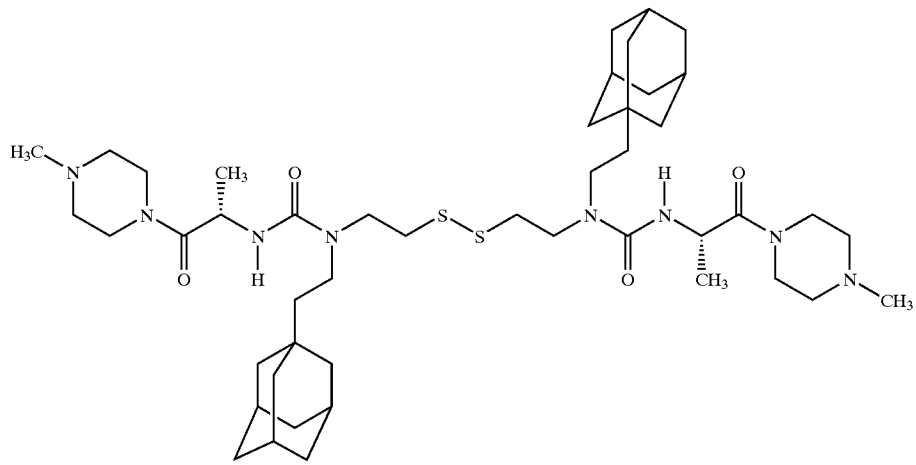

30) 1,1'-[(2S,2'S)-2,2'-[3,3'-Bis(2-cyclopentylethyl)-3,3'-[2,2'-(dithio)diethyl]diureido]dipropionyl]-4,4'-dimethyldipiperazine

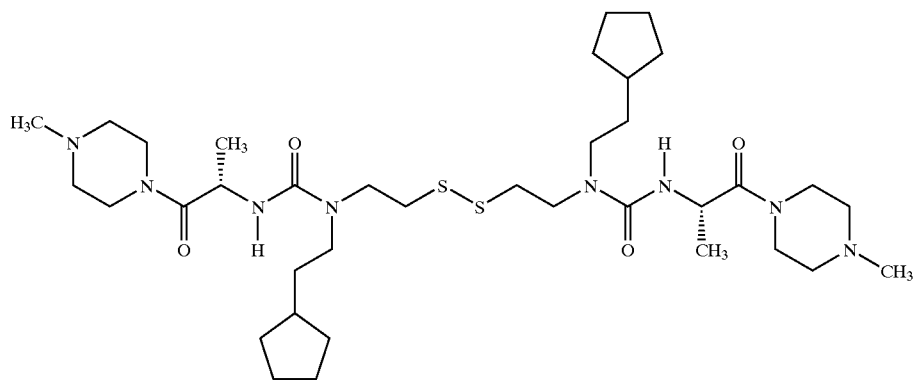

Since the present synthetic intermediate is selected corresponding to the chemical structure of the present A typical synthesis route scheme of the present compound is shown below.

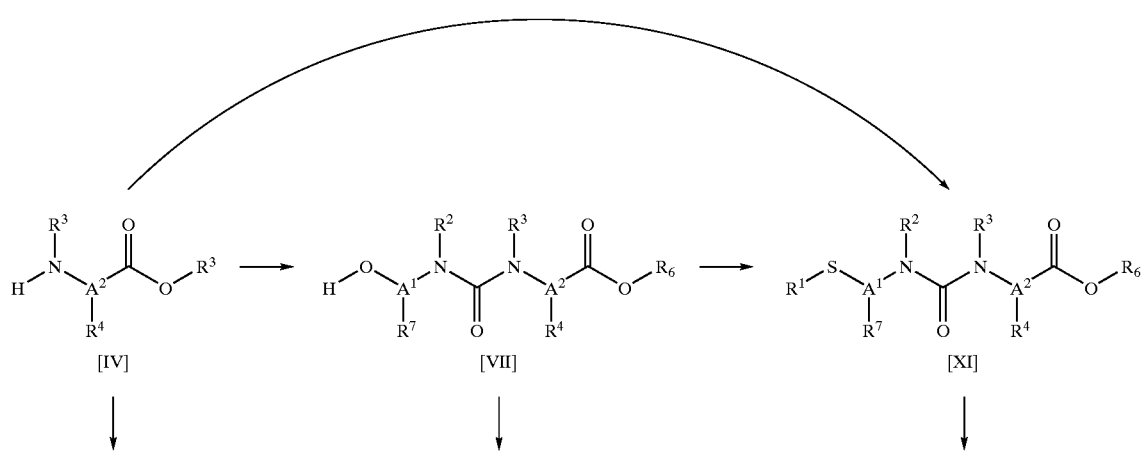

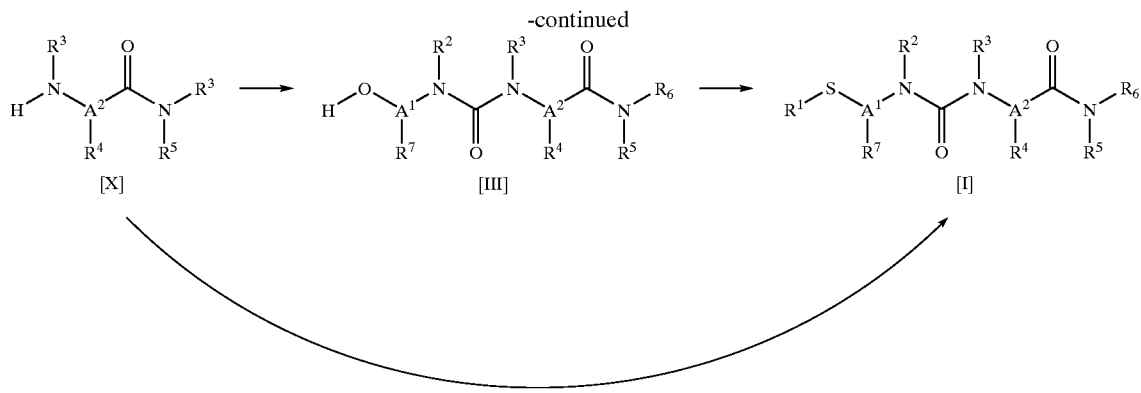

The present compound [I] can be synthesized through various synthesis routes, for example, as shown in the above reaction route scheme. These synthesis methods are shown every route below. However, these routes exemplify routes and do not show all methods. Detailed synthesis methods are described in Examples later.

Route A) [IV]→[VII]→[III]→[I]
Route B) [IV]→[X]→[III]→[I]
Route C) [IV]→[VII]→[XI]→[I]
Route D) [IV]→[XI]→[I]
Route E) [IV]→[X]→[I]

The synthesis methods of these routes are described in more detail below.

Route A)

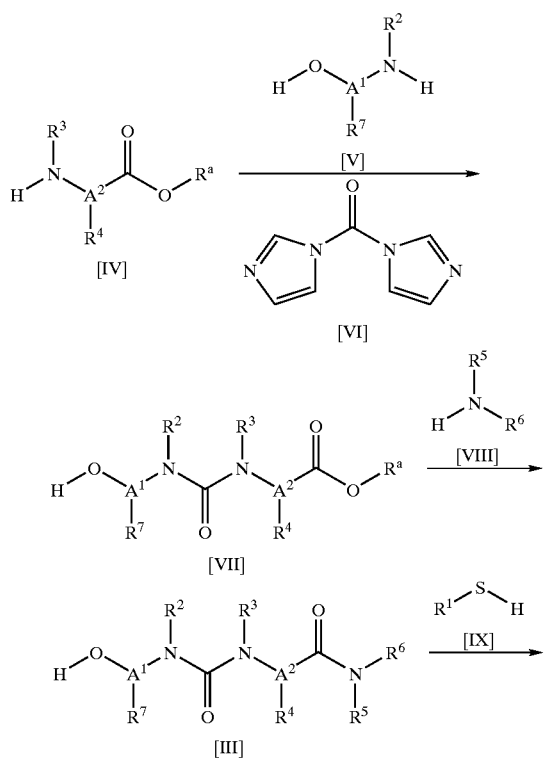

[wherein $R^a$ is hydrogen, lower alkyl, phenyl or benzyl. The same definitions are applied hereinafter.]

The ester derivative [IV] is reacted with the amino alcohol derivative [V] in the presence of the condensation agent (for example, 1,1'-carbonyldiimidazole [VI]) and the base to convert it into the urea derivative [VII], and the resulting urea derivative is reacted with the amine derivative [VIII] to give the compound represented by the formula [III] (the present synthetic intermediate). Then, the obtained compound [III] is condensed with the thiol derivative [IX] by Mitsunobu reaction to give the present compound [I].

Route B)

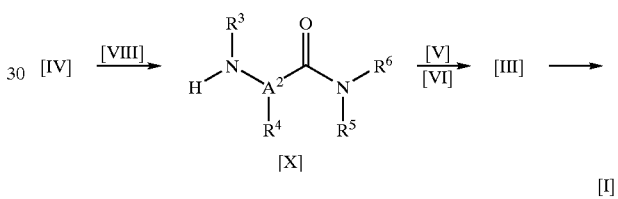

The ester derivative [IV] is reacted with the amine derivative [VIII] to convert it into the amide derivative [X], and the resulting amide derivative is reacted with the amino alcohol derivative [V] in the presence of the condensation agent (for example, 1,1'-carbonyldiimidazole [VI]) and the base to give the compound represented by the formula [III] (the present synthetic intermediate). Then, the present compound [I] is obtained in the same manner as by the route A).

Route C)

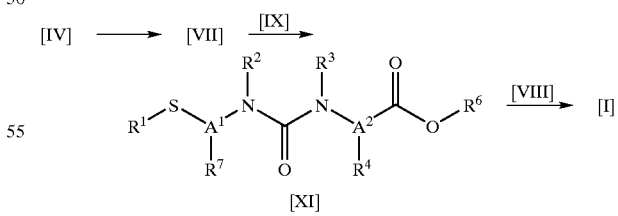

The urea derivative [VII] obtained according to the method of the route A) is condensed with the thiol derivative [IX] by Mitsunobu reaction to give the compound represented by the formula [XI]. Then, the obtained compound [XI] is condensed with the amine derivative [VIII] by the conventional method to give the present compound [I].

Route D)

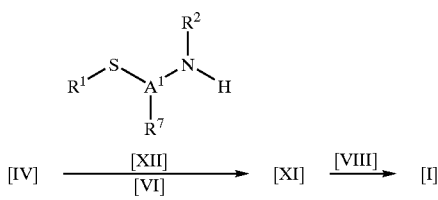

[IV] $\xrightarrow[\text{[VI]}]{\text{[XII]}}$ [XI] $\xrightarrow{\text{[VIII]}}$ [I]

The ester derivative [IV] is reacted with the aminothiol derivative [XII] in the presence of the condensation agent (for example, 1,1'-carbonyldiimidazole [VI]) and the base to give the compound [XI]. Then, the obtained compound [XI] is condensed with the amine derivative [VIII] by the conventional method to give the present compound [I].

Route E)

[IV] $\longrightarrow$ [X] $\xrightarrow[\text{[VI]}]{\text{[XII]}}$ [I]

The amide derivative [X] obtained by the method of the route B) is reacted with the aminothiol derivative [XII] in the presence of the condensation agent (for example, 1,1'-carbonyldiimidazole [VI]) and the base to give the present compound [I].

In the above-mentioned synthesis methods, when the reactant has a hydroxy, thiol or amino group in its molecule, these groups can be protected with suitable protecting groups, if necessary, and these protecting groups can also be removed by the conventional method after reaction. When the reactant has a carboxyl group in its molecule, the carboxyl group can be esterified, if necessary, and the ester can also be converted into a carboxylic acid by hydrolysis or acidolysis.

In the present compound, when R joins with sulfur adjacent to $A^1$ to form a thiolactone ring or a dithiolane ring, the present compound can also be synthesized by the following methods other than the above-mentioned routes.

When $R^7$ is $R^E$—OCO— and $R^1$ is hydrogen in the formula [I], the thiolactone ring can also be synthesized by condensing these groups.

When $R^7$ is mercapto and $R^1$ is hydrogen in the formula [I], the dithiolane ring can be synthesized by joining these groups. Namely, the dithiolane ring is synthesized by forming intramolecular disulfide.

The compounds obtained by the above-mentioned methods can be converted into the above-mentioned salts by the conventional method.

The chemical structural feature of the present compounds is that the compounds have urea structure as basic structure and have a sulfur atom and an amide bond in side chains. Few studies of such drugs having the urea structure as basic skeleton have been reported. Moreover, no drug having a sulfur atom in a side chain has hitherto practically been reported. Limiting drugs to those having the TNF-α production inhibitory effects, which is an object of the present invention, no drug having a chemical structure similar to the present compound is known at all.

The present inventors precisely studied the synthesis of the compounds having the urea structure as basic structure which thus had been hitherto hardly studied, prepared the many novel compounds, found that these novel compounds have the excellent TNF-α production inhibitory effects, and completed the present invention. The present inventors found also the novel compounds which are useful as the synthetic intermediates of the present compounds in the process of the study of the synthesis of the present compounds. The present compounds exhibit the effects both in state where the sulfur atom in the side chain joins with various groups (represented by $R^1$ in the formula [I] except for hydrogen) and in the state where the sulfur atom takes the form of SH ($R^1$ in the formula [I] is hydrogen). When $R^1$ is used as a protecting group of the SH group, the protecting group is sometimes removed by hydrolysis and the like and the resulting form of SH exhibits the effects. When the present compounds contain a carboxylate in their molecule, the present compounds exhibit the effects even in the ester state. The ester linkage is sometimes subject to hydrolysis and the like and the resulting form of a carboxylic acid exhibits the effects. When the present compounds contain a group which is converted into a free hydroxy or amino group, the present compounds can be administered in state where these groups are protected with suitable protecting groups. The present compounds can be administered in state where these protecting groups are removed.

The TNF-α production inhibitory effects of the present compounds were examined in order to study utility of the present compounds. Details will be described in the item of pharmacological test below. Studying in vitro or in vivo inhibitory effects on liberation of TNF-α caused by stimulation of lipopolysaccharide (LPS), the present compounds exhibited the excellent TNF-α production inhibitory effects.

TNF-α production is known to be closely related to crises of autoimmune diseases such as rheumatoid arthritis, Crohn's disease and systemic lupus erythematosus, cachexia, acute infectious disease, allergy, pyrexia, anemia, diabetes and the like. Compounds which inhibit its production like the present compounds are expected to be useful for treatment of these various diseases.

The present compound can be administered orally or parnterally. Examples of dasage forms are tablets, capsules, granules, powders, injections and the like. The present compound can be formulated into preparations by the conventional methods. For example, oral preparations such as tablets, capsules, granules and powders can be produced by adding optionally diluents such as lactose, crystalline cellulose, starch and vegetable oil; lubricants such as magnesium stearate and talc; binders such as hydroxypropylcellulose and polyvinyl pyrrolidone; disintegrator such as calcium carboxymethylcellulose or low-substituted hydroxypropylmethylcellulose; coating agent such as hydroxypropylmethylcellulose, macrogol or silicone resin; or film forming agent such as gelatin film.

The dosage of the present compound can be selected suitably according to the symptom, age, dosage form and the like. In case of the oral preparation, the present compound can be administered once to several times per day with a daily dose of 0.1 to 5000 mg, preferably 1 to 1000 mg.

Examples of preparations and formulations and results of pharmacological test of the present invention are shown below. These examples do not limit the scope of the invention, but are intended to make the invention more clearly understandable.

BEST MODE FOR CARRYING OUT THE INVENTION

Preparation of Compounds

REFERENCE EXAMPLE 1

L-2-Phenylglycine t-Butyl Ester (Reference Compound No. 1-1)

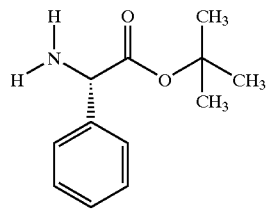

1) To isobutene (5 ml) in a pressure tube are added N-benzyloxycarbonyl-L-2-phenylglycine (4.2 g), anhydrous methylene chloride (10 ml) and concentrated sulfuric acid (0.5 ml) successively under a nitrogen atmosphere and dry ice-methanol cooling, the tube is stoppered, and then the mixture is stirred at room temperature overnight. The cooled reaction mixture is introduced into a vessel containing a 10% aqueous sodium hydrogencarbonate solution and ice, and the mixture is stirred. Ethyl acetate is added to the mixture, and the whole is extracted. The organic layer is washed with water and saturated brine successively, dried over anhydrous magnesium sulfate and concentrated under reduced pressure. The resulting residue is purified by silica gel column chromatography to give 3.5 g (75%) of N-benzyloxycarbonyl-L-2-phenylglycine t-butyl ester.

IR (Film, $cm^{-1}$) 3352, 2978, 1722, 1498, 1455, 1369, 1331, 1228, 1151, 1050.

2) Under a nitrogen atmosphere, 20% palladium hydroxide on carbon (200 mg) is added to a solution of N-benzyloxycarbonyl-L-2-phenylglycine t-butyl ester (3.4 g) obtained in 1) in tetrahydrofuran (18 ml)-methanol (18 ml). The mixture is stirred under a hydrogen atmosphere for two days. Palladium hydroxide on carbon is filtered out with Celite, and the filtrate is concentrated under reduced pressure to give 1.3 g (63%) of the titled compound (Reference compound No. 1-1) as crystals. (Reference compound No. 1-1)

mp 220.9~223.5° C.; IR (KBr, $cm^{-1}$) 3411, 2980, 2931, 1732, 1496, 1394, 1372, 1250, 1157, 750.

The following compounds are obtained by a method similar to Reference Example 1.

L-Phenylalanine t-butyl ester (Reference compound No. 1-2)

mp 160~190° C. (decomp.); $[\alpha]_D^{20}$ +15.6° (c=0.98, methanol); IR (KBr, $cm^{-1}$) 2834, 1734, 1507, 1244, 116.0, 703.

D-Alanine t-butyl ester (Reference compound No. 1-3)
IR (Film, $cm^{-1}$) 3376, 2978, 1731, 1368, 1251.

t-Butyl L-2-aminobutyrate (Reference compound No. 1-4)
IR (Film, $cm^{-1}$) 3381, 2975, 2935, 2878, 1729, 1479, 1459, 1393, 1368, 1253, 1157, 849.

L-Norvaline t-butyl ester (Reference compound No. 1-5)
IR (Film, $cm^{-1}$) 3381, 2961, 2934, 2874, 1728, 1368, 1256, 1156, 847, 756.

DL-3-(t-Butoxy)alanine t-butyl ester hydrochloride (Reference compound No. 1-6)
mp 150.7~151.3° C.; IR (KBr, $cm^{-1}$) 2979, 1747, 1497, 1248, 1156.

REFERENCE EXAMPLE 2

L-3-(4-Nitrophenyl)alanine Phenyl Ester Hydrochloride (Reference Compound No. 2-1)

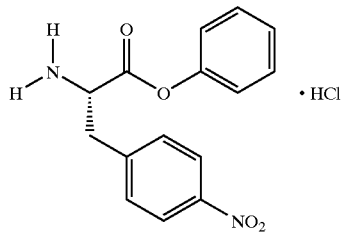

1) In anhydrous methylene chloride (174 ml) are dissolved N-(t-butoxycarbonyl)-L-3-(4-nitrophenyl)alanine (21.6 g), phenol (7.86 g) and dimethylaminopyridine (0.85 g) under a nitrogen atmosphere. Then, 1,3-dicyclohexylcarbodiimide (17.2 g) is added to the solution under ice cooling, and the mixture is stirred at room temperature for one hour. The resulting precipitate is filtered out, and then the filtrate is washed with a 5% aqueous sodium hydrogencarbonate solution, water, a 5% aqueous citric acid solution, water and saturated brine successively. The filtrate is dried over anhydrous magnesium sulfate and concentrated under reduced pressure to give 21.25 g (79%) of N-(t-butoxycarbonyl)-L-3-(4-nitrophenyl) alanine phenyl ester as crystals.

mp 115.0~116.0° C.; $[\alpha]_D^{20}$ −21.6° (c=1.0, methanol); IR (KBr, $cm^{-1}$) 3385, 1744, 1688, 1523, 1347, 1231, 1191, 949, 745, 695.

2) A 4.6 N solution of hydrogen chloride in ethyl acetate (11 ml) is added to a solution of N-(t-butoxycarbonyl)-L-3-(4-nitrophenyl)alanine phenyl ester (1.93 g) obtained in 1) in chloroform (10 ml), and the mixture is stirred at room temperature for one hour. Ether is added to the reaction mixture, and the resulting precipitate is filtered off to give 1.50 g (93%) of the titled compound (Reference compound No. 2-1) as crystals. (Reference compound No. 2-1).

mp 202.5~204.6° C. (decomp.); $[\alpha]_D^{20}$ +42.7° (c=1.0, methanol); IR (KBr, $cm^{-1}$) 2866, 1758, 1602, 1525, 1483, 1357, 1228, 1207, 761, 698.

The following compounds are obtained by a method similar to Reference Example 2.

L-Phenylalanine phenyl ester hydrochloride (Reference compound No. 2-2)
mp 187~190° C.; $[\alpha]_D^{20}$ +37.3° (c=0.98, methanol); IR (KBr, $cm^{-1}$) 2864, 2646, 2610, 1764, 1616, 1591, 1455, 1226, 1208.

L-3-(4-Fluorophenyl)alanine phenyl ester hydrochloride (Reference compound No. 2-3)
mp 208.0~209.5° C.; $[\alpha]_D^{20}$ +30.2° (c=0.51, methanol); IR (KBr, $cm^{-1}$) 2873, 1763, 1600, 1510, 1222, 1157, 823, 759, 695.

L-3-(4-Methoxyphenyl)alanine phenyl ester hydrochloride (Reference compound No. 2-4)
mp 178.5~185.0° C. (decomp.); $[\alpha]_D^{20}$ +27.4° (c=0.51, methanol); IR (KBr, $cm^{-1}$) 2865, 1766, 1513, 1225, 1209.

L-3-(2-Naphthyl)alanine phenyl ester hydrochloride (Reference compound No. 2-5)
mp 190.0~193.2° C,; $[\alpha]_D^{20}$ +37.1° (c=0.49, dimethyl sulfoxide); IR (KBr, $cm^{-1}$) 3467, 2853, 1776, 1759, 1491, 1222, 1199.

L-3-(4-Biphenylyl)alanine phenyl ester hydrochloride (Reference compound No. 2-6)

mp 215.0~216.5° C.; $[\alpha]_D^{20}$ +56.8° (c=0.53, dimethyl sulfoxide); IR (KBr, cm$^{-1}$) 2863, 1771, 1590, 1486, 1409, 1340, 1251, 1196.

L-3-(2-Thienyl)alanine phenyl ester hydrochloride (Reference compound No. 2-7)

mp 167.0~167.6° C.; $[\alpha]_D^{20}$ +12.9° (c=0.99, methanol); IR (KBr, cm$^{-1}$) 2843, 1764, 1731, 1588, 1524, 1495, 1456, 1240, 1201, 1164, 1139, 750, 699, 691.

L-Tyrosine phenyl ester tosylate (Reference compound No. 2-8)

mp 213.0~217.0° C. (decomp.); $[\alpha]_D^{20}$ +21.4° (c=0.49, methanol); IR (KBr, cm$^{-1}$) 3355, 2835, 1740, 1614, 1595, 1516, 1169, 1123, 1035, 1010, 818, 758, 688.

N$^G$-Tosyl-L-arginine benzyl ester hydrochloride (Reference compound No. 2-9) $[\alpha]_D^{20}$ +1.6° (c=1.0, methanol); IR (KBr, cm$^{-1}$) 2927, 1971, 1747, 1677, 1620, 1362, 1215, 1170, 1088, 907, 816, 744.

REFERENCE EXAMPLE 3

L-3-(4-Nitrophenyl)alanine Benzyl Ester Tosylate (Reference Compound No. 3-1)

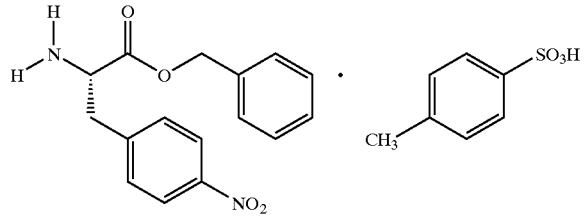

Into a reaction vessel equipped with a Deanstark apparatus are introduced L-3-(4-nitrophenyl)alanine (2.0 g), benzyl alcohol (27 ml), benzene (29 ml) and tosic acid monohydrate (2.0 g), and the mixture is refluxed overnight with stirring. Ether is added to the reaction mixture under ice cooling, and the resulting precipitate is filtered off to give 4.12 g (quantitatively) of the titled compound (Reference compound No. 3-1) as crystals.

(Reference compound No. 3-1)

mp 183.5~186.5° C.; $[\alpha]_D^{20}$ 10.1° (c=1.0, methanol); IR (KBr, cm$^{-1}$) 3085, 2669, 1746, 1601, 1518, 1348, 1208, 1175.

The following compounds are obtained by a method similar to Reference Example 3.

L-Phenylalanine benzyl ester tosylate (Reference compound No. 3-2)

mp 166.6~167.9° C.; $[\alpha]_D^{20}$ −6.9° ( c=1.0, methanol); IR (KBr, cm$^{-1}$) 3032, 1741, 1525, 1498, 1206, 1129, 1037, 1013.

L-3-(4-Chlorophenyl)alanine benzyl ester tosylate (Reference compound No. 3-3)

mp 171.0~177.5° C.; $[\alpha]_D^{20}$ −8.9° (c=1.0, methanol); IR (KBr, cm$^{-1}$) 2950, 1916, 1743, 1587.

L-3-(4-Methoxyphenyl)alanine benzyl ester tosylate (Reference compound No. 3-4)

mp 152.0~162.0° C.; $[\alpha]_D^{20}$ −12.8° (c=1.0, methanol); IR (KBr, cm$^{-1}$) 3000, 1742, 16 13, 1514, 1177.

L-2-Phenylglycine benzyl ester tosylate (Reference compound No. 3-5)

mp 170.08~176.0° C.; $[\alpha]_D^{20}$ +44.4° (c=1.0 methanol); IR (KBr, cm$^{-1}$) 3039, 1748, 1598, 1497, 1222, 1173, 906, 697.

L-3-(2-Naphthyl)alanine benzyl ester tosylate (Reference compound No. 3-6)

mp 174.8~184.5° C.; $[\alpha]_D^{20}$ −23.0° (c=1.0, methanol); IR (KBr, cm$^{-1}$) 3059, 1742, 1514, 1222, 1156.

L-Alanine benzyl ester tosylate (Reference compound No. 3-7)

mp 92.0~100.1° C.; $[\alpha]_D^{20}$ −3.40° (c=1.0, methanol); IR (KBr, cm$^{-1}$) 3031, 1765, 1737, 1612, 1284, 1211, 1127, 1039, 1013.

L-(3-Cyclohexyl)alanine benzyl ester tosylate (Reference compound No. 3-8)

mp 157.1~161.7° C.; $[\alpha]_D^{20}$ −2.2° (c=1.0, methanol); IR (KBr, cm$^{-1}$) 2931, 1754, 1287, 1124.

S-Methyl-L-cysteine benzyl ester tosylate (Reference compound No. 3-9)

mp 105.0~110.3° C.; $[\alpha]_D^{20}$ −8.1° (c=1.0, methanol); IR (KBr, cm$^{-1}$) 3093, 1748, 1523, 1218, 1178, 1125, 1038, 1013, 816, 736.

S-Benzyl-L-cysteine benzyl ester tosylate (Reference compound No. 3-10)

mp 141.8~153.3° C.; $[\alpha]_D^{20}$ −19.4° (c=1.0, methanol); IR (KBr, cm$^{-1}$) 3027, 1756, 1613, 1542, 1453, 1277, 1244, 1221, 1161, 1128, 1107, 1069, 1034, 1009, 976, 817, 740.

S-Benzyl-DL-penicillamine benzyl ester hydrochloride (Reference compound No. 3-11)

IR (Film, cm$^{-1}$) 3390, 2967, 1744, 1585, 1496, 1455, 1396, 1376, 1308, 1219.

N-Methyl-L-alanine benzyl ester hydrochloride (Reference compound No. 3-12)

mp 179.0~180.8° C.; $[\alpha]_D^{20}$ −12.0° (c=1.0, methanol); IR (KBr, cm$^{-1}$) 2992, 2734, 2643, 2470, 1732, 1497, 1482, 1239, 1207.

4-Aza-DL-leucine ethyl ester ditosylate (Reference compound No. 3-13)

mp 104~110° C.; IR (KBr, cm$^{-1}$) 3424, 2986, 1756, 1740, 1469, 1376, 1190, 1124, 1035, 1011, 815, 685.

D-Phenylalanine benzyl ester tosylate (Reference compound No. 3-14), enantiomer of Reference compound No. 3-2

$[\alpha]_D^{20}$ +6.8° (c=1.0, methanol); IR (KBr, cm$^{-1}$) 3033, 1741, 1609, 1206, 1129.

DL-Homophenylalanine benzyl ester tosylate (Reference compound No. 3-15)

Methyl 2-amino-2-methylpropionate hydrochloride (Reference compound No. 3-16)

mp 186.0~186.5° C.(decomp.); IR (KBr, cm$^{-1}$) 2960, 1748, 1596, 1522, 1468, 1438, 1388, 1366, 1318, 1282, 1239, 1195, 1087.

Benzyl 1-amino-1-cyclopropanecarboxylate tosylate (Reference compound No. 3-17)

mp 90~110° C. (decomp.); IR (KBr, cm$^{-1}$) 2938, 1746, 1215, 684.

Benzyl 1-amino-1-cyclopentanecarboxylate tosylate (Reference compound No. 3-18)

mp 175~189° C. (decomp.); IR (KBr, cm$^{-1}$) 2960, 2718, 1741, 1525, 1213, 1124, 1013.

REFERENCE EXAMPLE 4

N-Phenethyl-L-phenylalanine Benzyl Ester Hydrochloride (Reference Compound No. 4-1)

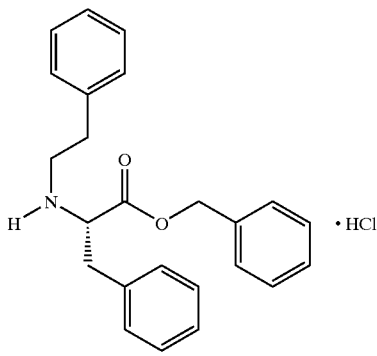

To a solution of L-phenylalanine benzyl ester tosylate (Reference compound No. 3-2, 1.0 g) in anhydrous dimethylformamide (18 ml) are added phenethyl bromide (0.49 ml), anhydrous potassium carbonate (1.2 g) and sodium iodide (2.7 g), and the mixture is stirred overnight while heating at 60° to 70° C. Water is added to the reaction mixture under ice cooling, and the whole is extracted with ethyl acetate. The organic layer is washed with water and saturated brine successively, dried over anhydrous magnesium sulfate and concentrated under reduced pressure. The residue is purified by silica gel column chromatography, and the resulting oily matter is dissolved in ether. A 4 N solution of hydrogen chloride in ethyl acetate (4 ml) is added thereto under ice cooling, and the resulting precipitate is filtered off to give 646 mg (45%) of the titled compound (Reference compound No. 4-1) as crystals.

(Reference compound No. 4-1)

mp 142~159° C.; $[\alpha]_D^{20}$ +10.7° (c=1.0, methanol); IR (KBr, cm$^{-1}$) 2578, 1748, 1554, 1230, 1183.

The following compound is obtained by a method similar to Reference Example 4.

N-Isoamyl-DL-homophenylalanine benzyl ester (Reference compound No. 4-2)

IR (Film, cm$^{-1}$) 2955, 1732, 1497, 1455, 1167, 750, 698.

REFERENCE EXAMPLE 5

N-Isoamyl-3-(phenylthio)-DL-alanine Ethyl Ester Hydrochloride (Reference Compound No. 5-1)

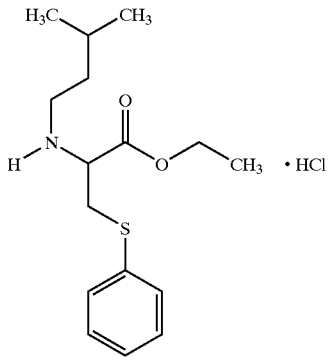

A solution of N-isovaleryl-3-(phenylthio)-DL-alanine ethyl ester (1.0 g) in anhydrous tetrahydrofuran (3.2 ml) is added to a 1 M solution of a borane-tetrahydrofuran complex salt in tetrahydrofuran (4.85 ml) dropwise under a nitrogen atmosphere and ice cooling, and the mixture is refluxed with stirring for one hour. A 3 N solution of hydrogen chloride in ethanol (2 ml) is added to the reaction mixture under ice cooling, and the mixture is further refluxed for one hour. The reaction mixture is concentrated under reduced pressure, 5% sodium hydrogencarbonate is added to the concentrate, and the whole is extracted with ether. The organic layer is washed with saturated brine, dried over anhydrous magnesium sulfate and concentrated under reduced pressure. The residue is purified by silica gel column chromatography, and the resulting oily matter is dissolved in ether. A 4.6 N solution of hydrogen chloride in ethyl acetate is added thereto under ice cooling, and the resulting precipitate is filtered off to give 163 mg (15%) of the titled compound (Reference compound No. 5-1) as crystals.

(Reference Compound No. 5-1)

mp 113.0~115.5° C.; IR (KBr, cm$^{-1}$) 3459, 2963, 2660, 1747, 1737, 1560, 1472, 1330, 1254, 1213, 1033.

REFERENCE EXAMPLE 6

N-Cyclohexyl-N-methylethylenediamine Dihydrochloride (Reference Compound No. 6-1)

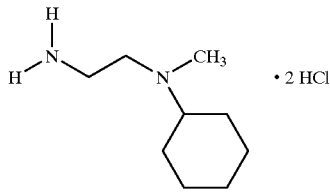

1) To a solution of N-(t-butoxycarbonyl)-2-bromoethylamine (1.0 g) in anhydrous dimethylformamide (15 ml) are added N-methylcyclohexylamine (0.64 ml), anhydrous potassium carbonate (0.9 g) and sodium iodide (2.0 g), and the mixture is stirred at room temperature for three days. Water is added to the reaction mixture, and the whole is extracted with ether. The organic layer is washed with a 10% aqueous sodium hydrogencarbonate solution, water and saturated brine successively, dried over anhydrous magnesium sulfate and concentrated under reduced pressure. The resulting residue is purified by silica gel column chromatography to give 0.82 g (72%) of N-(t-butoxycarbonyl)-N'-cyclohexyl-N'-methylethylenediamine as oily matter.

IR (Film, cm$^{-1}$) 3360, 2929, 1715, 1494, 1452, 1365, 1250, 1172, 1050.

2) N-(t-Butoxycarbonyl)-N'-cyclohexyl-N'-methylethylenediamine (793 mg) obtained in 1) is dissolved in a 4 N solution of hydrogen chloride in dioxane (20 ml), and the solution is stirred at room temperature overnight. The reaction mixture is concentrated uner reduced pressure, and ethyl acetate is added to the residue. The resulting precipitate is filtered off to give 463 mg (65%) of the titled compound (Reference compound No. 6-1) as crystals.

(Reference Compound No. 6-1)

mp 197.0~198.3° C.; IR (KBr, cm$^{-1}$) 2859, 2603, 1601, 1521, 1472, 1454, 1339, 1016.

The following compounds are obtained by a method similar to Reference Example 6.

N-Methyl-N-phenylethylenediamine monohydrochloride (Reference compound No.6-2)

mp 210.0~211.0° C. (decomp.); IR (KBr, cm$^{-1}$) 3012, 2466, 1601, 1512, 1495, 1414, 1347, 1196, 1170, 1110, 1027.

N-(2-Aminoethyl)phthalimide hydrochloride (Reference compound No. 6-3)

mp 250° C. or higher; IR (KBr, cm$^{-1}$) 2909, 1708, 1507, 1428, 1396, 1361, 1324, 1072, 1045, 879, 718.

1-(2-Aminoethyl)-4-methylpiperazine dihydrochloride (Reference compound No. 6-4)

mp 250° C. or higher; IR (KBr, cm$^{-1}$) 2978, 1468, 1440, 1161, 1069, 1024, 975, 958, 793, 772.

1-Cyclohexylpiperazine dihydrochloride (Reference compound No. 6-5)

mp 250° C. or higher: IR (KBr, cm$^{-1}$) 3487, 2932, 2679, 2578, 1434, 1397, 1315.

1-(Carboxymethyl)piperazine bis(hydrogen trifluoroacetate) (Reference compound No. 6-6)

mp 173~175° C.; IR (KBr, cm$^{-1}$) 2794, 1744, 1664, 1196, 1133.

1-(Trifluoroacetyl)piperazine hydrochloride (Reference compound No. 6-7)

mp 120° C.; IR (KBr, cm$^{-1}$) 3524, 2937, 2753, 2480, 1716, 1699, 1457, 1216, 1189, 1182, 1169, 1151, 1130, 1022, 1013, 896, 754.

REFERENCE EXAMPLE 7

4-(Dimethylamino)butylamine (Reference Compound No. 7-1)

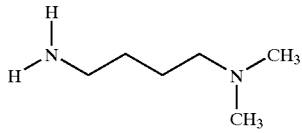

1) To a solution of N-(benzyloxycarbonyl)-4-(mesyloxy) butylamine (2.51 g) in anhydrous dimethylformamide (28 ml) are added 2.0 M dimethylamine THF solution 12.5 ml. anhydrous potassium carbonate (1.72 g) and sodium iodide (3.74 g), and the mixture is stirred at room temperature overnight. Water is added to the reaction mixture, and the whole is extracted with ether. The organic layer is washed with water and saturated brine successively, dried over anhydrous magnesium sulfate and concentrated under reduced pressure. The resulting residue is purified by silica gel column chromatography to give 1.59 g (76%) of N-(benzyloxycarbonyl)-4-(dimethylamino) butylamine.

IR (Film, cm$^{-1}$) 3331, 2942, 1715, 1536, 1455, 1260, 1037, 739, 698.

2) Under a nitrogen atmosphere, 20% palladium hydroxide on carbon (200 mg) is added to a solution of N-(benzyloxycarbonyl)-4-(dimethylamino)butylamine (1.39 g) obtained in 1) in ethanol (19 ml). The mixture is stirred under a hydrogen atmosphere for three days. Palladium hydroxide on carbon is filtered out with Celite, and the filtrate is concentrated under reduced pressure to give 706 mg (quantitatively) of the titled compound (Reference compound No. 7-1) as noncrystalline powder. (Reference Compound No. 7-1) IR (Film, cm$^{-1}$) 3408, 2361, 1633, 1480.

REFERENCE EXAMPLE 8

(2S)-2-Amino-N$^1$-methyl-4-phenylbutyramide Hydrochloride (Reference Compound No. 8-1)

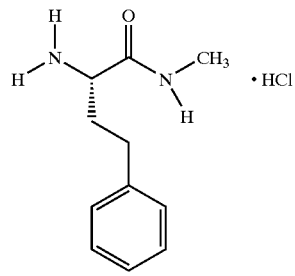

1) In anhydrous methylene chloride (7 ml) are suspended (2S)-2-(t-butoxycarboxamido)-4-phenylbutyric acid (400 mg), methylamine hydrochloride (193 mg) and 1-hydroxybenzotriazole (193 mg) under a nitrogen atmosphere. To the suspension are added N-methylmorpholine (0.52 ml) and 1-ethyl-3-(3-dimethylaminopropyl) carbodiimide hydrochloride (356 mg) successively under ice cooling, and the mixture is stirred at room temperature overnight. The reaction mixture is concentrated under reduced pressure, water is added to the resulting oily matter, and the whole is extracted with ethyl acetate. The organic layer is washed with water and saturated brine successively, dried over anhydrous sodium sulfate and concentrated under reduced pressure. Hexane is added to the resulting oily matter, and the resulting precipitate is filtered off to give 370 mg (89%) of (2S)-2-(t-butoxycarboxamido)-N'-methyl-4-phenylbutyramide as crystals.

mp 102.8~104.7° C.; $[\alpha]_D^{20}$ −2.8° (c=0.49, chloroform); IR (KBr, cm$^{-1}$) 3338, 2969, 1682, 1656, 1524, 1454, 1368, 1283, 1173.

2) A 4.6 N solution of hydrogen chloride in ethyl acetate (2 ml) is added to a solution of (2S)-2-(t-butoxycarboxamido)-N$^1$-methyl-4-phenylbutyramide (332 mg) obtained in 1) in ethyl acetate (2 ml)-chloroform (1 ml), and the mixture is stirred at room temperature for one hour. The reaction mixture is concentrated under reduced pressure, and ethyl acetate is added to the residue. The resulting precipitate is filtered off to give 247 mg (95%) of the titled compound (Reference compound No. 8-1) as crystals.

(Reference Compound No. 8-1)

mp 2211.5~214.0° C.; $[\alpha]_D^{20}$ +35.5° (c=0.51, methanol); IR (KBr, cm$^{-1}$) 3346, 2861, 2005, 1658, 1570, 1523, 1500, 1420, 749, 702.

The following compounds are obtained by a method similar to Reference Example 8.

(2S)-2-Amino-N$^1$-methyl-3-phenylpropionamide hydrochloride (Reference compound No. 8-2)

mp 197.0~199.6° C.; $[a]_D^{20}$ +64.5° (c=1.0, methanol); IR (KBr, cm$^{-1}$) 3342, 2884, 2602, 1665, 1603, 1569, 1501, 1457, 1336, 1265, 1118.

(2S)-2-Amino-N$^1$,N$^1$-dimethyl-3-phenylpropionamide hydrochloride (Reference compound No. 8-3)

mp 207.5~219.5° C. (decomp.); $[a]_D^{20}$ +76.3° (c=1.0, methanol); IR (KBr, cm$^{-1}$) 3419, 3029, 1960, 1653, 1446, 1398, 1366, 1139, 1096, 1035, 767, 748, 700.

1-[(2S)-2-Amino-3-phenylpropionyl]-4-methylpiperazine dihydrochloride (Reference compound No. 8-4)

[α]$_D^{20}$ +41.5° (c=1.0, methanol); IR (Film, cm$^{-1}$) 3423, 2938, 1655, 1494, 1456, 1366, 1255, 1167.

(2S)-2-Amino-N$^1$-methylpropionamide hydrochloride (Reference compound No.8-5)

mp 200~205° C. (decomp.); [α]$_D^{20}$ +11.6° (c=1.0, methanol); IR (KBr, cm$^{-1}$) 3261, 2862, 2641, 1666, 1611, 1510, 1413, 1278, 1121, 1013, 701.

1-[(2S)-2-Aminopropionyl]-4-methylpiperazine dihydrochloride (Reference compound No. 8-6) [α]$_D^{20}$ +3.9° (c=1.0. methanol);

(2S)-2-Amino-N$^1$-butyl-3-(4-biphenylyl)propionamide hydrochloride (Reference compound No. 8-7)

mp 167.5~170.0° C.; [α]$_D^{20}$ +52.9° (c=1.0 methanol); IR (KBr, cm$^{-1}$) 3331, 2955, 2643, 2587, 1659, 1601, 1568, 1486, 1259, 1166, 759, 696.

(2S)-2-Amino-N$^1$-[2-(dimethylamino)ethyl]-3-phenylpropionamide dihydrochloride (Reference compound No. 8-8)

[α]$_D^{20}$ +60.1° (c=1.0, methanol); IR (Film, cm$^{-1}$) 3417, 3211, 2958, 1684, 1564, 1495, 1262, 1169, 750, 703.

2-(Isoamylamino)-N$^1$-[2-(dimethylamino)ethyl]acetamide dihydrochloride (Reference compound No. 8-9)

mp 154.5~157.5° C.; IR (KBr, cm$^{-1}$) 3228, 2958, 1676, 1570, 1468, 1443, 1277.

4-[(2S)-2-Aminopropionyl]morpholine hydrochloride (Reference compound No. 8-10)

mp 250° C. or higher; [α]$_D^{20}$ +5.1° (c=1.0, methanol); IR (KBr, cm$^{-1}$) 3007, 2787, 2719, 2626, 2580, 1645, 1517, 1480, 1380, 1271, 1246, 1114.

REFERENCE EXAMPLE 9

(2S)-2-(Isoamylamino)-N$^1$-[2-(dimethylamino)ethyl]-3-phenylpropionamide Dihydrochloride (Reference Compound No. 9-1)

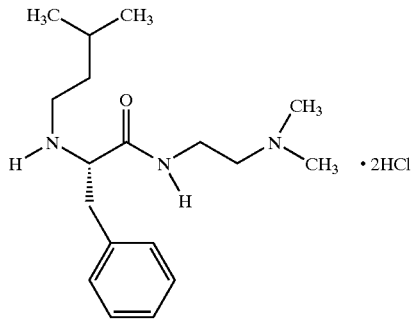

Anhydrous potassium carbonate (3.32 g) and molecular sieves 3A (5 g) are added successively to a solution of (2S)-2-amino-N$^1$-[2-(dimethylamino)ethyl]-3-phenylpropionamide dihydrochloride (Reference compound No. 8-8, 2.47 g) and isovaleraldehyde (0.69 g) in ethanol (40 ml), and the mixture is stirred at room temperature for two hours. Sodium cyanoborohydride (0.55 g) is further added thereto, and the mixture is stirred at room temperature for two hours. Water is added to the reaction mixture, and the mixture is filtered with Celite. The filtrate is concentrated under reduced pressure, saturated brine is added to the residue, and the whole is extracted with ethyl acetate. The organic layer is washed with a 10% aqueous sodium hydrogencarbonate solution and saturated brine successively, dried over anhydrous sodium sulfate and concentrated under reduced pressure. The residue is purified by silica gel column chromatography, and the resulting oily matter is dissolved in ether (5 ml). A 4.6 N solution of hydrogen chloride in ethyl acetate (4 ml) is added thereto, and the resulting precipitate is filtered off to give 0.40 g (13%) of the titled compound (Reference compound No. 9-1) as crystals.

(Reference compound No. 9-1)

mp 163.0~166.5° C.; [α]$_D^{20}$ +58.9° (c=0.50, methanol); IR (KBr, cm$^{-1}$) 3496, 3394, 3211, 2964, 2805, 2681, 1666, 1565, 1453, 1387, 1278, 750, 703.

REFERENCE EXAMPLE 10

2-Amino-N$^1$,N$^1$-diisopropylacetamide (Reference Compound No. 10-1)

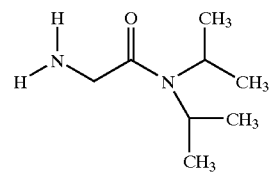

1) In anhydrous methylene chloride (84 ml) are suspended N-(benzyloxycarbonyl)glycine (7.0 g), diisopropylamine (6.6 ml) and 1-hydroxybenzotriazole (4.52 g) under a nitrogen atmosphere. To the suspension are added N-methylmorpholine (5.5 ml) and 1-ethyl-3-(3-dimethylaminopropyl)carbodiimide hydrochloride (9.62 g) successively, and the mixture is stirred at room temperature overnight. The reaction mixture is concentrated under reduced pressure, water is added to the resulting oily matter, and the whole is extracted with chloroform. The organic layer is washed with a 10% aqueous sodium hydrogencarbonate solution, water and saturated brine successively, dried over anhydrous magnesium sulfate and concentrated under reduced pressure. The resulting residue is purified by silica gel column chromatography to give 2.74 g (28%) of 2-(benzyloxycarboxamido)-N$^1$,N$^1$-diisopropylacetamide.

IR (Film, cm$^{-1}$) 3403, 2968, 1719, 1645, 1214, 1044, 698.

2) Under a nitrogen atmosphere, 20% palladium hydroxide on carbon (200 mg) is added to a solution of 2-(benzyloxycarboxamido)-N$^1$,N$^1$-diisopropylacetamide (2.61 g) obtained in 1) in ethanol (22 ml). The mixture is stirred under a hydrogen atmosphere for two days. Palladium hydroxide on carbon is filtered out with Celite, and the filtrate is concentrated under reduced pressure to give 0.92 g (65%) of the titled compound (Reference compound No. 10-1) as crystals.

(Reference Compound No. 10-1)

mp 225~230° C. (decomp.); IR (KBr, cm$^{-1}$) 2971, 1652, 1456, 1326, 1213, 1135, 1038, 913, 885.

The following compounds are obtained by a method similar to Reference Example 10.

2-Amino-N$^1$,N$^1$-dicyclohexylacetamide (Reference compound No. 10-2)

IR (Film, cm$^{-1}$) 3422, 2932, 1645, 1480, 1446.

1-Methyl-4-[(2S)-2-(phenethylamino)propionyl]piperazine (Reference compound No. 10-3)

[α]$_D^{20}$ −9.0° (c=0.98, methanol); IR (Film, cm$^{-1}$) 2935, 2791, 1642, 1435, 1140.

REFERENCE EXAMPLE 11

N,N-Diisopropylethylenediamine Dihydrochloride
(Reference Compound No. 11-1)

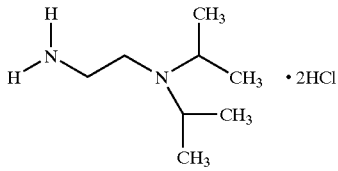

Lithium aluminum hydride (408 mg) is suspended in anhydrous ether (13 ml) under a nitrogen atmosphere and ice cooling, and a suspension of 2-amino-$N^1$,$N^1$-diisopropylacetamide (Reference compound No. 10-1, 850 mg) in anhydrous tetrahydrofuran (13 ml) is added dropwise thereto. The mixture is stirred at room temperature for one hour. A tetrahydrofuran (2 ml) solution containing water (0.8 ml) is added dropwise to the reaction mixture under ice cooling. A 4 N aqueous sodium hydroxide solution is added thereto, and the whole is extracted with chloroform. The organic layer is washed with saturated brine, dried over anhydrous magnesium sulfate and concentrated under reduced pressure. The resulting oily matter is dissolved in chloroform (2 ml), and a 4.6 N solution of hydrogen chloride in ethyl acetate (3 ml) is added thereto. The mixture is concentrated under reduced pressure, isopropyl ether is added to the concentrate, and the resulting precipitate is filtered off to give 734 mg (63%) of the titled compound (Reference compound No. 11-1) as crystals.

(Reference Compound No. 11-1)
mp 145~150° C. (decomp.); IR (KBr, $cm^{-1}$) 2990, 1699, 1520, 1397.

The following compound is obtained by a method similar to Reference Example 11.

N,N-Dicyclohexylethylenediamine dihydrochloride (Reference compound No. 11-2)
mp 72~80° C. (decomp.); IR (KBr, $cm^{-1}$) 3406, 2938, 1454, 1024, 988.

REFERENCE EXAMPLE 12

(1S)-1-Benzyl-2-(benzyloxy)ethylamine
Hydrochloride (Reference Compound No. 12-1)

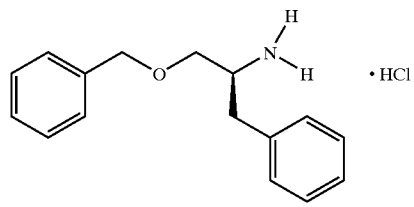

(1S)-1-Benzyl-2-(benzyloxy)-N-(t-butoxycarbonyl)ethylamine (205 mg) is dissolved in a 2.3 N solution of hydrogen chloride in methanol (3 ml), and the solution is stirred for one hour. The reaction mixture is concentrated under reduced pressure, ether is added to the concentrate, and the resulting precipitate is filtered off to give 143 mg (99%) of the titled compound (Reference compound No. 12-1) as crystals.

(Reference Compound No. 12-1)
mp 155.3~156.4° C.; $[\alpha]_D^{20}$ +34.7° (c=1.0, methanol); IR (KBr, $cm^{-1}$) 2863, 1598, 1509, 1496, 1453, 1362, 1171, 1117, 1086, 739, 697.

The following compounds are obtained by a method similar to Reference Example 12.

(1R)-1-Benzyl-2-(benzyloxy)ethylamine hydrochloride (Reference compound No. 12-2), enantiomer of Reference compound No. 12-1.
mp 153.9~154.6° C.; $[\alpha]_D^{20}$ −33.1° (c=1.0, methanol); IR (KBr, $cm^{-1}$) 2862, 1598, 1509, 1496, 1453, 1362, 1171, 1116, 1086, 1074, 1060.

2-(Benzyloxy)ethylamine hydrochloride (Reference compound No. 12-3)
mp 125~137° C.; IR (KBr, $cm^{-1}$) 2907, 2034, 1606, 1508, 1496, 1457, 1360, 1126, 1049, 1027, 1006, 735, 696.

(2S)-2-Amino-4-butanolide hydrochloride (Reference compound No. 12-4)

2-(Methylthio)ethylamine hydrochloride (Reference compound No. 12-5)
mp 139~145° C.; IR (KBr, $cm^{-1}$) 2963, 2597, 1579, 1466, 1139, 1082.

2-(Phenylthio)ethylamine hydrochloride (Reference compound No. 12-6)
mp 111.3~114.0° C.; IR (KBr, $cm^{-1}$) 2892, 2582, 1994, 1588, 1504, 1473, 1096, 897, 753, 697.

2-(Phenyldithio)ethylamine hydrochloride (Reference compound No. 12-7)
mp 130.0~132.0° C.; IR (KBr, $cm^{-1}$) 2977, 1600, 1475, 733, 686.

2-(Benzylthio)ethylamine hydrochloride (Reference compound No. 12-8)
mp 118~120° C.; IR (KBr, $cm^{-1}$) 2670, 2575, 2440, 1960, 1586, 1490, 1452, 1096, 700.

2-Methyl-2-(benzylthio)propylamine hydrochloride (Reference compound No. 12-9)
mp 113~116° C.; IR (KBr, $cm^{-1}$) 2934, 2612, 2031, 1601, 1522, 1494, 1461, 1435, 1398, 1376, 1149, 784, 721, 698.

REFERENCE EXAMPLE 13

2-Cyclohexyl-N-(2-hydroxyethyl)ethylamine
Hydrochloride (Reference Compound No. 13-1)

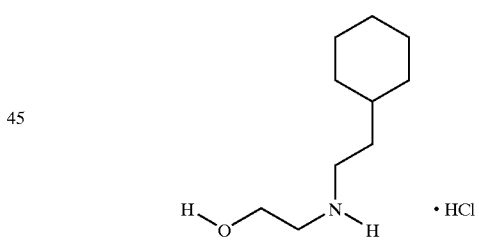

Anhydrous potassium carbonate (3.5 g) and sodium iodide (9.4 g) are added to a solution of 2-aminoethanol (1.9 ml) and 2-cyclohexylethyl bromide (4.0 g) in ethanol (42 ml), and the mixture is refluxed for 17 hours with stirring. A saturated aqueous ammonium chloride solution is added to the reaction mixture, and the mixture is washed with ether. A 4 N aqueous sodium hydroxide solution is added to the aqueous layer, and the whole is extracted with chloroform. The organic layer is washed with saturated brine, dried over anhydrous magnesium sulfate and concentrated under reduced pressure. The resulting residue is dissolved in ethyl acetate. To the solution are added a 4 N solution of hydrogen chloride in ethyl acetate (4 ml) and then ether (10 ml) under ice cooling, and the resulting precipitate is filtered off to give 2.2 g (51%) of the titled compound (Reference compound No. 13-1) as crystals.

(Reference Compound No. 13-1)

mp 158.5~160.2° C.; IR (KBr, cm$^{-1}$) 3316, 2922, 2856, 1560, 1467, 1454, 1407, 1351, 1084, 1058, 1049, 1001, 932.

The following compounds are obtained by a method similar to Reference Example 13.

N-(2-Hydroxyethyl)isoamylamine hydrochloride (Reference compound No. 13-2)

mp 150~162° C.; IR (KBr, cm$^{-1}$) 3376, 2961, 2471, 1595, 1472, 1369, 1075, 1004, 961, 775.

N-(2-Hydroxyethyl)isobutylamine (Reference compound No. 13-3) IR (Film, cm$^{-1}$) 3311, 2955, 1465, 1388, 1367, 1243, 1215, 1115, 1057, 755.

3,3-Dimethyl-N-(2-hydroxyethyl)butylamine hydrochloride (Reference compound No. 13-4)

mp 115~133° C.; IR (KBr, cm$^{-1}$) 3386, 2960, 1751, 1593, 1478, 1368, 1248, 1092, 1069, 997.

N-(2-Hydroxyethyl)-4-methylpentylamine hydrochloride (Reference compound No. 13-5)

mp 163.5~166.0° C.; IR (KBr, cm$^{-1}$) 3378, 2959, 2505, 2418, 1595, 1469, 1074.

N-(2-Hydroxyethyl)-3-butenylamine hydrochloride (Reference compound No. 13-6)

N-(3-Hydroxypropyl)isoamylamine (Reference compound No. 13-7) IR (Film, cm$^{-1}$) 3281, 2955, 1468, 1367, 1116, 1072.

N-(4-Hydroxybutyl)isoamylamine (Reference compound No. 13-8)

IR (Film, cm$^{-1}$) 2955, 1470, 1367, 1115.

N-[(1RS)-2-Hydroxy-1-phenylethyl]isoamylamine hydrochloride (Reference compound No. 13-9)

IR (Film, cm$^{-1}$) 3350, 2958, 1587, 1458, 1076, 761, 703.

N-[(1R)-1-Benzyl-2-hydroxyethyl]isoamylamine hydrochloride (Reference compound No. 13-10)

mp 171~183° C.; $[\alpha]_D^{20}$ +8.3° (c=1.0, methanol); IR (KBr, cm$^{-1}$) 3321, 2961, 2468, 1604, 1568, 1456, 1055, 987, 747, 708.

N-(2-Hydroxyethyl)phenethylamine hydrochloride (Reference compound No.13-11)

mp 134.7~138.5° C.; IR (KBr, cm$^{-1}$) 3386, 2791, 2464, 1590, 1498, 1453, 1336, 1070, 1014, 743.

N-(2-Hydroxyethyl)-4-methylphenethylamine hydrochloride (Reference compound No. 13-12)

mp 148° C.; IR (KBr, cm$^{-1}$) 3283, 2956, 2784, 2461, 1516, 1451, 1082, 1063, 1008, 808.

2-(4-Biphenylyl)-N-(2-hydroxyethyl)ethylamine (Reference compound No. 13-13)

mp 82~87° C.; IR (KBr, cm$^{-1}$) 3029, 2925, 2887, 2825, 1488, 1126, 1098, 1071, 1048, 909, 870.

4-Fluoro-N-(2-hydroxyethyl)phenethylamine hydrochloride (Reference compound No. 13-14)

mp 120° C.; IR (KBr, cm$^{-1}$) 3313, 2957, 2793, 1600, 1577, 1515, 1448, 1232, 1063, 826.

4-Chloro-N-(2-hydroxyethyl)phenethylamine hydrochloride (Reference compound No. 13-15)

mp 125.0~126.0° C.; IR (KBr, cm$^{-1}$) 3312, 2960, 2793, 2462, 1591, 1536, 1495, 1453, 1411, 1080, 1016, 918, 825, 804.

N-(2-Hydroxyethyl)-4-nitrophenethylamine (Reference compound No. 13-16)

mp 67.2~68.8° C.; IR (KBr, cm$^{-1}$) 3271, 2828, 1596, 1510, 1461, 1441, 1347, 1063, 1035, 941, 846, 724.

N-(2-Hydroxyethyl)-4-methoxyphenethylamine hydrochloride (Reference compound No. 13-17)

mp 135° C.; IR (KBr, cm$^{-1}$) 3404, 2966, 2793, 2462, 1612, 1516, 1303, 1246, 1028, 833, 815.

N-(2-Hydroxyethyl)benzylamine hydrochloride (Reference compound No. 13-18)

mp 95° C.; IR (KBr, cm$^{-1}$) 3374, 2940, 2795, 1579, 1458, 1072.

N-(2-Hydroxyethyl)-3-phenylpropylamine hydrochloride (Reference compound No. 13-19)

mp 97~103° C.; IR (KBr, cm$^{-1}$) 3382, 2957, 2789, 1454, 1069, 1023, 748, 699.

3-(4-Fluorophenyl)-N-(2-hydroxyethyl)propylamine hydrochloride (Reference compound No. 13-20)

mp 78~84° C.; IR (KBr, cm$^{-1}$) 3364, 3277, 2949, 2751, 1599, 1511, 1446, 1222, 1075, 821.

3-(4-Chlorophenyl)-N-(2-hydroxyethyl)propylamine hydrochloride (Reference compound No. 13-21)

mp 107° C.; IR (KBr, cm$^{-1}$) 3422, 2966, 2784, 1607, 1494, 1472, 1411, 1316, 1303, 1085, 1055, 930, 812.

N-(2-Hydroxyethyl)-2-phenoxyethylamine hydrochloride (Reference compound No. 13-22)

mp 131.8~133.9° C.; IR (KBr, cm$^{-1}$) 3355, 2959, 2744, 2534, 1927, 1599, 1500, 1072, 1036.

(E)-N-(2-Hydroxyethyl)-3-phenyl-2-propenylamine (Reference compound No.13-23)

IR (Film, cm$^{-1}$) 3298, 2838, 1495, 1448, 1357, 1120, 1049, 969, 747, 693.

N-(3-Hydroxypropyl)phenethylamine hydrochloride (Reference compound No.13-24)

IR (KBr, cm$^{-1}$) 3358, 2950, 2786, 2489, 2427, 1738, 1605, 1498, 1456, 1250, 1100, 1063, 1006, 745, 697.

N-[(2RS)-2-Hydroxypropyl]phenethylamine hydrochloride (Reference compound No. 13-25)

mp 153.5~155.4° C.; IR (KBr, cm$^{-1}$) 3420, 2972, 2798, 2523, 2450, 1590, 1497, 1456, 1404, 1282, 1147, 1076, 1052, 1020, 936, 744, 697.

N-Isoamylserinol hydrochloride (Reference compound No. 13-26)

mp 80~89° C.; IR (KBr, cm$^{-1}$) 3340, 2969, 1566, 1466, 1098, 1072, 1007, 968, 941, 777.

N-[2-(Cyclohexyl)ethyl]-2-(methylthio)ethylamine hydrochloride (Reference compound No. 13-27)

mp 210~225° C. (decomp.); IR (KBr, cm$^{-1}$) 2920, 2783, 1450.

N-Isoamyl-2-(methylthio)ethylamine (Reference compound No. 13-28)

IR (Film, cm$^{-1}$) 3298, 2954, 1464, 1284, 1122, 957, 752.

2-(Methylthio)-N-(phenethyl)ethylamine hydrochloride (Reference compound No. 13-29)

mp 222~228° C.; IR (KBr, cm$^{-1}$) 2944, 2774, 2447, 1476, 1450, 1430, 1090, 991, 889, 788, 743, 696.

N-Isoamyl-2-(phenylthio)ethylamine (Reference compound No. 13-30)

IR (Film, cm$^{-1}$) 3300, 2954, 1584, 1466, 1120, 740, 692.

N-Phenethyl-2-(phenyldithio)ethylamine hydrochloride (Reference compound No. 13-31)

mp 149~160° C. (decomp.); IR (KBr , cm$^{-1}$) 2776, 1591, 1475, 739, 710.

2-(Benzylthio)-N-(phenethyl)ethylamine hydrochloride (Reference compound No. 13-32)

mp 150~155° C.; IR (KBr, cm$^{-1}$) 2935, 2767, 2452, 1584, 1494, 1452, 1241, 1029, 984, 780, 748, 698.

2-(Benzylthio)-2-methyl-N-(phenethyl)propylamine hydrochloride (Reference compound No. 13-33)

mp 157. 4~159.5° C.; IR (KBr, cm$^{-1}$) 2956, 2708, 1590, 1571, 1496, 1470, 1460, 1420, 1372, 1291, 1146, 1064, 1030, 780, 748, 711, 697.

N-[4-(Benzyloxy)phenethyl]-2-(benzylthio)ethylamine hydrochloride (Reference compound No. 13-34)

mp 177~181° C.; IR (KBr, cm⁻¹) 3061, 3029, 2948, 2769, 1610, 1582, 1513, 1494, 1455, 1380, 1338, 1300, 1280, 1245, 1177, 1113, 1006.

2-Cyclopentyl-N-(2-hydroxyethyl)ethylamine hydrochloride (Reference compound No. 13-35)

2-Cycloheptyl-N-(2-hydroxyethyl)ethylamine hydrochloride (Reference compound No. 13-36)

mp 138.5~140.1° C.; IR (KBr, cm⁻¹) 3305, 2924, 2853, 1565, 1465.

2-(1-Adamantyl)-N-(2-hydroxyethyl)ethylamine hydrochloride (Reference compound No. 13-37)

mp 195~205° C.; IR (KBr, cm⁻¹) 3359, 2901, 2845, 1450, 1085.

N-(2-Hydroxyethyl)-3-methyl-3-butenylamine hydrochloride (Reference compound No. 13-38)

mp 141~146° C.; IR (KBr, cm⁻¹) 3366, 2972, 2802, 1449, 1068, 893.

2-Cyclohexyl-N-(3-hydroxypropyl)ethylamine hydrochloride (Reference compound No. 13-39)

mp 115° C.; IR (KBr, cm⁻¹) 3746, 3676, 3364, 2923, 2853, 2796, 2900, 24245, 1578, 1451.

2-(1-Adamantyl)-N-(2-hydroxyethyl)ethylamine (Reference compound No. 13-40)

mp 63.9~66.5° C.; IR (KBr, cm⁻¹) 3283, 3104, 2903, 2842, 1450, 1437, 1063, 853.

2-(1-Adamantyl)-N-[2-(methylthio)ethyl]ethylamine (Reference compound No. 13-41)

IR (Film, cm⁻¹) 2902, 2844, 1450.

2-Cyclopentyl-N-[2-(methylthio)ethyl]ethylamine (Reference compound No. 13-42)

IR (Film, cm⁻¹) 3296, 2947, 2865, 1451, 1125.

REFERENCE EXAMPLE 14

N-[2-(t-Butyldimethylsiloxy)ethyl]-2-methoxyethylamine (Reference Compound No. 14-1)

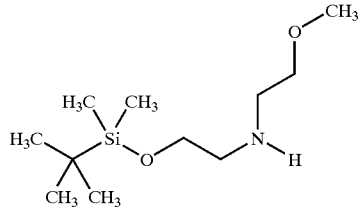

Sodium iodide (14.48 g) is added to a solution of 2-methoxyethylamine (14 ml) and 2-(t-butyldimethylsiloxy)ethyl bromide (7.00 g) in ethanol (65 ml), and the mixture is refluxed overnight with stirring. The reaction mixture is concentrated under reduced pressure, water is added to the residue, and the whole is extracted with chloroform. The organic layer is washed with saturated brine, dried over anhydrous sodium sulfate and concentrated under reduced pressure. The resulting residue is purified by silica gel column chromatography to give 4.13 g (55%) of the titled compound (Reference compound No. 14-1).

(Reference Compound No. 14-1) IR (Film, cm⁻¹) 2930, 2858, 1464, 1254, 1109, 952, 835, 777.

The following compounds are obtained by a method similar to Reference Example 14.

N-[2-(t-Butyldimethylsiloxy)ethyl]-2-(4-pyridyl)ethylamine (Reference compound No. 14-2) IR (Film, cm⁻¹) 3308, 2930, 2856, 1602, 1465, 1414, 1254, 1088, 938, 836, 778.

2-Hydroxy-N-phenylethylamine (Reference compound No. 14-3)

IR (Film, cm⁻¹) 3395, 3051, 3022, 1603, 1506, 1057.

N-(2-Hydroxyethyl)-2-(2-pyridyl)ethylamine dihydrochloride (Reference compound No. 14-4)

IR (KBr, cm⁻¹) 3385, 2760, 1619, 1470, 772.

N-[(1RS)-1-(Hydroxymethyl)-2-phenoxyethyl]isoamylamine hydrochloride (Reference compound No. 14-5)

mp 91~110° C.; IR (KBr, cm⁻¹) 3213, 2962, 1601, 1567, 1499, 1471, 1450, 1252, 1078, 1045, 753.

N-[2-(t-Butyldimethylsiloxy)ethyl]-2-(1-cyclohexenyl)ethylamine (Reference compound No. 14-6) IR (Film, cm⁻¹) 2928, 2856, 1462, 1256, 1087, 836, 811, 777.

N-[2-(t-Butyldimethylsiloxy)ethyl]-2-cyclopropylethylamine (Reference compound No. 14-7)

IR (Film, cm⁻¹) 2928, 2857, 1463, 1256, 1098, 835, 776.

N-[2-(t-Butyldimethylsiloxy)ethyl]-2-cyclobutylethylamine (Reference compound No. 14-8)

IR (Film, cm⁻¹) 3282, 2928, 2857, 1472, 1256, 1099, 835, 777.

2-[3,5-Di(t-butyl)-4-(methoxymethoxy)phenyl]-N-(2-hydroxyethyl)ethylamine (Reference compound No. 14-9).

REFERENCE EXAMPLE 15

N-(2-Hydroxyethyl)-2-(2-naphthyl)ethylamine (Reference Compound No. 15-1)

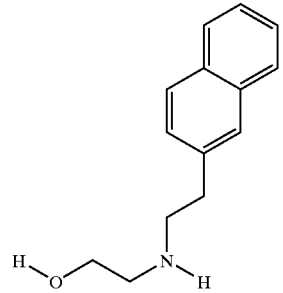

Lithium aluminum hydride (0.66 g) is suspended in anhydrous ether (10 ml) under a nitrogen atmosphere and ice cooling, and a solution of 2-hydroxy-N-(2-naphthylacetyl)ethylamine (2.00 g) in anhydrous tetrahydrofuran (50 ml) is added dropwise to the suspension. The mixture is stirred at room temperature for one hour and then refluxed for one hour. A water-containing tetrahydrofuran solution is added dropwise to the reaction mixture under ice cooling. A 4 N aqueous sodium hydroxide solution is further added thereto, and the whole is extracted with chloroform. The organic layer is washed with saturated brine, dried over anhydrous magnesium sulfate and concentrated under reduced pressure. The resulting oily matter is purified by silica gel column chromatography to give 0.45 g (21%) of the titled compound (Reference compound No. 15-1) as crystals. (Reference compound No. 15-1)

mp 122~128° C.; IR (KBr, cm⁻¹) 3132, 2902, 2834, 1442, 1357, 1118, 1058, 930, 899, 857, 823, 754.

The following compounds are obtained by a method similar to Reference Example 15.

N-[(1RS)-1-(Dimethylaminomethyl)-2-hylroxyethyl] phenethylamine (Reference compound No. 15-2)

IR (Film, cm$^{-1}$) 3300, 2941, 2820, 1635, 1603, 1496, 1455, 1264, 1128, 1043, 840, 750, 700.

N-[(2RS)-3-Hydroxy-2-methylpropyl]phenethylamine hydrochloride (Reference compound No. 15-3)

mp 67~78° C.;

IR (KBr, cm$^{-1}$) 3381, 2964, 1560, 1457, 1241, 1105, 1041, 7513, 700.

N-[(1RS)-1-(Hydroxymethyl)-3-phenylpropyl] isoamylamine hydrochloride (Reference compound No. 15-4)

IR (KBr, cm$^{-1}$) 3312, 3030, 2961, 2844, 1559, 1457, 1336, 998, 750, 699.

N-[(1RS)-1-((Hydroxymethyl)-2-(phenylthio)ethyl] isoamylamine hydrochloride (Reference compound No. 15-5)

mp 104~106° C.;

IR (KBr, cm$^{-1}$) 3306, 2963, 2824, 1560, 1460, 1106, 1066, 999, 924, 738, 689.

(2RS)-2-(Benzylthio)-3-methyl-2-(phenethyl)butylamine hydrochloride (Reference compound No. 15-6)

mp 79~88° C.; IR (KBr, cm$^{-1}$) 3062, 3028, 2963, 2693, 1602, 1558, 1494, 1454, 1388, 1368, 1336, 128.

REFERENCE EXAMPLE 16

2-(Benzylthio)-1-(benzylthiomethyl)-N-(phenethyl) ethylamine (Reference Compound No. 16-1)

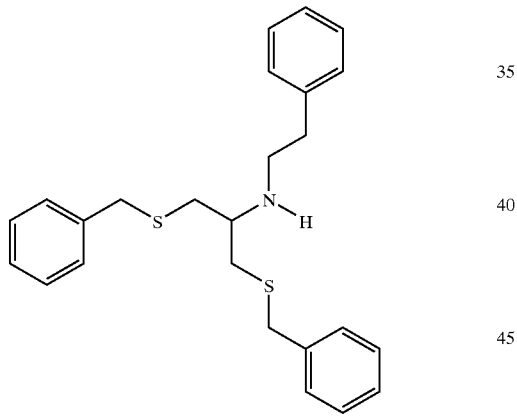

1) A solution of methanesulfonyl chloride (2.7 ml) in anhydrous methylene chloride (5 ml) is added dropwise to a solution of 2-hydroxy-1-(hydroxymethyl)-N-(phenethyl) ethylamine hydrochloride (2.42 g) and diisopropylethylamine (9.1 ml) in anhydrous methylene chloride (30 ml) under a nitrogen atmosphere and ice-methanol cooling, and the mixture is stirred as it is for 20 minutes. Water is added to the reaction mixture, and the whole is extracted with ethyl acetate. The organic layer is washed with 1 N hydrochloric acid, water and saturated brine successively, dried over anhydrous sodium sulfate and concentrated under reduced pressure. The resulting residue is purified by silica gel column chromatography to give 2.19 g (61%) of N-mesyl-2-(mesyloxy)-1-[(mesyloxy)methyl]-N-(phenethyl)ethylamine.

IR (Film, cm$^{-1}$) 1357, 1175, 1146, 962, 830, 757.

2) A solution of benzylmercaptan (1.80 g) in anhydrous dimethylformamide (5 ml) is added dropwise to a suspension of sodium hydride 60% dispersion in mineral oil (636 mg) in anhydrous methylformamide (14 ml) under a nitrogen atmosphere. Then, a solution of N-mesyl-2-(mesyloxy)-1-[(mesyloxy)methyl]-N-(phenethyl) ethylamine (2.07 g) obtained in 1) in anhydrous dimethylformamide (5 ml) is added dropwise thereto. The mixture is stirred at room temperature for two hours, water is added to the reaction mixture, and the whole is extracted with ether. The organic layer is washed with a 1 N aqueous sodium hydroxide solution, 1 N hydrochloric acid, water and saturated brine successively, dried over anhydrous magnesium sulfate and concentrated under reduced pressure. The resulting residue is purified by silica gel column chromatography to give 1.84 g (79%) of 2-(benzylthio)-1-[(benzylthio)methyl]-N-mesyl-N-(phenethyl)ethylamine.

IR (Film, cm$^{-1}$) 3026, 1497, 1453, 1330, 1144, 960, 768, 701.

3) A 65% bis(2-methoxyethoxy)aluminum lithium hydride toluene solution (3.3 ml) is added to a solution of 2-(benzylthio)-1-[(benzylthio)methyl]-N-mesyl-N-(phenethyl)ethylamine (1.34 g) obtained in 2) in anhydrous toluene (5 ml) under a nitrogen atmosphere, and the mixture is refluxed overnight. A 2 N aqueous sodium hydroxide solution is added to the reaction mixture under ice cooling, and the whole is extracted with ether. The organic layer is washed with a 2 N aqueous sodium hydroxide solution, water and saturated brine successively, dried over anhydrous magnesium sulfate and concentrated under reduced pressure. The resulting residue is purified by silica gel column chromatography to give 0.80 g (71%) of the titled compound (Reference compound No. 16-1).

(Reference Compound No. 16-1)

IR (Film, cm$^{-1}$) 3026, 2913, 1602, 1494, 1452, 1238, 1114, 1071, 1028, 752, 699.

REFERENCE EXAMPLE 17

N-(2-Mercaptoethyl)phenethylamine Hydrochloride (Reference Compound No. 17-1)

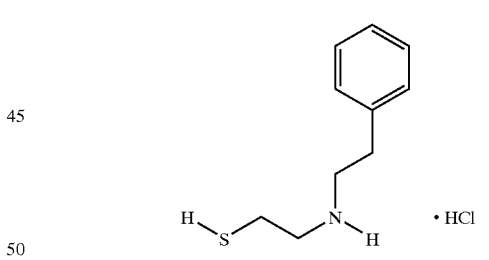

1) Phenethyl bromide (5.4 ml) is added to a solution of 2-methylthiazoline (2.0 g) in chlorobenzene (20 ml) under a nitrogen atmosphere, and the mixture is refluxed for six hours with stirring. Water is added to the reaction mixture under ice cooling, and the mixture is washed with chloroform.

A solution of sodium hydroxide (1.6 g) in water (5 ml) is added to the aqueous layer under a nitrogen atmosphere and ice cooling, and the mixture is stirred for 10 minutes. To the reaction mixture is added 6 N hydrochloric acid to acidify it, and then the whole is extracted with ether. The organic layer is washed with saturated brine, dried over anhydrous sodium sulfate and concentrated under reduced pressure to give 2.45 g (55%) of N-acetyl-N-(2-mercaptoethyl)phenethylamine.

IR (Film, cm$^{-1}$) 3447, 2933, 1637, 1477, 1420, 1364, 1291, 1243, 1204, 1150.

2) Concentrated hydrochloric acid (5 ml) is added to a solution of N-acetyl-N-(2-mercaptoethyl)phenethylamine (500 mg) in acetic acid (5 ml) under a nitrogen atmosphere, and the mixture is refluxed for 24 hours. The reaction mixture is concentrated under reduced pressure, and then a 10% aqueous sodium carbonate solution is added to the concentrate. Weak basicity of the liquid is confirmed, and the whole is extracted with ethyl acetate. The organic layer is washed with saturated brine and dried over anhydrous sodium sulfate. A 4 N solution of hydrogen chloride in ethyl acetate is added to the organic layer, and the mixture is concentrated under reduced pressure. Ether is added to the concentrate, and the resulting precipitate is filtered off to give 244 mg (50%) of the titled compound (Reference compound No. 17-1) as crystals.

(Reference Compound No. 17-1)

mp 163~171° C.; IR (KBr, cm$^{-1}$) 3028, 2944, 2770, 2433, 2361, 1589, 1454, 743, 696.

The following compounds are obtained by a method similar to Reference Example 17.

2-Cyclohexyl-N-(2-mercaptoethyl)ethylamine hydrochloride (Reference compound No. 17-2)

mp 205~230° C.; IR (KBr, cm$^{-1}$) 2924, 2787, 2610, 2499, 2433, 1589, 1478, 1452.

2-(1-Adamantyl)-N-(2-mercaptoethyl)ethylamine hydrochloride (Reference compound No. 17-3)

mp 250° C. or higher; IR (KBr, cm$^{-1}$) 2906, 2844, 2785, 1453.

REFERENCE EXAMPLE 18

Ethyl (3RS)-3-(Isoamylamino)-4-(phenylthio) butyrate (Reference Compound No. 18-1)

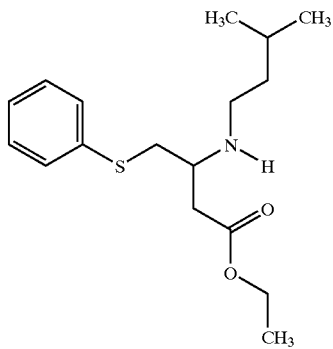

Isoamylamine (0.32 ml) is added to a solution of ethyl (E, Z)-4-(phenylthio)crotonate (908 mg) in ethanol (12 ml) under a nitrogen atmosphere, and the mixture is refluxed for 24 hours with stirring. The reaction mixture is concentrated under reduced pressure, and the resulting residue is purified by silica gel column chromatography to give 360 mg (50%) of the titled compound (Reference compound No. 18-1).

(Reference Compound No. 18-1)

IR (Film, cm$^{-1}$) 2955, 1731, 1584, 1479, 1437, 1370, 1194.

The following compounds are obtained by a method similar to Reference Example 18.

t-Butyl (2RS)-2-(isoamylamino)methyl-3-(phenylthio) propionate (Reference compound No. 18-2)

IR (Film, cm$^{-1}$) 3337, 2956, 1726, 1584, 1252, 1150.

t-Butyl (2RS)-2-(isobutylamino)methyl-3-(phenylthio) propionate (Reference compound No. 18-3)

IR (Film, cm$^{-1}$) 3346, 2954, 1726, 1584, 1367, 1252, 1150.

REFERENCE EXAMPLE 19 bis[2-[N-(2-Cyclohexylethyl)amino]ethyl]disulfide (Reference Compound No. 19-1)

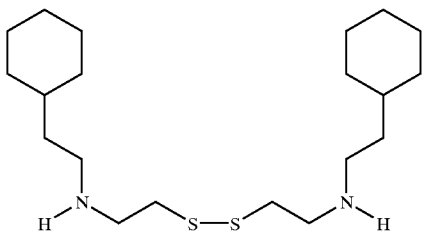

1) To a solution of thiazolidine (605 mg) in acetonitrile (15 ml) are added triethylamine (0.81 ml) and 2-cyclohexylethyl methanesulfonate (1.0 g), and the mixture is refluxed overnight with stirring. The reaction mixture is concentrated under reduced pressure, water is added to the concentrate, and the whole is extracted with ether. The organic layer is washed with saturated brine, dried over anhydrous magnesium sulfate and concentrated under reduced pressure. The resulting residue is purified by silica gel column chromatography to 594 mg (61%) of N-(2-cyclohexylethyl)thiazolidine.

IR (Film, cm$^{-1}$) 2920, 2849, 1308.

2) A solution of iodine (378 mg) in methanol (5 ml) is added dropwise to a solution of N-(2-cyclohexylethyl) thiazolidine (594 mg) in methanol (10 ml) at room temperature with stirring. After the dropping, the mixture is stirred at room temperature for 30 minutes. A 4 N aqueous sodium hydroxide solution (10 ml) is added to the reaction mixture, and the mixture is concentrated under reduced pressure. Chloroform is added to the concentrate, and the whole is extracted. The organic layer is washed with saturated brine, dried over anhydrous magnesium sulfate and concentrated under reduced pressure to give 571 mg (51%) of the titled compound (Reference compound No. 19-1).

The following compounds are obtained by a method similar to Reference Example 19.

Bis[2-[N-[2-(1-adamantyl)ethyl]amino]ethyl]disulfide (Reference compound No. 19-2)

IR (Film, cm$^{-1}$) 2899, 2844, 1450.

Bis[2-(N-phenethylamino)ethyl]disulfide (Reference compound No. 19-3)

Bis[2-[N-(2-cyclohexylethyl)amino]ethyl]disulfide dihydriodate (Reference compound No. 19-4)

mp 225.5~229.0° C.; IR (KBr, cm$^{-1}$) 3442, 2921, 2851, 2800, 1566.

EXAMPLE 1 t-Butyl (2S)-2-[3-(2-cyclohexylethyl)-3-(2-hydroxyethyl)ureido]propionate (Compound No. 1-1)

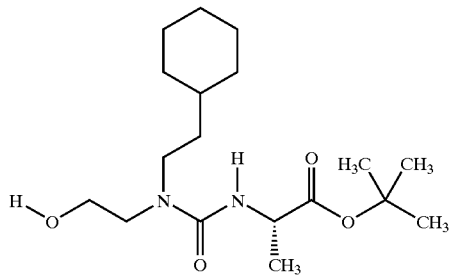

Tetrahydrofuran (11 ml) is added to a mixture of L-alanine t-butyl ester hydrochloride (787 mg), 1,1'-carbonyldiimidazole (983 mg) and imidazole (295 mg) under a nitrogen atmosphere, and the mixture is stirred at room temperature for 30 minutes.

N-(2-Hydroxyethyl)-2-cyclohexylethylamine hydrochloride (Reference compound No. 13-1, 900 mg) is added to the reaction mixture, and the mixture is refluxed for one hour. A 5% aqueous citric acid solution is added to the reaction mixture under ice cooling, and the whole is extracted with ethyl acetate. The organic layer is washed with water and saturated brine successively, dried over anhydrous magnesium sulfate and concentrated under reduced pressure. The resulting oily matter is purified by silica gel column chromatography to give 1.5 g (quantitatively) of the titled compound (Compound No. 1-1).

(Compound No. 1-1)
$[\alpha]_D^{20}$ −5.9° (c=1.0, methanol); IR (Film, cm$^{-1}$) 3359, 2977, 2924, 2851, 1729, 1629, 1531, 1450, 1409, 1368, 1221, 1157, 1054.

The following compounds are obtained by a method similar to Example 1.

t-Butyl (2S)-2-[3-(2-hydroxyethyl)-3-phenethylureido]propionate (Compound No. 1-2)
$[\alpha]_D^{20}$ −9.6° (c=0.97, methanol); IR (Film, cm$^{-1}$) 3342, 2977, 2934, 1732, 1633, 1454, 1368, 1156.

t-Butyl (2R)-2-[3-(2-hydroxyethyl)-3-phenethylureido]propionate (Compound No. 1-3)
$[\alpha]_D^{20}$ +8.8° (c=1.0, methanol); IR (Film, cm$^{-1}$) 3336, 2977, 2933, 1733, 1631, 1533, 1221, 1156.

t-Butyl (2S)-2-[3-(4-fluorophenethyl)-3-(2-hydroxyethyl)ureido]propionate (Compound No. 1-4)
IR (Film, cm$^{-1}$) 3335, 2979, 2934, 1730, 1632, 1510, 1456, 1369, 1222, 1157.

t-Butyl (2S)-2-[3-(4-chlorophenethyl)-3-(2-hydroxyethyl)ureido]propionate (Compound No. 1-5)
$[\alpha]_D^{20}$ −10.4° (c=0.50, methanol); IR (Film, cm$^{-1}$) 3338, 2979, 1732, 1632, 1530, 1492, 1454, 1407, 1368, 1306, 1221, 1156, 1091, 1058, 1016, 757.

t-Butyl (2S)-2-[3-(2-hydroxyethyl)-3-(4-nitrophenethyl)ureido]propionate (Compound No. 1-6)
$[\alpha]_D^{20}$ −8.0° (c=0.50, methanol); IR (Film, cm$^{-1}$) 3340, 2979, 1732, 1633, 1519, 1368, 1346, 1156, 1058, 856, 750.

t-Butyl (2S)-2-[3-(2-hydroxyethyl)-3-(4-methoxyphenethyl)ureido]propionate (Compound No. 1-7)
$[\alpha]_D^{20}$ −11.4° (c=1.0, methanol); IR (Film, cm$^{-1}$) 3343, 2978, 2935, 1732, 1633, 1513, 1454, 1368, 1247, 1156, 1037.

t-Butyl (2S)-2-[3-(2-hydroxyethyl)-3-(4-methylphenethyl)ureido]propionate (Compound No. 1-8)
$[\alpha]_D^{20}$ +4.1° (c=1.0, chloroform); IR (Film, cm$^{-1}$) 3338, 2979, 2932, 1732, 1633, 1515, 1368, 1220, 1156, 1057, 755.

t-Butyl (2S)-2-[3-(2-hydroxyethyl)-3-(4-phenylphenethyl)ureido]propionate (Compound No. 1-9)
mp 91.4~94.44° C.; $[\alpha]_D^{20}$ −9.8° (c=1.0, methanol); IR (KBr, cm$^{-1}$) 3282, 3074, 2975, 2940, 1741, 1628, 1559, 1366, 1272, 1219, 1151, 762.

t-Butyl (2S)-2-[3-(2-hydroxyethyl)-3-[2-(2-pyridyl)ethyl]ureido]propionate (Compound No. 1-10)
$[\alpha]_D°$ −4.9° (c=0.23, methanol); IR (Film, cm$^{-1}$) 3328, 2978, 1734, 1634, 1595, 1533, 1476, 1456, 1368, 1220, 1156.

t-Butyl (2S)-2-[3-(2-hydroxyethyl)-3-[2-(2-naphthyl)ethyl]ureido]propionate (Compound No. 1-11)
$[\alpha]_D°$ −8.8° (c=0.94, methanol); IR (Film, cm$^{-1}$) 3336, 2978, 2933, 1732, 1632, 1530, 1368, 1220, 1156, 750.

t-Butyl (2S)-2-[3-(2-hydroxyethyl)-3-(3-phenylpropyl)ureido]propionate (Compound No. 1-12)
$[\alpha]_D°$ −6.7° (c=0.50, methanol); IR (KBr, cm$^{-1}$) 3346, 2977, 2938, 1733, 1634, 1532, 1157, 1058, 751, 700.

t-Butyl (2S)-2-[3-[3-(4-fluorophenyl)propyl]-3-(2-hydroxyethyl)ureido]propionate (Compound No. 1-13)
$[\alpha]_D°$ −5.9° (c=0.50, methanol); IR (Film, cm$^{-1}$) 3337, 2979, 2935, 1732, 1632, 1510, 1369, 1221, 1157, 1058, 848, 757.

t-Butyl (2S)-2-[3-[3-(4-chlorophenyl)propyl]-3-(2-hydroxyethyl)ureido]propionate (Compound No. 1-14)
$[\alpha]_D°$ −6.9° (c=1.0, methanol); IR (Film, cm$^{-1}$) 3338, 2978, 2933, 1732, 1633, 1532, 1221, 1156, 1058, 848, 759.

t-Butyl (2S)-2-[3-(2-hydroxyethyl)-3-(3-phenyl-2-propenyl)ureido]propionate (Compound No. 1-15)
$[\alpha]_D°$ −5.0° (c=0.98, chloroform); IR (KBr, cm$^{-1}$) 3335, 2978, 1732, 1632, 1532, 1368, 1223, 1156, 1050, 969, 747.

t-Butyl (2S)-2-[3-(2-hydroxyethyl)-3-(2-phenoxyethyl)ureido]propionate (Compound No. 1-16)
$[\alpha]_D°$ −8.0° (c=1.0, methanol); IR (Film, cm$^{-1}$) 3368, 2978, 2877, 1732, 1633, 1600, 1498, 1242, 1158.

t-Butyl (2S)-2-[3-(2-hydroxyethyl)-3-phenylureido]propionate (Compound No. 1-17)
mp 94.5~97.4° C.; $[\alpha]_D°$ +34.0° (c=1.0, methanol); IR (KBr, cm$^{-1}$) 3452, 3284, 2978, 2939, 1728, 1642, 1594, 1526, 1452, 1367, 1235.

t-Butyl (2S)-2-[3-benzyl-3-(2-hydroxyethyl)ureido]propionate (Compound No. 1-18)

t-Butyl (2S)-2-[3-(3-butenyl)-3-(2-hydroxyethyl)ureido]propionate (Compound No. 1-19)
$[\alpha]_D°$ +6.4° (c=0.99, chloroform); IR (Film, cm$^{-1}$) 3305, 2978, 2934, 1728, 1628, 1537, 1479, 1456, 1368, 1224, 1155, 1059.

t-Butyl 2-[3-(2-hydroxyethyl)-3-phenethylureido]acetate (Compound No. 1-20)
mp 71.9~73.6° C.; IR (KBr, cm$^{-1}$) 3355, 2977, 2929, 1744, 1616, 1556, 1366, 1225.

t-Butyl 2-[3-(2-hydroxyethyl)-3-methylureido]acetate (Compound No. 1-21)
mp 85.5~87.0° C.; IR (KBr, cm$^{-1}$) 3357, 3254, 2950, 1749, 1630, 1555, 1390, 1365, 1224, 1153, 1056, 983, 857, 775, 756, 572.

t-Butyl (2S)-2-[3-(2-hydroxyethyl)-3-phenethylureido]butyrate (Compound No. 1-22)
$[\alpha]_D°$ −11.1° (c=1.0, methanol); IR (Film, cm$^{-1}$) 3326, 2973, 2934, 1732, 1632, 1530, 145, 1368, 115.

t-Butyl (2RS)-3-(t-butoxy)-2-[3-(2-hydroxyethyl)-3-phenethylureido]propionate (Compound No. 1-23)
IR (Film, cm$^{-1}$) 3367, 2974, 1736, 1633, 1519, 1367, 1158, 1054.

t-Butyl (2S)-2-[3-(2-hydroxyethyl)-3-phenethylureido]-2-phenylacetate (Compound No. 1-24)
mp 87.5~88.8° C.; $[\alpha]_D^\circ$ +48.0° (c=1.0, methanol); IR (KBr, cm$^{-1}$) 3289, 2981, 1739, 1629, 1538, 1370, 1149.

t-Butyl (2S)-2-[3-(2-hydroxyethyl)-3-methylureido]-3-phenylpropionate (Compound No. 1-25)
$[\alpha]_D^\circ$ +26.3° (c=0.50, chloroform); IR (Film, cm$^{-1}$) 3358, 2977, 2932, 1730, 1633, 1530, 1455, 1393, 1368, 1220, 1155, 1050, 742, 701.

t-Butyl (2S)-2-[3-(2-hydroxyethyl)-3-isoamylureido]-3-phenylpropionate (Compound No. 1-26)
IR (Film, cm$^{-1}$) 3354, 2956, 1732, 1632, 1524, 1455, 1409, 1368, 1221, 1156.

t-Butyl (2S)-2-[3-(2-cyclohexylethyl)-3-(2-hydroxyethyl)ureido]-3-phenylpropionate (Compound No. 1-27)
$[\alpha]_D^\circ$ +21.9° (c=0.95, chloroform); IR (Film, cm$^{-1}$) 3340, 2977, 2924, 1730, 1631, 1520, 1368, 1221, 1156, 1051, 755, 701.

t-Butyl 3-[3-(2-hydroxyethyl)-3-phenethylureido]propionate (Compound No. 1-28)
IR (Film, cm$^{-1}$) 3348, 2976, 2932, 1725, 1629, 1535, 1367, 1157, 1061, 751, 701.

t-Butyl (2S)-2-[3-[(2RS)-3-hydroxy-2-methylpropyl]-3-phenethylureido]-3-phenylpropionate (Compound No. 1-29)
IR (Film, cm$^{-1}$) 3324, 2974, 1734, 1631, 1522, 1497, 1455, 1410, 1368, 1221, 1155, 1031, 987, 752, 701.

t-Butyl (2S)-2-[3-(2-hydroxyethyl)-3-phenethylureido]-3-phenylpropionate (Compound No. 1-30)
$[\alpha]_D^\circ$ -2.8° (c=0.57, methanol); IR (Film, cm$^{-1}$) 3365, 2977, 2932, 1728, 1632, 1523, 1368, 1155, 1049, 752, 701.

Ethyl (2S)-2-[3-(2-hydroxyethyl)-3-phenethylureido]-4-methylvalerate (Compound No. 1-31)
$[\alpha]_D^\circ$ -12.2° (c=1.0, methanol); IR (Film, cm$^{-1}$) 3339, 2957, 1737, 1631, 1531, 1199.

Ethyl (2S)-2-[3-(3-hydroxypropyl)-3-phenethylureido]-3-phenylpropionate (Compound No. 1-32)
$[\alpha]_D^\circ$ +16.9° (c=9.96, chloroform); IR (Film, cm$^{-1}$) 3326, 2934, 1736, 1632, 1527, 1497, 1454, 1409, 1371, 1291, 1241, 1199, 1030, 751, 701.

Ethyl (2S)-2-[3-[(2RS)-2-hydroxypropyl]-3-phenethylureido]-3-phenylpropionate (Compound No. 1-33)
IR (Film, cm$^{-1}$) 3336, 2977, 1736, 1633, 1525, 1497, 1454, 1408, 1372, 1199, 1079, 1057, 1030, 752, 701.

Methyl (2RS)-2-[3-[(2R-hydroxyethyl)]-3-phenethylureido]-4-(methylthio)butyrate (Compound No. 1-34)
IR (Film, cm$^{-1}$) 3339, 2919, 1740, 1632, 1528, 1206, 1048, 750, 701.

Phenyl (2S)-2-[3-(2-hydroxyethyl)-3-phenethylureido]-3-(4-nitrophenyl)propionate (Compound No. 1-35)
$[\alpha]_D^\circ$ -3.5° (c=0.53, chloroform); IR (Film, cm$^{-1}$) 3308, 1761, 1634, 1520, 1492, 1346, 1192, 1165, 751, 700.

Benzyl (2S)-3-(4-chlorophenyl)-2-[3-(2-hydroxyethyl)-3-phenethylureido]propionate (Compound No. 1-36)
IR (Film, cm$^{-1}$) 3367, 2935, 1739, 1631, 1528, 1493, 1454, 1176.

Benzyl (2S)-2-[3-(2-hydroxyethyl)-3-isoamylureido]-3-(4-nitrophenyl)propionate (Compound No. 1-37)
$[\alpha]_D^\circ$ -31.2° (c=0.54, chloroform); IR (Film, cm$^{-1}$) 3321, 2955, 1740, 1634, 1520, 1456, 1346, 1180.

Benzyl (2S)-2-[3-(2-hydroxyethyl)-3-phenethylureido]-3-(2-nitro-4-biphenylyl)propionate (Compound No. 1-38)
$[\alpha]_D^\circ$ -14.5° (c=0.61, chloroform); IR (Film, cm$^{-1}$) 3339, 1738, 1633, 1530, 1358, 756, 700.

Benzyl (2S)-3-[4-(benzenesulfonyl)-3-nitrophenyl]-2-[3-(2-hydroxyethyl)-3-phenethylureido]propionate (Compound No. 1-39)
$[\alpha]_D^\circ$ -9.2+ (c=0.53, chloroform); IR (Film, cm$^{-1}$) 3338, 3028, 1740, 1636, 1545, 1161, 752.

Benzyl (2S)-2-[3-(2-hydroxyethyl)-3-phenethylureido]-3-(2-naphthyl)propionate (Compound No. 1-40)
$[\alpha]_D^\circ$ -18.2° (c=1.0, methanol); IR (Film, cm$^{-1}$) 3324, 1740, 1632, 1523, 1190, 1050.

Benzyl (2R)-2-[3-(2-hydroxyethyl)-3-phenethylureido]-3-(methylthio)propionate (Compound No. 1-41)
$[\alpha]_D^\circ$ -20.7° (c=0.52, methanol); IR (Film, cm$^{-1}$) 3350, 2921, 1742, 1632, 1524, 1454, 1409, 1190, 1049, 752, 700.

Benzyl (2R)-3-(benzylthio)-2-[3-(2-hydroxyethyl)-3-phenethylureido]propionate (Compound No. 1-42)
$[\alpha]_D^\circ$ -38.0° (c=0.53, methanol); IR (Film, cm$^{-1}$) 3354, 3027, 2926, 1741, 1632, 1523, 1454, 1410, 1309, 1186, 1048, 750, 699.

Benzyl (2S)-2-[3-(2-hydroxyethyl)-3-phenethylureido]-3-phenylpropionate (Compound No. 1-43)
$[\alpha]_D^\circ$ -14.4° (c=0.96, chloroform); IR (Film, cm$^{-1}$) 3327, 3028, 2934, 1740, 1632, 1526, 749, 699.

Benzyl (2R)-[3-(2-hydroxyethyl)-3-phenethylureido]-3-phenylpropionate (Compound No. 1-44), enantiomer of Compound No. 1-43
$[\alpha]_D^\circ$ +16.1° (c=0.51, methanol); IR (Film, cm$^{-1}$) 3328, 2933, 1740, 1630, 1528, 1178, 1048, 747, 699.

Benzyl (2S)-2-[3-(2-hydroxyethyl)-3-phenethylureido]-3-(4-isopropoxyphenyl)propionate (Compound No. 1-45)
$[\alpha]_D^\circ$ -18.7° (c=0.50, chloroform); IR (Film, cm$^{-1}$) 3344, 2975, 1739, 1632, 1509, 1242, 1184, 120, 955, 751, 700.

Benzyl (2S)-2-[3-[(1RS)-1-(dimethylaminomethyl)-2-hydroxyethyl]-3-phenethylureido]-3-phenylpropionate (Compound No. 1-46)
$[\alpha]_D^\circ$ -14.1° (c=1.0, methanol); IR (Film, cm$^{-1}$) 3378, 2945, 1739, 1634, 1455, 1187.

Benzyl (2S)-2-[3-(2-hydroxyethyl)-3-isoamylureido]-3-phenylpropionate (Compound No. 1-47)
$[\alpha]_D^\circ$ -19.2° (c=1.0, chloroform); IR (Film, cm$^{-1}$) 3341, 2955, 2870, 1740, 1631, 1527, 1189, 1051, 753, 699.

Benzyl (2S)-2-[3-(2-hydroxyethyl)-3-isoamylureido]-3-(4-methoxyphenyl)propionate (Compound No. 1-48)
$[\alpha]_D^\circ$ -19.5° (c=0.55, chloroform); IR (Film, cm$^{-1}$) 3336, 2956, 1741, 1632, 1585, 1249, 1179, 1110, 755, 699.

Benzyl (2S)-2-[3-(2-hydroxyethyl)-3-isoamylureido]-2-phenylacetate (Compound No. 1-49)
mp 77.5~79.6° C.; $[\alpha]_D^\circ$ +33.7° (c=0.50, chloroform); IR (KBr, cm$^{-1}$) 3228, 2952, 1745, 1705, 1631, 1560, 1455, 1370, 1239, 1180, 1163.

Benzyl (2S)-2-[3-(2-hydroxyethyl)-3-isoamylureido]-4-methylvalerate (Compound No. 1-50)
$[\alpha]_D^\circ$ -22.9° (c=0.97, chloroform); IR (Film, cm$^{-1}$) 3325, 2956, 1742, 1634, 1538, 1170, 1051, 752, 697.

Benzyl 2-[3-(2-hydroxyethyl)-3-isoamylureido]acetate (Compound No. 1-51)
IR (Film, cm$^{-1}$) 3353, 2955, 1747, 1633, 1537, 1188, 1049, 754, 698.

Benzyl (2S)-3-cyclohexyl-2-[3-(2-hydroxyethyl)-3-isoamylureido]propionate (Compound No. 1-52)

$[\alpha]_D^\circ$ −21.8° (c=0.52, chloroform); IR (Film, cm$^{-1}$) 3307, 2924, 1742, 1631, 1531, 1449, 1169, 1051.

Benzyl (2S)-2-[3-(2-hydroxyethyl)-3-isoamylureido]-3-(4-imidazolyl)propionate (Compound No. 1-53)

$[\alpha]_D^\circ$ −9.5° (c=0.53, chloroform); IR (KBr, cm$^{-1}$) 3198, 2955, 1742, 1630, 1532, 1174, 1051, 754, 698.

Benzyl (2S)-2-[3-(2-hydroxyethyl)-3-isoamylureido]-5-(3-tosylguanidino)valerate (Compound No. 1-54)

$[\alpha]_D^\circ$ +1.6° (c=0.51, chloroform); IR (Film, cm$^{-1}$) 3336, 2954, 1738, 1626, 1548, 1261, 1170, 1132, 1082, 815, 753.

Benzyl (2S)-2-[3-[4-(benzyloxy)phenethyl]-3-[2-(benzylthio)ethyl]ureido]propionate (Compound No. 1-55)

$[\alpha]_D^\circ$ −8.4° (c=0.98, chloroform); IR (Film, cm$^{-1}$) 350, 3062, 3030, 2934, 1740, 1641, 1583, 1511, 1453, 1401, 1300, 1239, 1191, 1025.

Benzyl (2S)-2-[3-[2-(benzylthio)-2-methylpropyl]-3-phenethylureido]propionate (Compound No. 1-56)

$[\alpha]_D^{20}$ 9.8° (c=0.52, methanol); IR (Film, cm$^{-1}$) 3348, 3028, 2962, 1741, 1639, 1521, 1453, 1385, 1364, 1305, 1264, 1188, 1089, 1070, 1029, 1004, 967, 912, 749, 698.

Benzyl (2S)-2-[3-[(2RS)-2-(benzylthio)-3-methylbutyl]-3-phenethylureido]propionate (Compound No. 1-57)

IR (Film, cm$^{-1}$) 3359, 3062, 3027, 2958, 1740, 1646, 1603, 1522, 1453, 1402, 1383, 1364, 1306, 1168.

Benzyl (2RS)-3-(benzylthio)-2-[3-[2-(benzylthio)ethyl]-3-phenethylureido]-3-methylbutyrate (Compound No. 1-58)

IR (Film, cm$^{-1}$) 3378, 3061, 3028, 2966, 2930, 1736, 1656, 1602, 1495, 1454, 1367, 1320, 1189.

Phenyl (2S)-2-[3-(2-hydroxyethyl)-3-phenethylureido]-3-phenylpropionate (Compound No. 1-59)

$[\alpha]_D^\circ$ −3.8° (c=0.30, chloroform); IR (Film, cm$^{-1}$) 3334, 1760, 1633, 1527, 1493, 1454, 1408, 1367, 1192, 1047, 751, 700.

Phenyl (2S)-3-(4-fluorophenyl)-2-[3-(2-hydroxyethyl)-3-phenethylureido]propionate (Compound No. 1-60)

$[\alpha]_D^\circ$ −4.1° (c=0.31, chloroform); IR (Film, cm$^{-1}$) 3305, 2932, 1762, 1632, 1510, 1223, 1192, 1163, 751, 701.

Phenyl (2S)-2-[3-(2-hydroxyethyl)-3-phenethylureido]-3-(4-hydroxyphenyl)propionate (Compound No. 1-61)

$[\alpha]_D^\circ$ −4.6° (c=0.33, chloroform); IR (Film, cm$^{-1}$) 3409, 1757, 1630, 1516, 1493, 1454, 1411, 1368, 1191, 1047, 831, 751, 701.

Phenyl (2S)-2-[3-(2-hydroxyethyl)-3-phenethylureido]-3-(4-methoxyphenyl)propionate (Compound No. 1-62)

mp 91.2~94.0° C.; $[\alpha]_D^\circ$ −4.9° (c=1.0, chloroform); IR (KBr, cm$^{-1}$) 3310, 2935, 1761, 1633, 1513, 1249, 1192, 1164, 701.

Phenyl (2S)-2-[3-(2-hydroxyethyl)-3-phenethylureido]-3-(2-thienyl)propionate (Compound No. 1-63)

$[\alpha]_D^\circ$ −9.4° (c=0.66, chloroform); IR (Film, cm$^{-1}$) 3323, 1761, 1633, 1523, 1492, 1192, 1046, 750, 700.

Phenyl (2S)-2-[3-(2-hydroxyethyl)-3-phenethylureido]-3-(2-naphthyl)propionate (Compound No. 1-64)

$[\alpha]_D^\circ$ −8.6° (c=0.54, chloroform); IR (Film, cm$^{-1}$) 3312, 2931, 1760, 1634, 1524, 1493, 1192, 1164, 750.

Phenyl (2S)-3-(4-biphenylyl)-2-[3-(2-hydroxyethyl)-3-phenethylureido]propionate (Compound No. 1-65)

$[\alpha]_D^\circ$ −22.3° (c=0.55, dimethyl sulfoxide); IR (Film, cm$^{-1}$) 3305, 2930, 1763, 1633, 1520, 1487, 1192, 1164, 759, 699.

Phenyl (2S)-2-[3-(2-hydroxyethyl)-3-isoamylureido]-3-(4-nitrophenyl)propionate (Compound No. 1-66)

$[\alpha]_D^\circ$ −6.1° (c=0.54, chloroform); IR (Film, cm$^{-1}$) 3306, 2956, 1761, 1633, 1520, 1492, 1346, 1192, 1165, 753.

Phenyl (2S)-3-(4-biphenylyl)-2-[3-(2-hydroxyethyl)-3-isoamylureido]propionate (Compound No. 1-67)

$[\alpha]_D^\circ$ −2.3° (c=0.98, chloroform); IR (Film, cm$^{-1}$) 3306, 2955, 1763, 1633, 1519, 1487, 1192, 1164, 760, 698.

t-Butyl (2S)-2-[3-phenethyl-3-[2-(phenyldithio)ethyl]ureido]-3-phenylpropionate (Compound No. 1-68)

$[\alpha]_D^\circ$ −7.5° (c=0.32, methanol); IR (Film, cm$^{-1}$) 3369, 2977, 1729, 1649, 1512, 1155, 741, 700.

(2S)-2-[3-(2-Mercaptoethyl)-3-phenethylureido]-4-butanolide (Compound No. 1-69)

Ethyl (2S)-2-[3-[2-(methylthio)ethyl]-3-phenethylureido]-3-phenylpropionate (Compound No. 1-70)

$[\alpha]_D^\circ$ −2.3° (c=0.32, methanol); IR (Film, cm$^{-1}$) 3368, 2980, 2919, 1736, 1644, 1514, 1454, 1405, 1369, 1195, 1092, 1029, 752, 701.

Benzyl (2R)-3-(benzylthio)-2-[3-[2-(benzylthio)ethyl]-3-phenethylureido]propionate (Compound No. 1-71)

$[\alpha]_D^\circ$ −38.1° (c=0.50, methanol); IR (Film, cm$^{-1}$) 3027, 2920, 1740, 1649, 1495, 1453, 1190, 753, 700.

Benzyl (2S)-2-[3-[2-(benzylthio)-1-[(benzylthio)methyl]ethyl]-3-phenethylureido]-3-phenylpropionate (Compound No. 1-72)

$[\alpha]_D^\circ$ +2.4° (c=0.51, chloroform); IR (Film, cm$^{-1}$) 3027, 1737, 1650, 1495, 1454, 1346, 1257, 1191, 753, 700.

Benzyl (2S)-6-(benzyloxycarboxamido)-2-[3-(2-hydroxyethyl)-3-isoamylureido]hexanoate (Compound No. 1-73)

$[\alpha]_D^\circ$ −14.9° (c=0.47, chloroform); IR (Film, cm$^{-1}$) 3319, 2953, 1712, 1633, 1531, 1455, 1410, 1367, 1256, 1174, 1052.

Benzyl (2S)-2-[3-(2-hydroxyethyl)-3-phenethylureido]-3-[4-(benzyloxy)phenyl]propionate (Compound No. 1-74)

$[\alpha]_D^\circ$ +3.2° (c=0.51, methanol); IR (Film, cm$^{-1}$) 3324, 1740, 1632, 1511, 1241, 1026.

t-Butyl 2-[3-(2-cyclohexylethyl)-3-(2-hydroxyethyl)ureido]acetate (Compound No. 1-75)

IR (Film, cm$^{-1}$) 3354, 2977, 2924, 2851, 17 43, 1632, 1536, 1368, 1221, 1157, 754.

t-Butyl (2S)-2-[3-(2-cyclohexylethyl)-3-(3-hydroxypropyl)ureido]propionate (Compound No. 1-76)

t-Butyl (2S)-2-[3-(2-cyclohexylethyl)-3-(3-hydroxypropyl)ureido]propionate (Compound No. 1-77) $[\alpha]_D^\circ$ −5.2° (c=1.0, methanol); IR (Film, cm$^{-1}$) 3350, 2977, 2922, 2854, 1738, 1633, 1531, 1455.

t-Butyl (2S)-2-[3-[2-(1-adamantyl)ethyl]-3-(2-hydroxypropyl)ureido]propionate (Compound No. 1-78) $[\alpha]_D^\circ$ −3.5° (c=1.0, methanol); IR (Film, cm$^{-1}$) 3340, 2978, 2902, 2847, 1732, 1633, 1530, 1451, 1218, 1156.

Ethyl (2S)-2-[3-(2-hydroxyethyl)-3-(methyl-3-butenyl)ureido]propionate (Compound No. 1-79) IR (Film, cm$^{-1}$) 3344, 2980, 2937, 1734, 1634, 1533, 1204, 1060, 889.

Phenyl (2S)-3-(4-biphenylyl)-2-[3-[(1RS)-1-ethoxycarbonylmethyl)-2-(phenylthio)ethyl]-3-isoamylureido]propionate (Compound No. 1-80) IR (Film, cm$^{31\ 1}$) 3344, 2980, 2937, 1734, 1634, 1533, 1204, 1060, 888.

t-Butyl (2S)-2-[3-[2-(methylthio)ethyl]-3-(phenethyl)ureido]propionate (Compound No. 1-81) IR (Film, cm$^{-1}$) 3354, 3026, 2978, 2919, 1732, 1634, 1520, 1215, 1155.

Methyl 2-[3-(2-cyclohexylethyl)-3-(2-hydroxyethyl) ureido]-2-methylpropionate (Compound No. 1-82) IR (Film, cm$^{-1}$) 3306, 2985, 2923, 2851, 1741, 1632, 1536, 1284, 1152, 1054, 756.

Benzyl 1-[3-(2-cyclohexylethyl)-3-(2-hydroxyethyl) ureido]-1-cyclopropanecarboxylate (Compound No. 1-83) mp 101~108° C.; IR (Film, cm$^{-1}$) 3403, 3345, 2919, 2850, 1731, 1614, 1527, 1275, 1166, 1036, 748, 705.

Benzyl 1-[3-(2-cyclohexylethyl)-3-(2-hydroxyethyl) ureido]-1-cyclopentanecarboxylate (Compound No. 1-84) mp 66.7~68.5° C.; IR (KBr, cm$^{-1}$) 3220, 2926, 1785, 1624, 1560, 1475, 1448, 1412, 1274, 1249, 1077, 732.

t-Butyl (2S)-2-[3-(2-cyclohexylethyl)-3-(3-hydroxypropyl)ureido]propionate (Compound No. 1-85) $[\alpha]_D^\circ$ −5.7° (c=1.0, methanol); IR (Film, cm$^{-1}$) 3326, 2977, 2923, 2851, 1737, 1632, 1536, 1450, 1368, 1304, 1218, 1157.

t-Butyl (2R)-2-[3-(2-cyclohexylethyl)-3-(2-hydroxyethyl)ureido]propionate (Compound No. 1-86) $[\alpha]_D^\circ$ +6.3° (c=1.0, methanol); IR (Film, cm$^{-1}$) 3340, 2977, 2923, 1732, 1632, 1531, 1449, 1368, 1157.

t-Butyl 2-[3-[2-(1-adamantyl)ethyl]-3-(2-hydroxyethyl) ureido]acetate (Compound No. 1-87) mp 120.0~120.5° C. IR (KBr, cm$^{-1}$) 3289, 2901, 2843, 1751, 1630, 1567, 1223, 1155.

t-Butyl (2S)-2-[3-[2-[3,5-di(t-butyl)-4-(methoxymethoxy)phenyl]ethyl]-3-(2-hydroxyethyl) ureido]propionate (Compound No. 1-88) $[\alpha]_D^\circ$ −16.2° (c=1.0, methanol); IR (Film, cm$^{-1}$) 3347, 2958, 1731, 1630, 1530, 1452, 1260, 1164.

EXAMPLE 2

Benzyl (2S)-2-[3-(2-hydroxyethyl)-1-methyl-3-phenethylureido]propionate (Compound No. 2-1)

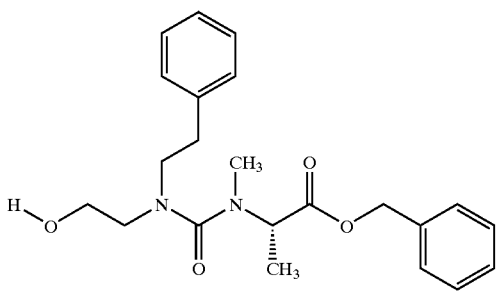

N,N-Diisopropylethylamine (3.5 ml) is added to a solution of triphosgene (5.5 g) in carbon tetrachloride (20 ml) under a nitrogen atmosphere and ice-methanol cooling. A solution of a free base obtained from N-methyl-L-alanine benzyl ester hydrochloride (Reference compound No. 3-12, 2.10 g) in carbon tetrachloride (5 ml) is added dropwise to the mixture while keeping temperature at −5° C., and the mixture is stirred for 30 minutes after the dropping. A solution of a free base obtained from N-(2-hydroxyethyl) phenethylamine hydrochloride (Reference compound No. 13-11, 5.5 g) in carbon tetrachloride (5 ml) is added to the reaction mixture, and the mixture is stirred at room temperature for 30 minutes and then refluxed for 1.5 hours. A 10% aqueous sodium hydrogencarbonate solution is added to the reaction mixture under ice cooling, and the whole is extracted with ether. The organic layer is washed with a 10% aqueous citric acid solution, water and saturated brine successively, dried over anhydrous magnesium sulfate and concentrated under reduced pressure. The resulting oily matter is purified by silica gel column chromatography to give 2.74 g (78%) of the titled compound (Compound No. 2-1).

(Compound No. 2-1) $[\alpha]_D^\circ$ −19.3° (c=1.0, methanol); IR (Film, cm$^{-1}$) 3410, 3062, 3027, 2941, 1740, 1620, 1454, 1164, 1089.

EXAMPLE 3 t-Butyl (2S)-2-[3-[2-(t-butyldimethylsiloxy)ethyl]-3-(2-methoxyethyl)ureido]propionate (Compound No. 3-1)

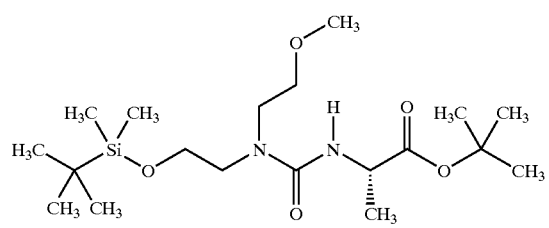

In anhydrous tetrahydrofuran (11 ml) are suspended L-alanine t-butyl ester hydrochloride (1.70 g), 1,1'-carbonyldiimidazole (1.54 g) and imidazole (0.47 g) under a nitrogen atmosphere, and the suspension is stirred at room temperature for 30 minutes. A solution of N-[2-(t-butyldimethylsiloxy)ethyl]-2-methoxyethylamine (Reference compound No. 14-1, 1.77 g) in anhydrous tetrahydrofuran (6 ml) is added to the reaction mixture, and the mixture is refluxed for one hour. After allowing to stand, the reaction mixture is concentrated under reduced pressure. Water is added to the resulting oily matter, and the whole is extracted with ether. The organic layer is washed with saturated brine, dried over anhydrous magnesium sulfate and concentrated under reduced pressure. The resulting oily matter is purified by silica gel column chromatography to give 2.91 g (95%) of the titled compound (Compound No. 3-1).

(Compound No. 3-1) $[\alpha]_D^\circ$ +6.3° (c=1.1, chloroform); IR (Film, cm$^{-1}$) 3348, 2931, 2858, 1737, 1650, 1530, 1462, 1368, 1225, 1159, 1117, 838, 779.

The following compounds are obtained by a method similar to Example 3.

t-Butyl (2S)-2-[3-[2-(t-butyldimethylsiloxy)ethyl]-3-[2-(4-pyridyl)ethyl]ureido]propionate (Compound No. 3-2)

Ethyl (2S)-2-[3-[2-(t-butyldimethylsiloxy)ethyl]-3-[2-(1-cyclohexenyl)ethyl]ureido]propionate (Compound No. 3-3) IR (Film, cm$^{-1}$) 3361, 2929, 2857, 1737, 1634, 1532, 1472, 1373, 1253, 1185, 1104, 836, 778.

t-Butyl (2S)-2-[3-[2-(t-butyldimethylsiloxy)ethyl]-3-(2-cyclopropylethyl)ureido]propionate (Compound No. 3-4) IR (Film, cm$^{-1}$) 3358, 2930, 2857, 1736, 1644, 1525, 1472, 1368, 1256, 1221, 1158, 1104, 837.

t-Butyl (2S)-2-[3-[2-(t-butyldimethylsiloxy)ethyl]-3-(2-cyclobutylethyl)ureido]propionate (Compound No. 3-5) $[\alpha]_D^\circ$ −4.3° (c=1.1, methanol); IR (Film, cm$^{-1}$) 3359, 2930, 2857, 1736, 1644, 1524, 1472, 1392, 1368, 1255, 1220, 1158, 1104, 1063, 928, 837, 778.

EXAMPLE 4 t-Butyl (2S)-2-[3-(2-hydroxyethyl)-3-(2-methoxyethyl)ureido]propionate (Compound No. 4-1)

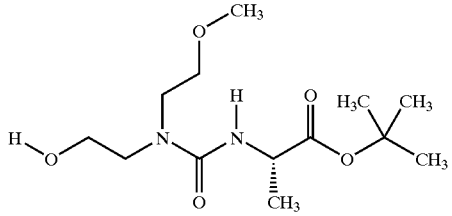

t-Butyl (2S)-2-[3-[2-(t-butyldimethylsiloxy)ethyl]-3-(2-methoxyethyl)ureido]propionate (Compound No. 3-1, 2.79 g) is dissolved in anhydrous tetrahydrofuran (11 ml) under a nitrogen atmosphere. Tetra-n-butylammonium fluoride (7.3 ml) is added to the solution at room temperature with stirring, and the mixture is stirred for one hour. Water is added to the reaction mixture, and the whole is extracted with ethyl acetate. The organic layer is washed with saturated brine, dried over anhydrous magnesium sulfate and concentrated under reduced pressure. The resulting oily matter is purified by silica gel column chromatography to give 2.14 g (quantitatively) of the titled compound (Compound No. 4-1).

(Compound No. 4-1) $[\alpha]_D°$ -2.0° (c=1.0, chloroform); IR (Film, cm$^{-1}$) 3334, 2979, 2933, 1732, 1633, 1537, 1455, 1405, 1368, 1159, 1118, 1057, 756.

The following compounds are obtained by a method similar to Example 4.

t-Butyl (2S)-2-[3-(2-hydroxyethyl)-3-[2-(4-pyridyl)ethyl]ureido]propionate (Compound No. 4-2) IR (Film, cm$^{-1}$) 3338, 2978, 1732, 1634, 1606, 1532, 1368, 1222, 1155, 1058, 848, 810, 758.

Ethyl (2S)-2-[3-[2-(1-cyclohexenyl)ethyl]-3-(2-hydroxyethyl)ureido]propionate (Compound No. 4-3) $[\alpha]_D°$ -7.5° (c=0.53, methanol); IR (Film, cm$^{-1}$) 3338, 2980, 2928, 1738, 1632, 1531, 1449, 1408, 1183, 1058.

t-Butyl (2S)-2-[3-(2-cyclopropylethyl)-3-(2-hydroxyethyl)ureido]propionate (Compound No. 4-4) $[\alpha]_D°$ -8.2° (c=1.0, methanol); IR (Film, cm$^{-1}$) 3342, 2979, 2933, 1732, 1632, 1530, 1456, 1368, 1223, 1158, 1056, 756.

t-Butyl (2S)-2-[3-(2-cyclobutylethyl)-3-(2-hydroxyethyl)ureido]propionate (Compound No. 4-5) $[\alpha]_D°$ -7.2° (c=0.54, methanol); IR (Film, cm$^{-1}$) 3339, 2974, 1732, 1633, 1532, 1455, 1368, 1222, 1158, 1055, 756.

EXAMPLE 5 t-Butyl (2S)-2-[3-[2-(Acetylthio)ethyl]-3-(2-cyclohexylethyl)ureido]propionate (Compound No. 5-1)

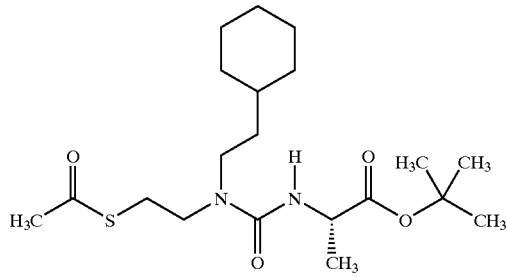

Anhydrous tetrahydrofuran (6 ml) is added to a mixture of t-butyl (2S)-2-[3-(2-cyclohexylethyl)-3-(2-hydroxyethyl)ureido]propionate (Compound No. 1-1, 1.0 g) and triphenylphosphine (1.5 g) under a nitrogen atmosphere, and the mixture is stirred for 30 minutes under salt-ice cooling. Diisopropyl azodicarboxylate (1.2 ml) is added dropwise to the mixture while keeping liquid temperature at 5° C., and then thioacetic acid (0.4 ml) is added dropwise thereto over 20 minutes. The mixture is stirred for 20 minutes, a 10% aqueous sodium hydrogencarbonate solution (30 ml) is added to the reaction mixture, and the whole is extracted with ether. The organic layer is washed with a 10% aqueous sodium hydrogencarbonate solution, water and saturated brine successively, dried over anhydrous magnesium sulfate and concentrated under reduced pressure. The resulting oily matter is purified by silica gel column chromatography to give the titled compound (Compound No. 5-1).

The following compounds are obtained by a method similar to Example 5.

t-Butyl (2S)-2-[3-[2-(acetylthio)ethyl]-3-phenethylureido]propionate (Compound No. 5-2) $[\alpha]_D°$ -4.1° (c=0.52, methanol); IR (Film, cm$^{-1}$) 2928, 1735, 1680, 1650, 1368, 1216, 1154.

t-Butyl (2R)-2-[3-[2-(acetylthio)ethyl]-3-phenethylureido]propionate (Compound No. 5-3), enantiomer of Compound No. 5-2 t-Butyl (2S)-2-[3-[2-(acetylthio)ethyl]-3-(4-fluorophenethyl)ureido]propionate (Compound No. 5-4) $[\alpha]_D°$ +5.20° (c=0.99, chloroform); IR (Film, cm$^{-1}$) 2980, 1732, 1681, 1642, 1510, 1368, 1220, 1155, 1110.

t-Butyl (2S)-2-[3-[2-(acetylthio)ethyl]-3-(4-chlorophenethyl)ureido]propionate (Compound No. 5-5)

t-Butyl (2S)-2-[3-[2-(acetylthio)ethyl]-3-(4-nitrophenethyl)ureido]propionate (Compound No. 5-6)

t-Butyl (2S)-2-[3-[2-(acetylthio)ethyl]-3-(4-methoxyphenethyl)ureido]propionate (Compound No. 5-7)

t-Butyl (2S)-2-[3-[2-(acetylthio)ethyl]-3-(4-methylphenethyl)ureido]propionate (Compound No. 5-8)

t-Butyl (2S)-2-[3-[2-(acetylthio)ethyl]-3-(4-phenylphenethyl)ureido]propionate (Compound No. 5-9)

t-Butyl (2S)-2-[3-[2-(acetylthio)ethyl]-3-[2-(2-pyridyl)ethyl]ureido]propionate (Compound No. 5-10) $[\alpha]_D°$ -

1.7° (c=0.58, methanol); IR (Film, cm$^{-1}$) 3390, 2978, 1732, 1683, 1651, 1531, 1437, 1367, 1216, 1154, 1119, 722, 542.

t-Butyl (2S)-2-[3-[2-(acetylthio)ethyl]-3-[2-(2-naphthyl)ethyl]ureido]propionate (Compound No. 5-11) IR (Film, cm$^{-1}$) 3383, 2981, 1737, 1682, 1641, 1530, 1368, 1255, 1155.

t-Butyl (2S)-2-[3-[2-(acetylthio)ethyl]-3-(3-phenylpropyl)ureido]propionate (Compound No. 5-12) [α]$_D^°$+10.1° (c=0.51, chloroform); IR (Film, cm$^{-1}$) 3385, 2979, 2935, 1735, 1683, 1644, 1529, 1255, 1217, 155, 752, 700.

t-Butyl (2S)-2-[3-[2-(acetylthio)ethyl]-3-[3-(4-fluorophenyl)propyl]ureido]propionate (Compound No. 5-13)

t-Butyl (2S)-2-[3-[2-(acetylthio)ethyl]-3-[3-(4-chlorophenyl)propyl]ureido]propionate (Compound No. 5-14)

t-Butyl (2S)-2-[3-[2-(acetylthio)ethyl]-3-(3-phenyl-2-propenyl)ureido]propionate (Compound No. 5-15)

t-Butyl (2S)-2-[3-[2-(acetylthio)ethyl]-3-(2-phenoxyethyl)ureido]propionate (Compound No. 5-16) [α]$_D^°$+2.2° (c=1.0, methanol); IR (Film, cm$^{-1}$) 3379, 2979, 2935, 1735, 1682, 1654, 1600, 1529, 1498, 1243, 1155, 1110.

t-Butyl (2S)-2-[3-[2-(acetylthio)ethyl]-3-phenylureido]propionate (Compound No. 5-17) [α]$_D^°$+19.9° (c=0.98, methanol); IR (Film, cm$^{-1}$) 3419, 2979, 2934, 1732, 1692, 1666, 1596, 1495, 1453, 1259, 1227, 1157, 1110.

t-Butyl (2S)-2-[3-[2-(acetylthio)ethyl]-3-benzylureido]propionate (Compound No. 5-18)

t-Butyl (2S)-2-[3-[2-(acetylthio)ethyl]-3-(3-butenyl)ureido]propionate (Compound No. 5-19)

t-Butyl 2-[3-[2-(acetylthio)ethyl]-3-phenethylureido]acetate (Compound No. 5-20)

t-Butyl 2-[3-[2-(acetylthio)ethyl]-3-methylureido]acetate (Compound No. 5-21)

t-Butyl (2S)-2-[3-[2-(acetylthio)ethyl]-3-phenethylureido]butyrate (Compound No. 5-22) [α]$_D^°$-7.1° (c=1.0, methanol); IR (Film, cm$^{-1}$) 3390, 2974, 2934, 1732, 1682, 1651, 1525, 1455, 1367, 1255, 1153.

t-Butyl (2RS)-2-[3-[2-(acetylthio)ethyl]-3-phenethylureido]-3-(t-butoxy)propionate (Compound No. 5-23) IR (Film, cm$^{-1}$) 2975, 1738, 1691, 1653, 1509, 1366, 1251, 1155, 1098.

t-Butyl (2S)-2-[3-[2-(acetylthio)ethyl]-3-phenethylureido]-2-phenylacetate (Compound No. 5-24) IR (Film, cm$^{-1}$) 3391, 2978, 1734, 1685, 1652, 1497, 1368, 1208, 1152, 700.

t-Butyl (2S)-2-[3-[2-(acetylthio)ethyl]-3-methylureido]-3-phenylpropionate (Compound No. 5-25)

t-Butyl (2S)-2-[3-[2-(acetylthio)ethyl]-3-isoamylureido]-3-phenylpropionate (Compound No. 5-26) IR (Film, cm$^{-1}$) 3389, 2956, 1731, 1689, 1653, 1516, 1368, 1258, 1156, 1102.

t-Butyl (2S)-2-[3-[2-(acetylthio)ethyl]-3-(2-cyclohexylethyl)ureido]-3-phenylpropionate (Compound No. 5-27) [α]$_D^°$+16.2° (c=1.0, chloroform); IR (Film, cm$^{-1}$) 3389, 2923, 1730, 1690, 1653, 1514, 1367, 1214, 1155, 701.

t-Butyl 3-[3-[2-(acetylthio)ethyl]-3-phenethylureido]propionate (Compound No. 5-28) IR (Film, cm$^{-1}$) 3392, 2978, 2932, 1726, 1691, 1634, 1531, 1367, 1256, 1157, 951, 751, 701, 628.

t-Butyl (2S)-2-[3-[(2RS)-3-(acetylthio)-2-methylpropyl]-3-phenethylureido]-3-phenylpropionate (Compound No. 5-29) IR (Film, cm$^{-1}$) 3436, 2975, 2930, 1728, 1693, 1650, 1510, 1454, 1368, 1256, 1155, 956, 846, 751, 701, 629.

t-Butyl (2S)-2-[3-[2-(acetylthio)ethyl]-3-phenethylureido]-3-phenylpropionate (Compound No. 5-30) [α]$_D^°$-9.5° (c=0.98, methanol); IR (Film, cm$^{-1}$) 3383, 2977, 1732, 1653, 1521, 1370, 1154, 701.

t-Butyl (2S)-2-[3-[2-(acetylthio)ethyl]-3-(2-methoxyethyl)ureido]propionate (Compound No. 5-31)

t-Butyl (2S)-2-[3-[2-(acetylthio)ethyl]-3-[2-(4-pyridyl)ethyl]ureido]propionate (Compound No. 5-32) IR (Film, cm$^{-1}$) 3382, 1732, 1682, 1644, 1602, 1530, 1367, 1217, 1154.

t-Butyl 2-[3-[2-(acetylthio)ethyl]-3-(2-cyclohexylethyl)ureido]acetate (Compound No. 5-33)

t-Butyl (2S)-2-[3-[2-(acetylthio)ethyl]-3-(2-cyclopentylethyl)ureido]propionate (Compound No. 5-34)

t-Butyl (2S)-2-[3-[2-(acetylthio)ethyl]-3-(2-cycloheptylethyl)ureido]propionate (Compound No. 5-35) [α]$_D^°$+1.0° (c=1.0, methanol); IR (Film, cm$^{-1}$) 3389, 2978, 2923, 2853, 1734, 1684, 1646, 1526, 1456.

t-Butyl (2S)-2-[3-[2-(acetylthio)ethyl]-3-[2-(1-adamantyl)ethyl]ureido]propionate (Compound No. 5-36) mp 111~113° C.; [α]$_D^°$+2.2° (c=1.0, methanol); IR (KBr, cm$^{-1}$) 3376, 2972, 2901, 2847, 1749, 1683, 1651, 1534, 1453, 1211, 1152.

t-Butyl (2S)-2-[3-[2-(acetylthio)ethyl]-3-(2-cyclopropylethyl)ureido]propionate (Compound No. 5-37)

t-Butyl (2S)-2-[3-[2-(acetylthio)ethyl]-3-(2-cyclobutylethyl)ureido]propionate (Compound No. 5-38) IR (Film, cm$^{-1}$) 3390, 2978, 1738, 1682, 1644, 1530, 1454, 1368, 1258, 1156, 1108.

t-Butyl (2S)-2-[3-[3-(acetylthio)propyl]-3-(2-cyclohexylethyl)ureido]propionate (Compound No. 5-39) [α]$_D^°$-4.3° (c=1.0, methanol); IR (Film, cm$^{-1}$) 3362, 2978, 2924, 2852, 1732, 1694, 1633, 1520, 1450, 1407, 1368, 1258, 1215, 1156.

t-Butyl (2R)-2-[3-[2-(acetylthio)ethyl]-3-(2-cyclohexylethyl)ureido]propionate (Compound No. 5-40) [α]$_D^°$-8.9° (c=1.0, methanol); IR (Film, cm$^{-1}$) 3390, 2980, 2924, 1737, 1682, 1644, 1530, 1450, 1368, 1216, 1156.

t-Butyl 2-[3-[2-(acetylthio)ethyl]-3-[2-(1-adamantyl)ethyl]ureido]acetate (Compound No. 5-41) IR (Film, cm$^{-1}$) 3390, 2978, 2903, 2846, 1743, 1692, 1643, 1536, 1366, 1217, 1156, 755.

t-Butyl (2S)-2-[3-[2-(acetylthio)ethyl]-3-[2-[3,5-di(t-butyl)-4-(methoxymethoxy)phenyl]ethyl]ureido]propionate (Compound No. 5-42) [α]D$^°$+2.0° (c=1.0, methanol); IR (Film, cm$^{-1}$) 3390, 2963, 1737, 1683, 1645, 1526, 1481, 1453, 1430, 1392, 1367, 1260, 1164.

EXAMPLE 6 t-Butyl (2S)-2-[3-[2-(Acetylthio)ethyl]-3-phenethylureido]-3-methylbutyrate (Compound No. 6-1)

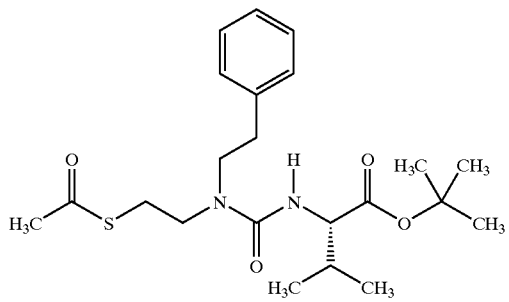

In anhydrous tetrahydrofuran (72 ml) are suspended L-valine t-butyl ester hydrochloride (1.5 g), 1,1'-carbonyldiimidazole (1.4 g) and imidazole (0.49 g) under a nitrogen atmosphere, and the suspension is stirred at room temperature for 30 minutes.

N-(2-Mercaptoethyl)phenethylamine hydrochloride (Reference compound No. 17-1, 1.77 g) is added to the reaction mixture, and the mixture is refluxed for one hour. Water is added to the reaction mixture under ice cooling, and the whole is extracted with ether. The organic layer is washed with water, a 10% aqueous citric acid solution, water and saturated brine successively, dried over anhydrous magnesium sulfate and concentrated under reduced pressure. The resulting oily matter is dissolved in chloroform (14 ml) under a nitrogen atmosphere, triethylamine (1.5 ml) is added to the solution under ice cooling. Acetic anhydride (0.81 ml) is added thereto, and the mixture is stirred as it is for 30 minutes. Water is added to the reaction mixture under ice cooling, and the whole is extracted with ether. The organic layer is washed with a 10% aqueous citric acid solution, water and saturated brine successively, dried over anhydrous magnesium sulfate and concentrated under reduced pressure. The resulting oily matter is purified by silica gel column chromatography to give 1.95 g (65%) of the titled compound (Compound No. 6-1).

(Compound No. 6-1) $[\alpha]_D^\circ$ -5.1° (c=1.0, methanol); IR (Film, cm$^{-1}$) 3392, 2967, 2932, 1729, 1684, 1653, 1519, 1256, 1210, 1151.

The following compound is obtained by a method similar to Example 6.

t-Butyl (2S)-2-[3-[2-(acetylthio)ethyl]-3-phenethylureido]valerate (Compound No. 6-2) $[\alpha]_D^\circ$ +5.9° (c=1.0, chloroform); IR (Film, cm$^{-1}$) 3385, 2962, 2873, 1732, 1681, 1644, 1530, 1454, 1367, 1214, 1153, 753, 701.

EXAMPLE 7

(2S)-2-[3-[2-(Acetylthio)ethyl]-3-(2-cyclohexylethyl)ureido]propionic Acid (Compound No. 7-1)

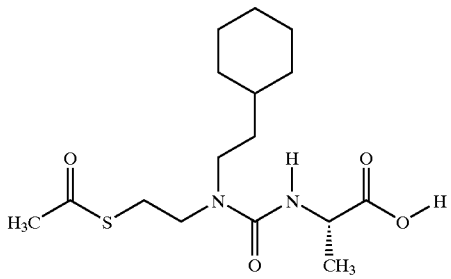

A 4.0 N hydrogen chloride/dioxane solution (14 ml) is added to t-butyl (2S)-2-[3-[2-(acetylthio)ethyl]-3-(2-cyclohexylethyl)ureido]propionate (Compound No. 5-1, 2.3 g), and the mixture is stirred at room temperature overnight. The reaction mixture is concentrated under reduced pressure, to the resulting oily matter are added a 5% aqueous sodium hydrogencarbonate solution (30 ml) and ethyl acetate (30 ml), and the aqueous layer is separated from the organic layer. A 5% aqueous citric acid solution is added to the aqueous layer to acidify it, and the whole is extracted with ethyl acetate. The organic layer is washed with water and saturated brine successively, dried over anhydrous magnesium sulfate and concentrated under reduced pressure. The resulting oily matter is purified by silica gel column chromatography to give 826 mg (42%) of the titled compound (Compound No. 7-1) as crystals.

(Compound No. 7-1) mp 89.5~90.5° C.; $[\alpha]_D^\circ$ +7.7° (c=1.0, methanol); IR (KBr, cm$^{-1}$) 3382, 2926, 2853, 1715, 1674, 1600, 1549, 1485, 1454, 1421, 1381, 1355, 1328, 1298, 1223, 1168, 1136, 1106.

The following compounds are obtained by a method similar to Example 7.

(2S)-2-[3-[2-(Acetylthio)ethyl]-3-phenethylureido]propionic acid (Compound No. 7-2)

(2R)-2-[3-[2-(Acetylthio)ethyl]-3-phenethylureido]propionic acid (Compound No. 7-3), enantiomer of Compound No. 7-2 mp 113.0~114.7° C.; $[\alpha]_D^\circ$ -2.7° (c=1.0, methanol); IR (Film, cm$^{-1}$) 3368, 2940, 1716, 1675, 1598, 1548, 1298.

(2S)-2-[3-[2-(Acetylthio)ethyl]-3-(4-fluorophenethyl)ureido]propionic acid (Compound No. 7-4) $[\alpha]_D^\circ$ -28.6° (c=1.0, chloroform); IR (Film, cm$^{-1}$) 2938, 1729, 1679, 1605, 1535, 1510, 1220, 1157.

(2S)-2-[3-[2-(Acetylthio)ethyl]-3-(4-chlorophenethyl)ureido]propionic acid (Compound No. 7-5) $[\alpha]_D^\circ$ +1.8° (c=1.0, methanol); IR (Film, cm$^{-1}$) 3376, 2938, 1732, 1681, 1614, 1537, 1492, 1205, 1143.

(2S)-2-[3-[2-(Acetylthio)ethyl]-3-(4-nitrophenethyl)ureido]propionic acid (Compound No. 7-6) $[\alpha]_D^\circ$ -19.40° (c=0.54, chloroform); IR (Film, cm$^{-1}$) 3372, 2938, 1735, 1680, 1603, 1519, 1345, 1206, 7514.

(2S)-2-[3-[2-(Acetylthio)ethyl]-3-(4-methoxyphenethyl)ureido]propionic acid (Compound No. 7-7) $[\alpha]_D^\circ$ -37.9° (c=1.0, chloroform); IR (Film, cm$^{-1}$) 3380, 2937, 1732, 1682, 1613, 1513, 1455, 1247, 1178, 1035, 756.

(2S)-2-[3-[2-(Acetylthio)ethyl]-3-(4-methylphenethyl)ureido]propionic acid (Compound No. 7-8) $[\alpha]_D^\circ$ -

44.1° (c=0.58, chloroform); IR (Film, cm$^{-1}$) 3377, 2937, 1731, 1682, 1614, 1537, 1215, 1143, 810, 757, 631.

(2S)-2-[3-[2-(Acetylthio)ethyl]-3-(4-phenylphenethyl) ureido]propionic acid (Compound No. 7-9) IR (Film, cm$^{-1}$) 3377, 325, 1732, 1681, 1614, 1537, 1486, 1216, 1142, 761.

(2S)-2-[3-[2-(Acetylthio)ethyl-3-2-(2-pyridyl)ethyl] ureido]propionic acid (Compound No. 7-10) IR (Film, cm$^{-1}$) 3392, 1682, 1594, 1531, 1409.

(2S)-2-[3-[2-(Acetylthio)ethyl]-3-[2-(2-naphthyl)ethyl] ureido]propionic (Compound No. 7-11) [α]$_D$°−38.5° (c=0.22, chloroform); IR (Film, cm$^{-1}$) 3375, 2921, 1734, 1679, 1609, 1533, 1205, 1141, 752.

(2S)-2-[3-[2-(Acetylthio)ethyl]-3-(3-phenylpropyl) ureido]propionic acid (Compound No. 7-12) [α]$_D$°+4.9° (c=0.50, methanol); IR (Film, cm$^{-1}$) 3378, 2938, 1732, 1682, 1614, 1536, 1207, 1140, 753, 700, 631.

(2S)-2-[3-[2-(Acetylthio)ethyl]-3-[3-(4-fluorophenyl) propyl]ureido]propionic acid (Compound No. 7-13) [α]$_D$°−31.6° (c=1.0, chloroform); IR (Film, cm$^{-1}$) 3377, 2938, 1736, 1680, 1604, 1535, 1510, 1219, 952, 832, 760, 630.

(2S)-2-[3-[2-(Acetylthio)ethyl]-3-[3-(4-chlorophenyl) propyl]ureido]propionic acid (Compound No. 7-14) [α]$_D$°−33.1° (c=1.0, chloroform); IR (Film, cm$^{-1}$) 3377, 2938, 1736, 1680, 1612, 1536, 1203, 951, 833, 759, 630.

(2S)-2-[3-[2-(Acetylthio)ethyl]-3-(3-phenyl-2-propenyl) ureido]propionic acid (Compound No. 7-15) [α]$_D$°−35.3° (c=1.0, chloroform); IR (Film, cm$^{-1}$) 3375, 2985, 1730, 1680, 1611, 1534, 1210, 751, 629.

(2S)-2-[3-[2-(Acetylthio)ethyl]-3-(2-phenoxyethyl) ureido]propionic acid (Compound No. 7-16) [α]$_D$°+5.1° (c=0.99, methanol); IR (Film, cm$^{-1}$) 3374, 2938, 1737, 1680, 1600, 1535, 1496, 1239.

(2S)-2-[3-[2-(Acetylthio)ethyl]-3-phenylureido] propionic acid (Compound No. 7-17) [α]$_D$°+26.0° (c=0.98, methanol); IR (Film, cm$^{-1}$) 3408, 2985, 1736, 1692, 1625, 1594, 1453.

(2S)-2-[3-[2-(Acetylthio)ethyl]-3-benzylureido]propionic acid (Compound No. 7-18) [α]$_D$°+6.5° (c=0.5, methanol); IR (Film, cm$^{-1}$) 3375, 2985, 1730, 1679, 1612, 1534, 1496, 1452, 1410, 1357, 1211, 1140, 755, 630.

(2S)-2-[3-[2-(Acetylthio)ethyl]-3-(3-butenyl)ureido] propionic acid (Compound No. 7-19) IR (Film, cm$^{-1}$) 3378, 2980, 2938, 1732, 1682, 1614, 1535, 1456, 1411, 1356, 1297, 1210, 1137.

2-[3-[2-(Acetylthio)ethyl]-3-phenethylureido]acetic acid (Compound No. 7-20) mp 132.5~134.5° C. (decomp.); IR (KBr, cm$^{-1}$) 2937, 1740, 1680, 1606, 1555, 1204.

2-[3-[2-(Acetylthio)ethyl]-3-methylureido]acetic acid (Compound No. 7-21) mp 94.8~101.0° C.; IR (KBr, cm$^{-1}$) 3385, 2926, 1756, 1684, 1603, 1560, 1398, 1220, 1142, 1099, 912, 766, 694, 628.

(2S)-2-[3-[2-(Acetylthio)ethyl]-3-phenethylureido] butyric acid (Compound No. 7-22) mp 101.0~104.2° C.; [α]$_D$°−2.5° (c=1.0, methanol); IR (KBr, cm$^{-1}$) 3385, 2942, 1716, 1676, 1609, 1546, 1411, 1301, 1254, 1217, 700.

(2RS)-2-[3-[2-(Acetylthio)ethyl]-3-phenethylureido]-3-hydroxypropionic acid (Compound No. 7-23) mp 113.0~119.0° C.; IR (KBr, cm$^{-1}$) 3156, 2942, 1741, 1682, 1630, 1546, 1212, 1018.

(2S)-2-[3-[2-(Acetylthio)ethyl]-3-phenethylureido]-2-phenylacetic acid (Compound No. 7-24) [α]$_D$°+51.2° (c=1.0, methanol); IR (Film, cm$^{-1}$) 3378, 3027, 1732, 1686, 1613, 1519, 1454, 1356, 1216, 1139, 754.

(2S)-2-[3-[2-(Acetylthio)ethyl]-3-methylureido]-3-phenylpropionic acid (Compound No. 7-25) [α]$_D$°−19.6° (c=0.47, methanol); IR (Film, cm$^{-1}$) 3369, 2928, 1730, 1691, 1612, 1530, 1397, 1355, 1301, 1209, 1136, 1048, 952, 756, 701, 627.

(2S)-2-[3-[2-(Acetylthio)ethyl]-3-isoamylureido]-3-phenylpropionic acid (Compound No. 7-26) [α]$_D$°−18.9° (c=0.97, methanol); IR (Film, cm$^{-1}$) 3376, 2955, 1734, 1690, 1612, 1527, 1420, 1356, 1211, 1135.

(2S)-2-[3-[2-(Acetylthio)ethyl]-3-(2-cyclohexylethyl) ureido]-3-phenylpropionic acid (Compound No. 7-27) [α]$_D$°−33.9° (c=1.0, chloroform); IR (Film, cm$^{-1}$) 3376, 2923, 2851, 1732, 1691, 1613, 1527, 1202, 1134, 950, 755, 701, 627.

3-[3-[2-(Acetylthio)ethyl]-3-phenethylureido]propionic acid (Compound No. 7-28) mp 110.4~113.6° C.; IR (KBr, cm$^{-1}$) 3364, 2948, 1708, 1679, 1599, 1556, 1228, 952, 744, 702.

(2S)-2-[3-[(2RS)-3-(Acetylthio)-2-methylpropyl]-3-phenethylureido]-3-phenylpropionic acid (Compound No. 7-29) IR (Film, cm$^{-1}$) 3433, 2928, 1732, 1692, 1606, 1523, 1454, 1418, 1356, 1202, 1135, 955, 752, 701, 628.

(2S)-2-[3-[2-(Acetylthio)ethyl]-3-phenethylureido]-3-phenylpropionic acid (Compound No. 7-30) [α]$_D$°−17.4° (c=0.51, methanol); IR (Film, cm$^{-1}$) 3369, 3027, 2927, 1734, 1678, 1612, 1529, 1201, 751, 701.

(2S)-2-[3-[2-(Acetylthio)ethyl]-3-(2-methoxyethyl) ureido]-3-phenylpropionic acid (Compound No. 7-31) [α]$_D$°−60.3° (c=1.0, chloroform); IR (Film, cm$^{-1}$) 3370, 2936, 1732, 1682, 1633, 1538, 1455, 1409, 1357, 1205, 1115, 1066, 1008, 952, 758.

(2S)-2-[3-[2-(Acetylthio)ethyl]-3-[2-(4-pyridyl)ethyl] ureido]propionic acid (Compound No. 7-32)

(2S)-2-[3-[2-(Acetylthio)ethyl]-3-phenethylureido]-3-methylbutyric acid (Compound No. 7-33) [α]$_D$°+9.1° (c=1.0, chloroform); IR (Film, cm$^{-1}$) 3854, 3386, 2964, 1730, 1684, 1615, 1526, 1454, 1416, 1203.

(2S)-2-[3-[2-(Acetylthio)ethyl]-3-phenethylureido] valeric acid (Compound No. 7-34) [α]$_D$°−22.0° (c=1.0, chloroform); IR (Film, cm$^{-1}$) 3375, 2960, 2873, 1728, 1680, 1616, 1534, 1454, 1203, 1143, 952, 701.

(2S)-2-[3-Phenethyl-3-[2-(phenyldithio)ethyl]ureido]-3-phenylpropionic acid (Compound No. 7-35) [α]$_D$°−6.0° (c=1.0, methanol); IR (Film, cm$^{-1}$) 3434, 2925, 1728, 1603, 1524, 1199, 740, 700.

2-[3-[2-(Acetylthio)ethyl]-3-(2-cyclohexylethyl)ureido] acetic acid (Compound No. 7-36) IR (Film, cm$^{-1}$) 3386, 2923, 2851, 1732, 1692, 1614, 1538, 1417, 757.

(2S)-2-[3-[2-(Acetylthio)ethyl]-3-(2-cyclopentylethyl) ureido]propionic acid (Compound No. 7-37) IR (Film, cm$^{-1}$) 3378, 2947, 2867, 1732, 1682, 1614, 1532, 1454, 1413, 1374, 1356, 1298, 1216, 1138, 1110, 757.

(2S)-2-[3-[2-(Acetylthio)ethyl]-3-(2-cycloheptylethyl) ureido]propionic acid (Compound No. 7-38) [α]$_D$°+4.6° (c=1.0, methanol); IR (Film, cm$^{-1}$) 3379, 2922, 2853, 1729, 1685, 1602, 1534, 1457, 1413.

(2S)-2-[3-[2-(Acetylthio)ethyl]-3-[2-(1-adamantyl)ethyl] ureido]propionic acid (Compound No. 7-39) [α]$_D$°+4.6° (c=1.0, methanol); IR (Film, cm$^{-1}$) 3380, 2902, 2846, 1734, 1684, 1527, 1452, 1418, 1207.

(2S)-2-[3-[2-(Methylthio)ethyl]-3-phenethylureido]propionic acid (Compound No. 7-40) IR (Film, cm$^{-1}$) 3368, 2919, 1727, 1603, 1529, 1203.

(2S)-2-[3-[2-(Acetylthio)ethyl]-3-(2-cyclopropylethyl)ureido]propionic acid (Compound No. 7-41) [α]$_D^°$ + 7.0° (c=0.52, methanol); IR (Film, cm$^{-1}$) 3379, 2998, 1732, 1682, 1614, 1536, 1454, 1413, 1212, 1135, 757.

(2S)-2-[3-[2-(Acetylthio)ethyl]-3-(2-cyclobutylethyl)ureido]propionic acid (Compound No. 7-42) [α]$_D^°$ + 5.3° (c=0.49, methanol); IR (Film, cm$^{-1}$) 3379, 2936, 1729, 1690, 1612, 1533, 1454, 1412, 1204, 1134.

(2S)-2-[3-[3-(Acetylthio)propyl]-3-(2-cyclohexylethyl)ureido]propionic acid (Compound No. 7-43) [α]$_D^°$ − 35.8° (c=1.0, chloroform); IR (Film, cm$^{-1}$) 3418, 2923, 2852, 1731, 1693, 1614, 1524, 1454, 1415, 1207.

(2R)-2-[3-[2-(Acetylthio)ethyl]-3-(2-cyclohexylethyl)ureido]propionic acid (Compound No. 7-44) [α]$_D^°$ − 5.2° (c=1.0, methanol); IR (Film, cm$^{-1}$) 3380, 2923, 2851, 1732, 1682, 1614, 1531, 1450, 1206.

2-[3-[2-(Acetylthio)ethyl]-3-[2-(1-adamantyl)ethyl]ureido]acetic acid (Compound No. 7-45) IR (Film, cm$^{-1}$) 3390, 2902, 2846, 1732, 1689, 1640, 1538, 1211, 756.

(2S)-2-[3-[2-(Acetylthio)ethyl]-3-[2-[3,5-di(t-butyl)-4-hydroxyphenyl]ethyl]ureido]propionic acid (Compound No. 7-46) [α]$_D^°$ −11.9° (c=0.52, methanol); IR (KBr, cm$^{-1}$) 3639, 3582, 3391, 2958, 1743, 1684, 1609, 1540, 1435, 1236, 1197.

EXAMPLE 8

(2S)-4-Hydroxy-2-[3-(2-mercaptoethyl)-3-phenethylureido]butyric Acid (Compound No. 8-1)

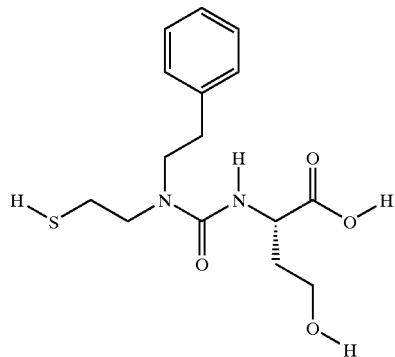

(2S)-2-[3-(2-Mercaptoethyl)-3-phenethylureido]-4-butanolide (Compound No. 1-69, 2.9 g) is dissolved in methanol (19 ml) under a nitrogen atmosphere. A 2 N aqueous lithium hydroxide solution (5.6 ml) is added thereto under ice cooling, and the mixture is stirred under ice cooling for 50 minutes and further at room temperature for 35 minutes. The reaction mixture is concentrated under reduced pressure, a 10% aqueous citric acid solution is added to the concentrate, and the whole is extracted with ethyl acetate. The organic layer is washed with water and saturated brine successively, dried over anhydrous magnesium sulfate and concentrated under reduced pressure to give 1.5 g (48%) of the titled compound (Compound No. 8-1).

The following compounds are obtained by a method similar to Example 8.

(2S)-2-[3-[2-(Methylthio)ethyl]-3-phenethylureido]-3-phenylpropionic acid (Compound No. 8-2) [α]$_D^°$ −2.8° (c=0.49, methanol); IR (Film, cm$^{-1}$) 3435, 3027, 2918, 1728, 1604, 1522, 1454, 1201, 752, 701.

(2R)-3-(Benzylthio)-2-[3-[2-(benzylthio)ethyl]-3-phenethylureido]propionic acid (Compound No. 8-3) [α]$_D^°$ −32.4° (c=0.48, methanol); IR (Film, cm$^{-1}$) 3426, 3026, 2920, 1729, 1602, 1520, 1453, 1422, 1364, 1303, 1201, 1071, 1028, 753, 701.

EXAMPLE 9

(2S)-2-[3-[2-Mercapto-1-(mercaptomethyl)ethyl]-3-phenethylureido]-3-phenylpropionic acid (Compound No. 9-1)

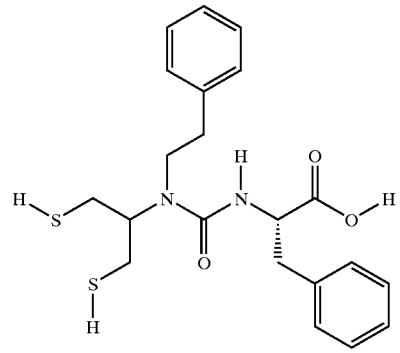

A solution of benzyl (2S)-2-[3-[2-(benzylthio)-1-[(benzylthio)methyl]ethyl]-3-phenethylureido]-3-phenylpropionate (Compound No. 1-72, 996 mg) in anhydrous tetrahydrofuran (20 ml) is added dropwise to liquid ammonia (80 ml) under a nitrogen atmosphere and dry ice-methanol cooling. Then, metallic sodium (300 mg) by portions is added thereto until coloration does not disappear, and the mixture is stirred as it is for one hour. Ammonium chloride by portions is added to the reaction mixture to decolorize it, and then a nitrogen gas is bubbled through the mixture at room temperature to evaporate ammonia. To the resulting residue is added 1 N hydrochloric acid to acidify it, and the whole is extracted with ethyl acetate. The organic layer is washed with water and saturated brine successively, dried over anhydrous magnesium sulfate and concentrated under reduced pressure to give the titled compound (Compound No. 9-1).

EXAMPLE 10

(2S)-2-[3-(1,2-Dithiolan-4-yl)-3-phenethylureido]-3-phenylpropionic Acid (Compound No. 10-1)

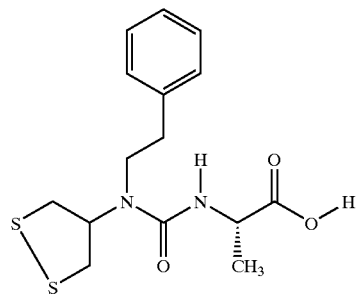

(2S)-2-[3-[2-Mercapto-1-(mercaptomethyl)ethyl]-3-phenethylureido]-3-phenylpropionic acid (Compound No. 9-1, 780 mg) is dissolved in methanol (2 ml). To the solution are added 1 N aqueous ammonia (10 ml) and a 1% aqueous ferric chloride solution (0.5 ml), and the mixture is stirred at room temperature for two hours while bubbling air through it. The reaction mixture is concentrated under reduced pressure, 2 N hydrochloric acid is added to the concentrate under ice cooling to acidify it, and the whole is extracted with ethyl acetate. The organic layer is washed with water and saturated brine successively, dried over anhydrous sodium sulfate and concentrated under reduced pressure. The resulting oily matter is purified by silica gel column chromatography to give 514 mg (66%) of the titled compound (Compound No. 10-1) as oily matter.

(Compound No. 10-1) $[\alpha]_D^\circ$ −8.4° (c=0.50, methanol); IR (Film, cm$^{-1}$) 3437, 3339, 3026, 2934, 1732, 1603, 1520, 1454, 1417, 1345, 1215, 753, 701.

EXAMPLE 11

(2S)-2-[3-(2-Mercaptoethyl)-3-phenethylureido]-3-phenylpropionic Acid (Compound No. 11-1)

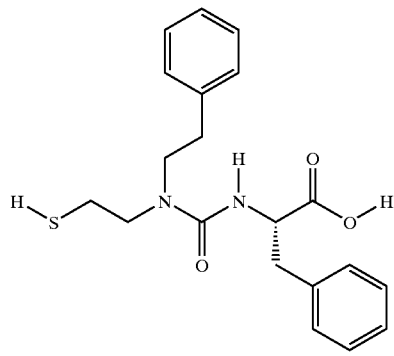

(2S)-2-[3-[2-(Acetylthio)ethyl]-3-phenethylureido]-3-phenylpropionic acid (Compound No. 7-30, 646 mg) is dissolved in 28% aqueous ammonia (15 ml) under a nitrogen atmosphere, and the solution is stirred at room temperature for one hour. To the reaction mixture are added water and ethyl acetate, and the aqueous layer is separated from the organic layer. To the aqueous layer is added 6 N hydrochloric acid under ice cooling to acidify it, and the whole is extracted with ethyl acetate. The organic layer is washed with water and saturated brine successively, dried over anhydrous sodium sulfate and concentrated under reduced pressure. The resulting oily matter is purified by silica gel column chromatography to give 415 mg (81%) of the titled compound (Compound No. 11-1).

(Compound No. 11-1) $[\alpha]_D^\circ$ −8.6° (c=0.15, methanol); IR (Film, cm$^{-1}$) 3368, 3027, 2933, 1727, 1604, 1526, 1203, 752, 701.

The following compound is obtained by a method similar to Example 11.

(2S, 2'S)-2,2'-[3,3'-Diphenethyl-3,3'-(2,2'-dithiodiethyl) diureido]-3,3'-diphenyldi(propionic acid) (Compound No. 11-2) $[\alpha]_D^\circ$ −10.0° (c=0.43, methanol); IR (Film, cm$^{-1}$) 3372, 3026, 2926, 1726, 1604, 1524, 1202, 752, 701.

EXAMPLE 12

(2S)-2-[3-[2-(Benzyloxycarbonylthio)ethyl]-3-phenethylureido]-3-phenylpropionic acid (Compound No. 12-1)

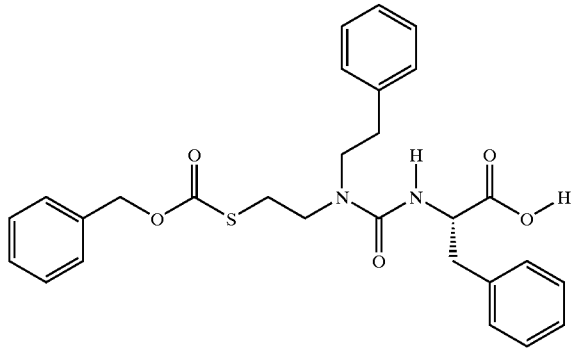

(2S)-2-[3-(2-Mercaptoethyl)-3-phenethylureido]-3-phenylpropionic acid (Compound No. 11-1, 108 mg) is dissolved in anhydrous methylene chloride (1.5 ml) under a nitrogen atmosphere, and the solution is stirred. To the solution are added N,N-diisopropylethylamine (0.07 ml) and benzyloxycarbonyl chloride (0.05 ml) successively under ice cooling, and the mixture is stirred at room temperature overnight. The reaction mixture is concentrated under reduced pressure, water is added to the residue, and the whole is extracted with ethyl acetate. The organic layer is washed with a 10% aqueous citric acid solution, water and saturated brine successively, dried over anhydrous sodium sulfate and concentrated under reduced pressure. The resulting oily matter is purified by silica gel column chromatography to give 102 mg (69%) of the titled compound (Compound No. 12-1).

(Compound No. 12-1) $[\alpha]_D^\circ$ −14.9° (c=0.34, methanol); IR (Film, cm$^{-1}$) 3381, 3028, 1698, 1614, 1530, 1144, 751, 699.

The following compound is obtained by a method similar to Example 12.

(2S)-2-[3-[2-(t-Butoxycarbonylthio)ethyl]-3-phenethylureido]-3-phenylpropionic acid (Compound No. 12-2)

EXAMPLE 13

1-[(2S)-2-[3-[2-(Acetylthio)ethyl]-3-(2-cyclohexylethyl)ureido]propionyl]-4-methylpiperazine (Compound No. 13-1)

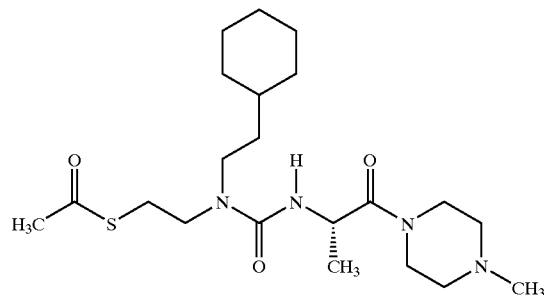

In anhydrous methylene chloride (5 ml) are dissolved (2S)-2-[3-[2-(acetylthio)ethyl]-3-(2-cyclohexylethyl)

ureido]propionic acid (Compound No. 7-1, 826 mg), N-methylpiperazine (0.27 ml) and 1-hydroxybenzotriazole (357 mg) under a nitrogen atmosphere. To the solution are added N-methylmorpholine (0.29 ml) and 1-ethyl-3-(3-dimethylaminopropyl)carbodiimide hydrochloride (506 mg) successively under ice cooling, and the mixture is stirred at room temperature overnight. The reaction mixture is concentrated under reduced pressure, a 5% aqueous sodium hydiogencarbonate solution (30 ml) is added to the resulting oily matter, and the whole is extracted with ethyl acetate. The organic layer is washed with water and saturated brine successively, dried over anhydrous magnesium sulfate and concentrated under reduced pressure. The resulting oily matter is purified by silica gel column chromatography to give 801 mg (78%) of the titled compound (Compound No. 13-1).

(Compound No. 13-1). $[\alpha]_D^{\circ}$ +25.2° (c=0.99, chloroform); IR (Film, cm$^{-1}$) 3378, 2923, 2850, 1691, 1633, 1519, 1448, 1292, 1215, 1140, 754.

The following compounds are obtained by a method similar to Example 13.

1-[(2S)-2-[3-[2-(Acetylthio)ethyl]-3-phenethylureido] propionyl]-4-methylpiperazine (Compound No. 13-2) $[\alpha]_D^{\circ}$ +11.9° (c=0.50, methanol); IR (Film, cm$^{-1}$) 3377, 2976, 2938, 2794, 1688, 1636, 1530, 1448, 1356, 1292, 1249, 1216, 1172, 1141, 1032, 1002, 952, 752, 702, 628.

1-[(2R)-2-[3-[2-(Acetylthio)ethyl]-3-phenethylureido] propionyl]-4-methylpiperazine (Compound No. 13-3), enantiomer of Compound No. 13-2 $[\alpha]_D^{\circ}$ −11.4° (c=1.0, methanol); IR (Film, cm$^{-1}$) 3376, 2938, 1688, 1634, 1529, 1449, 1292, 1215, 1141.

1-[(2S)-2-[3-[2-(Acetylthio)ethyl]-3-(4-fluorophenethyl) ureido]propionyl]-4-methylpiperazine (Compound No. 13-4) $[\alpha]_D^{\circ}$ +10.4° (c=1.0, methanol); IR (Film, cm$^{-1}$) 2939, 1687, 1632, 1510, 1448, 1292, 1220, 1142, 1002, 754.

1-[(2S)-2-[3-[2-(Acetylthio)ethyl]-3-(4-chlorophenethyl) ureido]propionyl]-4-methylpiperazine (Compound No. 13-5) $[\alpha]_D^{\circ}$ +10.7° (c=0.53, methanol); IR (Film, cm$^{-1}$) 3369, 2938, 2794, 1688, 1635, 1532, 1492, 1448, 1292, 1216, 1141, 750.

1-[(2S)-2-[3-[2-(Acetylthio)ethyl]-3-(4-nitrophenethyl) ureido]propionyl]-4-methylpiperazine (Compound No. 13-6) $[\alpha]_D^{\circ}$ +13.2° (c=0.55, methanol); IR (Film, cm$^{-1}$) 3370, 2938, 2795, 1688, 1633, 1519, 1345, 1291, 1216, 1141, 750.

1-[(2S)-2-[3-[2-(Acetylthio)ethyl]-3-(4-methoxyphenethyl)ureido]propionyl]-4-methylpiperazine (Compound No. 13-7) $[\alpha]_D^{\circ}$ +8.8° (c=0.99, methanol); IR (Film, cm$^{-1}$) 3378, 2937, 2794, 1688, 1632, 1513, 1463, 1292, 1247, 1215, 1141, 1002.

1-[(2S)-2-[3-[2-(Acetylthio)ethyl]-3-(4-methylphenethyl) ureido]propionyl]-4-methylpiperazine (Compound No. 13-8) $[\alpha]_D^{\circ}$ +24.3° (c=1.0, chloroform); IR (Film, cm$^{-1}$) 3370, 2937, 1689, 1632, 1514, 1447, 1291, 1214, 1141, 1102, 627.

1-[(2S)-2-[3-[2-(Acetylthio)ethyl]-3-(4-phenylphenethyl) ureido]propionyl]-4-methylpiperazine (Compound No. 13-9) $[\alpha]_D^{\circ}$ +10.0° (c=0.55, methanol); IR (Film, cm$^{-1}$) 3378, 2937, 2794, 1687, 1633, 1518, 1447, 1141, 1002, 756.

1-[(2S)-2-[3-[2-(Acetylthio)ethyl]-3-[2-(2-pyridyl)ethyl] ureido]propionyl]-4-methylpiperazine (Compound No. 13-10) $[\alpha]_D^{\circ}$ +11.0° (c=0.52, methanol); IR (Film, cm$^{-1}$) 3377, 2936, 2794, 1689, 1637, 1441, 1292, 1141, 1001.

1-[(2S)-2-[3-[2-(Acetylthio)ethyl]-3-[2-(2-naphthyl) ethyl]ureido]propionyl-]4-methylpiperazine (Compound No. 13-11) $[\alpha]_D^{\circ}$ +8.7° (c=0.96, methanol); IR (Film, cm$^{-1}$) 3376, 687, 1633, 1508, 1446, 1141, 751.

1-[(2S)-2-[3-[2-(Acetylthio)ethyl]-3-(3-phenylpropyl) ureido]propionyl]-4-methylpiperazine (Compound No. 13-12) $[\alpha]_D^{\circ}$ +15.5° (c=0.50, methanol); IR (Film, cm$^{-1}$) 3368, 2937, 2793, 1689, 1632, 1530, 1450, 1291, 1141, 751.

1-[(2S)-2-[3-[2-(Acetylthio)ethyl]-3-[3-(4-fluorophenyl) propyl]ureido]propionyl]-4-methylpiperazine (Compound No. 13-13) $[\alpha]_D^{\circ}$ +27.3° (c=1.0, chloroform); IR (Film, cm$^{-1}$) 3369, 2938, 1689, 1636, 1510, 1448, 1292, 1219, 1141, 755.

1-[(2S)-2-[3-[2-(Acetylthio)ethyl]-3-[3-(4-chlorophenyl) propyl]ureido]propionyl]-4-methylpiperazine (Compound No. 13-14) $[\alpha]_D^{\circ}$ +26.2° (c=0.95, chloroform); IR (Film, cm$^{-1}$) 3369, 2937, 1689, 1633, 1530, 1492, 1292, 1214, 1141, 754, 628.

1-[(2S)-2-[3-[2-(Acetylthio)ethyl]-3-(3-phenyl-2-propenyl)ureido]propionyl]-4-methylpiperazine (Compound No. 13-15) $[\alpha]_D^{\circ}$ +30.0° (c=1.0, chloroform); IR (Film, cm$^{-1}$) 3374, 2937, 2794, 1689, 1632, 1529, 1448, 1292, 1141, 752.

1-[(2S)-2-[3-[2-(Acetylthio)ethyl]-3-(2-phenoxyethyl) ureido]propionyl-4-methylpiperazine (Compound No. 13-16) $[\alpha]_D^{\circ}$ +14.6° (c=1.0, methanol); IR (Film, cm$^{-1}$) 3369, 2794, 1688, 1638, 1497, 1462, 1242.

1-[(2S)-2-[3-[2-(Acetylthio)ethyl]-3-phenylureido] propionyl]-4-methylpiperazine (Compound No. 13-17) $[\alpha]_D^{\circ}$ +35.1° (c=1.0, methanol); IR (Film, cm$^{-1}$) 3400, 2976, 2938, 1693, 1640, 1596, 1494, 1447.

1-[(2S)-2-[3-[2-(Acetylthio)ethyl]-3-benzylureido] propionyl]-4-methylpiperazine (Compound No. 13-18) $[\alpha]_D^{\circ}$ +12.1° (c=0.5, methanol); IR (Film, cm$^{-1}$) 3376, 2937, 1687, 1530, 1451, 1291, 1217, 1141, 1002, 753.

1-[(2S)-2-[3-[2-(Acetylthio)ethyl]-3-(3-butenyl)ureido] propionyl]-4-methylpiperazine (Compound No. 13-19) $[\alpha]_D^{\circ}$ +15.2° (c=1.0, methanol); IR (Film, cm$^{-1}$) 3350, 2976, 2937, 2793, 1690, 1637, 1530, 1447, 1292, 1218, 1140.

1-[2-[3-[2-(Acetylthio)ethyl]-3-phenethylureido]acetyl]-4-methylpiperazine (Compound No. 13-20) IR (Film, cm$^{-1}$) 2937, 1688, 1640, 1507, 1442, 1291, 1141.

1-[2-[3-[2-(Acetylthio)ethyl]-3-methylureido]acetyl]-4-methylpiperazine (Compound No. 13-21) mp 74.6~77.0° C.; IR (KBr, cm$^{-1}$) 3361, 2937, 2794, 1688, 1653, 1633, 1547, 1459, 1348, 1289, 1228, 1145, 1054, 1042, 998, 956, 629, 574.

1-[(2S)-2-[3-[2-(Acetylthio)ethyl]-3-phenethylureido] butyryl]-4-methylpiperazine (Compound No. 13-22) $[\alpha]_D^{\circ}$ +10.1° (c=1.0, methanol); IR (Film, cm$^{-1}$) 3368, 2967, 2936, 1689, 1633, 1528, 1453, 1293, 1141.

1-[(2RS)-2-[3-[2-(Acetylthio)ethyl]-3-phenethylureido]-3-hydroxypropionyl]-4-methylpiperazine (Compound No. 13-23) IR (Film, cm$^{-1}$) 3376, 2939, 1689, 1628, 1520, 1454, 1292, 1142, 1001.

1-[(2S)-2-[3-[2-(Acetylthio)ethyl]-3-phenethylureido]-2-phenylacetyl]-4-methylpiperazine (Compound No. 13-24) $[\alpha]_D^{\circ}$ +36.4° (c=1.0 methanol); IR (Film, cm$^{-1}$) 3390, 2939, 1689, 1636, 1497, 1445, 1293, 1142, 1001, 753, 701.

1-[(2S)-2-[3-[2-(Acetylthio)ethyl]-3-methylureido]-3-phenylpropionyl]-4-methylpiperazine (Compound No.

13-25) $[\alpha]_D^\circ$ +29.7° (c=0.50, chloroform); IR (Film, cm$^{-1}$) 3329, 2938, 2797, 1691, 1632, 1531, 1454, 1386, 1355, 1292, 1250, 1217, 1141, 1033, 1002, 752, 701, 626.

1-[(2S)-2-[3-[2-(Acetylthio)ethyl]-3-isoamylureido]-3-phenylpropionyl]-4-methylpiperazine (Compound No. 13-26) $[\alpha]_D^\circ$ +27.5° (c=1.0, methanol); IR (Film, cm$^{-1}$) 3345, 2951, 1690, 1630, 1528, 1449, 1357, 1292, 1217, 1140.

1-[(2S)-2-[3-[2-(Acetylthio)ethyl]-3-(2-cyclohexylethyl) ureido]-3-phenylpropionyl]-4-methylpiperazine (Compound No. 13-27) $[\alpha]_D^\circ$ +30.3° (c=1.0, chloroform); IR (Film, cm$^{-1}$) 3350, 2922, 1691, 1632, 1526, 1448, 1292, 1249, 1215, 753, 700, 627.

1-[3-[3-[2-(Acetylthio)ethyl]-3-phenethylureido] propionyl]-4-methylpiperazine (Compound No. 13-28) mp 81.3~84.8° C.; IR (KBr, cm$^{-1}$) 3312, 2936, 2789, 1694, 1626, 1532, 1477, 1292, 1140, 1003, 700, 629.

1-[(2S)-2-[3-[(2RS)-3-Acetylthio-2-methylpropyl]-3-phenethylureido]-3-phenylpropionyl]-4-methylpiperazine (Compound No. 13-29) IR (Film, cm$^{-1}$) 3360, 2934, 2794, 1691, 1631, 1497, 1454, 1291, 1141, 1002, 751, 700, 628.

1-[(2S)-2-[3-[2-(Acetylthio)ethyl]-3-phenethylureido]-3-phenylpropionyl]-4-ethylpiperazine (Compound No. 13-30) $[\alpha]_D^\circ$ +21.1° (c=1.0, methanol); IR (Film, cm$^{-1}$) 3368, 2970, 2930, 1689, 1632, 1526, 1454, 1353, 1285, 1138.

1-[(2S)-2-[3-[2-(Acetylthio)ethyl]-3-phenethylureido-3-phenylpropionyl]-4-(2-hydroxyethyl)piperazine (Compound No. 13-31) $[\alpha]_D^\circ$ +18.4° (c=1.0, methanol); IR (Film, cm$^{-1}$) 3374, 2936, 1688, 1627, 1526, 1454, 1354, 1217, 1138.

1-[(2S)-2-[3-[2-(Acetylthio)ethyl]-3-phenethylureido]-3-phenylpropionyl]-4-(carboxymethyl)piperazine (Compound No. 13-32) mp 230° C. (decomp.); IR (KBr, cm$^{-1}$) 3373, 1636, 1522, 1123.

1-[(2S)-2-[3-[2-(Acetylthio)ethyl]-3-phenethylureido]-3-phenylpropionyl]-4-methylhomopiperazine (Compound No. 13-33) $[\alpha]_D^\circ$ +17.7° (c=1.0, methanol); IR (Film, cm$^{-1}$) 3363, 2940, 1688, 1628, 1527, 1496, 1454, 1357, 1288, 1202, 1134.

(2S)-2-[3-[2-(Acetylthio)ethyl]-3-phenethylureido]-N-(4-pyridyl)propionamide (Compound No. 13-34) $[\alpha]_D^\circ$ -27.2° (c=1.0, chloroform); IR (Film, cm$^{-1}$) 3266, 3184, 3026, 1686, 1628, 1595, 1530, 1415, 1290, 1194, 1140, 754.

(2S)-2-[3-[2-(Acetylthio)ethyl]-3-phenethylureido]-N-(3-pyridyl)propionamide (Compound No. 13-35) $[\alpha]_D^\circ$ -34.0° (c=1.0, chloroform); IR (Film, cm$^{-1}$) 3263, 3026, 1682, 1621, 1538, 1483, 1424, 1286, 1200, 1137, 752.

1-[(2S)-2-[3-[2-(Acetylthio)ethyl]-3-(2-methoxyethyl) ureido]propionyl]-4-methylpiperazine (Compound No. 13-36) $[\alpha]_D^\circ$ +30.0° (c=0.33, chloroform); IR (Film, cm$^{-1}$) 3368, 2978, 2936, 1690, 1636, 1530, 1463, 1141, 114, 1002, 628.

1-[(2S)-2-[3-[2-(Acetylthio)ethyl]-3-[2-(4-pyridyl)ethyl] ureido]propionyl]-4-methylpiperazine (Compound No. 13-37) $[\alpha]_D^\circ$ +8.1° (c=1.0, methanol); IR (Film, cm$^{-1}$) 2981, 1687, 1636, 1603, 1448, 1142, 754.

1-[(2S)-2-[3-[2-(Acetylthio)ethyl]-3-phenethylureido]-3-methylbutyryl]-4-methylpiperazine (Compound No. 13-38) $[\alpha]_D^\circ$ +31.4° (c=1.1, chloroform); IR (Film, cm$^{-1}$) 3387, 2937, 2794, 1689, 1633, 1519.

1-[(2S)-2-[3-[2-(Acetylthio)ethyl]-3-phenethylureido] valeryl]-4-methylpiperazine (Compound No. 13-39) $[\alpha]_D^\circ$ +22.4° (c=1.0, chloroform); IR (Film, cm$^{-1}$) 3370, 2938, 1688, 1632, 1531, 1454, 1291, 1217, 1141, 753.

1-[(2S)-2-[3-[2-(Benzyloxycarbonylthio)ethyl]-3-phenethylureido]-3-phenylpropionyl]-4-methylpiperazine (Compound No. 13-40) $[\alpha]_D^\circ$ +8.7° (c=0.51, methanol); IR (Film, cm$^{-1}$) 3382, 2937, 1705, 1633, 1454, 1142, 751, 700.

1-[(2S)-2-[3-[2-(t-Butoxycarbonylthio)ethyl]-3-phenethylureido]-3-phenylpropionyl]-4-methylpiperazine (Compound No. 13-41) IR (Film, cm$^{-1}$) 3367, 2979, 1698, 1632, 1528, 1453, 1204, 1130, 752, 701.

1-[(2S)-2-[3-Phenethyl-3-[2-(phenyldithio)ethyl]ureido]-3-phenylpropionyl]-4-methylpiperazine (Compound No. 13-42) $[\alpha]_D^\circ$ +16.4° (c=0.96, methanol); IR (Film, cm$^{-1}$) 3340, 2936, 1627, 1530, 1454, 746, 700.

1-[(2S)-4-Hydroxy-2-[3-(2-mercaptoethyl)-3-phenethylureido]butyryl]-4-methylpiperazine (Compound No. 13-43)

1-Methyl-4-[(2S)-2-[3-[2-(methylthio)ethyl]-3-phenethylureido]-3-phenylpropionyl]piperazine (Compound No. 13-44) $[\alpha]_D^\circ$ +15.1° (c=0.52, methanol); IR (Film, cm$^{-1}$) 3346, 2918, 1628, 1497, 1452, 1291, 1214, 1144, 1002, 750, 700.

1-[(2R)-3-(Benzylthio)-2-[3-[2-(benzylthio)ethyl]-3-phenethylureido]propionyl]-4-methylpiperazine (Compound No. 13-45) $[\alpha]_D^\circ$ -19.9° (c=0.48, methanol); IR (Film, cm$^{-1}$) 3349, 3026, 2937, 2794, 1632, 1495, 1452, 1365, 1293, 1206, 1143, 1072, 1029, 1001, 753, 701.

1-[(2S)-2-[3-(1,2-Dithiolan-4-yl)-3-phenethylureido]-3-phenylpropionyl]-4-methylpiperazine (Compound No. 13-46) $[\alpha]_D^\circ$ +16.2° (c=0.50, chloroform); IR (Film, cm$^{-1}$) 3344, 2938, 2796, 1628, 1497, 1454, 1291, 1248, 1217, 1143, 1001, 752, 701.

1,1'-Dimethyl-4,4'-[(2S, 2'S)-2,2'-[3,3'-diphenethyl-3,3'-(2,2'-dithiodiethyl)diureido]-3,3'-diphenyldipropionyl] dipiperazine (Compound No. 13-47) $[\alpha]_D^\circ$ +3.0° (c=0.86, methanol); IR (Film, cm$^{-1}$) 3341, 3026, 1628, 1514, 1452, 750, 700.

1-[(2S)-2-[3-[2-(Acetylthio)ethyl]-3-phenethylureido]-3-phenylpropionyl]-4-(trifluoroacetyl)piperazine (Compound No. 13-48) $[\alpha]_D^\circ$ +33.1° (c=0.52, methanol); IR (Film, cm$^{-1}$) 3370, 3026, 2928, 1694, 1644, 1524, 1454, 1366, 1284, 1243, 1200, 1142, 1010, 952, 753, 701.

1-[(2S)-2-[3-[2-(Acetylthio)ethyl]-3-(2-cyclohexylethyl) ureido]propionyl]piperidine (Compound No. 13-49) $[\alpha]_D^\circ$ +29.3° (c=0.47, chloroform); IR (Film, cm$^{-1}$) 3379, 2923, 2852, 1691, 1632, 1530, 1447, 1214, 1135, 752.

4-[(2S)-2-[3-[2-(Acetylthio)ethyl]-3-(2-cyclohexylethyl) ureido]propionyl]morpholine (Compound No. 13-50) $[\alpha]_D^\circ$ +26.1° (c=0.49, chloroform); IR (Film, cm$^{-1}$) 3370, 2922, 2851, 1690, 1635, 1526, 1447, 1270, 1116, 1030, 755.

(2S)-2-[3-[2-(Acetylthio)ethyl]-3-(2-cyclohexylethyl) ureido-N-[2-(dimethylamino)ethyl]-N-methylpropionamide (Compound No. 13-51) $[\alpha]_D^\circ$ +6.2° (c=1.0, methanol); IR (Film, cm$^{-1}$) 3341, 2923, 2851, 1692, 1634, 1490, 1448, 1418, 1355, 1295, 1223, 1184, 1135, 1043.

(2S)-2-[3-[2-(Acetylthio)ethyl]-3-(2-cyclohexylethyl) ureido]-N-[2-(dimethylamino)ethyl]propionamide (Compound No. 13-52) $[\alpha]_D^\circ$ +12.7° (c=0.99, methanol); IR (Film, cm$^{-1}$) 3296, 3089, 2923, 2851, 2818, 2768, 1691, 1662, 1626, 1535, 1448, 1409, 1355, 1225, 1135.

(2S)-2-[3-[2-(Acetylthio)ethyl]-3-(2-cyclohexylethyl)ureido]-N,N-dimethylpropionamide (Compound No. 13-53) $[\alpha]_D^\circ$ +10.1° (c=1.0, methanol); IR (Film, cm$^{-1}$) 3350, 2924, 2851, 1691, 1642, 1503, 1448, 1419, 1356, 1297, 1227, 1184, 1135.

1-[(2S)-2-[3-[2-(Acetylthio)ethyl]-3-(2-cyclohexylethyl)ureido]propionyl]-4-methylhomopiperazine (Compound No. 13-54) $[\alpha]_D^\circ$ +21.9° (c=1.1, chloroform); IR (Film, cm$^{-1}$) 3350, 2922, 2849, 1691, 1633, 1527, 1449, 1203, 1134, 951, 755.

1-[(2S)-2-[3-[2-(Acetylthio)ethyl]-3-(2-cyclohexylethyl)ureido]propionyl]-3-pyrroline (Compound No. 13-55) $[\alpha]_D^\circ$ +19.7° (c=1.0, chloroform); IR (Film, cm$^{-1}$) 3338, 2980, 2922, 2851, 1690, 1644, 1621, 1530, 1460, 1357, 1294, 1221, 1136, 950, 754.

1-[2-[3-[2-(Acetylthio)ethyl]-3-(2-cyclohexylethyl)ureido]acetyl]-4-methylpiperazine (Compound No. 13-56) IR (Film, cm$^{-1}$) 3400, 2922, 2850, 1691, 1641, 1508, 1444, 1292, 1142.

1-[(2S)-2-[3-[2-(Acetylthio)ethyl]-3-(2-cyclopentylethyl)ureido]propionyl]-4-methylpiperazine (Compound No. 13-57) $[\alpha]_D^\circ$ +13.5° (c=1.0, methanol); IR (Film, cm$^{-1}$) 3377, 2942, 2865, 2794, 1690, 1632, 1510, 1448, 1292, 1216, 1141.

1-[(2S)-2-[3-[2-(Acetylthio)ethyl]-3-(2-cycloheptylethyl)ureido]propionyl]-4-methylpiperazine (Compound No. 13-58) $[\alpha]_D^\circ$ +12.2° (c=0.97, methanol); IR (Film, cm$^{-1}$) 3378, 2923, 2852, 1692, 1632, 1446, 1292.

1-[(2S)-2-[3-[2-(Acetylthio)ethyl]-3-[2-(1-adamantyl)ethyl]ureido]propionyl]-4-methylpiperazine (Compound No. 13-59) $[\alpha]_D^\circ$ +14.0° (c=1.0, methanol); IR (Film, cm$^{-1}$) 3380, 2902, 2845, 1690, 1636, 1507, 1448, 1292.

1-[(2S)-2-[3-[2-(Acetylthio)ethyl]-3-(2-cyclopropylethyl)ureido]propionyl]-4-methylpiperazine (Compound No. 13-60) $[\alpha]_D^\circ$ +9.4° (c=1.5, methanol); IR (Film, cm$^{-1}$) 3369, 2997, 2938, 1691, 1632, 1510, 1447, 1141, 1002, 753.

1-[(2S)-2-[3-[2-(Acetylthio)ethyl]-3-(2-cyclobutylethyl)ureido]propionyl]-4-methylpiperazine (Compound No. 13-61) $[\alpha]_D^\circ$ +13.9° (c=0.53, methanol); IR (Film, cm$^{-1}$) 3368, 2938, 1691, 1632, 1530, 1447, 1140, 754.

1-[(2S)-2-[3-[2-(Acetylthio)ethyl]-3-(2-cyclohexylethyl)ureido]propionyl]-4-cyclohexylpiperazine (Compound No. 13-62) $[\alpha]_D^\circ$ +13.6° (c=1.0, methanol); IR (Film, cm$^{-1}$) 3382, 2925, 2852, 1693, 1632, 1510, 1448, 1298, 1276, 1238, 1216, 1138.

(2S)-2-[3-[2-(Acetylthio)ethyl]-3-(2-cyclohexylethyl)ureido]-N-(2-pyridylmethyl)propionamide (Compound No. 13-63) $[\alpha]_D^\circ$ +16.0° (c=1.0, methanol); IR (Film, cm$^{-1}$) 3293, 2923, 1682, 1632, 1594, 1531, 1449, 754.

(2S)-2-[3-[2-(Acetylthio)ethyl]-3-(2-cyclohexylethyl)ureido]-N-(4-pyridylmethyl)propionamide (Compound No. 13-64) $[\alpha]_D^\circ$ +17.1° (c=1.0, methanol); IR (Film, cm$^{-1}$) 3286, 2923, 2851, 1682, 1632, 1531, 1449, 1416.

2-[3-[2-(Acetylthio)ethyl]-3-(2-cyclohexylethyl)ureido]-N-(2-hydroxyethyl)acetamide (Compound No. 13-65) IR (Film, cm$^{-1}$) 3334, 2923, 2851, 1633, 1538, 755.

1-[(2S)-2-[3-[3-(Acetylthio)propyl]-3-(2-cyclohexylethyl)ureido]propionyl]-4-methylpiperazine (Compound No. 13-66) $[\alpha]_D^\circ$ +5.9° (c=1.0, methanol); IR (Film, cm$^{-1}$) 3354, 2922, 2850, 2793, 1693, 1632, 1507, 1448, 1292, 1214, 1140.

1-[(2R)-2-[3-[2-(Acetylthio)ethyl]-3-(2-cyclohexylethyl)ureido]propionyl]-4-methylpiperazine (Compound No. 13-67) $[\alpha]_D^\circ$ −11.9° (c=1.0, methanol); IR (Film, cm$^{-1}$) 3380, 2923, 2851, 1692, 1633, 1447, 1292, 1140.

1-[2-[3-[2-(Acetylthio)ethyl]-3-[2-(1-adamantyl)ethyl]ureido]acetyl]-4-methylpiperazine (Compound No. 13-68) IR (Film, cm$^{-1}$) 3400, 2902, 2846, 2795, 1692, 1640, 1510, 1443, 754.

1-[(2S)-2-[3-[2-(Acetylthio)ethyl]-3-[2-[3,5-di(t-butyl)-4-hydroxyphenyl]ethyl]ureido]propionyl]-4-methylpiperazine (Compound No. 13-69)

EXAMPLE 14

1-[(2S)-2-[3-[4-(Acetoxy)phenethyl]-3-[2-(acetylthio)ethyl]ureido]propionyl]-4-methylpiperazine (Compound No. 14-1)

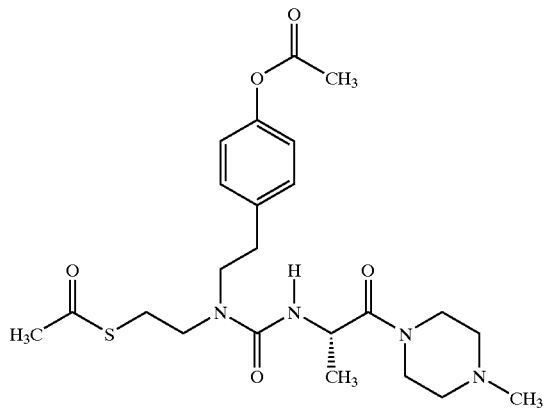

A solution of benzyl (2S)-2-[3-[4-(benzyloxy)phenethyl]-3-[2-(benzylthio)ethyl]ureido]propionate (Compound No. 1-55, 843 mg) in anhydrous tetrahydrofuran (10 ml) is added dropwise to liquid ammonia (40 ml) under a nitrogen atmosphere and dry ice-methanol cooling. Then, metallic sodium (300 mg) by portions is added to the mixture until coloration does not disappear, and the mixture is stirred as it is for one hour. Ammonium chloride is added to the reaction mixture to decolorize it, and then a nitrogen gas is bubbled through the mixture at room temperature to evaporate ammonia. To the resulting residue is added 1 N hydrochloric acid (50 ml), and the whole is extracted with ethyl acetate. The organic layer is washed with saturated brine, dried over anhydrous magnesium sulfate and concentrated under reduced pressure.

The resulting oily matter is dissolved in anhydrous methylene chloride (7.2 ml) under a nitrogen atmosphere, and N-methylpiperazine (0.32 ml) and 1-hydroxybenzotriazole (192 mg) are added to the solution. 1-Ethyl-3-(3-dimethylaminopropyl)carbodiimide hydrochloride (360 mg) is added to the mixture under ice cooling, and the mixture is stirred at room temperature overnight while shading. The reaction mixture is concentrated under reduced pressure, a 10% aqueous sodium hydrogencarbonate solution (50 ml) is added to the resulting oily matter, and the whole is extracted with ethyl acetate. The organic layer is washed with saturated brine, dried over anhydrous magnesium sulfate and concentrated under reduced pressure.

The resulting oily matter is dissolved in acetone (10 ml)-water (10 ml) under a nitrogen atmosphere, tri-n- butylphosphine (0.25 ml) is added to the solution, and the mixture is stirred for 15 minutes. To the mixture are added triethylamine (0.61 ml) and acetic anhydride (0.41 ml) successively under ice cooling, and the mixture is stirred at room temperature for 30 minutes. Ethyl acetate is added to the reaction mixture. The organic layer is washed with a 10% aqueous sodium hydrogencarbonate and saturated brine successively, dried over anhydrous sodium sulfate and concentrated under reduced pressure. The resulting oily matter is purified by silica gel column chromatography to give 324 mg (47%) of the titled compound (Compound No. 14-1).

(Compound No. 14-1); $[\alpha]_D°$ +21.8° (c=0.98, chloroform); IR (Film, cm$^{-1}$) 3375, 2937, 2794, 1762, 1688, 1636, 1508, 1447, 1368, 1292, 1195, 1141.

The following compounds are obtained by a method similar to

EXAMPLE 14

1-[(2S)-2-[3-[2-(Acetylthio)-2-methylpropyl]-3-phenethylureido]propionyl]-4-methylpiperazine (Compound No. 14-2)

$[\alpha]_D^{20}$+11.5° (c=0.53, methanol); IR (Film, cm$^{-1}$) 3420, 2970, 2937, 2793, 1680, 1636, 1498, 1448, 1364, 1292, 1202, 1142, 1112, 1002, 751, 702.

1-[(2S)-2-[3-[(2RS)-2-(Acetylthio)-3-methylbutyl]-3-phenethylureido]propionyl-4-methylpiperazine (Compound No. 14-3)

IR (Film, cm$^{-1}$) 3382, 2960, 2794, 1687, 1633, 1505, 1462, 1366, 1292, 1230, 1173, 1142.

1-[(2RS)-3-(Acetylthio)-2-[3-[2-(acetylthio)ethyl]-3-phenethylureido]-3-methylbutyryl]-4-methylpiperazine (Compound No. 14-4)

EXAMPLE 15

(2S)-2-[3-(2-Hydroxyethyl)-3-phenethylureido]-4-methylvaleric Acid (Compound No. 15-1)

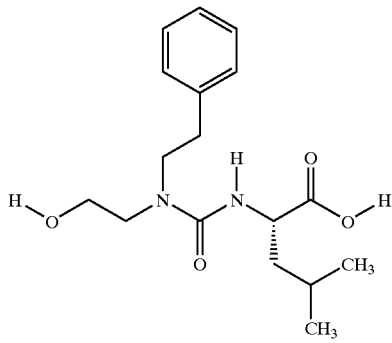

Ethyl (2S)-2-[3-(2-hydroxyethyl)-3-phenethylureido]-4-methylvalerate (Compound No. 1-31, 1.00 g) is dissolved in a mixed solvent of tetrahydrofuran (3.5 ml)-ethanol (2.8 ml). A 2 N aqueous lithium hydroxide solution (1.7 ml) is added thereto under ice cooling, and the mixture is stirred under ice cooling for 25 minutes and further at room temperature for one hour. A 5% aqueous citric acid solution is added to the reaction mixture, and the whole is extracted with ethyl acetate. The organic layer is washed with water and saturated brine successively, dried over anhydrous magnesium sulfate and concentrated under reduced pressure to give 1.02 g (quantitatively) of the titled compound (Compound No. 15-1).

(Compound No. 15-1)

$[\alpha]_D^{20}$-4.7° (c=0.95, methanol); IR (Film, cm$^{-1}$) 3340, 2957, 1724, 1620, 1536, 1217.

The following compounds are obtained by a method similar to Example 15.

(2S)-2-[3-(3-Hydroxypropyl)-3-phenethylureido]-3-phenylpropionic acid (Compound No. 15-2)

$[\alpha]_D^{20}$-12.4° (c=0.50, methanol); IR (Film, cm$^{-1}$) 3340, 3027, 2933, 1728, 1622, 2526, 1496, 1454, 1418, 1357, 1216, 1079, 1054, 1031, 946, 753, 701.

(2S)-2-[3-[(2RS)-2-Hydroxypropyl]-3-phenethylureido]-3-phenylpropionic acid (Compound No. 15-3)

IR (Film, cm$^{-1}$) 3362, 3027, 2970, 1728, 1622, 1526, 1497, 1455, 1416, 1375, 1217, 1079, 1057, 753, 701.

(2RS)-2-[3-(2-Hydroxyethyl)-3-phenethylureido]-4-(methylthio)butyric acid (Compound No. 15-4)

IR (Film, cm$^{-1}$) 3374, 2918, 1732, 1614, 1532, 1219, 1047, 752, 701.

(2S)-2-[3-(2-Hydroxyethyl)-3-phenethylureido]-3-(4-nitrophenyl)propionic acid (Compound No. 15-5)

$[\alpha]_D^{20}$34.4° (c=0.52, chloroform); IR (Film, cm$^{-1}$) 3384, 2934, 1752, 1605, 1519, 1454, 1346, 1047.

(2S)-3-(4-Chlorophenyl)-2-[3-(2-hydroxyethyl)-3-phenethylureido]propionic acid (Compound No. 15-6)

$[\alpha]_D^{20}$-46.4° (c=0.50, chloroform); IR (Film, cm$^{-1}$) 3353, 2933, 1721, 1622, 1529, 1493, 1362, 1217.

(2S)-2-[3-(2-Hydroxyethyl)-3-isoamylureido]-3-(4-nitrophenyl)propionic acid (Compound No. 15-7)

$[\alpha]_D^{20}$-28.6° (c=0.96, chloroform); IR (Film, cm$^{-1}$) 3352, 2955, 1725, 1606, 1520, 1468, 1346, 1219, 1049.

(2S)-2-[3-(2-Hydroxyethyl)-3-phenethylureido]-3-(2-nitro-4-biphenylyl propionic acid (Compound No. 15-8)

$[\alpha]_D^{20}$-30.6° (c=0.51, chloroform); IR (Film, cm$^{-1}$) 3371, 2933, 1726, 1620, 1529, 1358, 1218, 756, 701.

(2S)-3-[4-(Benzenesulfonyl)-3-nitrophenyl]-2-[3-(2-hydroxyethyl)-3-phenethylureido]propionic acid (Compound No. 15-9)

$[\alpha]_D^{20}$-24.7° (c=0.48, chloroform); IR (Film, cm$^{-1}$) 3390, 2932, 1728, 1604, 1544, 1159, 752.

(2S)-2-[3-(2-Hydroxyethyl)-3-phenethylureido]-3-(2-naphthyl)propionic acid (Compound No. 15-10)

$[\alpha]_D^{20}$+3.1° (c=1.1, methanol); IR (Film, cm$^{-1}$) 3366, 3025, 2932, 1727, 1620, 1530, 1217, 1047.

(2R)-2-[3-(2-Hydroxyethyl)-3-phenethylureido]-3-(methylthio)propionic acid (Compound No. 15-11)

$[\alpha]_D^{20}$+6.2° (c=0.5, methanol); IR (Film, cm$^{-1}$) 3369, 2921, 1729, 1616, 1526, 1454, 1420, 1367, 1213, 1047, 751, 701.

(2R)-3-(Benzylthio)-2-[3-(2-hydroxyethyl)-3-phenethylureido]propionic acid (Compound No. 15-12)

$[\alpha]_D^{20}$-31.8° (c=0.50, methanol); IR (Film, cm$^{-1}$) 3382, 2926, 1730, 1615, 1524, 1454, 1418, 1366, 1305, 1210, 1047, 752, 701.

(2S)-2-[3-(2-Hydroxyethyl)-3-phenethylureido]-3-[4-(benzyloxy)phenyl]propionic acid (Compound No. 15-13)

$[\alpha]_D^{20}$+1.2° (c=0.95, methanol); IR (KBr, cm$^{-1}$) 3364, 2932, 1728, 1613, 1511, 1241, 1043.

(2S)-2-[3-[2-(1-Cyclohexenyl)ethyl]-3-(2-hydroxyethyl) ureido]propionic acid (Compound No. 15-14)

IR (Film, cm$^{-1}$) 3374, 2929, 1732, 1614, 1537, 1216, 757.

(2S)-2-[3-(2-Hydroxyethyl)-3-(3-methyl-3-butenyl) ureido]propionic acid (Compound No. 15-15)

$[\alpha]_D^{20}$ −66.8° (c=0.52, chloroform); IR (Film, cm$^{-1}$) 3370, 2937, 1728, 1614, 1536, 1218, 1046, 893, 758.

2-[3-(2-Cyclohexylethyl)-3-(2-hydroxyethyl)ureido]-2-methylpropionic acid (Compound No. 15-16)

IR (Film, cm$^{-1}$) 3308, 2923, 2851, 1716, 1623, 1530, 1411, 1363, 1276, 1168, 1051, 757.

1-[3-(2-Cyclohexylethyl)-3-(2-hydroxyethyl)ureido]-1-cyclopropanecarboxylic acid (Compound No. 15-17)

IR (Film, cm$^{-1}$) 3360, 2923, 2851, 1714, 1632, 1529, 1448, 1416, 1273, 1194, 1050, 756.

1-[3-(2-Cyclohexylethyl)-3-(2-hydroxyethyl)ureido]-1-cyclopentanecarboxylic acid (Compound No. 15-18)

mp 126.0~127.5° C.(decomp.); IR (KBr, cm$^{-1}$) 3300, 2923, 1670, 1629, 1533, 1302.

EXAMPLE 16

(2S)-2-[3-(2-Hydroxyethyl)-3-phenethylureido]-3-phenylpropionic Acid (Compound No. 16-1)

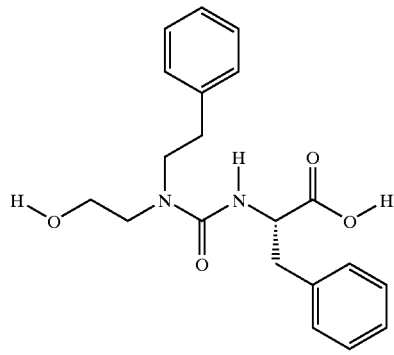

Under a nitrogen atmosphere, 20% palladium hydroxide on carbon (200 mg) is added to a solution of benzyl (2S)-2-[3-(2-hydroxyethyl)-3-phenethylureido]-4-phenylpropionate (Compound No. 1-43, 1.92 g) in tetrahydrofuran (14 ml). The mixture is stirred under a hydrogen atmosphere for 2.5 days. Palladium hydroxide on carbon is filtered out with Celite, and the filtrate is concentrated under reduced pressure to give 1.50 g (98%) of the titled compound (Compound No. 16-1).

(Compound No. 16-1)

$[\alpha]_D^{20}$−4.6° (c=0.49, methanol); IR (Film, cm$^{-1}$) 3357, 2934, 1726, 1623, 1528, 1216, 1047, 752, 701.

The following compounds are obtained by a method similar to Example 16.

(2R)-2-[3-(2-Hydroxyethyl)-3-phenethylureido]-3-phenylpropionic acid (Compound No. 16-2), enantiomer of Compound No. 16-1

$[\alpha]_D^{20}$+5.1° (c=0.52, methanol); IR (Film, cm$^{-1}$) 3339, 3027, 2931, 1726, 1619, 1530, 1216, 1047, 753, 701.

(2S)-2-[3-(2-Hydroxyethyl)-3-phenethylureidol]-3-(4-isopropoxyphenyl)propionic acid (Compound No. 16-3)

$[\alpha]_D^{20}$−53.0° (c=0.36, chloroform); IR (Film, cm$^{-1}$) 3369, 2977, 1732, 1614, 1510, 1243, 1184, 1121, 1048, 955, 755, 701.

(2S)-2-[3-[(1RS)-1-(Dimethylaminomethyl)-2-hydroxyethyl]-3-phenethylureido]-3-phenylpropionic acid (Compound No. 16-4)

$[\alpha]_D^{20}$−9.8° (c=0.5, methanol); IR (Film, cm$^{-1}$) 3344, 2951, 1722, 1632, 1514, 1402, 1217, 753.

(2S)-2-[3-(2-Hydroxyethyl)-3-isoamylureido]-3-phenylpropionic acid (Compound No. 16-5)

$[\alpha]_D^{20}$−43.5° (c=0.98, methanol); IR (Film, cm$^{-1}$) 3339, 2955, 1727, 1611, 1529, 1217, 1049, 757, 701.

(2S)-2-[3-(2-Hydroxyethyl)-3-isoamylureido]-3-(4-methoxyphenyl)propionic acid (Compound No. 16-6)

$[\alpha]_D^{20}$−40.8° (c=0.53, chloroform); IR (Film, cm$^{-1}$) 3367, 2956, 1732, 1614, 1513, 1249, 1179, 1037, 758.

(2S)-2-[3-(2-Hydroxyethyl)-3-isoamylureido]-2-phenylacetic acid (Compound No. 16-7)

$[\alpha]_D^{20}$+57.3° (c=0.45, chloroform); IR (Film, cm$^{-1}$) 3307, 2956, 1727, 1615, 1520, 1217, 1187, 1049, 758, 698.

(2S)-2-[3-(2-Hydroxyethyl)-3-isoamylureido]-4-methylvaleric acid (Compound No. 16-8)

$[\alpha]_D^{20}$−60.1° (c=0.98, chloroform); IR (Film, cm$^{-1}$) 3342, 2955, 1720, 1612, 1529, 1219, 1048, 756.

2-[3-(2-Hydroxyethyl)-3-isoamylureido]acetic acid (Compound No. 16-9)

IR (Film, cm$^{-1}$) 3357, 2957, 1730, 1613, 1538, 1415, 1219, 1048, 759.

(2S)-3-Cyclohexyl-2-[3-(2-hydroxyethyl)-3-isoamylureido]propionic acid (Compound No. 16-10)

mp 68.5~71.5° C.; $[\alpha]_D^{20}$−62.7° (c=0.96, chloroform); IR (KBr, cm$^{-1}$) 2926, 2611, 1750, 1725, 1620, 1538, 1450, 1367, 1223, 1054.

(2S)-2-[3-(2-Hydroxyethyl)-3-isoamylureido]-3-(4-imidazolyl)propionic acid hydrochloride (Compound No. 16-11)

$[\alpha]_D^{20}$−21.1° (c=0.53, methanol); IR (KBr, cm$^{-1}$) 3311, 3133, 2961, 1739, 1621, 1531, 1238, 1046, 832, 760.

(2S)-2-[3-(2-Hydroxyethyl)-3-isoamylureido]-5-(3-tosylguanidino)valeric acid (Compound No. 16-12)

$[\alpha]_D^{20}$−13.9° (c=0.52, chloroform); IR (Film, cm$^{-1}$) 3340, 2956, 1723, 1625, 1548, 1412, 1255, 1132, 1082, 815, 756.

(2S)-2-[3-(2-Hydroxyethyl)-1-methyl-3-phenethylureido]propionic acid (Compound No. 16-13)

$[\alpha]_D^{20}$−25.8° (c=1.0, methanol); IR (Film, cm$^{-1}$) 3368, 3001, 1738, 1615, 1496.

EXAMPLE 17

(2S)-6-(t-Butoxycarboxamido)-2-[3-(2-hydroxyethyl)-3-isoamylureido]hexanoic Acid (Compound No. 17-1)

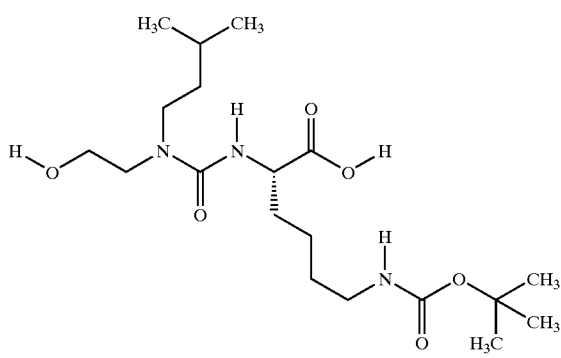

Under a nitrogen atmosphere, 1 N hydrochloric acid (12 ml) and 20% palladium hydroxide on carbon (285 mg) are added to a solution of benzyl (2S)-6-(benzyloxycarboxamido)-2-[3-(2-hydroxyethyl)-3- isoamylureido]hexanoate (Compound No. 1-73, 2.85 g) in tetrahydrofuran (60 ml). The mixture is stirred under a hydrogen atmosphere for two hours. Palladium hydroxide on carbon is filtered out with Celite.

A 4 N aqueous sodium hydroxide solution (3 ml) is added to the obtained filtrate under ice cooling. Then, to the mixture are added triethylamine (1.09 g) and a solution of di-t-butyl dicarbonate (2.36 g) in tetrahydrofuran (10 ml) dropwise successively, and the mixture is further stirred at room temperature for four hours. The reaction mixture is concentrated under reduced pressure, a 10% aqueous citric acid solution is added to the residue, and the whole is extracted with ethyl acetate. The organic layer is washed with a 10% aqueous citric acid solution, water and saturated brine successively, dried over anhydrous sodium sulfate and concentrated under reduced pressure. The resulting oily matter is purified by silica gel column chromatography to give 1.92 g (88%) of the titled compound (Compound No. 17-1).

(Compound No. 17-1)

$[\alpha]_D^{20}$ −37.1° (c=0.53, chloroform); IR (Film, cm$^{-1}$) 3330, 2956, 1712, 1694, 1631, 1530, 1367, 1251, 1172, 1051, 757.

EXAMPLE 18

1-[(2S)-2-[3-(2-Hydroxyethyl)-3-phenethylureido]-4-methylvaleryl]-4-methylpiperazine (Compound No. 18-1)

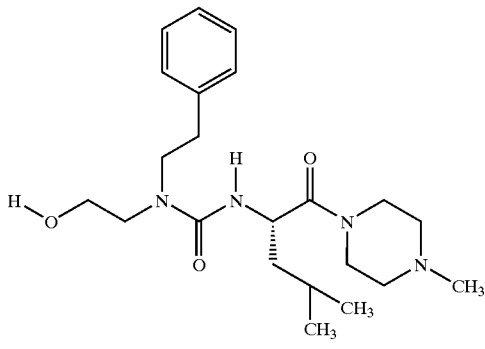

In anhydrous methylene chloride (10 ml) are dissolved (2S)-2-[3-(2-hydroxyethyl)-3-phenethylureido]-4-methylvaleric acid (Compound No. 15-1, 700 mg), N-methylpiperazine (0.25 ml) and 1-hydroxybenzotriazole (440 mg) under a nitrogen atmosphere. Then, to the solution are added N-methylmorpholine (0.29 ml) and 1-ethyl-3-(3-dimethylaminopropyl) carbodiimide hydrochloride (504 mg) successively under ice cooling. The mixture is stirred under ice cooling for 30 minutes and then at room temperature for two hours. The reaction mixture is concentrated under reduced pressure, a 5% aqueous sodium hydrogencarbonate solution is added to the resulting oily matter, and the whole is extracted with ethyl acetate. The organic layer is washed with water and saturated brine successively, dried over anhydrous magnesium sulfate and concentrated under reduced pressure. The resulting oily matter is purified by silica gel column chromatography to give 808 mg (92%) of the titled compound (Compound No. 18-1).

(Compound No. 18-1)

$[\alpha]_D^{20}$ +1.6° (c=0.99, methanol); IR (Film, cm$^{-1}$) 3346, 2950, 1631, 1449, 1291, 1223, 1171, 1143.

The following compounds are obtained by a method similar to Example 18.

1-[(2S)-2-[3-(3-Hydroxypropyl)-3-phenethylureido]-3-phenylpropionyl]-4-methylpiperazine (Compound No. 18-2)

$[\alpha]_D^{20}$ +16.6° (c=0.50, methanol); IR (Film, cm$^{-1}$) 3358, 2937, 1624, 1528, 1496, 1453, 1290, 1249, 1144, 1001, 750, 701.

1-[(2S)-2-[3-[(2RS)-2-Hydroxypropyl]-3-phenethylureido]-3-phenylpropionyl]-4-methylpiperazine (Compound No. 18-3)

IR (Film, cm$^{-1}$) 3362, 2937, 1625, 1522, 1454, 1291, 1234, 1144, 1001, 751, 701.

1-[(2RS)-2-[3-(2-Hydroxyethyl)-3-phenethylureido]-4-(methylthio)butyryl]-4-methylpiperazine (Compound No. 18-4)

mp 115.7~117.2° C.; IR (KBr, cm$^{-1}$) 3421, 3289, 2932, 2794, 1621, 1532, 1449, 1255, 1218, 1053, 1002, 754, 704.

1-(t-Butoxycarbonyl)-4-[(2S)-2-[3-(2-hydroxyethyl)-3-phenethylureido]-3-(4-nitrophenyl)propionyl]piperazine (Compound No. 18-5)

$[\alpha]_D^{20}$ +11.4° (c=1.0, chloroform); IR (Film, cm$^{-1}$) 3400, 2931, 1691, 1630, 1521, 1456, 1420, 1346, 1236, 1167.

1-[(2S)-2-[3-(2-Hydroxyethyl)-3-phenethylureido]-3-(4-nitrophenyl)propionyl]-4-methylpiperazine (Compound No. 18-6)

$[\alpha]_D^{20}$ +2.6° (c=0.53, chloroform); IR (Film, cm$^{-1}$) 3376, 2941, 1627, 1519, 1451, 1346, 1291, 1224, 1144, 1049, 1000, 751, 700.

1-Cyclohexyl-4-[(2S)-2-[3-(2-hydroxyethyl)-3-phenethylureido]-3-(4-nitrophenyl)propionyl]piperazine (Compound No. 18-7)

$[\alpha]_D^{20}$ +6.1° (c=1.0, chloroform); IR (Film, cm$^{-1}$) 3341, 2930, 2855, 1627, 1520, 1451, 1346, 1225.

1-[(2S)-2-[3-(2-Hydroxyethyl)-3-phenethylureido]-3-(4-nitrophenyl)propionyl]-4-phenylpiperazine (Compound No. 18-8)

IR (Film, cm$^{-1}$) 3412, 2928, 1627, 1602, 1519, 1346, 1228, 755, 698.

1-Benzyl-4-[(2S)2-[3-(2-hydroxyethyl)-3-phenethylureido]-3-(4-nitrophenyl)propionyl]piperazine (Compound No. 18-9)

$[\alpha]_D^{20}$ +7.7° (c=1.0, chloroform); IR (Film, cm$^{-1}$) 3371, 2936, 1626, 1519, 1453, 1346, 1221, 750, 700.

(2S)-N-[2-(Diisopropylamino)ethyl]-2-[3-(2-hydroxyethyl)-3-phenethylureido]-3-(4-nitrophenyl)propionamide (Compound No. 18-10)

$[\alpha]_D^{20}$ −12.9° (c=1.0, chloroform); IR (Film, cm$^{-1}$) 3389, 2968, 1630, 1520, 1346, 751, 700.

(2S)-N-[2-(Dicyclohexylamino)ethyl]-2-[3-(2-hydroxyethyl)-3-phenethylureido]-3-(4-nitrophenyl)propionamide (Compound No. 18-11)

$[\alpha]_D^{20}$ −10.3° (c=0.50, chloroform); IR (Film, cm$^{-1}$) 3301, 2929, 1634, 1520, 1346, 755.

(2S)-2-[3-(2-Hydroxyethyl)-3-phenethylureido]-N-[2-(4-methylpiperazin-1-yl)ethyl]-3-(4-nitrophenyl)propionamide (Compound No. 18-12)

mp 89.0~91.5° C.; $[\alpha]_D^{20}$ −20.0° (c=0.50, chloroform); IR (KBr, cm$^{-1}$) 3289, 2939, 2804, 1668, 1617, 1518, 1455, 1347, 1284, 1235, 1165, 1012, 700.

(2S)-N-[2-(t-Butoxycarboxamido)ethyl]-2-[3-(2-hydroxyethyl)-3-phenethylureido]-3-(4-nitrophenyl)propionamide (Compound No. 18-13)

$[\alpha]_D^{20}$ −25.9° (c=1.0, chloroform); IR (Film, cm$^{-1}$) 3304, 2976, 2933, 1693, 1625, 1519, 1346, 1168, 753.

1-[(2S)-2-[3-(2-Hydroxyethyl)-3-phenethylureido]-3-(4-nitrophenyl)propionyl]piperidine (Compound No. 18-14)

$[\alpha]_D^{20}$+11.1° (c=0.53, chloroform); IR (Film, cm$^{-1}$) 3348, 2939, 1622, 1519, 1346, 1221, 1050, 1016, 855, 750, 700.

4-[(2S)-2-[3-(2-Hydroxyethyl)-3-phenethylureido]-3-(4-nitrophenyl)propionyl]morpholine (Compound No. 18-15)

$[\alpha]_D^{20}$+9.4° (c=1.0, chloroform); IR (Film, cm$^{-1}$) 3415, 2927, 2860, 1626, 1519, 1346, 751.

(2S)-N-(t-Butoxycarbonylmethyl)-2-[3-(2-hydroxyethyl)-3-phenethylureido]-3-(4-nitrophenyl)propionamide (Compound No. 18-16)

$[\alpha]_D^{20}$−17.7° (c=0.54, methanol); IR (Film, cm$^{-1}$) 3292, 2979, 2933, 1740, 1663, 1624, 1521, 1346, 1225, 1156, 752.

(2S)-3-(4-Chlorophenyl)-N-[2-(dimethylamino)ethyl]-2-[3-(2-hydroxyethyl)-3-phenethylureido]propionamide (Compound No. 18-17)

$[\alpha]_D^{20}$−20.7° (c=0.51, chloroform); IR (Film, cm$^{-1}$) 3291, 2944, 1714, 1626, 1534, 1493, 1365, 1232, 1092.

(2S)-2-[3-(2-Hydroxyethyl)-3-isoamylureido]-N-methyl-3-(4-nitrophenyl)propionamide (Compound No. 18-18)

$[\alpha]_D^{20}$−18.4° (c=0.50, chloroform); IR (KBr, cm$^{-1}$) 3304, 2957, 1670, 1616, 1519, 1408, 1348, 1047.

(2S)-N-[2-(Dimethylamino)ethyl]-2-[3-(2-hydroxyethyl)-3-phenethylureido]-3-(2-nitro-4-biphenylyl)propionamide (Compound No. 18-19)

$[\alpha]_D^{20}$−21.9° (c=0.50, chloroform); IR (Film, cm$^{-1}$) 3305, 2945, 1626, 1529, 755, 701.

(2S)-3-[4-(Benzenesulfonyl)-3-nitrophenyl]-N-[2-(dimethylamino)ethyl]-2-[3-(2-hydroxyethyl)-3-phenethylureido]propionamide (Compound No. 18-20)

$[\alpha]_D^{20}$ −21.0° (c=0.50, chloroform); IR (Film, cm$^{-1}$) 3297, 2943, 1625, 1544, 752.

1-[(2S)-2-[3-(2-Hydroxyethyl)-3-phenethylureidol]-3-(2-naphthyl)propionyl]-4-methylpiperazine (Compound No. 18-21)

$[\alpha]_D^{20}$+2.0° (c=1.0, methanol); IR (Film, cm$^{-1}$) 3348, 2937, 1626, 1524, 1447, 1225.

1-[(2R)-2-[3-(2-Hydroxyethyl)-3-phenethylureido]-3-(methylthio)propionyl]-4-methylpiperazine (Compound No. 18-22)

$[\alpha]_D^{20}$4.1° (c=0.51, methanol); IR (Film, cm$^{-1}$) 3352, 2921, 1628, 1521, 1455, 1365, 1293, 1224, 1170, 1143, 1047, 100, 752, 701.

1-[(2R)-3-(Benzylthio)-2-[3-(2-hydroxyethyl)-3-phenethylureido]propionyl]-4-methylpiperazine (Compound No. 18-23)

mp 88.2~90.7° C.; $[\alpha]_D^{20}$+25.2° (c=0.50, methanol); IR (KBr, cm$^{-1}$) 3423, 3309, 2941, 2788, 1620, 1549, 1451, 1293, 1229, 1141, 1060, 1002, 786, 754, 710.

1-[(2S)-2-[3-(2-Hydroxyethyl)-3-phenethylureido]-3-phenylpropionyl]-4-methylpiperazine (Compound No. 18-24)

$[\alpha]_D^{20}$+14.7° (c=0.46, methanol); IR (Film, cm$^{-1}$) 3354, 2938, 1626, 1526, 1452, 751, 701.

1-[(2R)-2-[3-(2-Hydroxyethyl)-3-phenethylureidol]-3-phenylpropionyl]-4-methylpiperazine (Compound No. 18-25), enantiomer of Compound No. 18-24

$[\alpha]_D^{20}$−14.6° (c=0.53, methanol); IR (Film, cm$^{-1}$) 3348, 2935, 1626, 1526, 1450, 750, 701.

(2S)-N-[2-(Dimethylamino)ethyl]-2-[3-(2-hydroxyethyl)-3-phenethylureido]-3-(4-isopropoxyphenyl)propionamide (Compound No. 18-26)

mp 87.5~100.0° C.; $[\alpha]_D^{20}$−14.9° (c=0.32, chloroform); IR (KBr, cm$^{-1}$) 3276, 2975, 1669, 1614, 1550, 1510, 1238, 1183, 1119, 1053, 956, 748, 701.

1-[(2S)-2-[3-[(1RS)-1-(Dimethylaminomethyl)-2-hydroxyethyl]-3-phenethylureido]-3-phenylpropionyl]-4-methylpiperazine (Compound No. 18-27)

$[\alpha]_D^{20}$+14.3° (c=1.30, methanol); IR (Film, cm$^{-1}$) 3420, 2941, 1626, 1496, 1291, 1145, 752.

(2S)-N-[2-(Dimethylamino)ethyl]-2-[3-(2-hydroxyethyl)-3-isoamylureido]-3-phenylpropionamide (Compound No. 18-28)

$[\alpha]_D^{20}$−21.3° (c=1.0, chloroform); IR (Film, cm$^{-1}$) 3305, 2954, 1630, 1530, 1234, 1051, 754, 701.

(2S)-2-[3-(2-Hydroxyethyl)-3-isoamylureido]-N-[(1S)-1-(methylcarbamoyl)ethyl]-3-phenylpropionamide (Compound No. 18-29)

mp 106.5~111.0° C.; $[\alpha]_D^{20}$−13.2° (c=1.0, chloroform); IR (KBr, cm$^{-1}$) 3276, 2950, 1647, 1554, 1456, 1410, 1050, 701.

(2S)-2-[3-(2-Hydroxyethyl)-3-isoamylureido]-3-(4-methoxyphenyl)-N-methylpropionamide (Compound No. 18-30)

mp 96.5~99.0° C.; $[\alpha]_D^{20}$+5.2° (c=0.50, chloroform); IR (KBr, cm$^{-1}$) 3270, 2955, 1668, 1620, 1550, 1513, 1410, 1246, 1177, 1042, 824.

(2S)-2-[3-(2-Hydroxyethyl)-3-isoamylureido]-N-methyl-2-phenylacetamide (Compound No. 18-31)

mp 164.5~165.5° C.; $[\alpha]_D^{20}$+1.7° (c=0.50, methanol); IR (KBr, cm$^{-1}$) 3410, 3274, 2961, 1659, 1618, 1539, 1375, 1361, 1232, 1160, 1087, 727, 700.

1-[(2S)-2-[3-(2-Hydroxyethyl)-3-isoamylureido]-4-methylvaleryl]-4-methylpiperazine (Compound No. 18-32)

$[\alpha]_D^{20}$ +2.2° (c=1.0, methanol); IR (Film, cm$^{-1}$) 3344, 2954, 2868, 1633, 1463, 1172, 1144.

(2S)-N, 4-Dimethyl-2-[3-(2-hydroxyethyl)-3-isoamylureido]valeramide (Compound No. 18-33)

$[\alpha]_D^{20}$ −23.4° (c=0.48, chloroform); IR (Film, cm$^{-1}$) 3294, 2956, 2871, 1626, 1535, 1469, 1410, 1236, 1051, 756.

2-[3-(2-Hydroxyethyl)-3-isoamylureido]-N-methylacetamide (Compound No. 18-34)

mp 124.5~126.0° C.; IR (KBr, cm$^{-1}$) 3420, 3352, 3272, 2955, 1668, 1616, 1533, 1413, 1237, 1078, 751.

(2S)-3-Cyclohexyl-2-[3-(2-hydroxyethyl)-3-isoamylureido]-N-methylpropionamide (Compound No. 18-35)

$[\alpha]_D^{20}$−21.9° (c=0.51, chloroform); IR (Film, cm$^{-1}$) 3297, 2924, 1630, 1535, 1468, 1448, 1411, 1235, 1051.

(2S)-2-[3-(2-Hydroxyethyl)-3-isoamylureido]-3-(4-imidazolyl)-N-methylpropionamide (Compound No. 18-36)

mp 94.0~97.0° C.; $[\alpha]_D^{20}$ +14.3° (c=0.33, dimethyl sulfoxide); IR (KBr, cm$^{-1}$) 3270, 2956, 1663, 1412, 1241, 1070, 977, 770.

(2S)-2-[3-(2-Hydroxyethyl)-3-isoamylureido]-N-methyl-5-(3-tosylguanidino)valeramide (Compound No. 18-37)

$[\alpha]_D^{20}$ +11.6° (c=0.50, chloroform); IR (Film, cm$^{-1}$) 3335, 2955, 1627, 1550, 1410, 1258, 1132, 1082, 814, 755.

1-[(2S)-2-[3-(2-Hydroxyethyl)-1-methyl-3-phenethylureido]propionyl]-4-methylpiperazine (Compound No. 18-38)

$[\alpha]_D^{20}$ −11.4° (c=0.97, chloroform); IR (Film, cm$^{-1}$) 3417, 2938, 1634, 1455, 1291, 1252, 1077, 1034.

(2S)-6-(t-Butoxycarboxamido)-2-[3-(2-hydroxyethyl)-3-isoamylureido]-N-methylhexanamide (Compound No. 18-39)

$[\alpha]_D^{20}$ −6.2° (c=0.51, chloroform); IR (Film, cm$^{-1}$) 3308, 2956, 1693, 1632, 1530, 1366, 1251, 1172, 052, 756.

1-[(2S)-3-[4-(Benzyloxy)phenyl]-2-[3-(2-hydroxyethyl)-3-phenethylureido]propionyl]-4-methylpiperazine (Compound No. 18-40)

$[\alpha]_D^{20}$ +2.2° (c=0.50, methanol); IR (Film, cm$^{-1}$) 3354, 2938, 1623, 1510, 1454, 1240, 1038.

(2S)-N-[2-(t-Butoxycarbonyl)ethyl]-2-[3-(2-hydroxyethyl)-3-phenethylureido]-3-(4-nitrophenyl)propionamide (Compound No. 18-41)

mp 109.0~111.5° C.; $[\alpha]_D^{20}$ −27.2° (c=0.49, chloroform); IR (KBr, cm$^{-1}$) 3271, 3078, 2937, 1729, 1653, 1617, 1521, 1347, 1155, 844, 749, 702.

1-[(2S)-2-[3-[2-(1-Cyclohexenyl)ethyl]-3-(2-hydroxyethyl)ureido]propionyl]-4-methylpiperazine (Compound No. 18-42)

$[\alpha]_D^{20}$ +8.3° (c=0.99, methanol); IR (Film, cm$^{-1}$) 3361, 2930, 1632, 1520, 1447, 1292, 1225, 754.

1-[(2S)-2-[3-(2-Hydroxyethyl)-3-(3-methyl-3-butenyl)ureido]propionyl]-4-methylpiperazine (Compound No. 18-43)

$[\alpha]_D^{20}$ +10.3° (c=0.47, methanol); IR (Film, cm$^{-1}$) 3355, 2937, 1632, 1526, 1448, 1292, 1225, 1144, 1034, 1002, 890, 757.

1-[2-[3-(2-Cyclohexylethyl)-3-(2-hydroxyethyl)ureido]-2-methylpropionyl]-4-methylpiperazine (Compound No. 18-44)

mp 50~60° C.; IR (KBr, cm$^{-1}$) 3294, 2924, 1645, 1627, 1546, 1421, 1356, 1284, 1170, 1140, 1048, 1001, 749.

1-[1-[3-(2-Cyclohexylethyl)-3-(2-hydroxyethyl)ureido]-1-cyclopropanecarbonyl]-4-methylpiperazine (Compound No. 18-45)

IR (Film, cm$^{-1}$) 3338, 2921, 2850, 2796, 1633, 1520, 1446, 1288, 1213, 1143, 1050, 1002, 753.

1-[1-[3-(2-Cyclohexylethyl)-3-(2-hydroxyethyl)ureido]-1-cyclopentanecarbonyl]-4-methylpiperazine (Compound No. 18-46)

mp 128.5~131.4° C.; IR (KBr, cm$^{-1}$) 3306, 2927, 1652, 1542, 1444, 1418, 1284, 995, 779.

EXAMPLE 19

(2S)-N-[2-(Dimethylamino)ethyl]-2-[3-(2-hydroxyethyl)-3-phenethylureido]-3-(4-nitrophenyl)propionamide (Compound No. 19-1)

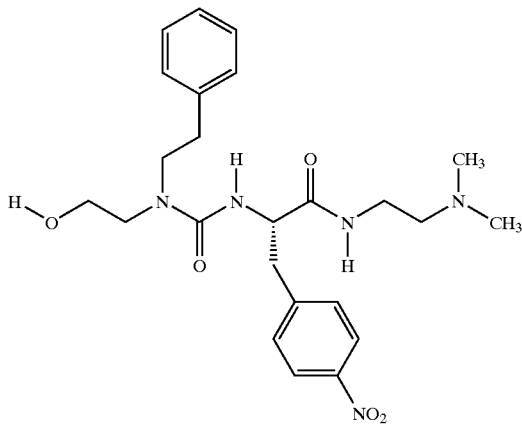

A solution of 2-(dimethylamino)ethylamine (362 mg) in tetrahydrofuran (3 ml) is added to a solution of phenyl (2S)-2-[3-(2-hydroxyethyl)-3-phenethylureido]-3-(4-nitrophenyl)propionate (Compound No. 1-35, 392 mg) in tetrahydrofuran (5 ml) under ice cooling, and the mixture is stirred at room temperature for 1.5 hours. The reaction mixture is concentrated under reduced pressure, water is added to the concentrate, and the whole is extracted with ethyl acetate. The organic layer is washed with water and saturated brine successively, dried over andhydrous sodium sulfate and concentrated under reduced pressure. The resulting oily matter is purified by silica gel column chromatography to give 314 mg (81%) of the titled compound (Compound No. 19-1).

(Compound No. 19-1)

$[\alpha]_D^{20}$ −39.3° (c=0.27, chloroform); IR (Film, cm$^{-1}$) 3293, 2943, 1625, 1519, 1346, 1231, 1044, 856, 751, 701.

The following compounds are obtained by a method similar to Example 19.

(2S)-N-[3-(Dimethylamino)propyl]-2-[3-(2-hydroxyethyl)-3-phenethylureido]-3-(4-nitrophenyl)propionamide (Compound No. 19-2)

$[\alpha]_D^{20}$ −35.2° (c=0.50, chloroform); IR (Film, cm$^{-1}$) 3270, 3100, 2943, 1664, 1615, 1519, 1350, 749.

(2S)-2-[3-(2-Hydroxyethyl)-3-phenethylureido]-N-[2-(4-morpholinyl)ethyl]-3-(4-nitrophenyl)propionamide (Compound No. 19-3)

$[\alpha]_D^{20}$ −17.2° (c=1.0, chloroform); IR (Film, cm$^{-1}$) 3295, 2941, 1627, 1519, 1346, 1116, 752.

(2S)-2-[3-(2-Hydroxyethyl)-3-phenethylureido]-3-(4-nitrophenyl)-N-[2-(phthalimido)ethyl]propionamide (Compound No. 19-4)

$[\alpha]_D^{20}$ −33.6° (c=0.49, chloroform); IR (Film, cm$^{-1}$) 3289, 1712, 1622, 1519, 1395, 1346, 1229, 1037, 752, 720.

(2S)-2-[3-(2-Hydroxyethyl)-3-phenethylureido]-N-[2-[(N-methyl)cyclohexylamino]ethyl]-3-(4-nitrophenyl)propionamide (Compound No. 19-5)

$[\alpha]_D^{20}$ −16.5° (c=0.53, chloroform); IR (Film, cm$^{-1}$) 3296, 2930, 1624, 1520, 1453, 1409, 1345, 1230, 1048.

(2S)-N-[2-(Diethylamino)ethyl]-2-[3-(2-hydroxyethyl)-3-phenethylureido]-3-(4-nitrophenyl)propionamide (Compound No. 19-6)

mp 89.0~92.5° C.; $[\alpha]_D^{20}$ −17.6° (c=0.49, chloroform); IR (KBr, cm$^{-1}$) 3274, 2971, 1663, 1617, 1517, 1440, 1347.

(2S)-2-[3-(2-Hydroxyethyl)-3-phenethylureido]-N-[2-[(N-methyl)phenylamino]ethyl]-3-(4-nitrophenyl)propionamide (Compound No. 19-7)

$[\alpha]_D^{20}$ −26.3° (c=0.51, chloroform); IR (Film, cm$^{-1}$) 3290, 2935, 1660, 1624, 1601, 1519, 1346, 1216.

(2S)-N-[4-(Dimethylamino)butyl]-2-[3-(2-hydroxyethyl)-3-phenethylureido]-3-(4-nitrophenyl)propionamide (Compound No. 19-8)

$[\alpha]_D^{20}$ −81.5° (c=0.51, chloroform); IR (Film, cm$^{-1}$) 3291, 2940, 1625, 1519, 1346, 750.

(2S)-2-[3-(2-Hydroxyethyl)-3-phenethylureido]-3-(4-nitrophenyl)-N-[2-(2-pyridyl)ethyl]propionamide (Compound No. 19-9)

mp 112.0~118.0° C.; $[\alpha]_D^{20}$ −26.0° (c=0.51, chloroform); IR (KBr, cm$^{-1}$) 3277, 3090, 2937, 1666, 1612, 1516, 1436, 1347, 1279, 1224, 1049, 748, 703.

(2S)-2-[3-(2-Hydroxyethyl)-3-phenethylureido]-N-[3-(1-imidazolyl)propyl]-3-(4-nitrophenyl)propionamide (Compound No. 19-10)

$[\alpha]_D^{20}$ −46.3° (c=1.0, chloroform); IR (Film, cm$^{-1}$) 3416, 2938, 1628, 1518, 1346, 750.

(2S)-2-[3-(2-Hydroxyethyl)-3-phenethylureido]-3-(4-nitrophenyl)-N-[2-(1-piperidyl)ethyl]propionamide (Compound No. 19-11)

$[\alpha]_D^{20}$ −15.9° (c=0.49, chloroform); IR (Film, cm$^{-1}$) 3404, 2937, 1633, 1519, 1345, 749, 700.

(2S)-N-[2-(Dimethylamino)ethyl]-2-[3-(2-hydroxyethyl)-3-phenethylureido]-3-phenylpropionamide (Compound No. 19-12)

mp 97.5~101.2° C.; $[\alpha]_D^{20}$ −13.2° (c=0.51, chloroform); IR (KBr, cm$^{-1}$) 3271, 3087, 2942, 1667, 1617, 1546, 1498, 1455, 1280, 1230, 1048, 748, 699.

(2S)-N-[2-(Dimethylamino)ethyl]-3-(4-fluorophenyl)-2-[3-(2-hydroxyethyl)-3-phenethylureido]propionamide (Compound No. 19-13)

mp 108.5~111.0° C.; $[\alpha]_D^{20}$ −15.7° (c=0.53, chloroform); IR (KBr, cm$^{-1}$) 3268, 3088, 2945, 1666, 1614, 1549, 1456, 1417, 1373, 1280, 1227, 1049, 828, 748, 699.

(2S)-N-[2-(Dimethylamino)ethyl]-2-[3-(2-hydroxyethyl)-3-phenethylureido]-3-(4-hydroxyphenyl)propionamide (Compound No. 19-14)

$[\alpha]_D^{20}$ −4.7° (c=0.50, chloroform); IR (Film, cm$^{-1}$) 3293, 2947, 1629, 1515, 1454, 1367, 1238, 1047, 752, 701.

(2S)-N-[2-(Dimethylamino)ethyl]-2-[3-(2-hydroxyethyl)-3-phenethylureido]-3-(4-methoxyphenyl)propionamide (Compound No. 19-15)

$[\alpha]_D^{20}$ −10.8° (c=0.50, chloroform); IR (Film, cm$^{-1}$) 3287, 2939, 1622, 1513, 1247, 1037, 751.

(2S)-N-[2-(Dimethylamino)ethyl]-2-[3-(2-hydroxyethyl)-3-phenethylureido]-3-(2-thienyl)propionamide (Compound No. 19-16)

$[\alpha]_D^{20}$ −17.4° (c=0.51, chloroform); IR (Film, cm$^{-1}$) 3295, 2944, 1629, 1531, 1454, 1408, 1231, 1043, 751, 700.

(2S)-N-[2-(Dimethylamino)ethyl]-2-[3-(2-hydroxyethyl)-3-phenethylureido]-3-(2-naphthyl)propionamide (Compound No. 19-17)

$[\alpha]_D^{20}$ −8.1° (c=0.97, chloroform); IR (Film, cm$^{-1}$) 3296, 2945, 1629, 1532, 1233, 1045, 751.

(2S)-3-(4-Biphenylyl)-N-[2-(dimethylamino)ethyl]-2-[3-(2-hydroxyethyl)-3-phenethylureido]propionamide (Compound No. 19-18)

$[\alpha]_D^{20}$ −14.4° (c=1.0, chloroform); IR (Film, cm$^{-1}$) 3290, 2943, 1626, 1534, 1230, 1094, 757, 699.

(2S)-N-[2-(Dimethylamino)ethyl]-2-[3-(2-hydroxyethyl)-3-isoamylureido]-3-(4-nitrophenyl)propionamide (Compound No. 19-19)

$[\alpha]_D^{20}$ −31.4° (c=0.29, chloroform); IR (Film, cm$^{-1}$) 3290, 2954, 1660, 1624, 1521, 1467, 1346, 1233, 1052, 856, 755.

(2S)-3-(4-Biphenylyl)-N-butyl-2-[3-(2-hydroxyethyl)-3-isoamylureido]propionamide (Compound No. 19-20)

EXAMPLE 20

(2S)-2-[3-(2-Hydroxyethyl)-3-isoamylureido]-N-methyl-3-phenylpropionamide (Compound No. 20-1)

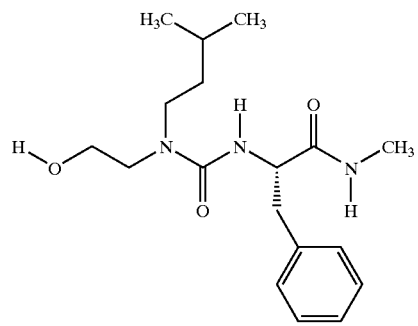

In anhydrous tetrahydrofuran (7 ml) are suspended N-methyl-L-phenylalanine amide hydrochloride (Reference compound No. 8-2, 429 mg), 1,1'-carbonyldiimidazole (422 mg) and imidazole (136 mg) under a nitrogen atmosphere, and the suspension is stirred at room temperature for 20 minutes. A solution of N-(2-hydroxyethyl)isoamylamine (Reference compound No. 13-2, 525 mg) in anhydrous tetrahydrofuran (3 ml) is added to the reaction mixture, and the mixture is refluxed for 0.5 hour. The reaction mixture is concentrated under reduced pressure, a 10% aqueous citric acid solution is added to the concentrate, and the whole is extracted with ethyl acetate. The organic layer is washed with a 10% aqueous citric acid solution, water and saturated brine successively, dried over anhydrous magnesium sulfate and concentrated under reduced pressure. The resulting oily matter is purified by silica gel column chromatography to give 626 mg (93%) of the titled compound (Compound No. 20-1).

(Compound No. 20-1)

$[\alpha]_D^{20}$ +9.4° (c=0.24, methanol); IR (Film, cm$^{-1}$) 3295, 2955, 1625, 1537, 1234, 1051.

The following compounds are obtained by a method similar to Example 20.

(2S)-2-[3-(2-Hydroxyethyl)-3-isobutylureido]-N-methyl-3-phenylpropionamide (Compound No. 20-2)

$[\alpha]_D^{20}$ +8.3° (c=0.54, methanol); IR (Film, cm$^{-1}$) 3296, 2958, 1626, 1531, 1339, 1269, 1042.

(2S)-2-[3-(2-Hydroxyethyl)-3-(4-methylpentyl)ureido]-N-methyl-3-phenylpropionamide (Compound No. 20-3)

$[\alpha]_D^{20}$ −3.5° (c=0.56, chloroform); IR (Film, cm$^{-1}$) 3340, 2954, 1630, 1531, 1468, 1411, 1367, 1231, 1164, 1051.

(2S)-2-[3-(3,3-Dimethylbutyl)-3-(2-hydroxyethyl)ureido]-N-methyl-3-phenylpropionamide (Compound No. 20-4)

IR (Film, cm$^{-1}$) 3294, 2954, 2360, 1625, 1534, 1411, 1365, 1246, 1051, 754, 699.

(2S)-2-[3-(2-Hydroxyethyl)-3-phenethylureido]-N-methyl-3-phenylpropionamide (Compound No. 20-5)

$[\alpha]_D^{20}$ −3.0° (c=0.49, chloroform); IR (Film, cm$^{-1}$) 3294, 2929, 1626, 1537, 1497, 1410, 1232, 750, 700.

(2S)-2-[3-[2-Hydroxy-1-(hydroxymethyl)ethyl]-3-isoamylureido]-N-methyl-3-phenylpropionamide (Compound No. 20-6)

$[\alpha]_D^{20}$ +4.6° (c=0.36, chloroform); IR (Film, cm$^{-1}$) 3305, 2955, 1626, 1519, 1455, 1411, 1367, 1239, 1048, 754, 700.

(2S)-2-[3-[(1RS)-2-Hydroxy-1-(phenylthiomethyl)ethyl]-3-isoamylureido]-N-methyl-3-phenylpropionamide (Compound No. 20-7)

IR (Film, cm$^{-1}$) 3297, 2955, 1626, 1519, 1237, 1088, 1026, 748, 699.

(2S)-N,N-Dimethyl-2-[3-(2-hydroxyethyl)-3-isoamylureido]-3-phenylpropionamide (Compound No. 20-8)

$[\alpha]_D^{20}$ +45.1° (c=0.99, chloroform); IR (Film, cm$^{-1}$) 3349, 2955, 1632, 1530, 1422, 1235, 1054, 754, 701.

(2S)-N,N-Dimethyl-2-[3-(3-hydroxypropyl)-3-isoamylureido]-3-phenylpropionamide (Compound No. 20-9)

$[\alpha]_D^{20}$ +43.2° (c=1.0, chloroform); IR (Film, cm$^{-1}$) 3418, 2955, 1634, 1538, 1240, 1058, 946, 752, 702.

(2S)-N,N-Dimethyl-2-[3-(4-hydroxybutyl)-3-isoamylureido]-3-phenylpropionamide (Compound No. 20-10)

IR (Film, cm$^{-1}$) 3418, 2927, 1628, 1522, 754, 701.

(2S)-N,N-Dimethyl-2-[3-[(1RS)-2-hydroxy-1-phenylethyl]-3-isoamylureido]-3-phenylpropionamide (Compound No. 20-11)

IR (Film, cm$^{-1}$) 3406, 2955, 1626, 1495, 753, 701.

(2S)-N,N-Dimethyl-2-[3-[(1RS)-1-(hydroxymethyl)-3-phenylpropyl]-3-isoamylureido]-3-phenylpropionamide (Compound No. 20-12)

(2S)-N,N-Dimethyl-2-[3-[(1RS)-2-hydroxy-1-(phenoxymethyl)ethyl]-3-isoamylureido]-3-phenylpropionamide (Compound No. 20-13)
IR (Film, cm$^{-1}$) 3413, 2955, 1628, 1497, 1243, 754.

(2S)-2-[3-(2-Hydroxyethyl)-3-isoamylureido]-N-methyl-4-phenylbutyramide (Compound No. 20-14)
$[\alpha]_D^{20}$ −17.3° (c=0.5, chloroform); IR (Film, cm$^{-1}$) 3292, 2955, 1624, 1537, 1410, 1234, 1052, 754, 700.

(2S)-2-[3-[(1R)-1-Benzyl-2-hydroxyethyl]-3-isoamylureido]-3-(4-biphenylyl)-N-butylpropionamide (Compound No. 20-15)
$[\alpha]_D^{20}$ +22.6° (c=0.70, dimethyl sulfoxide); IR (Film, cm$^{-1}$) 3421, 2957, 2060, 1626, 1558, 1520, 1291, 760, 698.

4-[(2S)-2-[3-[2-(1-Adamantyl)ethyl]-3-(2-hydroxyethyl)ureido]propionyl]morpholine (Compound No. 20-16)
$[\alpha]_D^{20}$ +6.1° (c=0.97, methanol); IR (Film, cm$^{-1}$) 3372, 2902, 2846, 1628, 1520, 1448, 1361, 1346, 1300, 1270, 1224, 1117, 1030, 754.

4-[(2S)-2-[3-(2-Cyclohexylethyl)-3-(2-hydroxyethyl)ureido]propionyl]morpholine (Compound No. 20-17)
$[\alpha]_D^{20}$ +6.5° (c=1.0, methanol); IR (Film, cm$^{-1}$) 3360, 2922, 2851, 1632, 1520, 1446, 1372, 1301, 1270, 1226, 1116, 1030, 754.

1-[(2S)-2-[3-[2-(1-Adamantyl)ethyl]-3-(2-hydroxyethyl)ureido]propionyl]-4-methylpiperazine (Compound No. 20-18)
IR (Film, cm$^{-1}$) 3356, 2902, 2846, 2796, 1628, 1522, 1448, 1374, 1292, 1221, 1144, 1051, 1002, 754.

EXAMPLE 21

(2S)-2-[3-[2-(Benzyloxy)ethyl]-1-isoamylureido]-N-[2-(dimethylamino)ethyl]-3-phenylpropionamide (Compound No. 21-1)

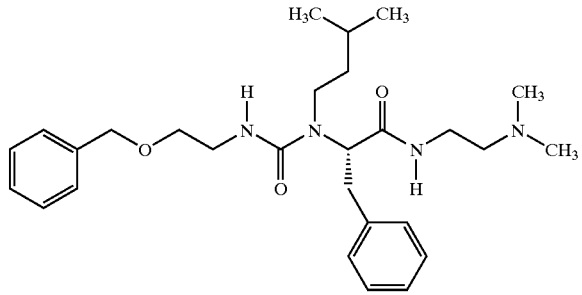

In anhydrous tetrahydrofuran (9 ml) are suspended 2-(benzyloxy)ethylamine hydrochloride (Reference compound No. 12-3, 203 mg), 1,1'-carbonyldiimidazole (233 mg) and imidazole (74 mg) under a nitrogen atmosphere, and the suspension is stirred at room temperature for 15 minutes. N$^1$-[2-(Dimethylamino)ethyl]-N$^2$-isoamyl-L-phenylalanine amide dihydiochloride (Reference compound No. 9-1, 341 mg) is added to the reaction mixture, and the mixture is refluxed overnight. The reaction mixture is concentrated under reduced pressure, a 10% aqueous sodium hydiogencarbonate solution is added to the concentrate, and the whole is extracted with ethyl acetate. The organic layer is washed with a 10% aqueous sodium hydrogencarbonate solution and saturated brine successively, dried over anhydrous sodium sulfate and concentrated under reduced pressure. The resulting oily matter is purified by silica gel column chromatography to give 386 mg (89%) of the titled compound (Compound No. 21-1).

(Compound No. 21-1)
$[\alpha]_D^{20}$ −43.5° (c=0.5, chloroform); IR (Film, cm$^{-1}$) 3294, 2952, 1634, 1524, 1455, 1366, 1289, 1099, 748, 699.

The following compounds are obtained by a method similar to Example 21.

2-[3-[(1R)-1-Benzyl-2-(benzyloxy)ethyl]-1-isoamylureido]-N-[2-(dimethylamino)ethyl]acetamide (Compound No. 21-2)
$[\alpha]_D^{20}$ +21.1° (c=(0.49, chloroform); IR (Film, cm$^{-1}$) 3384, 2956, 1634, 1527, 751.

2-[3-[(1S)-1-Benzyl-2-(benzyloxy)ethyl]-1-isoamylureido]-N-[2-(dimethylamino)ethyl]acetamide (Compound No. 21-3), enantiomer of Compound No. 21-2
$[\alpha]_D^{20}$ −21.8° (c=0.48, chloroform); IR (Film, cm$^{-1}$) 3295, 2953, 1633, 1533, 746, 699.

EXAMPLE 22

(2S)-N-[2-(Dimethylamino)ethyl]-2-[3-(2-hydroxyethyl)-1-isoamylureido]-3-phenylpropionamide (Compound No. 22-1)

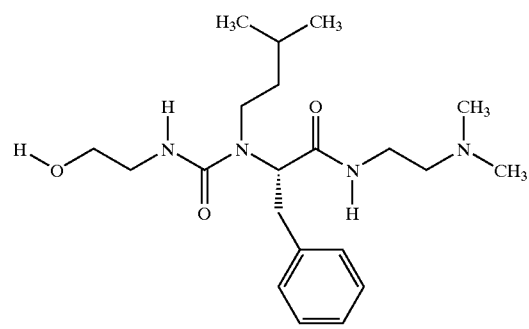

Under a nitrogen atmosphere, 20% palladium hydroxide on carbon (30 mg) is added to a solution of (2S)-2-[3-[2-(benzyloxy)ethyl]-1-isoamylureido]-N-[2-(dimethylamino)ethyl]-3-phenylpropionamide (Compound No. 21-1, 300 mg) in methanol (10 ml). The mixture is stirred under a hydrogen atmosphere for 4.5 hours. Palladium hydroxide on carbon is filtered out with Celite, and the filtrate is concentrated under reduced pressure. The concentrate is dissolved in ethyl acetate. The solution is washed with a 10% aqueous sodium hydrogencarbonate solution, water and saturated brine successively, dried over anhydrous sodium sulfate and concentrated under reduced pressure. The resulting oily matter is purified by silica gel column chromatography to give 167 mg (68%) of the titled compound (Compound No. 22-1).

(Compound No. 22-1)
$[\alpha]_D^{20}$ −44.8° (c=0.47, chloroform); IR (Film, cm$^{-1}$) 3320, 2953, 1657, 1629, 1531 , 1457, 1291, 1076, 751, 700.

The following compounds are obtained by a method similar to Example 22.

2-[3-[(1R)-1-Benzyl-2-hydroxyethyl]-1-isoamylureido]-N-[2-(dimethylamino)ethyl]acetamide (Compound No. 22-2)
$[\alpha]_D^{20}$ +17.8° (c=0.31, methanol); IR (Film, cm$^{-1}$) 3386, 2958, 1656, 1546, 1466, 1273, 1032, 750, 701.

2-[3-[(1S)-1-Benzyl-2-hydroxyethyl]-1-isoamylureido]-N-[2-(dimethylamino)ethyl]acetamide (Compound No. 22-3), enantiomer of Compound No. 22-2
$[\alpha]_D^{20}$ −40.6° (c=0.22, dimethyl sulfoxide); IR (KBr, cm$^{-1}$) 3413, 2957, 1636, 1542, 1248, 1088, 701.

EXAMPLE 23

1-[(2S)-2-[3-(2-Hydroxyethyl)-3-phenethylureido]-3-(4-hydroxyphenyl)propionyl]-4-methylpiperazine (Compound No. 23-1)

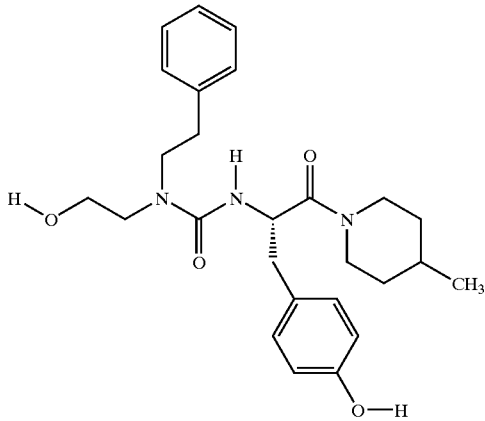

Under a nitrogen atmosphere, 20% palladium hydroxide on carbon (200 mg) is added to a solution of 1-[(2S)-2-[3-(2-hydroxyethyl)-3-phenethylureido]-3-[4-(benzyloxy)phenyl]propionyl]-4-methylpiperazine (Compound No. 18-40, 1.09 g) in tetrahydrofuran (2 ml)-methanol (2 ml). The mixture is stirred under a hydrogen atmosphere for three days. Palladium hydroxide on carbon is filtered out with Celite, and the filtrate is concentrated under reduced pressure to give 685 mg (75%) of the titled compound (Compound No. 23-1) as noncrystalline powder.

(Compound No. 23-1)

$[\alpha]_D^{20}$ +20.0° (c=0.54, methanol); IR (Film, cm$^{-1}$) 3364, 1626, 1515, 1452, 1229, 1029.

EXAMPLE 24

(2S)-3-(4-Aminophenyl)-N-[2-(dimethylamino)ethyl]-2-[3-(2-hydroxyethyl)-3-phenethylureido]propionamide (Compound No. 24-1)

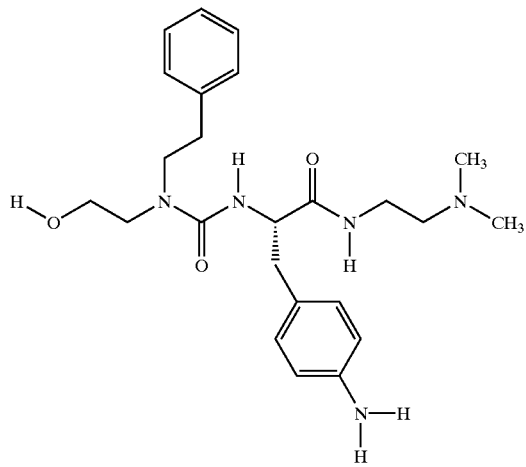

Under a nitrogen atmosphere, 5% palladium-carbon (92 mg) is added to a solution of (2S)-N-[2-(dimethylamino)ethyl]-2-[3-(2-hydroxyethyl)-3-phenethylureido]-3-(4-nitrophenyl)propionamide (Compound No. 19-1, 921 mg) in ethanol (30 ml). The mixture is stirred under a hydrogen atmosphere for three hours. Palladium-carbon is filtered out with Celite, and the filtrate is concentrated under reduced pressure. The resulting oily matter is purified by silica gel column chromatography to give 418 mg (49%) of the titled compound (Compound No. 24-1) as noncrystalline powder.

(Compound No. 24-1)

$[\alpha]_D^{20}$ −23.8° (c=0.48, chloroform); IR (Film, cm$^{-1}$) 3346, 2945, 1627, 1517, 1408, 1367, 1274, 1181, 1043, 753, 702.

EXAMPLE 25

(2S)-2-[3-(2-Acetoxyethyl)-3-phenethylureido]-3-[4-(acetylamino)phenyl]-N-[2-(dimethylamino)ethyl]propionamide (Compound No. 25-)

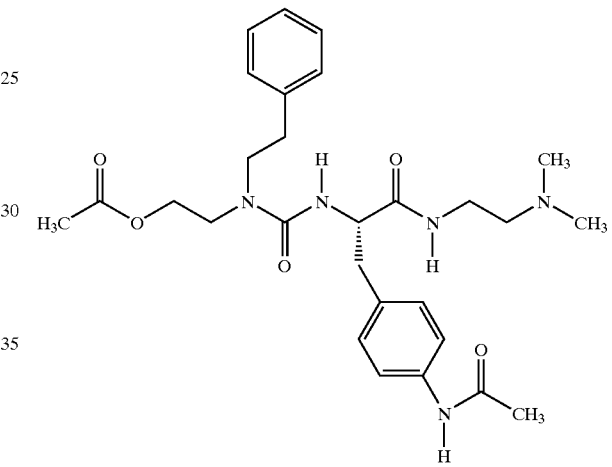

(2S)-3-(4-Aminophenyl)-N-[2-(dimethylamino)ethyl]-2-[3-(2-hydroxyethyl)-3-phenethylureido]propionamide (Compound No. 24-1, 265 mg) is dissolved in anhydrous methylene chloride (5 ml) under a nitrogen atmosphere, and the solution is stirred. To the solution are added triethylamine (152 mg) and then a solution of acetic anhydride (123 mg) in anhydrous methylene chloride (1 ml) dropwise under ice cooling, and the mixture is stirred as it is for 30 minutes and further at room temperature for 1.5 hours. The reaction mixture is concentrated under reduced pressure, a 10% aqueous sodium hydrogencarbonate solution is added to the residue, and the whole is extracted with ethyl acetate. The organic layer is washed with water and saturated brine successively, dried over anhydrous sodium sulfate and concentrated under reduced pressure. The resulting oily matter is purified silica gel column chromatography to give 200 mg (63%) of the titled compound (Compound No. 25-1) as crystals.

(Compound No. 25-1)

mp 87.0~100° C.; $[\alpha]_D^{20}$ −2.7° (c=0.50, chloroform); IR (KBr, cm$^{-1}$) 3292, 2943, 1742, 1665, 1625, 1539, 1455, 1412, 1370, 1319, 1232, 1040, 748, 702.

EXAMPLE 26

(2S)-3-[4-(Acetylamino)phenyl]-N-[2-(dimethylamino)ethyl]-2-[3-(2-hydroxyethyl)-3-phenethylureido]propionamide (Compound No. 26-1)

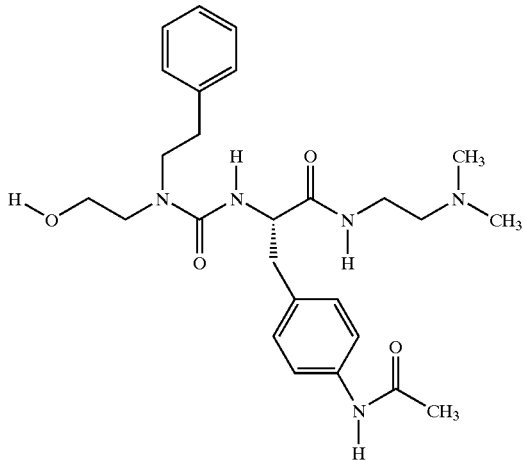

(2S)-2-[3-(2-Acetoxyethyl)-3-phenethylureidol]-3-[4-(acetylamino)phenyl]-N-[2-(dimethylamino)ethyl]propionamide (Compound No. 25-1, 158 mg) is dissolved in tetrahydrofuran (3 ml). A 1 N aqueous lithium hydroxide solution (1.7 ml) is added thereto under ice cooling, and the mixture is stirred for 40 minutes. The reaction mixture is extracted with chloroform. The organic layer is washed with saturated brine, dried over anhydrous sodium sulfate and concentrated under reduced pressure to give 140 mg (97%) of the titled compound (Compound No. 26-1) as crystals.

(Compound No. 26-1)

mp 132.0~137.0° C.; $[\alpha]_D^{20}$ −4.2° (c=0.51, chloroform); IR (KBr, cm$^{-1}$) 3288, 3095, 2939, 1667, 1613, 1541, 1411, 1372, 1320, 1242, 1052, 754, 700.

EXAMPLE 27

1-[(2S)-2-[3-[2-(Acetylthio)ethyl]-3-phenethylureido]-4-methylvaleryl]-4-methylpiperazine (Compound No. 27-1)

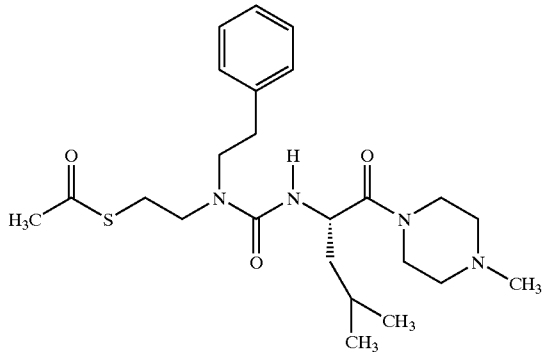

In anhydrous tetrahydrofuran (3 ml) are dissolved 1-[(2S)-2-[3-(2-hydroxyethyl)-3-phenethylureido]-4-methylvaleryl]-4-methylpiperazine (Compound No. 18-1, 500 mg) and triphenylphosphine (654 mg) under a nitrogen atmosphere, and the solution is stirred under salt-ice cooling for 30 minutes. To the solution are added a solution of diethyl azodicarboxylate (435 mg) in anhydrous tetrahydrofuran (1 ml) and a solution of thioacetic acid (0.2 ml) in anhydrous tetrahydrofuran (2 ml) successively dropwise while keeping liquid temperature at 5° C. The mixture is stirred for one hour, a 10% aqueous sodium hydrogencarbonate solution is added to the reaction mixture, and the whole is extracted with ether. The organic layer is washed with a 10% aqueous sodium hydrogencarbonate solution, water and saturated brine, dried over anhydrous magnesium sulfate and concentrated under reduced pressure. The resulting oily matter is purified by silica gel column chromatography to give 472 mg (82%) of the titled compound (Compound No. 27-1).

(Compound No. 27-1)

$[\alpha]_D^{20}$ +1.2° (c=1.0, methanol); IR (Film, cm$^{-1}$) 2953, 1689, 1633, 1447, 1290, 1217, 1172, 1141.

The following compounds are obtained by a method similar to Example 27.

1-[(2S)-2-[3-[3-(Acetylthio)propyl]-3-phenethylureido]-3-phenylpropionyl]-4-methylpiperazine (Compound No. 27-2)

$[\alpha]_D^{20}$ +10.4° (c=1.0, methanol); IR (Film, cm$^{-1}$) 3351, 2939, 1690, 1628, 1496, 1454, 1291, 1249, 1217, 1142, 1002, 753, 701.

1-[(2S)-2-[3-[(2RS)-2-(Acetylthio)propyl]-3-phenethylureido]-3-phenylpropionyl]-4-methylpiperazine (Compound No. 27-3)

IR (Film, cm$^{-1}$) 3370, 2937, 1684, 1633, 1497, 1454, 1355, 1291, 1248, 1218, 1143, 1116, 1002, 751, 701.

1-[(2RS)-2-[3-[2-(Acetylthio)ethyl]-3-phenethylureido]-4-(methylthio)butyryl]-4-methylpiperazine (Compound No. 27-4)

IR (Film, cm$^{-1}$) 3367, 2936, 2792, 1688, 1634, 1522, 1445, 1294, 1213, 1002, 750, 701.

1-[(2S)-2-[3-[2-(Acetylthio)ethyl]-3-phenethylureido]-3-(4-nitrophenyl)propionyl]-4-(t-butoxycarbonyl)piperazine (Compound No. 27-5)

$[\alpha]_D^{20}$ +6.9° (c=1.50, chloroform); IR (Film, cm$^{-1}$) 3368, 2977, 2929, 1694, 1640, 1520, 1417, 1365, 1346, 1286, 1235, 1167.

1-[(2S)-2-[3-[2-(Acetylthio)ethyl]-3-phenethylureidol]-3-(4-nitrophenyl)propionyl]-4-methylpiperazine (Compound No. 27-6)

$[\alpha]_D^{20}$ −2.0° (c=0.49, chloroform); IR (Film, cm$^{-1}$) 3368, 2939, 1687, 1633, 1519, 1447, 1346, 1291, 1217, 1142, 752, 700.

1-[(2S)-2-[3-[2-(Acetylthio)ethyl]-3-phenethylureido]-3-(4-nitrophenyl)propionyl]-4-cyclohexylpiperazine (Compound No. 27-7)

$[\alpha]_D^{20}$ −28.8° (c=0.53, dimethyl sulfoxide); IR (Film, cm$^{1}$) 3366, 2929, 1690, 1633, 1519, 1452, 1345, 1281, 1217, 1138.

1-[(2S)-2-[3-[2-(Acetylthio)ethyl]-3-phenethylureido]-3-(4-nitrophenyl)propionyl]-4-phenylpiperazine (Compound No. 27-8)

IR (Film, cm$^{-1}$) 3429, 1536, 1519, 1345, 1228, 757, 698.

1-[(2S)-2-[3-[2-(Acetylthio)ethyl]-3-phenethylureido]-3-(4-nitrophenyl)propionyl]-4-benzylpiperazine (Compound No. 27-9)

$[\alpha]_D^{20}$ −6.7° (c=1.0, chloroform); IR (Film, cm$^{-1}$) 3426, 1634, 1519, 1345, 744.

2S)-2-[3-[2-(Acetylthio)ethyl]-3-phenethylureido]-N-[2-diisopropylamino)ethyl]-3-(4-nitrophenyl)propionamide (Compound No. 27-10)

[α]$_D^{20}$ −38.1° (c=0.99, chloroform); IR (Film, cm$^{−1}$) 3442, 2968, 1628, 1521, 1345.

2S)-2-[3-[2-(Acetylthio)ethyl]-3-phenethylureido]-N-[2-(dicyclohexylamino)ethyl]-3-(4-nitrophenyl) propionamide (Compound No. 27-11)

[α]$_D^{20}$ −27.0° (c=0.52, chloroform); IR (Film, cm$^{−1}$) 3428, 2929, 1628, 1520, 1345.

2S)-2-[3-[2-(Acetylthio)ethyl]-3-phenethylureido]-N-[2-(4-mehylpiperazin-1-yl)ethyl]-3-(4-nitrophenyl) propionamide (Compound No. 27-12)

mp 103.0~105.5° C. (decomp.); [α]$_D^{20}$ −19.4° (c=0.50, chloroform); IR (KBr, cm$^{−1}$) 3289, 2936, 2794, 1694, 1664, 1619, 1519, 1347, 1284, 1166, 747, 699.

(2S)-2-[3-[2-(Acetylthio)ethyl]-3-phenethylureido]-N-[2-(t-butoxycarboxamido)ethyl-3-(4-nitrophenyl) propionamide (Compound No. 27-13)

mp 66.4~73.7° C.; [α]$_D^{20}$ −11.3° (c=1.52, methanol); IR (KBr, cm$^{−1}$) 3305, 2977, 2932, 1711, 1697, 1658, 1622, 1520, 1346, 750.

1-[(2S)-2-[3-[2-(Acetylthio)ethyl]-3-phenethylureido]-3-(4-nitrophenyl)propionyl]piperidine (Compound No. 27-14)

[α]$_D^{20}$ +3.5° (c=0.51, chloroform); IR (Film, cm$^{−1}$) 3369, 2939, 1688, 1633, 1519, 1445, 1345, 1215, 1136, 749, 700.

4-[(2S)-2-[3-[2-(Acetylthio)ethyl]-3-phenethylureido]-3-(4-nitrophenyl)propionyl]morpholine (Compound No. 27-15)

[α]$_D^{20}$ −2.6° (c=0.50, chloroform); IR (Film, cm$^{−1}$) 3422, 1634, 1519, 1346, 1114, 749, 700.

(2S)-2-[3-[2-(Acetylthio)ethyl]-3-phenethylureido]-N-(t-butoxycarbonyl)methyl-3-(4-nitrophenyl) propionamide (Compound No. 27-16)

mp 125.5~130.0° C.; [α]$_D^{20}$ −39.2° (c=0.53, chloroform); IR (KBr, cm$^{−1}$) 3299, 2981, 1741, 1674, 1620, 1522, 1348, 1222, 1155.

(2S)-2-[3-[2-(Acetylthio)ethyl]-3-phenethylureido]-3-(4-chlorophenyl)-N-[2-(dimethylamino)ethyl] propionamide (Compound No. 27-17)

mp 111.0~115.0° C.; [α]$_D^{20}$ −12.0° (c=0.31, chloroform); IR (KBr, cm$^{−1}$) 3290, 2939, 1663, 1618, 1545, 1493, 1454, 1355, 1229.

(2S)-2-[3-[2-(Acetylthio)ethyl]-3-isoamylureido]-N-methyl-3-(4-nitrophenyl) propionamide (Compound No. 27-18)

mp 109.0~116.0° C.; [α]$_D^{20}$ −35.0° (c=0.50, chloroform); IR (KBr, cm$^{−1}$) 3303, 2957, 1694, 1668, 1617, 1516, 1469, 1346, 1237, 1134, 1109.

(2S)-2-[3-[2-(Acetylthio)ethyl]-3-phenethylureido]-N-[2-(dimethylamino)ethyl]-3-(2-nitro-4-biphenylyl) propionamide (Compound No. 27-19)

mp 90° C.; [α]$_D^{20}$ −24.1° (c=0.52, chloroform); IR (KBr, cm$^{−1}$) 3286, 2940, 1692, 1664, 1621, 1530, 1355, 700.

(2S)-2-[3-[2-(Acetylthio)ethyl]-3-phenethylureido]-3-[4-(benzenesulfonyl)-3-nitrophenyl]-N-[2-(dimethylamino)ethyl]propionamide (Compound No. 27-20)

[α]$_D^{20}$ −22.3° (c=0.55, chloroform); IR (Film, cm$^{−1}$) 3305, 2943, 1668, 1628, 1544, 1160, 753.

1-[(2S)-2-[3-[2-(Acetylthio)ethyl]-3-phenethylureido]-3-(2-naphthyl)propionyl]-4-methylpiperazine (Compound No. 27-21)

[α]$_D^{20}$ +14.5° (c=1.1, methanol); IR (Film, cm$^{−1}$) 2937, 1688, 1632, 1527, 1447, 1216, 1142.

1-[(2R)-2-[3-[2-(Acetylthio)ethyl]-3-phenethylureido]-3-(methylthio)propionyl]-4-methylpiperazine (Compound No. 27-22)

[α]$_D^{20}$ −6.0° (c=0.5, methanol); IR (Film, cm$^{−1}$) 3368, 2937, 2794, 1689, 1636, 1525, 1446, 1356, 1292, 1253, 1212, 1142, 1001, 751, 701.

1-[(2R)-2-[3-[2-(Acetylthio)ethyl]-3-phenethylureido]-3-(benzylthio)propionyl]-4-methylpiperazine (Compound No. 27-23)

[α]$_D^{20}$ −23.4° (c=0.50, methanol); IR (Film, cm$^{−1}$) 3367, 2938, 2794, 1689, 1633, 1494, 1453, 1356, 1293, 1213, 1141, 1002, 753, 701.

1-[(2S)-2-[3-[2-(Acetylthio)ethyl]-3-phenethylureido]-3-phenylpropionyl]-4-methylpiperazine (Compound No. 27-24)

[α]$_D^{20}$ +19.6° (c=0.52, methanol); IR (Film, cm$^{−1}$) 3359, 2937, 1689, 1631, 1526, 1453, 1215, 1142, 751, 700.

1-Methyl-4-[(2S)-2-[3-phenethyl-3-[2-(pivaloylthio)ethyl]ureido]-3-phenylpropionyl]piperazine (Compound No. 27-25)

[α]$_D^{20}$ +19.3° (c=0.98, methanol); IR (Film, cm$^{−1}$) 3349, 2968, 2936, 1675, 1632, 1525, 1455, 950, 750, 700.

1-Methyl-4-[(2S)-2-[3-[2-(nicotinoylthio)ethyl]-3-phenethylureido]-3-phenylpropionyl]piperazine (Compound No. 27-26)

[α]$_D^{20}$ +17.3° (c=0.57, methanol); IR (Film, cm$^{31\ 1}$) 3370, 2938, 1632, 1528, 1453, 1218, 916, 751, 701.

1-[(2R)-2-[3-[2-(Acetylthio)ethyl]-3-phenethylureido]-3-phenylpropionyl]-4-methylpiperazine (Compound No. 27-27), enantiomer of Compound No. 27-24

[α]$_D^{20}$ −18.1° (c=0.52, methanol); IR (Film, cm$^{−1}$) 3364, 2937, 2794, 1687, 1636, 1522, 1496, 1453, 1291, 1142, 750, 700.

(2S)-2-[3-[2-(Acetylthio)ethyl]-3-phenethylureido]-N-[2-(dimethylamino)ethyl]-3-(4-isopropoxyphenyl) propionamide (Compound No. 27-28)

mp 110.0~112.5° C.; [α]$_D^{20}$ −4.3° (c=0.30, chloroform); IR (KBr, cm$^{−1}$) 3283, 2974, 1695, 1664, 1618, 1550, 1510, 1240, 1132, 954, 750, 702.

1-[(2S)-2-[3-[(1RS)-2-(Acetylthio)-1-(dimethylaminomethyl)ethyl]-3-phenethylureido]-3-phenylpropionyl]-4-methylpiperazine (Compound No. 27-29)

[α]$_D^{20}$ +11.8° (c=0.56, methanol); IR (Film, cm$^{−1}$) 2939, 2793, 1690, 1633, 1455, 1292, 1142, 752.

(2S)-2-[3-[2-(Acetylthio)ethyl]-3-isoamylureido]-N-[2-(dimethylamino)ethyl]-3-phenylpropionamide (Compound No. 27-30)

[α]$_D^{20}$ +5.5° (c=0.50, chloroform); IR (Film, cm$^{−1}$) 3285, 2954, 1694, 1659, 1620, 1544, 1228, 1135.

(2S)-2-[3-[2-(Acetylthio)ethyl]-3-isoamylureido]-N-[(1S)-1-(methylcarbamoyl)ethyl]-3-phenylpropionamide (Compound No. 27-31)

[α]$_D^{20}$ −7.6° (c=1.0, chloroform); IR (Film, cm$^{−1}$) 3293, 3064, 1629, 1534, 1227, 1135, 754, 700.

(2S)-2-[3-[2-(Acetylthio)ethyl]-3-isoamylureido]-3-(4-methoxyphenyl)-N-methylpropionamide (Compound No. 27-32)

mp 113.0~118.0° C.; [α]$_D^{20}$ −9.1° (c=0.52, chloroform); IR (KBr, cm$^{−1}$) 3309, 2959, 1695, 1667, 1616, 1545, 1514, 1247, 1136, 1036, 948, 832.

(2S)-2-[3-[2-(Acetylthio)ethyl]-3-isoamylureido]-N-methyl-2-phenylacetamide (Compound No. 27-33)

[α]$_D^{20}$ +1.3° (c=0.79, chloroform); IR (Film, cm$^{−1}$) 3304, 2956, 2360, 1688, 1629, 1513, 1411, 1355, 1214, 1135, 950, 755, 698.

1-[(2S)-2-[3-[2-(Acetylthio)ethyl]-3-isoamylureido]-4-methylvaleryl]-4-methylpiperazine (Compound No. 27-34)

[α]$_D^{20}$ +8.0° (c=0.51, methanol); IR (Film, cm$^{-1}$) 2954, 2868, 1691, 1632, 1462, 1291, 1140.

(2S)-2-[3-[2-(Acetylthio)ethyl]-3-isoamylureido]-N,4-dimethylvaleramide (Compound No. 27-35)

[α]$_D^{20}$ −24.4° (c=0.97, chloroform); IR (Film, cm$^{-1}$) 3295, 2956, 1661, 1623, 1537, 1235, 1136, 757.

2-[3-[2-(Acetylthio)ethyl]-3-isoamylureido]-N-methylacetamide (Compound No. 27-36)

IR (Film, cm$^{-1}$) 3399, 2956, 1633, 1535, 1412, 1299, 1236, 1136, 951, 756.

(2S)-2-[3-[2-(Acetylthio)ethyl]-3-isoamylureido]-3-cyclohexyl-N-methylpropionamide (Compound No. 27-37)

[α]$_D^{20}$ −23.1° (c=0.54, chloroform); IR (Film, cm$^{-1}$) 3295, 2923, 1693, 1660, 1623, 1537, 1489, 1448, 1355, 1235, 1136.

(2S)-2-[3-[2-(Acetylthio)ethyl]-3-isoamylureido]-3-(4-imidazolyl)-N-methylpropionamide (Compound No. 27-38)

[α]$_D^{20}$ −16.1° (c=0.12, chloroform); IR (Film, cm$^{-1}$) 3292, 2956, 2361, 1633, 1532, 1411, 1236, 1135, 950, 756.

(2S)-2-[3-[2-(Acetylthio)ethyl]-3-isoamylureido]-N-methyl-5-(3-tosylguanidino)valeramide (Compound No. 27-39)

[α]$_D^{20}$ −7.2° (c=0.51, chloroform); IR (Film, cm$^{-1}$) 3338, 2955, 1630, 1549, 1410, 1259, 1132, 1083, 755.

1-[(2S)-2-[3-[2-(Acetylthio)ethyl]-1-methyl-3-phenethylureido]propionyl]-4-methylpiperazine (Compound No. 27-40)

[α]$_D^{20}$ −14.6° (c=1.0, chloroform); IR (Film, cm$^{-1}$) 2937, 2792, 1692, 1644, 1548, 1141, 1076.

(2S)-2-[3-[2-(Acetylthio)ethyl]-3-phenethylureido]-N-[2-(dimethylamino)ethyl]-3-(4-nitrophenyl)propionamide (Compound No. 27-41)

mp 71~86° C.; [α]$_D^{20}$ −30.7° (c=0.49, chloroform); IR (KBr, cm$^{-1}$) 3292, 3085, 1693, 1664, 1621, 1519, 1347, 1287, 1227, 1135, 951, 860, 748, 700.

(2S)-2-[3-[2-(Benzoylthio)ethyl]-3-phenethylureido]-N-[2-(dimethylamino)ethyl]-3-(4-nitrophenyl)propionamide (Compound No. 27-42)

[α]$_D^{20}$ −56.5° (c=0.47, chloroform); IR (Film, cm$^{-1}$) 3408, 1632, 1519, 1345, 1208, 913, 750, 690.

(2S)-2-[3-[2-(Acetylthio)ethyl]-3-phenethylureido]-N-[3-(dimethylamino)propyl]-3-(4-nitrophenyl)propionamide (Compound No. 27-43)

IR (Film, cm$^{-1}$) 3282, 2942, 1691, 1663, 1618, 1520, 1346, 750.

(2S)-2-[3-[2-(Acetylthio)ethyl]-3-phenethylureido]-N-[2-(4-morpholinyl)ethyl]-3-(4-nitrophenyl)propionamide (Compound No. 27-44)

[α]$_D^{20}$ −31.4° (c=0.50, chloroform); IR (Film, cm$^{-1}$) 3368, 2941, 1667, 1631, 1519, 1454, 1346, 1116, 701.

(2S)-2-[3-[2-(Acetylthio)ethyl]-3-phenethylureido]-3-(4-nitrophenyl)-N-[2-(phthalimido)ethyl]propionamide (Compound No. 27-45)

mp 110° C.; [α]$_D^{20}$ −41.6° (c=0.53, chloroform); IR (KBr, cm$^{-1}$) 3284, 1716, 1668, 1618, 1519, 1395, 1345, 1280, 1227, 1137, 1108, 720, 703.

(2S)-2-[3-[2-(Acetylthio)ethyl]-3-phenethylureido]-N-[2-[(N-methyl)cyclohexylamino]ethyl]-3-(4-nitrophenyl)propionamide (Compound No. 27-46)

mp 90° C.; [α]$_D^{20}$ −29.7° (c=0.47, chloroform); IR (KBr, cm$^{-1}$) 3295, 2930, 1693, 1661, 1622, 1520, 1452, 1346, 1281, 1136.

(2S)-2-[3-[2-(Acetylthio)ethyl]-3-phenethylureido]-N-[2-(diethylamino)ethyl]-3-(4-nitrophenyl)propionamide (Compound No. 27-47)

mp 65° C.; [α]$_D^{20}$ −34.7° (c=0.49, chloroform); IR (KBr, cm$^{-1}$) 3293, 2970, 1692, 1620, 161 2, 1520, 1452, 1346, 1228, 1135.

(2S)-2-[3-[2-(Acetylthio)ethyl]-3-phenethylureido]-N-[2-[(N-methyl)phenylamino]ethyl]-3-(4-nitrophenyl)propionamide (Compound No. 27-48).

mp 129.0~131.0° C.; [α]$_D^°$ −44.1° (c=0.51, chloroform); IR (KBr, cm$^{-1}$) 3284, 2928, 1693, 1665, 1618, 1518, 1450, 1347, 1280, 1135.

(2S)-2-[3-[2-(Acetylthio)ethyl]-3-phenethylureido]-N-[4-(dimethylamino)butyl]-3-(4-nitrophenyl)propionamide (Compound No. 27-49)

[α]$_D^°$ −26° (c=0.53, chloroform); IR (Film, cm$^{-1}$) 3283, 2940, 1694, 1661, 1619, 1519, 1347, 748.

(2S)-2-[3-[2-(Acetylthio)ethyl]-3-phenethylureido]-3-(4-nitrophenyl)-N-[2-(2-pyridyl)ethyl]propionamide (Compound No. 27-50)

mp 106.0~112.5° C.; [α]$_D^°$ −39.5° (c=0.50, chloroform; IR (KBr, cm$^{-1}$) 3282, 3084, 2929, 1692, 1667, 1618, 1519, 1436, 1346, 1228, 1135, 1108, 749, 701.

(2S)-2-[3-[2-(Acetylthio)ethyl]-3-phenethylureido]-N-[3-(1-imidazolyl)propyl]-3-(4-nitrophenyl)propionamide (Compound No. 27-51) [α]$_D^°$ −33.9° (c=0.49, chloroform); IR (Film, cm1) 3294, 2938, 1672, 1630, 1519, 1346, 1227, 753.

(2S)-2-[3-[2-(Acetylthio)ethyl]-3-phenethylureido]-3-(4-nitrophenyl)-N-[2-(1-piperidyl)ethyl]propionamide (Compound No. 27-52)

mp 104.0~106.0° C.; [α]$_D^°$ −20.5° (c=0.53, chloroform); IR (KBr, cm$^{-1}$) 3291, 2934, 1694, 1664, 1620, 1520, 1347, 1132, 747, 700.

(2S)-2-[3-[2-(Acetylthio)ethyl]-3-phenethylureido]-N-[2-(dimethylamino)ethyl]-3-phenylpropionamide (Compound No. 27-53)

mp 11.51–114.5° C.; [α]$_D^°$ −3.7° (c=0.51, chloroform); IR (KBr, cm$^{-1}$) 3290, 2939, 1693, 1662, 1620, 1542, 1497, 1454, 1229, 1135, 749, 700.

(2S)-2-[3-[2-(Acetylthio)ethyl]-3-phenethylureido]-N-[2-(dimethylamino)ethyl]-3-(4-fluorophenyl)propionamide (Compound No. 27-54)

mp 90° C.; [α]$_D^°$ −6.1° (c=0.48, chloroform); IR (KBr, cm$^{-1}$) 3286, 2943, 1695, 1662, 1621, 1542, 1511, 1454, 1354, 1224, 1135, 949, 749, 700.

(2S)-2-[3-[2-(Acetylthio)ethyl]-3-phenethylureido]-N-[2-(dimethylamino)ethyl]-3-(4-hydroxyphenyl)propionamide (Compound No. 27-55) [α]$_D^°$ −20.8° (c=0.37, dimethyl sulfoxide); IR (Film, cm$^{-1}$) 3290, 2946, 1629, 1516, 1454, 1357, 1229, 1137, 1029, 952, 831, 753, 701.

(2S)-2-[3-[2-(Acetylthio)ethyl]-3-phenethylureido]-N-[2-(dimethylamino)ethyl]-3-(4-methoxyphenyl)propionamide (Compound No. 27-56)

mp 95.5~106.0° C. (decomp.) [α]$_D^°$ −5.3° (c=1.0, chloroform); IR (KBr, cm$^{-1}$) 3288, 2941, 1695, 1664, 1619, 1547, 1250.

(2S)-2-[3-[2-(Acetylthio)ethyl]-3-phenethylureido]-N-[2-(dimethylamino)ethyl]-3-(2-thienyl)propionamide (Compound No. 27-57)

mp 89.0~92.0° C. (decomp.); [α]$_D^°$ −8.4° (c=0.99, chloroform); IR (KBr, cm$^{-1}$) 3280, 2941, 1691, 1664, 1620, 1549, 1498, 1292, 1229, 1136, 700.

(2S)-2-[3-[2-(Acetylthio)ethyl]-3-phenethylureido]-N-[2-(dimethylamino)ethyl]-3-(2-naphthyl)propionamide (Compound No. 27-58)

[α]$_D^°$ −7.2° (c=0.50, chloroform); IR (Film, cm$^{-1}$) 3291, 2942, 1690, 1660, 1622, 1538, 751.

(2S)-2-[3-[2-(Acetylthio)ethyl]-3-phenethylureido]-3-(4-biphenylyl)-N-[2-(dimethylamino)ethyl]propionamide (Compound No. 27-59)

$[\alpha]_D°$ −10.5° (c=1.0, chloroform); IR (Film, cm$^{-1}$) 3294, 2942, 1663, 1626, 1535, 1488, 759, 700.

(2S)-2-[3-[2-(Acetylthio)ethyl]-3-isoamylureido]-N-[2-(dimethylamino)ethyl]-3-(4-nitrophenyl)propionamide (Compound No, 27-60)

mp 112.5~114.5° (decomp.); $[\alpha]_D°$ −20.1° (c=0.51, chloroform); IR (KBr, cm$^{-1}$) 3290, 2954, 1696, 1663, 1618, 1520, 1349, 1237, 1137, 954, 860.

(2S)-2-[3-[2-(Acetylthio)ethyl]-3-isoamylureido]-2-butylpropionamide (Compound No. 27-61)

mp 101.5~103.7° C.; $[\alpha]_D°$ −22.9(c0.51, dimethyl sulfoxide); IR (KBr, cm$^{-1}$) 3279, 3096, 2958, 1696, 1664, 1617, 1546, 1227, 1135, 759, 698.

(2S)-2-[3-[2-(Acetylthio)ethyl]-3-isoamylureido]-N-3-methyl-3-phenylpropionamide (Compound No. 27-62)

mp 116.5~120.5° C.; $[\alpha]_D°$ −16.5° (c=0.97, chloroform); IR (KBr, cm$^{-1}$) 3299, 3087, 2955, 1695, 1671, 1620, 1544, 1412, 1230, 1135, 700.

(2S)-2-[3-[2-(Acetylthio)ethyl]-3-isobutylureido]-N-methyl-3-phenylpropionamide (Compound No. 27-63)

$[\alpha]_D°$ −6.7° (c=0.02, methanol); IR (KBr, cm$^{-1}$) 3299, 2960, 1693, 1664, 1621, 1543, 1135, 950.

(2S)-2-[3-[2-(Acetylthio)ethyl]-3-(4-methylpentyl)ureido]-N-methyl-3-phenylpropionamide (Compound No. 27-64)

$[a_D°$ −20.9° (c=009, chloroform); IR (KBr, cm$^{-1}$) 3298, 2954, 1691, 1661, 1622, 1537, 1494, 1410, 1367, 1136.

(2S)-2-[3-[2-(Acetylthio)ethyl]-3-(3,3-dimethylbutyl)ureido]-N-methyl-3-phenylpropionamide (Compound No. 27-65)

$[\alpha]_D°$ −13.1° (c=0.33, chloroform); IR (Film, cm$^{-1}$) 3294, 2956, 1693, 1666, 1620, 1537, 1411, 1228, 1136, 756.

(2S)-2-[3-[2-(Acetylthio)ethyl]-3-phenethylureido]-N-methyl-3-phenylpropionamide (Compound No. 27-66)

$[\alpha]_D°$ −21.7° (c=0.68, chloroform); IR (Film, cm$^{-1}$) 3295, 2934, 1689, 1661, 1622, 1536, 1410, 1228, 1136, 753, 700.

(2S)-2-[3-[2-(Acetylthio)-1-(acetylthiomethyl)ethyl]-3-isoamylureido]-N-methyl-3-phenylpropionamide (Compound No. 27-67)

$[\alpha]_D°$ −8.8° (c=0.93, chloroform); IR (Film, cm$^{-1}$) 3307, 2956, 1694, 1630, 1516, 1355, 1134, 957, 756.

(2S)-2-[3-[2-(Acetylthio)-1-(phenylthiomethyl)ethyl]-3-isoamylureido]-N-methyl-3-phenylpropionamide (Compound No. 27-68)

IR (Film, cm$^{-1}$) 2955, 1690, 1624, 1513, 1439, 1354, 1231, 1132, 956, 743, 696.

(2S)-2-[3-[2-(Acetylthio)ethyl]-3-isoamylureido]-N,N-dimethyl-3-phenylpropionamide (Compound No. 27-69)

$[\alpha]_D°$ +47.6° (c=0.50, chloroform); IR (Film, cm$^{-1}$) 3340, 2955, 1692, 1633, 1531, 1421, 1136, 952, 754, 701.

(2S)-2-[3-[3-(Acetylthio)propyl]-3-isoamylureido]-N,N-dimethyl-3-phenylpropionamide (Compound No. 27-70)

$[\alpha]_D°$ +34.3° (c=1.0, chloroform); IR (Film, cm$^{-1}$) 3343, 2955, 1694, 1634, 1531, 1494, 1267, 1134, 954, 753, 701.

(2S)-2-[3-[4-(Acetylthio)butyl]-3-isoamylureido]-N,N-dimethyl-3-phenylpropionamide (Compound No. 27-71) IR (Film, cm$^{-1}$) 2962, 1732, 1694, 1634, 1505, 1255, 755.

(2S)-2-[3-[(1RS)-2-(Acetylthio)-1-phenylethyl]-3-isoamylureido]-N,N-dimethyl-3-phenylpropionamide (Compound No. 27-72)

IR (Film, cm$^{-1}$) 2927, 1694, 1634, 1495, 756, 701.

(2S)-2-[3-[(1RS)-1-(Acetylthiomethyl)-3-phenylpropyl]-3-isoamylureido]-N,N-dimethyl-3-phenylpropionamide (Compound No. 27-73)

IR (Film, cm$^{-1}$) 3423, 2927, 1691, 1634, 1496, 1260, 1133, 754, 700.

(2S)-2-[3-[(1RS)-2-(Acetylthio)-1-phenoxymethyl)ethyl]-3-isoamylureido]-N,N-dimethyl-3-phenylpropionamide (Compound No. 27-74)

IR (Film, cm$^{-1}$) 2955, 1693, 1634, 1495, 1242, 755.

(2S)-2-[3-[2-(Acetylthio)ethyl]-3-isoamylureido]-N-methyl-4-phenylbutyramide (Compound No. 27-75)

$[\alpha]_D°$ −9.9° (c=0.50, chloroform); IR (Film, cm$^{-1}$) 3291, 2955, 1694, 1660, 1621, 1538, 1410, 1225, 1134, 749, 699.

(2S)-2-[3-[(1R)-2-(Acetylthio)-1-biphenylyl)-N-butylpropionamide (Compound No. 27-76)

$[\alpha]_D°$ −16.7° (c=1.1, dimethyl sulfoxide);

IR (Film, cm$^{-1}$) 3422, 3306, 2957, 1689, 1661, 1624, 1512, 1225, 1133, 759, 699.

(2S)-2-[3-[2-(Acetylthio)ethyl]-1-isoamylureido]-N-2-(dimethylamino)ethyl]-3-phenylpropionamide (Compound No. 27-77)

$[\alpha]_D°$ −43.7° (c=0.30, chloroform); IR (KBr, cm$^{-1}$) 3350, 2954, 1690, 1661, 1632, 1528, 1466, 1365, 1243, 1133, 753, 700.

2-[3-[(1R)-2-(Acetylthio)-1-benzylethyl]-1-isoamylureido]-N-2-(dimethylamino)ethyl]acetamide (Compound No. 27-78)

2-[3-[(1S)-2-(Acetylthio)-1-benzylethyl]-1-isoamylureido]-N-[2-(dimethylamino)ethyl]acetamide (Compound No. 27-79), enantiomer of Compound No. 27-78

IR (Film, cm$^{-1}$) 3312, 2954, 1634, 1532, 1244, 752.

(2S)-2-[3-[2-(Acetylthio)ethyl]-3-isoamylureido]-6-(t-butoxycarboxamido)-N-methylhexanamide (Compound No. 27-80)

$[\alpha]_D°$ −14.6° (c=0.37, chloroform); IR (Film, cm$^{-1}$) 3305, 2955, 1693, 1624, 1534, 1365, 1248, 1172, 1136, 756.

1-[(2S)-2-[3-[2-(Acetylthio)ethyl]-3-phenethylureido]-3-(4-hydroxyphenyl)propionyl]-4-methylpiperazine (Compound No. 27-81)

$[\alpha]_D°$ +20.4° (c=0.50, methanol); IR (Film, cm$^{-1}$) 3232, 3009, 2940, 2800, 1684, 1626, 1515, 1450, 1248.

(2S)-3-[4-(Acetylamino)phenyl]-2-[3-[2-(acetylthio)ethyl]-3-phenethylureido]-N-[2-(dimethylamino)ethyl]propionamide (Compound No. 27-82)

mp 95° C. (decomp.); $[\alpha]_D°$ −5.3° (c=0.48, chloroform); IR (KBr, cm$^{-1}$) 3279, 2941, 1668, 1614, 1540, 1411, 1369, 1318, 1138, 750, 702.

(2S)-2-[3-[2-(Acetylthio)ethyl]-3-phenethylureido]-N-2-(t-butoxycarbonyl)ethyl]-3-(4-nitrophenyl)propionamide (Compound No. 27-83)

mp 142.0~143.5° C.; $[\alpha]_D°$ −35.0° (c=0.52, chloroform); IR (KBr, cm$^{-1}$) 3298, 1729, 1695, 1676, 1661, 1617, 1550, 1517, 1348, 1158, 747, 735, 697.

1-[(2S)-2-[3-[2-(Acetylthio)ethyl]-3-[2-(1-cyclohexenyl)ethyl]ureido]propionyl]-4-methylpiperazine (Compound No. 27-84)

$[\alpha]_D°$ +10.3° (c=1.1, methanol); IR (Film, cm$^{-1}$) 3370, 2929, 2793, 1690, 1632, 1529, 1447, 1292, 1214, 1140, 1002.

1-[(2S)-2-[3-[2-(Acetylthio)ethyl]-3-)3-butenyl)ureido]propionyl]-4-methylpiperazine (Compound No. 27-85)

$[\alpha]_D°$ +32.2° (c=0.50, chloroform); IR (Film, cm$^{-1}$) 3368, 2937, 1689, 1634, 1531, 31, 1447, 1291, 1214, 1141, 1002.

1-[2-[3-[2-(Acetylthio)ethyl]-3-(2-methylpropionyl)]-4-methylpiperazine (Compound No. 27-86)

IR (Film, cm$^{-1}$) 3369, 2923, 1644, 1524, 1426, 1291, 1224, 1169, 1139, 1004, 753.

1-[1-[3-[2-(Acetylthio)ethyl]-3-(2-cyclohexylethyl)ureido]-1-cyclopropanecarbonyl]-4-methylpiperazine (Compound No. 27-87) IR (Film, cm$^{-1}$) 3338, 2981, 2923, 2851, 1650, 1524, 1446, 1288, 1214, 1142, 1109, 754.

1-[1-[3-[2-(Acetylthio)ethyl]-3-(2-cyclohexylethyl)ureido]-1-cyclopentanecarbonyl]-4-methylpiperazine (Compound No. 27-88)

IR (Film, cm$^{-1}$) 3377, 2922, 2850, 2794, 1648, 1522, 1448, 1291, 1143, 1110, 753.

4-[(2S)-2-[3-[2-(Acetylthio)ethyl]-3-[2-(1-adamantyl)ethyl]ureido]propionyl]morpholine (Compound No. 27-89)

$[\alpha]_D^{\circ}$ +12.9° (c=1.0, methanol); IR (Film, cm$^{-1}$) 3380, 2902, 2847, 2677, 1692, 1633, 1514, 1446, 1357, 1296, 1271, 1238, 1214, 1116, 1030, 754.

4-[(2S)-2-[3-[2-(Acetylthio)ethyl]-3-(2-cyclohexylethyl)ureido]propionyl]morpholine (Compound No. 27-90)

1-[(2S)-2-[3-[2-(Acetylthio)ethyl]-3-[2-(1-adamantyl)ethyl]ureido]propionyl]-4-methylpiperazine (Compound No. 27-91)

EXAMPLE 28

(2S)-N,N-Dimethyl-2-[3-isoamyl-3-[2-methylthio)ethyl]ureido]-3-phenylpropionamide (Compound No. 28-1)

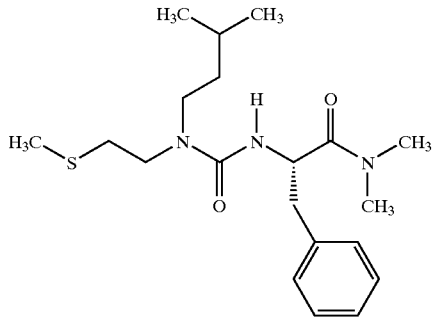

In anhydrous tetrahydrofuran (3.5 ml) are suspended N$^1$,N$^1$-dimethyl-L-phenylalanine amide hydrochloride (Reference compound No. 8-3, 206 mg), 1,1'-carbonyldiimidazole (190 mg) and imidazole (61 mg) under a nitrogen atmosphere, and the suspension is stirred at room temperature for 20 minutes. A solution of N-[2-(methylthio)ethyl]isoamylamine (Reference compound No. 13-28, 161 mg) in anhydrous tetrahydrofuran (1.5 ml) is added to the reaction mixture, and the mixture is refluxed for one hour. The reaction mixture is concentrated under reduced pressure, a 10% aqueous citric acid solution is added to the concentrate, and the whole is extracted with ether. The organic layer is washed with water and saturated brine successively, dried over anhydrous magnesium sulfate and concentrated under reduced pressure. The resulting oily matter is purified by silica gel column chromatography to give 306 mg (89%) of the titled compound (Compound No. 28-1).

(Compound No. 28-1)

$[\alpha]_D^{\circ}$ +39.1° (c=0.96, chloroform); IR (Film, cm$^{-1}$) 3338, 2955, 1632, 1496, 1420, 1295, 1236, 753, 701.

The following compounds are obtained by a method similar to Example 28.

(2S)-3-(4-Biphenylyl)-N-butyl-2-[3-isoamyl-3-[2-(methylthio)ethyl]ureido]propionamide (Compound No. 28-2)

mp 134.0~136.2° C.; $[\alpha]_D^{\circ}$ -17.5° (c=0.52, dimethyl sulfoxide); IR (KBr, cm$^{-1}$) 3284, 3090, 2957, 1667, 1617, 1546, 1236, 759, 697.

1-[(2S)-2-[3-(2-Cyclohexyl)ethyl-3-[2-(methylthio)ethyl]ureido]propionyl]-4-methylpiperazine (Compound No. 28-3)

IR (Film, cm$^{-1}$) 3352, 2921, 2850, 2794, 1633, 1506, 1447, 1292, 1213, 1142, 1002, 754.

1-[(2S)-2-[3-[2-(Methylthio)ethyl]-3-phenethylureido]propionyl]-4-methylpiperazine (Compound No. 28-4)

IR (Film, cm$^{-1}$) 3418, 2976, 2937, 2794, 1632, 1510, 1292, 1215.

(2S)-3-(4-Biphenylyl)-N-butyl-2-[3isoamyl-3-[2-(phenylthio)ethyl]ureido]propionamide (Compound No. 28-5)

mp 111.0~111.7° C.; $[\alpha]_D^{\circ}$ -15.2° (c=0.48, dimethyl sulfoxide); IR (KBr, cm$^{-1}$) 3284, 3078, 2956, 1666, 1617, 1550, 1234, 737, 690.

(2S)-3-(4-Biphenylyl)-N-butyl-2-[3-[(1RS)-1-(ethoxycarbonyl)-2-(phenylthio)ethyl]-3-isoamylureido]propionamide (Compound No. 28-6)

IR (Film, cm$^{-1}$) 3310, 2957, 1736, 1626, 1520, 1411, 1368, 1301, 1231, 1093.

(2S)-2-[3-[(2RS)-2-(t-Butoxycarbonyl)-3-(phenylthio)propyl]-3-isoamylureido]-N-methyl-3-phenylpropionamide (Compound No. 28-7)

$[\alpha]_D^{\circ}$ -28.2° (c=0.40, chloroform); IR (Film, cm$^{-1}$) 3299, 2956, 1712, 1664, 1624, 1536, 1150.

(2S)-2-[3-[(2RS)-2-(t-Butoxycarbonyl)-3-(phenylthio)propyl]-3-isobutylureido]-N-methyl-3-phenylpropionamide (Compound No. 28-8)

$[\alpha]_D^{\circ}$ -29.6° (c=0.48, chloroform); IR (Film, cm$^{-1}$) 3301, 2959, 1712, 1622, 1536, 1258, 1150.

1-[(2S)-2-[3-[2-(1-Adamantyl)ethyl]-3-[2-(methylthio)ethyl]ureido]propionyl]-4-methylpiperazine (Compound No. 28-9)

$[\alpha]_D^{\circ}$ +10° (c=1.0, methanol) IR (Film, cm$^{-1}$) 3419, 2903, 2846, 1632, 1508, 1448.

1-[(2S)-2-[3-(2-Cyclopentylethyl)-3-[2-(methylthio)ethyl]ureido]propionyl]-4-methylpiperazine (Compound No. 28-10)

$[\alpha]_D^{\circ}$ +8.3° (c=1.0, methanol); IR (Film, cm$^{-1}$) 3349, 2942, 1632, 1504, 1446.

1,1'-[(2S, 2'S)-2,2'-[3,3'-Bis(2-cyclohexylethyl)-3,3'-[2,2'-(dithio)diethyl]diureido]dipropionyl]-4,4'-dimethyldipiperazine (Compound No. 28-11)

IR (Film, cm$^{-1}$) 3350, 2922, 1632, 1510, 1447.

1,1'-[(2S, 2'S)-2,2'-[3,3'-Bis[2-(1-adamantyl)ethyl]-3,3'-2,2'-(dithio)diethyl]diureido]dipropionyl]-4,4'-dimethyldipiperazine (Compound No. 28-12)

1,1'-(Dimethyl)-4,4'-[(2S, 2'S)-2,2'-[3,3'-diphenethyl-3,3'-[2,2'-(dithio)diethyl]diureido]dipropionyl]dipiperazine (Compound No. 28-13)

IR (Film, cm$^{-1}$) 3352, 1632, 1454, 1292.

1,1'-Dimethyl-4,4'-[(2S, 2'S)-2,2'-[3,3'-[2,2'-(dithio)diethyl]diureido]dipropionyl]dipiperazine (Compound No. 28-14)

$[\alpha]_D^{\circ}$ -8.1° (c=1.0, methanol); IR (Film, cm$^{-1}$) 3341, 2976, 2938, 2796, 1632, 1555, 1446, 1367, 1293, 1237, 1173, 1144, 1074, 1034, 1002.

EXAMPLE 29

1-Methyl-4-[(2S)-2-[3-(3RS)-2-oxotetrahydrothiophen-3-yl]-1-phenethylureido]propionyl]piperazine (Compound No. 29-1)

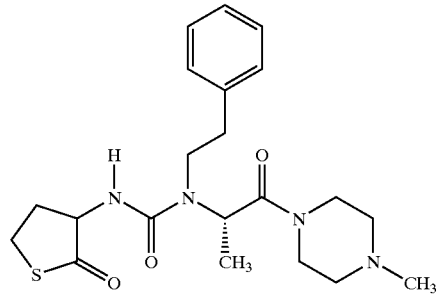

In anhydrous tetrahydrofuran (5 ml) are suspended DL-homocysteine thiolactone hydrochloride (280 mg), 1,1'-carbonyldiimidazole (324 mg) and imidazole (124 mg) under a nitrogen atmosphere, and the suspension is stirred at room temperature for 15 minutes. A solution of 1-methyl-4-[(2S)-2-(phenethylamino)propionyl]piperazine (Reference compound No. 10-3, 500 mg) in anhydrous tetrahydrofuran (5 ml) is added to the reaction mixture, and the mixture is refluxed for 20 minutes. A 10% aqueous sodium hydrogencarbonate solution is added to the reaction mixture, and the whole is extracted with ethyl acetate. The organic layer is washed with water and saturated brine successively, dried over anhydrous magnesium sulfate and concentrated under reduced pressure. The resulting oily matter is purified by silica gel column chromatography to give 592 mg (78%) of the titled compound (Compound No. 29-1).

(Compound No. 29-1)

IR (Film, cm$^{-1}$) 2940, 1704, 1632, 1524, 1454, 1291, 1253.

EXAMPLE 30

1-[(2S)-2-[3-(2-Mercaptoethyl)-3-phenethylureido]propionyl]-4-methylpiperazine (Compound No. 30-1)

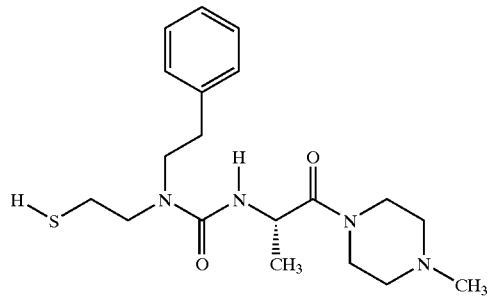

1-[(2S)-2-[3-[2-(Acetylthio)ethyl]-3-phenethylureido]propionyl]-4-methylpiperazine (Compound No. 13-2, 36.6 g) is dissolved in methanol (87 ml) under a nitrogen atmosphere, and the solution is cooled with ice. A 1 N aqueous sodium hydroxide solution (87 ml) is added dropwise thereto, and the mixture is stirred under ice cooling for 10 minutes. A 10% aqueous citric acid solution is added to the reaction mixture under ice cooling to adjust pH to 7. The mixture is concentrated under reduced pressure, a 10% aqueous sodium hydrogencarbonate solution (300 ml) is added to the concentrate, and the whole is extracted with ethyl acetate. The organic layer is washed with water and saturated brine successively, dried over anhydrous sodium sulfate and concentrated under reduced pressure. The resulting oily matter is purified by silica gel column chromatography to give the titled compound (Compound No. 30-1).

The following compounds are obtained by a method similar to Example 30.

1-[(2S)-2-[3-(2-Mercaptoethyl)-3-phenethylureido]butyryl]-4-methylpiperazine (Compound No. 30-2)

$[\alpha]_D^\circ$ +9.8° (c=0.44, methanol); IR (Film, cm$^{-1}$) 3345, 2936, 2793, 1630, 1529, 1451, 1293.

1-[(2S)-2-[3-(2-Mercaptoethyl)-3-phenethylureido]-3-phenylpropionyl]-4-methylpiperazine (Compound No. 30-3)

$[\alpha]_D^\circ$ +12.5° (c=0.52, methanol); IR (Film, cm$^{-1}$) 3343, 2937, 2795, 1628, 1528, 1452, 1291, 1215, 1144, 1002, 751, 700.

(2S)-6-(t-Butoxycarboxamido)-2-[3-isoamyl-3-(2-mercaptoethyl)ureido]-N-methylhexanamide (Compound No. 30-4)

mp 119.0~124.0° C.; $[\alpha]_D^\circ$ -14.5° (c=0.50, chloroform); IR (Film, cm$^{-1}$) 3322, 2934, 2545, 1711, 1653, 1619, 1530, 1410, 1366, 1246, 1166.

1-[(2S)-2-[3-(2-Mercaptoethyl)-3-phenethylureido]-3-phenylpropionyl]piperazine (Compound No. 30-5)

1-[(2S)-2-[3-(2-Cyclohexylethyl)-3-(2-mercaptoethyl)ureido]propionyl]-4-methylpiperazine (Compound No. 30-6)

mp 85.5~88.0° C.; IR (KBr, cm$^{-1}$) 2925, 2848, 2791, 2544, 1647, 1621, 1534, 1451, 1290, 1219, 1142.

1-[(2S)-2-[3-(2-Cyclopentylethyl)-3-(2-mercaptoethyl)ureido]propionyl]-4-methylpiperazine (Compound No. 30-7)

1-[(2S)-2-[3-[2-(1-Adamantyl)ethyl]-3-(2-mercaptoethyl)ureido]propionyl]-4-methylpiperazine (Compound No. 30-8)

EXAMPLE 31

1-[(2R)-3-Mercapto-2-[3-(2-mercaptoethyl)-3-phenethylureido]propionyl]-4-methylpiperazine (Compound No. 31-1)

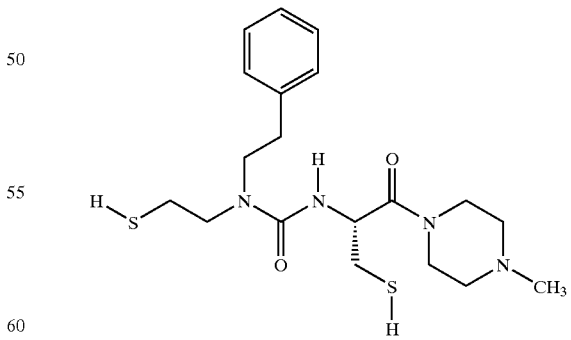

A solution of 1-[(2R)-3-(benzylthio)-2-[3-[2-benzylthio)ethyl]-3-phenethylureido]propionyl]-4-methylpiperazine (Compound No. 13-45, 1.05 g in anhydrous tetrahydrofuran (10 ml) is added dropwise to liquid ammonia (60 ml) under a nitrogen atmosphere and dry ice-methanol cooling metallic sodium (271 mg) by portions is added thereto until coloration does not disappear, and the mixture is stirred as it is for one hour. Crystalline ammonium chloride is added to the reaction mixture to decolorize it, and then a nitrogen gas is bubbled through the mixture at room temperature to evaporate ammonia. A 10% aqueous sodium hydrogencarbonate solution is added to the resulting residue, and the whole is extracted with ethyl acetate. The organic layer is washed with water and saturated brine successively, dried over anhydrous sodium sulfate and concentrated under reduced pressure to give the titled compound (Compound No. 31-1).

EXAMPLE 32

1-[(2S)-2-[3-[2-(Benzoylthio)ethyl]-3-phenethylureido]propionyl]-4-methylpiperazine
(Compound No. 32-1)

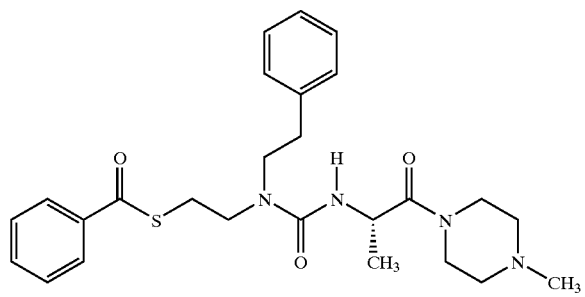

1-[(2S)-2-[3-(2-Mercaptoethyl)-3-phenethylureido]propionyl]-4-methylpiperazine (Compound No. 30-1, 32.9 g)is dissolved in chloroform (87 ml) under a nitrogen atmosphere, and the solution is stirred. To the solution are added triethylamine (13.3 ml) and then benzoyl chloride (10.1 ml )dropwise under ice cooling, and the mixture is stirred for 25 minutes. The reaction mixture is concentrated under reduced pressure, a 10% aqueous sodium hydrogencarbonate solution is added to the residue, and the whole is extracted with ethyl acetate. The organic layer is washed with a 10% aqueous sodium hydrogencarbonate solution, water and saturated brine successively, dried over anhydrous sodium sulfate and concentrated under reduced pressure. The resulting oily matter is purified by silica gel column chromatography to give the titled compound (Compound No. 32-1).

(Compound No. 32-1)

IR (Film, cm$^{-1}$) 3374, 2937, 2794, 1637, 1529, 1448, 1366, 1292, 1209, 1175, 1144, 1030, 1001.

The following compounds are obtained by a method similar to Example 32.

1-[(2S)-2-[3-[2-(Isopropylcarbamoylthio)ethyl]-3-phenethylureido]propionyl]-4-methylpiperazine
(Compound No. 32-2)

$[\alpha]_D^\circ$ +18.7° (c=1.0, chloroform); IR (Film, cm$^{-1}$) 3264, 2974, 2938, 2797, 1632, 1536, 1454, 1362, 1291, 1218, 1172, 1144.

1-[(2R)-3-(Acetylthio)-2-[3-[2-(acetylthio)ethyl]-3-phenethylureido]propionyl]-4-methylpiperazine
(Compound No. 32-3)

$[\alpha]_D^\circ$ -24.3° (c=0.53, methanol); IR (Film, cm$^{-1}$) 3363, 2937, 2794, 1689, 1638, 1528, 1450, 1355, 1293, 1255, 1212, 1138, 1001, 954, 752, 702.

EXAMPLE 33

(2S, 2'S)-N,N'-Bis[2-(t-butoxycarboxamido)ethyl]-3,3'-bis(4-nitrophenyl)-2,2'-[3,3'-diphenethyl-3,3'-[2,2'-(dithio)diethyl]diureido]bis(propionamide)
(Compound No. 33-1)

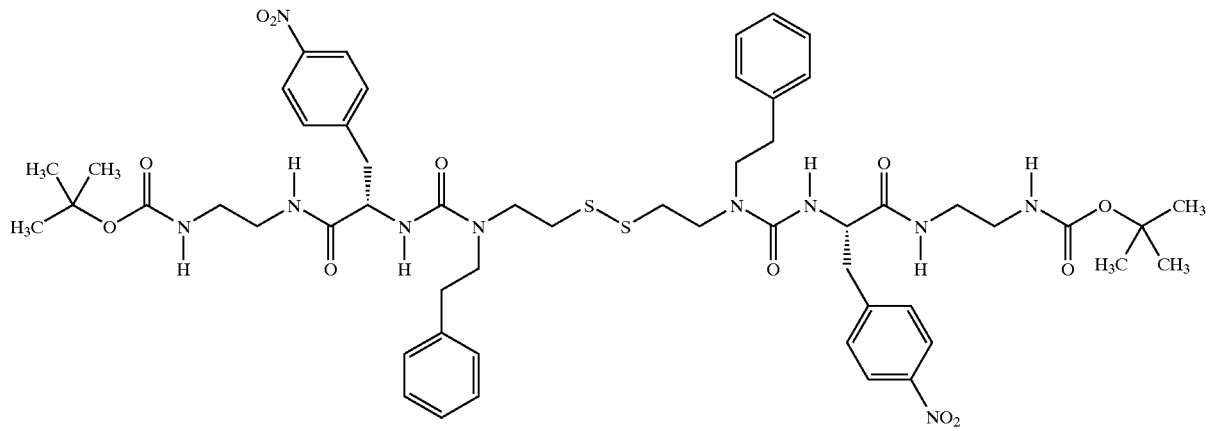

(2S)-2-[3-[2-(Acetylthio)ethyl]-3-phenethylureido]-N-[2-(t-butoxycarboxamido)ethyl]-3-(4-nitrophenyl) propionamide (Compound No. 27-13, 800 mg) is dissolved in tetrahydrofuran (5 ml), 1 N aqueous ammonium (7 ml) is added to the solution, and the mixture is stirred at room temperature for 3.5 days. Water is added to the reaction mixture, and the whole is extracted with ethyl acetate. The organic layer is washed with saturated brine, dried over anhydrous sodium sulfate and concentrated under reduced pressure. The resulting oily matter is purified by silica gel column chromatography to give 738 mg (99%) of the titled compound (Compound No. 33-1).

(Compound No. 33-1)

$[\alpha]_D^\circ$ -15.3° (c=0.57, methanol); IR (Film, cm$^{-1}$) 3293, 2977, 2933, 1708, 1660, 1619, 1520, 1346, 1168, 755.

The following compounds are obtained by a method similar to Example 33.

(2S, 2'S)-N,N'-Bis[2-(dimethylamino)ethyl]-3,3'-bis(4-nitrophenyl)-2,2'-[3,3'-diphenethyl-3,3'-[2,2'-(dithio)diethyl]diureido]bis(propionamide) (Compound No. 33-2)

$[\alpha]_D^\circ$ -21.0° (c=0.48, chloroform); IR (Film, cm$^{-1}$) 3291, 2940, 1658, 1620, 1520, 1346, 751.

(2S, 2'S)-2,2'-[3,3'-Diisobutyl-3,3'-[2,2'-(dithio)diethyl] diureido]-N,N-dimethyl-3,3'-diphenylbis(propionamide) (Compound No. 33-3)

IR (KBr, cm$^{-1}$) 3298, 3090, 2960, 1664, 1621, 1538, 1386, 1366.

(2S, 2'S)-2,2'-[3, 3'-Diisoamyl-3,3'-[2,2'-(dithio)diethyl] diureido]-N,N'-dimethyl-3,3'-diphenylbis(propionamide) (Compound No. 33-4)

IR (KBr, cm$^{-1}$) 3300, 3091, 2955, 1667, 1621, 1538, 1367, 1300.

(2S, 2'S)-N,N'-Bis[(1S)-1-(methylcarbamoyl)ethyl]-2,2'-[3,3'-diisoamyl-3,3'-[2, 2'-(dithio)diethyl]diureido]-3,3'-diphenylbis(propionamide)(Compound No. 33-5)

$[\alpha]_D^\circ$ -20.2° (c=0.19, chloroform); IR (KBr, cm$^{-1}$) 3305, 2956, 1668, 1626, 1541, 1228, 732, 699.

1,1'-Dimethyl-4,4'-[(2S, 2'S)-2,2'-[3,3'-diphenethyl-3,3'-[2RS, 2'RS)-2,2'-(dithio)dipropyl]diureido]-3,3'-diphenyldipropionyl]dipiperazine (Compound No. 33-6)

IR (Film, cm$^{-1}$) 3357, 2938, 1628, 1514, 1454, 1364, 1291, 1218, 1172, 1143, 1002, 752, 700.

1,1'-[(2S, 2'S)-2,2'-[3,3'-Bis(2-cyclopentylethyl)-3,3'-[2, 2'-(dithio)diethyl]diureido]dipropionyl]-4,4'-dimethyldipiperazine (Compound No. 33-7)

1,1'-[(2S, 2'S)-2,2'-[3,3'-Bis[2-(1-adamantyl)ethyl]-3,3'-[2,2'-(dithio)diethyl]diureido]dipropionyl]-4,4'-dimethyldipiperazine (Compound No. 33-8).

EXAMPLE 34

(2S)-6-Amino-2-[3-isoamyl-3-(2-mercaptoethyl) ureido]-N-methylhexanamide hydrochloride (Compound No. 34-1)

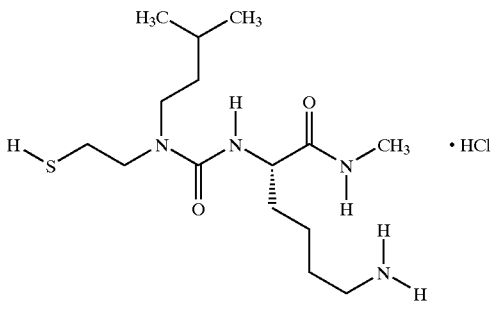

A 4.6 N solution of hydrogen chloride in ethyl acetate (2ml) is added to a solution of (2S)-6-(t-butoxycarboxamido)-2-[3-(2-mercaptoethyl)ureido]-N-methylhexanamide (Compound No. 30-4, 346 mg) in chloroform (4 ml) under a nitrogen atmosphere. The mixture is stirred for one hour and then concentrated under reduced pressure to give 292 mg (99%) of the titled compound (Compound No. 34-1).
(Compound No. 34-1)

$[\alpha]_D^\circ$ +10.4° (c=0.48, dimethyl sulfoxide); IR (Film, cm$^{-1}$) 3303, 2955, 1694, 1622, 1532, 1366, 1247, 1171, 757.

The following compound is obtained by a method similar to Example 34.

(2S, 2'S)-N,N'-Bis(2-aminoethyl)-3,3'-(4-nitrophenyl)-2, 2'-[3,3'-diphenethyl-3,3'-[2,2'-(dithio)diethyl]diureido] bis(propionamide) dihydrochloride (Compound No. 34-2)

$[\alpha]_D^\circ$ -15.3(c=0.99, methanol); IR (Film, cm$^{-1}$) 2929, 1624, 1518, 1345, 748, 700.

EXAMPLE 35

1-[(2S)-2-[3-[2-(Acetylthio)ethyl]-3-phenethylureido]-3-phenylpropionyl]-4-methylpiperazine hydrogen fumarate (Compound No. 35-1)

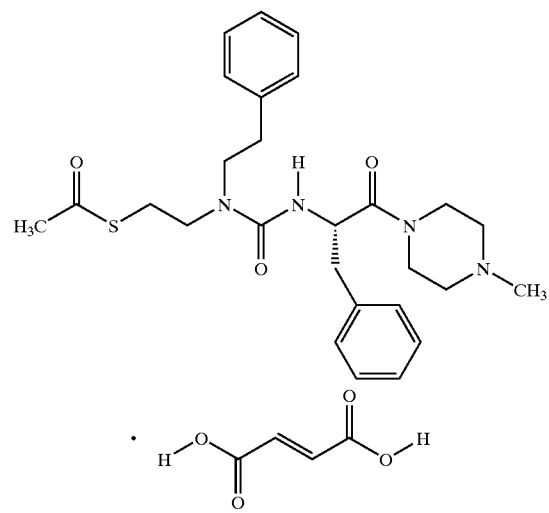

1-[(2S)-2-[3-[2-(Acetylthio)ethyl]-3-phenethylureido]-3-phenylpropionyl]-4-methylpiperazine (Compound No. 27-2, 16.39 g) is dissolved in ether (150 ml), and a solution of fumaric acid (3.83 g) in methanol (100 ml) is added thereto under ice cooling. The reaction mixture is concentrated under reduced pressure, the resulting oily matter is dissolved in diethyl ketone (40 ml), and the solution is allowed to stand in a refrigerator overnight to give 9.04 g (45%) of the titled compound (Compound No. 35-1) as crystals.
(Compound No. 35-1)

mp 17.5$^{18}$ $^{120.3\circ}$ C.; $[\alpha]_D^\circ$ +25.3° (c=0.99, methanol); IR (KBr, cm$^{-1}$) 3400, 3025, 2936, 2464, 1718, 1693, 1636, 1530, 1498, 1452, 1360, 1284, 1172, 979, 790, 754, 703.

The following compounds are obtained by a method similar to Example 35.

1-[(2RS)-3-(Acetylthio)-2-[3-[2-acetylthio)ethyl]3-phenethylureido]-3-methylbutyryl]-4-methylpiperazine hydrogen acetate (Compound No. 35-2)

IR (Film, cm$^{-1}$) 3391, 2936, 2794, 1686, 1636, 1509, 1453, 1364, 1294, 1249, 1202, 1143, 1110.

1-[(2S)-2-[3-(2-Mercaptoethyl)-3-phenethylureido]-3-phenylpropionyl]-4-methylpiperazine hydrogen fumarate (Compound No. 35-3)

$[\alpha]_D$ +14.9° (c=1.0, methanol); IR (Film, cm$^{-1}$) 3343, 3006, 2527, 1710, 1632, 1529, 1452, 1366, 1246, 979, 752, 702.

1-[(2S)-2-[3-[2-(Benzoylthio)ethyl]-3-phenethylureido] propionyl]-4-methylpiperazine hydrogen L-tartrate (Compound No. 35-4)

mp 126.5~131.5° C.; $[\alpha]_D^\circ$ +29.9° (c=1.0, methanol); IR (KBr, cm$^{-1}$) 3270, 3026, 1736, 1662, 1614, 1518, 1458, 1301, 1250, 1210, 1130, 1080, 1020, 976, 916, 688.

1-[(2S)-2-[3-(2-Mercaptoethyl)-3-phenethylureido]-3-phenylpropionyl]piperazine hydrogen fumarate (Compound No. 35-5)

$[\alpha]_D^\circ$ +16.1° (c=0.53, methanol); IR (KBr, cm$^{-1}$) 3348, 3027, 1717, 1636, 1522, 1455, 1369, 1247, 1083, 1029, 979, 750, 701.

1-[(2S)-2-[3-[2-(Acetylthio)ethyl]-3-(2-cyclohexylethyl)ureido]propionyl]-4-methylpiperazine hydrogen L-tartrate(Compound No. 35-6)

mp 106~111° C.; $[\alpha]_D^\circ$ +27.4° (c=1.0, methanol); IR (KBr, cm$^{-1}$) 3308, 2924, 2851, 1693, 1632, 1514, 1452, 1300, 1250, 1215, 1130, 1083, 1018.

1-[(2S)-2-[3-[2-(Acetylthio)ethyl]-3-(2-cyclohexylethyl)ureido]propionyl]-4-methylpiperazine hydrogen citrate (Compound No. 35-7)

mp 75° C. (decomp.); $[\alpha]_D^\circ$ +18.3° (c1.0, methanol); IR (KBr, cm$^{-1}$) 3392, 2925, 2852, 1733, 1691, 1628, 1531, 1456, 1219, 1135.

1-[(2S)-2-[3-[2-(Acetylthio)ethyl]-3-(2-cyclohexylethyl)ureido]propionyl]-4-methylpiperazine hydrogen fumarate (Compound No. 35-8)

mp 69~80° C.; $[\alpha]_D^\circ$ +20.6° (c=1.0, methanol); IR (KBr, cm$^{-1}$) 3385, 2925, 2852, 2471, 1710, 1690, 1652, 1526, 1448, 1247, 1137, 1057.

1-[(2S)-2-[3-[2-(Acetylthio)ethyl]-3-(2-cyclopentylethyl)ureido]propionyl]-4-methylpiperazine hydrogen L-tartrate (Compound No. 35-9)

mp 100° C.; $[\alpha]_D^\circ$ +27.8° (c=1.0, methanol); IR (KBr, cm$^{-1}$) 3325, 2948, 1633, 1526, 1454, 1217, 1133.

1-[(2S)-2-[3-[2-(Acetylthio)ethyl]-3-(2-cyclopentylethyl)ureido]propionyl]-4-methylpiperazine hydrogen diacetyl-L-tartrate (Compound No. 35-10)

mp 56~58° C.; $[\alpha]_D^\circ$ +11.4° (c=1.0, methanol); IR (KBr, cm$^{-1}$) 3392, 1740, 1636, 1540, 1457, 1374, 1222.

Bis[1-[(2S)-2-[3-[2-(acetylthio)ethyl]-3-(2-cyclopentylethyl)ureido]propionyl]-4-methylpiperazine] hydrogen dibenzoyl-L-tartrate (Compound No. 35-11)

mp 112.0$^{18}$ $^{115.3°}$ C.; $[\alpha]_D^\circ$ −17.5° (c=1.0, methanol); IR (KBr, cm$^{-1}$) 3412, 2949, 1717, 1694, 1636, 1522, 1452, 1374, 1268, 1116.

Bis[1-[(2S)-2-[3-[2-(acetylthio)ethyl]-3-(2-cyclopentylethyl)ureido]propionyl]-4-methylpiperazine] hydrogen toluoyl-L-tartrate (Compound No. 35-12)

mp 131~136° C. (decomp.); $[\alpha]_D^\circ$ −29.1° (c=1.0, methanol); IR (KBr, cm$^{-1}$) 3419, 2949, 2868, 1710, 1643, 1503, 1275, 1128.

1-[(2S)-2-[3-[2-(Acetylthio)ethyl]-3-(2-cyclopentylethyl)ureido]propionyl]-4-methylpiperazine hydrogen citrate (Compound No. 35-13)

mp 75~83° C.; $[\alpha]_D^\circ$ +18.4° (c=1.0, methanol); IR (KBr, cm$^{-1}$) 3391, 2952, 1693.

1-[(2S)-2-[3-[2-(Acetylthio)ethyl]-3-(2-cyclopentylethyl)ureido]propionyl]-4-methylpiperazine hydrogen 4-nitrobenzoate (Compound No. 35-14)

mp 76.5~78.5° C.; IR (KBr, cm$^{-1}$) 3390, 2947, 2360, 1691, 1631, 1516, 1350, 718.

1-[(2S)-2-[3-[2-(Acetylthio)ethyl]-3-(2-cycloheptylethyl)ureido]-4-methylpiperazine hydrogen L-tartrate (Compound No. 35-15)

mp 85~100° C.; $[\alpha]_D^\circ$ +24.5° (c=1.0, methanol); IR (KBr, cm$^{-1}$) 3322, 2922, 2853, 2699, 1693, 1632, 1528, 1460, 1303, 1264, 1216, 1135, 1068, 976.

1-[(2S)-2-[3-[2-(Acetylthio)ethyl]-3-[2-[3,5-di(t-butyl)-4-hydroxyphenyl]ethyl]ureido]propionyl]-4-methylpiperazine hydrogen L-tartrate (Compound No. 35-16)

mp 85° C. (decomp.); $[\alpha]_D^\circ$ +5.3° (c=1.0, methanol); IR (KBr, cm$^{-1}$) 3391, 2968, 1736, 1690, 1632, 1530, 1435, 1365, 1234, 1122.

1-[(2S)-2-[3-[2-(Acetylthio)ethyl]-3-[2-(1-adamantyl)ethyl]ureido]propionyl]-4-methylpiperazine hydrogen L-tartrate (Compound No. 35-17)

mp 125.5~130.0° C.; $[\alpha]_D^\circ$ +24.20c=1.0, methanol); IR (KBr, cm$^{-1}$) 3325, 2903, 2846, 1691, 1635, 1518, 1452, 1299, 1248, 1216, 1132, 1086, 976.

Bis[1-[(2S)-2-[3-[2-(acetylthio)ethyl]-3-[2-(1-adamantyl)ethyl]ureido]propionyl]-4-methylpiperazine]hydrogen dibenzoyl-L-tartrate (Compound No. 35-18)

mp 137.5~138.3° C. (decomp.); $[\alpha]_D^\circ$ −16.80c=1.0, methanol); IR (KBr, cm$^{-1}$) 3420, 2902, 2846, 2324, 1717, 1690, 1644, 1507, 1452, 1360, 1315, 1267, 1211, 1128.

1-[(2S)-2-[3-[2-(Acetylthio)ethyl]-3-[2-(1-adamantyl)ethyl]ureido]propionyl]-4-methylpiperazine hydrogen di-p-toluoyl-L-tartrate (Compound No. 35-19)

mp 136.0~140.0° C.; $[\alpha]_D^\circ$ −46.9° (c=1.0, methanol); IR (KBr, cm$^{-1}$) 3400, 2903, 2846, 1717, 1688, 1636, 1532, 1451, 1408, 1381, 1347, 1265, 1211, 1177, 1127, 1113, 1022.

Bis[1-[(2S)-2-[3-[2-(acetylthio)ethyl]-3-[2-(1-adamantyl)ethyl]ureido]propionyl]-4-methylpiperazine]hydrogen di-p-toluoyl-L-tartrate (Compound No. 35-20)

mp 135.0~138.5° C.; $[\alpha]_D^\circ$ −23.9° (c=1.0, methanol); IR (KBr, cm$^{-1}$) 3412, 2902, 2846, 2416, 2298, 1717, 1636, 1508, 1451, 1346, 1276, 1212, 1178, 1112, 1035, 980.

1-[(2S)-2-[3-[2-(Acetylthio)ethyl]-3-[2-(1-adamantyl)ethyl]ureido]propionyl]-4-methylpiperazine hydrogen citrate (Compound No. 35-21)

mp 80° C. (decomp.); $[\alpha]_D^\circ$ +15.1° (c=1.0, methanol); IR (KBr, cm$^{-1}$) 3392, 2903, 2846, 1728, 1636, 1534, 1451, 1218, 1136, 1055.

1-[(2S)-2-[3-[2-(Acetylthio)ethyl]-3-[2-(1-adamantyl)ethyl]ureido]propionyl]-4-methylpiperazine hydrogen fumarate (Compound No. 35-22)

mp 90° C. (decomp.); $[\alpha]_D^\circ$ +17.5° (c=1.0, methanol); IR (KBr, cm$^{-1}$) 3401, 2902, 2846, 2658, 1690, 1636, 1526, 1452, 1357, 1297, 1245, 1146, 1055, 979.

1-[(2S)-2-[3-[2-(Acetylthio)ethyl]-3-[2-(1-adamantyl)ethyl]ureido]propionyl]-4-methylpiperazine 4-nitrobenzoate (Compound No. 35-23)

mp 111.0~114.0° C.; $[\alpha]_D^\circ$ +16.0° (c=1.0, methanol); IR (KBr, cm$^{-1}$) 3391, 2900, 2845, 1691, 1633, 1516, 1477, 1403, 1352, 1319, 1288, 1245, 1217, 1137, 1104, 1039, 1010.

1-[(2S)-2-[3-(2-Cyclohexylethyl)-3-(2-mercaptoethyl)ureido]propionyl]-4-methylpiperazine hydrogen L-tartrate (Compound No. 35-24)

mp 70~90° C.; $[\alpha]_D^\circ$ +22.8° (c=1.0, methanol); IR (KBr, cm$^{-1}$) 3326, 2923, 2851, 1732, 1627, 1531, 1449, 1247, 1217, 1133, 1077.

1-[(2S)-2-[3-(2-Cyclopentylethyl)-3-(2-mercaptoethyl)ureido]propionyl]-4-methylpiperazine hydrogen L-tartrate (Compound No. 35-25)

mp 60~80° C.; $[\alpha]_D^\circ$ +23.1° (c=1.0, methanol); IR (KBr, cm$^{-1}$) 3322, 1627, 1529, 1453, 1304, 1216, 1135.

1-[(2S)-2-[3-[2-(1-Adamantyl)ethyl]-3-(2-mercaptoethyl)ureido]propionyl]-4-methylpiperazine hydrogen L-tartrate (Compound No. 35-26)

mp 84~130° C.; $[\alpha]_D^\circ$ +20.4° (c=1.0, methanol); IR (KBr, cm$^{-1}$) 3325, 2902, 2846, 2547, 1728, 1631, 1519, 1451, 1299, 1248, 1216, 1130, 1079.

1,1'-[(2S, 2'S)-2,2'-[3,3'-Bis(2-cyclopentylethyl)-3,3'-[2,2'-(dithio)diethyl]diureido]dipropionyl]-4,4'-dimethyldipiperazine bis hydrogen (L-tartrate) (Compound No. 35-27)

mp 55~70° C.; $[\alpha]_D^\circ$ +11.2° (c=0.55, methanol); IR (KBr, cm$^{-1}$) 3416, 2949, 1738, 1633, 1532, 1455, 1247, 1130.

1,1'-[(2S, 2'S)-2,2'-[3,3'-Bis[2-(1-adamantyl)ethyl]-3,3'-[2,2'-(dithio)diethyl]diureido]dipropionyl]-4,4'-dimethyldipiperazine bis hydrogen (L-tartrate) (Compound No. 35-28)

mp 73~90° C.; $[\alpha]_D^° +11.4°$ (c=0.54, methanol); IR (KBr, cm$^{-1}$) 3406, 2902, 2846, 1738, 1632, 1524, 1451, 1246, 1134, 1078, 978.

1-[(2S)-2-[3-[2-(1-Adamantyl)ethyl]-3-[2-(methylthio)ethyl]ureido]propionyl]-4-methylpiperazine hydrogen L-tartrate (Compound No. 35-29)

mp 95~105° C.; $[\alpha]_D^° +18.7°$ (c=1.0, methanol); IR (KBr, cm$^{-1}$) 3306, 2903, 2846, 1736, 1624, 1522, 1452, 1247, 1129, 1083.

1-[(2S)-2-[3-(2-Cyclohexylethyl)-3-[2-[2-(methoxycarbonyl)ethyl]thioethyl]ureido]propionyl]-4-methylpiperazine hydrogen L-tartrate (Compound No. 35-30)

$[\alpha]_D^° +16.3°$ (c=0.51, methanol); IR (KBr, cm$^{-1}$) 3418, 2923, 2851, 1738, 1632, 1526, 1450, 1361, 1247, 1130, 1078, 977.

1-[(2S)-2-[3-(2-Cyclopentylethyl)-3-[2-[2-(methoxycarbonyl)ethyl]thioethyl]ureido]propionyl]-4-methylpiperazine hydrogen L-tartrate (Compound No. 35-31)

mp 47~60° C.; $[\alpha]_D^° +17.6°$ (c=1.0, methanol); IR (KBr, cm$^{-1}$) 3321, 2950, 1738, 1634, 1520, 1436, 1304, 1249, 1134, 1068.

1-[(2S)-2-[3-[2-(1-Adamantyl)ethyl]-3-[2-[2-(methoxycarbonyl)ethyl]thioethyl]ureido]propionyl]-4-methylpiperazine hydrogen L-tartrate (Compound No. 35-32)

mp 73~100° C.; $[\alpha]_D^° +16.5°$ (c=0.51, methanol); IR (KBr, cm$^{-1}$) 3415, 2903, 2846, 1736, 1631, 1527, 1452, 1364, 1216, 1134, 1078, 1021, 977.

EXAMPLE 36

(2S)-2-[3-[2-(Acetylthio)ethyl]-3-phenethylureido]-N-(2-carboxyethyl)-3-(4-nitrophenyl)propionamide (Compound No. 36-1)

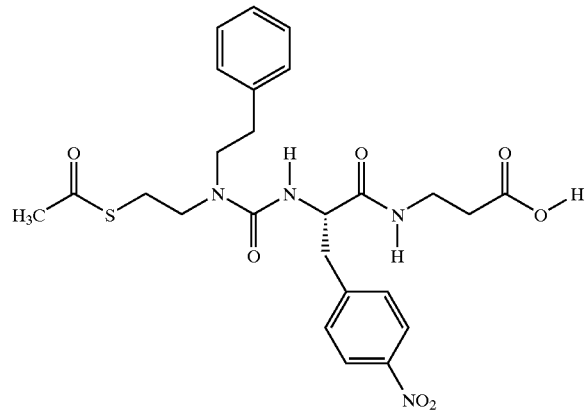

(2S)-2-[3-[2-(Acethylthio)ethyl]-3-phenethylureido]-N-[2-(t-butoxycarbonyl)ethyl]-3-(4-nitrophenyl)propionamide (Compound No. 27-83, 235 mg) is dissolved in a 4N solution of hydrogen chloride in dioxane (2 ml), and the solution is stirred overnight. The reaction mixture is concentrated under reduced pressure to give 146 mg (69%) of the titled compound (Compound No. 36-1) as crystals.

(Compound No. 36-1)

mp 113.5~1117.5° C.; $[\alpha]_D^° -20.1°$ (c=0.51, methanol); IR (KBr, cm$^{-1}$) 3346, 2929, 1699, 1664, 1603, 1510, 1345, 1201, 950, 891, 839, 750, 726, 698.

The following compounds are obtained by a method similar to Example 36.

(2S)-2-[3-[(2RS)-2-Carboxy-3-(phenylthio)propyl]-3-isoamylureido]-N-methyl-3-phenylpropionamide (Compound No. 36-2)

$[\alpha]_D^° -11.7°$ (c=0.35, chloroform); IR (KBr, cm$^{-1}$) 3305, 2957, 1707, 1621, 1534, 1228, 1165.

(2S)-2-[3-(2RS)-2-Carboxy-3-(phenylthio)propyl]-3-isobutylureido]-N-methyl-3-phenylpropionamide (Compound No. 36-3)

$[\alpha]_D^° -15.0°$ (c=0.34, chloroform); IR (KBr, cm$^{-1}$) 3306, 2958, 1707, 1624, 1531, 1265, 1165.

EXAMPLE 37

1-[(2S)-2-[3-[2-[2-(Methoxycarbonyl)ethyl]thioathyl]-3-phenethylureido]-3-phenylpropionyl]-4-methylpiperazine (Compound No. 37-1)

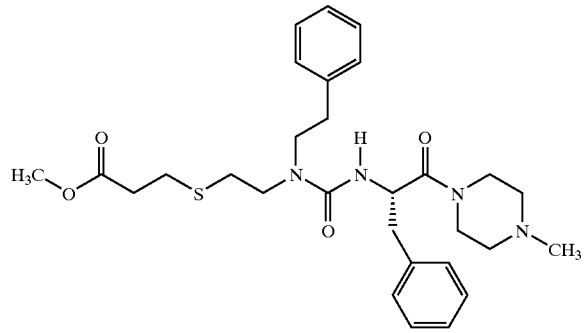

In tetrahydrofuran (3 ml) are dissolved 1-[(2S)-2-[3-[3-(acetylthio)ethyl-3-phenethylureido]propionyl]-4-methylpiperazine (Compound No. 27-24, 353 mg) and methyl acrylate (0.26 ml) under a nitrogen atmosphere, and the solution is cooled with ice. Concentrated aqueous ammonia (1 ml) is added dropwise to the solution, and the mixture is stirred under ice cooling for 30 minutes and further at room temperature for 3.5 hours. The reaction mixture is concentrated under reduced pressure, water is added to the concentrate, and the whole is extracted with ether. The organic layer is washed with water and saturated brine successively, dried over anhydrous magnesium sulfate and concentrated under reduced pressure. The resulting oily matter is purified by silica gel column chromatography to give 368 mg (96%) of the titled compound (Compound No, 37-1).

(Compound No. 37-1)

$[\alpha]_D^° +9.2°$ (c=0.98, methanol); IR (Film, cm$^{-1}$) 3347, 2937, 1737, 1630, 1497, 1448, 1360, 1291, 1214, 1144, 1001, 750, 701.

The following compounds are obtained by a method similar to Example 37.

1-[(2S)-2-[3-(2-Cyclohexylethyl)-3-[2-[2-(methoxycarbonyl)ethyl]thioethyl]ureido]propionyl]-4methylpiperazine (Compound No. 37-2)

1-[(2S)-2-[3-(2-Cyclopentylethyl)-3-[2-[2-(methoxycarbonyl)ethyl]thioethyl]ureido]propionyl]-4-methylpiperazine (Compound No. 37-3)

1-[(2S)-2-[3-[2-(1-Adamantyl)ethyl]-3-[2-[2-(methoxycarbonyl)ethyl]thioethyl]ureido]propionyl]-4-methylpiperazine (Compound No. 37-4)

EXAMPLE 38

(2S)-3-(4-Biphenylyl)-N-butyl-2-[3-[(1RS)-1-(ethoxycarbonylmethyl)-2-(phenylthio)ethyl]-3-isoamylureido]propionamide (Compound No. 38-1)

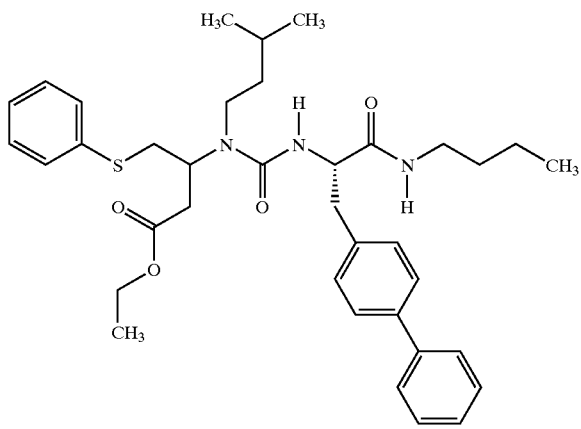

n-Butylamine (0.35 ml) is added to a solution of phenyl (2S)-3-(4-biphenylyl)-2-[3-[(1RS)-1-(ethoxycarbonylmethyl)-2-(phenylthio)ethyl]-3-isoamylureido]propionate (Compound No. 1-80, 464 mg) in tetrahydrofuran (7 ml), and the mixture is stirred at room temperature for 1.5 hours. The reaction mixture is concentrated under reduced pressure, water is added to the concentrate, and the whole is extracted with ethyl acetate. The organic layer is washed with water and saturated brine successively, dried over anhydrous sodium sulfate and concentrated under reduced pressure. The resulting oily matter is purified by silica gel column chromatography to give 402 mg (90%) of the titled compound (Compound No. 38-1).
(Compound No. 38-1)
IR (Film, cm$^{-1}$) 3306, 2957, 1733, 1664, 1622, 1520, 1369, 1299, 1207, 1027.

EXAMPLE 39

(2S)-3-(4-Biphenylyl)-N-butyl-2-[3-[(1RS)-1-(carboxymethyl)-2-(phenylthio)ethyl]-3-isoamylureido]propionamide (Compound No. 39-1)

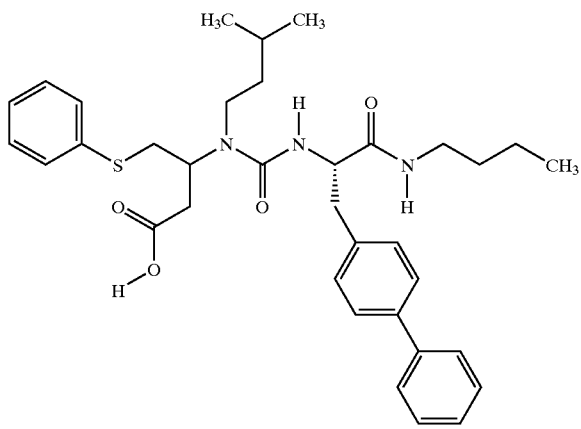

(2S)-3-(4-Biphenylyl)-N-butyl-2-[3-[(1RS)-1-(ethoxycarbonylmethyl)-2-(phenylthio)ethyl]-3-isoamylureido]propionamide (Compound No. 38-1, 402 mg) is dissolved in ethanol(2 ml), a 1 N aqueous lithium hydroxide solution (0.96 ml) is added thereto, and the mixture is stirred at room temperature for 45minutes. A 10% aqueous citric acid solution is added to the reaction mixture, and the whole is extracted with ether. The organic layer is washed with water and saturated brine successively, dried over anhydrous magnesium sulfate and concentrated under reduced pressure. The resulting oily matter is purified by silica gel column chromatography to give 386 mg (quantitatively) of the titled compound (Compound No. 39-1) as noncrystalline powder.
(Compound No. 39-1)
IR (KBr, cm$^{-1}$) 3306, 2957, 2871, 1705, 1623, 1520, 1439, 1366, 1295, 1225.

EXAMPLE 40

(2S)-2-[3-[(2RS)-2-(Hydroxycarbamoyl)-3-(phenylthio)propyl]-3-isoamylureido]-N-methyl-3-phenylpropionamide (Compound No. 40-1)

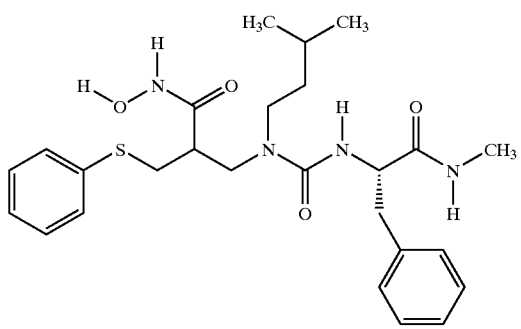

In anhydrous methylene chloride (4 ml) are dissolved (2S)-2-[3-[(2RS)-2-carboxy-3-(phenylthio)propyl]-3-isoamylureido]-N-methyl-3-phenylpropionamide (Compound No. 36-2, 100 mg), 1-hydroxybenzotriazole (68 mg) and 1-ethyl-3-(3-dimethylaminopropyl) carbodiimide hydrochloride (96 mg) under a nitrogen atmosphere. Then, N-methylmorpholine (0.05 ml) is added to the solution under ice cooling, and the mixture is stirred for 30 minutes. Next, to the mixture is added a solution containing hydroxylammonium chloride (52 mg) and N-methylmorpholine (0.08 ml) in dimethylformamide (1 ml), and the mixture is stirred under ice cooling for 10 minutes and then at room temperature overnight. A 5% aqueous citric acid solution is added to the reaction mixture, and the whole is extracted with ethyl acetate. The organic layer is washed with a 5% aqueous sodium hydrogencarbonate solution and saturated brine successively, dried over anhydrous magnesium sulfate and concentrated under reduced pressure. The resulting oily matter is purified by silica gel column chromatography to give 57 mg (54%) of the titled compound (Compound No. 40-1) as noncrystalline powder.
(Compound No. 40-1)
$[\alpha]_D$ +5.0° (c=0.34, chloroform); IR (KBr, cm$^{-1}$) 3291, 2955, 1625, 1529, 1234, 1165.
The following compounds are obtained by a method similar to Example 40.
(2S)-2-[3-[(2RS)-2-(Hydroxycarbamoyl)-3-(phenylthio) propyl]-3-isobutylureido]-N-methyl-3-phenylpropionamide (Compound No. 40-2)
IR (KBr, cm$^{-1}$) 3285, 2978, 1629, 1530, 1253, 1164.
(2S)-3-(4-Biphenylyl)-N-butyl-2-[3-[(1RS)-1-(hydroxycarbamoyl)methyl]-2-(phenylthio)ethyl]-3-isoamylureido]propionamide (Compound No, 40-3)

IR (Film, cm$^{-1}$) 3272, 2957, 2870, 1625, 1518, 1220, 1157, 1075.

EXAMPLE 41

1-[(2S)-2-[3-[2-(Acetylthio)ethyl]ureido]propionyl]-4-methylpiperazine (Compound No. 41-1)

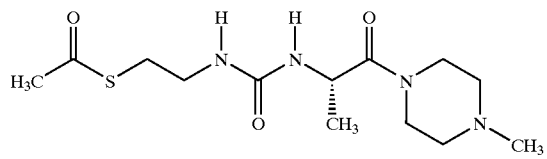

1,1'-Dimethyl-4,4'-[(2S, 2'S)-2,2'-(dithio)diethyl]diureido]dipropionyl]dipiperazine (Compound No. 28-14, 487 mg) is dissolved in acetone (10 ml)-water (2.5 ml), tri-n-butylphosphine (0.27 ml) is added to the solution, and the mixture is stirred at room temperature for 40 minutes. To the mixture are added triethylamine (0.31 ml) and acetic anhydride (0.21 ml) successively, and the mixture is stirred at room temperature for 20 minutes. The reaction mixture is concentrated under reduced pressure, and chloroform is added to the residue. The organic layer is washed with a 10% aqueous sodium hydrogencarbonate solution and saturated brine successively, dried over anhydrous sodium sulfate and concentrated under reduced pressure. The resulting oily matter is purified by silica gel column chromatography to give 448 mg (79%) of the titled compound (Compound No. 41-1).

(Compound No. 41-1)

$[\alpha]_D^\circ$ +3.6° (c=0.97, methanol); IR (Film, cm$^{-1}$) 3358, 2976, 2938, 2794, 1692, 1632, 1556, 1446, 1355, 1293, 1248, 1172, 1141, 1034, 1002.

Formulation

General formulation examples of oral preparations and injections using the present compounds are shown below.

1) Tablet

| Formulation 1 in 100 mg | |
|---|---|
| Present compound | 1 mg |
| Lactose | 66.4 mg |
| Cornstarch | 20 mg |
| Calcium carboxymethylcellulose | 6 mg |
| Hydroxypropylcellulose | 4 mg |
| Magnesium stearate | 0.6 mg |

Tablets according to the formulation as above are coated with 2 mg/tablet of a coating agent (this is a conventional coating agent such as hydroxypropylmethylcellulose, macrogol or silicone resin) to obtain desired coated tablets. (The same is applied to tablets mentioned below.)

| Formulation 2 in 100 mg | |
|---|---|
| Present compound | 5 mg |
| Lactose | 62.4 mg |
| Cornstarch | 20 mg |
| Calcium carboxymethylcellulose | 6 mg |
| Hydroxypropylcellulose | 4 mg |
| Magnesium stearate | 0.6 mg |
| Coating agent | 2 mg |
| Formulation 3 in 100 mg | |
| Present compound | 20 mg |
| Lactose | 51 mg |
| Cornstarch | 15 mg |
| Calcium carboxymethylcellulose | 5 mg |
| Hydroxypropylcellulose | 5 mg |
| Magnesium stearate | 1 mg |
| Talc | 1 mg |
| Coating agent | 2 mg |
| Formulation 4 in 100 mg | |
| Present compound | 40 mg |
| Lactose | 34 mg |
| Cornstarch | 10 mg |
| Calcium carboxymethylcellulose | 5 mg |
| Hydroxypropylcellulose | 5 mg |
| Magnesium stearate | 2 mg |
| Talc | 2 mg |
| Coating agent | 2 mg |
| Formulation 5 in 220 mg | |
| Present compound | 100 mg |
| Lactose | 67 mg |
| Cornstarch | 20 mg |
| Calcium carboxymethylcellulose | 10 mg |
| Hydroxypropylcellulose | 10 mg |
| Magnesium stearate | 4 mg |
| Talc | 4 mg |
| Coating agent | 5 mg |

2) Capsule

| Formulation 1 in 150 mg | |
|---|---|
| Present compound | 5 mg |
| Lactose | 145 mg |

Varying the mixing ratio of the present compound to lactose, capsules having the contents of the present compound of 10 mg/capsule, 30 mg/capsule, 50 mg/capsule and 100 mg/capsule are also prepared.

3) Granule

| Formulation 1 in 100 mg | |
|---|---|
| Present compound | 30 mg |
| Mannitol | 46.5 mg |
| Polyvinyl pyrrolidone K-30 | 7 mg |
| Eudragit RL | 15 mg |
| Triacetin | 1.5 mg |
| Formulation 2 in 130 mg | |
| Present compound | 50 mg |
| Lactose | 55 mg |
| White potato starch | 20 mg |
| Hydroxypropylcellulose | 4 mg |
| Talc | trace |

4) Injection

| Formulation 1 in 10 ml | |
|---|---|
| Present compound | 10–100 mg |
| Sodium chloride | 90 mg |

-continued

| Formulation 1 in 10 ml | |
| --- | --- |
| Sodium hydroxide | q.s. |
| Sterile purified water | q.s. |

Pharmacological Test

Inhibitory effects on TNF-α production induced by lipopolysaccharide (LPS) stimulation were studied by in vitro or in vivo tests according to the method of McGeehan et al. (Nature, 370, 558–661(1994)).

1) In vitro Test

Analyses were carried out by measuring TNF-α production from human monocytic line THP-1 by LPS stimulation.

As a medium, an RPMI1640medium containing a fetal bovine serum(10%), L-glutamine (2 mM), 2-mercaptoethanol (50 μM), penicillin (50 units/ml) and streptomycin (50 μg/ml) was used.

With respect to cells, human monocytic line THP-1 cells cultured in the above-mentioned medium were centrifuged at 100×g for five minutes to remove supernatant and then re-suspended in the medium. With respect to LPS, LPS from S. Typhimurium was dissolved in purified water and then diluted with the medium. Test compounds were dissolved in dimethyl sulfoxide (DMSO) and then diluted with the medium.

The cells ($10^6$/ml), LPS (2 μg/ml) and the test compound ($10^{-5}$ M) prepared as mentioned above were mixed, and this mixture was incubated at 37° C. for two hours and then centrifuged at 1000×g for TNF-α levels in cultured supernatant were measured with a human TNF-α specific ELISA kit. TNF-α production was not observed in the cultured supernatant in the absence of LPS (control).

TNF-α production inhibition rates of the test compounds were determined by the following equation.

Inhibition rate (%)=[(A-B)/A]×100

A: TNF-α level in supernatant of culture medium in the absence of test compound

B: TNF-α level in supernatant of culture medium in the presence of test compound Results Table 1 shows TNF-α inhibition rates (%) at a concentration of $10^{-5}$ M as examples of test results.

TABLE 1

| Test compound | Inhibition rate (%) |
| --- | --- |
| Compound No. 27-10 | 100 |
| Compound No. 27-17 | 93.5 |
| Compound No. 27-19 | 93.5 |
| Compound No. 27-41 | 93.8 |
| Compound No. 27-42 | 100 |
| Compound No. 27-46 | 100 |
| Compound No. 27-47 | 100 |
| Compound No. 27-56 | 96.9 |
| Compound No. 27-58 | 100 |
| Compound No. 27-59 | 100 |

As shown in Table 1, the present compound had an inhibitory effect on TNF-α production at low concentrations.

2) In vivo Test

Female rats (five per group), body weight of about 200 g, about eight weeks old, were used as test animals. With respect to LPS to be used, LPS from Salmonella was dissolved in physiological saline (1 mg/ml). Test compounds were dissolved or uniformly suspended in a 1% aqueous methylcellulose solution.

The above-mentioned LPS solution (0.5 ml/kg) was subcutaneously administered to the rat. Immediately after the LPS administration, the test compound preparation liquid (5 ml/kg, containing 50 mg/kg test compound) was orally administered. Two hours after the LPS administration, blood was collected from abdominal aorta and was centrifuged at 4° C. and 3000 rpm for ten minutes. TNF-α levels in the obtained plasma were measured with a rat TNF-α-specific ELISA kit. TNF-α was not observed in the plasma with respect to an LPS-nonadministered group (control).

TNF-α production inhibition rates of the test compounds were determined by the following equation.

Inhibition rate (%)=[(A-B)/A]×100

A: TNF-α level in plasma of test compound-nonadministered group

B: TNF-α level in plasma of test compound-administered group

Results

Table 2 shows TNF-α production inhibition rates (%) by oral administration of 50 mg/kg.

TABLE 2

| Test compound | Inhibition rate (%) |
| --- | --- |
| Compound No. 13-1 | 84.6 |
| Compound No. 13-3 | 66.8 |
| Compound No. 13-12 | 62.3 |
| Compound No. 13-16 | 54.1 |
| Compound No. 13-17 | 50.3 |
| Compound No. 13-20 | 66.6 |
| Compound No. 13-49 | 90.0 |
| Compound No. 13-50 | 93.5 |
| Compound No. 13-57 | 90.1 |
| Compound No. 27-4 | 60.9 |
| Compound No. 27-84 | 56.7 |

From the above-mentioned results, it is apparent that the present compounds exhibit excellent TNF-α production inhibitory effects and have various medical uses as therapeutic agents for diseases in which TNF-α participates, for example, autoimmune diseases such as rheumatoid arthritis, Crohn's disease and systemic lupus erythematosus, cachexia, acute infectious disease, allergy, pyrexia, anemia, diabetes and the like.

Industrial Applicability

The present invention provides novel urea derivatives which have TNF-α production inhibitory effects and are useful as therapeutic agents for various diseases, particularly as therapeutic agents for autoimmune diseases such as rheumatoid arthritis, and novel compounds which are useful as synthetic intermediates thereof.

What is claimed is:

1. A compound represented by the following general formula [I] or a salt thereof

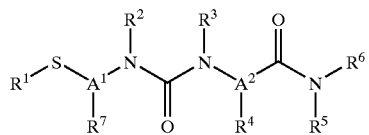

wherein $R^1$ is hydrogen, lower alkyl, an aromatic group, $R^A$—CO—, $R^C$—S— or a group of the following formula [II];

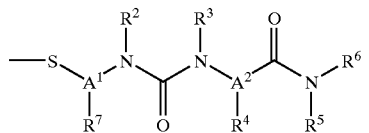

$R^2$, $R^3$ and $R^4$, being the same or different, are hydrogen, lower alkyl, lower alkenyl cycloalkyl, cycloalkenyl or an aromatic group; when $R^4$ is lower alkyl, terminal carbon of the lower alkyl can join with carbon to which the alkyl is bonded to form a cycloalkyl ring;

$R^5$ and $R^6$, being the same or different, are hydrogen, lower alkyl, lower alkenyl, cycloalkyl, cycloalkenyl or an aromatic group; when both $R^5$ and $R^6$ are lower alkyl, they can join each other to form a nonaromatic heterocyclic ring having nitrogen and/or oxygen in the ring, and the heterocyclic ring can be substituted by lower alkyl, lower alkenyl, cycloalkyl, cycloalkenyl, an aromatic group or $R^A$—CO—;

$R^7$ is hydrogen, lower alkyl, cycloalkyl, hydroxy, mercapto, phenyl, $R^B$—O—, $R^C$—S—, $R^D$—COS—, $R^E$—OCO—, $R^F$—N($R^G$)— or —CONHOH; or $R^7$ can join with sulfur adjacent to $A^1$ to form a nonaromatic heterocyclic ring with said sulfur adjacent to $A^1$ in the ring, and wherein the ring optionally contains a carbonyl in the ring;

$A^1$ is lower alkylene;

$A^2$ is lower alkylene;

each lower alkyl defined above can be substituted by hydroxy, a nonaromatic heterocyclic ring having nitrogen and/or oxygen in the ring, cycloalkyl, cycloalkenyl, adamantyl, an aromatic group, phthalimido, guanidino which can be substituted by lower alkylsulfonyl or aromatic sulfonyl, $R^A$—CO—, $R^B$—O—, $R^C$—S—, $R^D$—COS—, $R^E$—OCO—, $R^F$—N($R^G$)—, $R^H$—N($R^J$)CO—, $R^K$—CONH— or —CONHOH;

each lower alkenyl defined above can be substituted by hydroxy, lower alkyl, lower alkoxy, cycloalkyl, cycloalkenyl or an aromatic group;

each cycloalkyl defined above can be substituted by lower alkyl, hydroxy, oxo or $R^E$—OCO—;

each aromatic group defined above can be substituted by lower alkyl, hydroxy, lower alkoxy, lower alkanoyloxy, halogen, nitro, an aromatic group, lower alkylsulfonyl, aromatic sulfonyl, $R^E$—OCO—, $R^F$—N($R^G$)— or $R^K$—CONH—;

the nonaromatic heterocyclic ring having nitrogen and/or oxygen in the ring defined above can be substituted by lower alkyl, cycloalkyl, an aromatic group or $R^A$—CO—, and the lower alkyl can be substituted by hydroxy, cycloalkyl, cycloalkenyl, an aromatic group, $R^A$—CO—, $R^B$—O—, $R^E$—OCO— or $R^F$—N($R^G$)—;

$R^A$ is lower alkyl, halogen-lower alkyl, an aromatic group, lower alkoxy, aromatic-lower alkoxy or $R^F$—N($R^G$)—; $R^B$ is lower alkyl or an aromatic group; $R^C$ is hydrogen, lower alkyl or an aromatic group; $R^D$ is lower alkyl or an aromatic group; $R^E$ is hydrogen, lower alkyl or an aromatic group; $R^F$ and $R^G$, being the same or different, are hydrogen lower alkyl, cycloalkyl or an aromatic group; $R^H$ and $R^J$, being the same or different, are hydrogen, lower alkyl, cycloalkyl or an aromatic group; $R^K$ is lower alkyl, lower alkoxy or an aromatic group.

2. The compound or a salt thereof as claimed in claim 1, wherein the aromatic group is selected from phenyl, naphthyl, pyridyl, thienyl and imidazolyl, the nonaromatic heterocyclic ring having nitrogen and/or oxygen in the ring is selected from a morpholine ring, a piperidine ring, a piperazine ring, a pyrroline ring and a homopiperazine ring, and the nonaromatic heterocyclic ring having sulfur in the ring is selected from a thiolactone ring and a dithiolane ring.

3. The compound or a salt thereof as claimed in claim 1, wherein the group(s) in the general formula [I] is defined by anyone selected from the following 1) to 8) or any combinations consisting of 1) to 8), 1) $R^1$ is selected from hydrogen, lower alkyl, phenyl, $R^A$—CO—, $R^C$—S— and a group of the following formula [II],

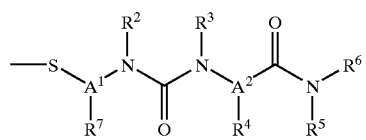

$R^A$ is selected from lower alkyl, lower alkoxy, phenyl, pyridyl, phenyl-lower alkoxy and $R^F$—N($R^G$)—, $R^C$ is selected from lower alkyl and phenyl, $R^F$ and $R^G$, being the same or different, are selected from hydrogen, lower alkyl and phenyl, each lower alkyl can be substituted by phenyl or lower alkoxycarbonyl, and each phenyl can be substituted by a group selected from lower alkyl, hydroxy, lower alkoxy, halogen and nitro;

2) $R^2$, $R^3$ and $R^4$, being the same or different, are selected from hydrogen, lower alkyl, lower alkenyl, cycloalkyl, cycloalkenyl, phenyl and naphthyl, the lower alkyl can be substituted by a group selected from hydroxy, cycloalkyl, cycloalkenyl, adamantyl, phenyl, naphthyl, pyridyl, thienyl, imidazolyl, guanidino which can be substituted by lower alkylsulfonyl or phenylsulfonyl, $R^B$—O—, $R^C$—S—, $R^D$—COS—, $R^E$—OCO—, $R^F$—N($R^G$)— and $R^K$—CONH—, the lower alkenyl can be substituted by lower alkyl, phenyl or naphthyl, $R^B$ is selected from lower alkyl and phenyl, $R^C$ is selected from hydrogen, lower alkyl and phenyl, $R^D$ is selected from lower alkyl and phenyl, $R^E$ is selected from hydrogen, lower alkyl and phenyl, $R^F$ and $R^G$, being the same or different, are selected from hydrogen, lower alkyl, cycloalkyl and phenyl, $R^K$ is selected from lower alkyl, lower alkoxy and phenyl, each phenyl can be substituted by a group selected from lower alkyl, hydroxy, lower alkoxy, lower alkanoyloxy, halogen, nitro, amino, lower alkylamino, lower alkanoylamino, lower alkylsulfonyl, phenylsulfonyl, phenyl and $R^E$—OCO—, and each cycloalkyl can be substituted by lower alkyl, hydroxy, oxo or $R^E$—OCO—;

3) $R^5$ and $R^6$, being the same or different, are selected from hydrogen, lower alkyl, lower alkenyl, cycloalkyl, cycloalkenyl, phenyl, naphthyl and pyridyl, the lower alkyl can be substituted by a group selected from hydroxy, lower alkoxy, cycloalkyl, cycloalkenyl, phenyl, naphthyl, pyridyl, thienyl, imidazolyl, phthalimido, piperidyl, piperazinyl, morpholinyl, $R^E$—OCO—, $R^F$—N($R^G$)—, $R^H$—N($R^J$)CO—, $R^K$—CONH— and —CONHOH, the piperidyl, piperazinyl or morpholinyl can be substituted by lower alkyl, phenyl or naphthyl, $R^E$ is selected from hydrogen, lower alkyl and phenyl, $R^F$ and $R^G$, being the same or different, are selected from hydrogen, lower alkyl, cycloalkyl and phenyl, $R^H$ and $R^J$, being the same or different, are selected from hydrogen, lower alkyl, cycloalkyl and phenyl, $R^K$ is selected from lower alkyl, lower alkoxy and phenyl, each phenyl can be substituted by a group selected from lower alkyl, hydroxy, lower alkoxy, lower alkanoyloxy, halogen, nitro, amino, lower alkylamino, lower alkanoylamino, lower alkylsulfonyl, phenylsulfonyl, phenyl and $R^E$—OCO—, and each cycloalkyl can be substituted by a group selected from lower alkyl, hydroxy, oxo and $R^E$—OCO—;

4) $R^5$ and $R^6$ join each other to form a nonaromatic heterocyclic ring selected from a morpholine ring, a piperidine ring, a piperazine ring, a pyrroline ring, and a homopiperazine ring, the nonaromatic heterocyclic ring can be substituted by lower alkyl, lower alkenyl, cycloalkyl, cycloalkenyl, phenyl, naphthyl or $R^A$—CO—, the lower alkyl can be substituted by hydroxy, phenyl, naphthyl, $R^B$—O—, $R^E$—OCO—, $R^F$—N($R^G$)— or —CONHOH, $R^A$ is lower alkyl, halogeno-lower alkyl, lower alkoxy or phenyl, $R^B$ is lower alkyl or phenyl, $R^E$ is hydrogen, lower alkyl or phenyl, $R^F$ and $R^G$, being the same or different, are hydrogen, lower alkyl, cycloalkyl or phenyl, each phenyl can be substituted by a group selected from lower alkyl, hydroxy, lower alkoxy, lower alkanoyloxy, halogen, nitro, amino, lower alkylamino, lower alkanoylamino, lower alkylsulfonyl, phenylsulfonyl, phenyl and $R^E$—OCO—, and each cycloalkyl can be substituted by a group selected from lower alkyl, hydroxy, oxo and $R^E$—OCO—;

5) $R^7$ is selected from hydrogen, lower alkyl, cycloalkyl, hydroxy, carboxy, mercapto, phenyl, $R^B$—O—, $R^C$—S—, $R^D$—COS—, $R^E$—OCO—, $R^F$—N($R^G$)— and —CONHOH, the lower alkyl can be substituted by a group selected from cycloalkyl, hydroxy, carboxy, mercapto, phenyl, $R^B$—O—, $R^C$—S—, $R^D$—COS—, $R^E$—OCO—, $R^F$—N($R^G$)— and —CONHOH, $R^B$ is lower alkyl or phenyl, $R^C$ is lower alkyl or phenyl, $R^D$ is lower alkyl or phenyl, $R^E$ is lower alkyl or phenyl, $R^F$ and $R^G$, being the same or different, are hydrogen, lower alkyl, cycloalkyl or phenyl, each phenyl can be substituted by a group selected from lower alkyl, hydroxy, lower alkoxy, lower alkanoyloxy, halogen, nitro, amino, lower alkylamino, lower alkanoylamino, lower alkylsulfonyl, phenylsulfonyl, phenyl and $R^E$—OCO—, and each cycloalkyl can be substituted by lower alkyl, hydroxy, oxo or $R^E$—OCO—;

6) $R^7$ joins with sulfur adjacent to $A^1$ to form a nonaromatic heterocyclic ring selected from a thiolactone ring and a dithiolane ring;

7) $A^1$ is lower alkylene; and

8) $A^2$ is lower alkylene.

4. The compound or a salt thereof as claimed in claim 1, wherein the group(s) in the general formula [I] is defined by anyone selected from the following 1) to 11) or any combinations consisting of 1) to 11), 1) $R^1$ is selected from hydrogen, lower alkyl, phenyl, $R^A$—CO—, $R^C$—S— and a group of the following formula [II], and the lower alkyl can be substituted by phenyl or lower alkoxycarbonyl,

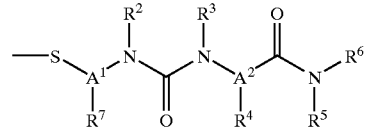

[II]

$R^A$ is selected from lower alkyl, lower alkoxy, phenyl, pyridyl, phenyl-lower alkoxy and $R^F$—N($R^G$)—, $R^C$ is phenyl, $R^F$ is lower alkyl, and $R^G$ is hydrogen;

2) $R^2$ is selected from hydrogen, lower alkyl, lower alkenyl and phenyl, the lower alkyl can be substituted by a group selected from lower alkoxy, cycloalkyl, cycloalkenyl, adamantyl, phenyl, naphthyl, pyridyl and $R^B$—O—, the phenyl can be substituted by a group selected from lower alkyl, hydroxy, lower alkoxy, lower alkanoyloxy, halogen, nitro and phenyl, the lower alkenyl can be substituted by phenyl, and $R^B$ is phenyl;

3) $R^3$ is selected from hydrogen and lower alkyl, and the lower alkyl can be substituted by phenyl;

4) $R^4$ is selected from hydrogen, lower alkyl and phenyl, the lower alkyl can be substituted by a group selected from hydroxy, cycloalkyl, phenyl, naphthyl, pyridyl, thienyl, imidazolyl, toluenesulfonylguanidino, $R^C$—S—, $R^D$—COS—, $R^F$—N($R^G$)— and $R^K$—CONH—, each phenyl can be substituted by a group selected from hydroxy, lower alkoxy, halogen, nitro, lower alkanoylamino, phenylsulfonyl and phenyl, $R^C$ is selected from hydrogen, lower alkyl and phenyl, $R^D$ is selected from lower alkyl and phenyl, $R^F$ and $R^G$ are hydrogen, and $R^K$ is lower alkoxy. When $R^4$ is lower alkyl, terminal carbon of the lower alkyl can join with carbon to which the alkyl is bonded to form a cycloalkyl ring;

5) $R^5$ is selected from hydrogen and lower alkyl;

6) $R^6$ is selected from lower alkyl and pyridyl, the lower alkyl can be substituted by a group selected from pyridyl, imidazolyl, phthalimido, piperidyl, piperazinyl, morpholinyl, $R^E$—OCO—, $R^F$—N($R^G$)—, $R^H$—N($R^J$)CO— and $R^K$—CONH—, $R^E$ is selected from hydrogen and lower alkyl, $R^F$ and $R^G$, being the same or different, are selected from hydrogen, lower alkyl, cycloalkyl, and phenyl, $R^H$ and $R^J$, being the same or different, are selected from hydrogen and lower alkyl, $R^K$ is lower alkoxy, and the piperazinyl can be substituted by lower alkyl;

7) $R^5$ and $R^6$ join each other to form a nonaromatic heterocyclic ring selected from a morpholine ring, a piperidine ring, a piperazine ring, a pyrroline ring and a homopiperazine ring, the piperazine ring or the homopiperazine ring can be substituted by lower alkyl, cycloalkyl, phenyl or $R^A$—CO—, the lower alkyl can be substituted by hydroxy, phenyl or $R^E$—OCO—, $R^A$ is lower alkyl, lower alkoxy or halogeno-lower alkyl, and $R^E$ is hydrogen or lower alkyl;

8) $R^7$ is selected from hydrogen, lower alkyl, hydroxy, mercapto, phenyl, $R^B$—O—, $R^C$—S—, $R^D$—COS—, $R^E$—OCO—, —CONHOH and $R^F$—N($R^G$), the lower alkyl can be substituted by a group selected from hydroxy, mercapto, phenyl, $R^B$—O—, $R^C$—S—, $R^D$—COS—, $R^E$—OCO—, —CONHOH and $R^F$—N($R^G$)—, $R^B$ is phenyl, $R^C$ is phenyl, $R^D$ is lower alkyl or phenyl, $R^E$ is hydrogen or lower alkyl, $R^F$ and $R^G$ are lower alkyl;

9) $R^7$ joins with sulfur adjacent to $A^1$ to form a nonaromatic heterocyclic ring selected from a thiolactone ring and a dithiolane ring;

10) $A^1$ is lower alkylene; and

11) $A^2$ is lower alkylene.

5. The compound or a salt thereof as claimed in claim 1, wherein the group(s)in the general formula [I] is defined by anyone selected from the following 1) to 10) or any combinations consisting of 1) to 10), 1) $R^1$ is selected from hydrogen, $R^A$—CO— and a group of the following formula [II],

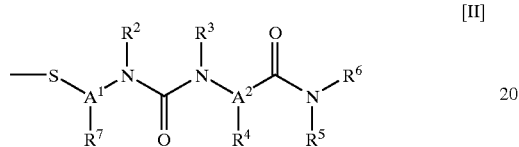

$R^A$ is selected from lower alkyl, phenyl and pyridyl;

2) $R^2$ is lower alkyl or phenyl, the lower alkyl can be substituted by a group selected from cycloalkyl, cycloalkenyl, adamantyl, phenyl and phenoxy, and the phenyl can be substituted by halogen;

3) $R^3$ is hydrogen;

4) $R^4$ is hydrogen or lower alkyl, the lower alkyl can be substituted by a group selected from phenyl, naphthyl, lower alkylthio and $R^D$—COS—, $R^D$ is lower alkyl, and the phenyl can be substituted by a group selected from hydroxy, lower alkoxy, halogen, nitro and phenyl;

5) $R^5$ is hydrogen;

6) $R^6$ is lower alkyl, the lower alkyl can be substituted by a group selected from pyridyl, piperidyl, piperazinyl and $R^F$—N($R^G$)—, $R^F$ and $R^G$, being the same or different, are selected from hydrogen, lower alkyl and cycloalkyl, and the piperazinyl can be substituted by lower alkyl;

7) $R^5$ and $R^6$ join each other to form a nonaromatic heterocyclic ring selected from a piperidine ring, a morpholine ring and a piperazine ring, the piperazine ring can be substituted by lower alkyl;

8) $R^7$ is hydrogen;

9) $A^1$ is lower alkylene; and

10) $A^2$ is lower alkylene.

6. The compound or a salt thereof as claimed in claim 1, wherein the group(s) in the general formula [I] is defined by anyone selected from the following 1) to 10) or any combinations consisting of 1) to 10), 1) $R^1$ is selected from acetyl, benzoyl and a group of the following formula [II];

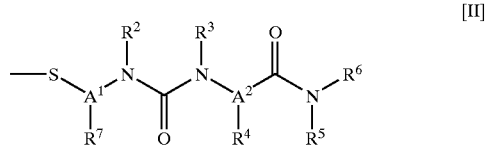

2) $R^2$ is selected from 2-cyclohexylethyl, 2-cyclopentylethyl, 2-(1-adamantyl)ethyl, 2-(cyclohexen-1-yl)ethyl, phenethyl and 3-(4-fluorophenyl)propyl;

3) $R^3$ is hydrogen;

4) $R^4$ is selected from methyl, acetylthiomethyl, benzyl, 2-naphthylmethyl, 4-fluorobenzyl, 4-chlorobenzyl, 4-biphenylylmethyl, 4-nitrobenzyl, 3-nitro-4-biphenylylmethyl, 4-methoxybenzyl and 4-isopropoxybenzyl;

5) $R^5$ is hydrogen;

6) $R^6$ is selected from 2-(dimethylamino)ethyl, 2-(diethylamino)ethyl, 2-(diisopropylamino)ethyl, N-methyl-2-(cyclohexylamino)ethyl, 2-(2-pyridyl)ethyl, 2-(1-piperidyl)ethyl and 2-(4-methylpiperazinyl)ethyl;

7) $R^5$ and $R^6$ join each other to form a group selected from 1-piperidyl, 4-morpholinyl and 4-methyl-1-piperazinyl;

8) $R^7$ is hydrogen;

9) $A^1$ is ethylene;

10) $A^2$ is methylene.

7. The compound or a salt thereof as claimed in claim 1, wherein $R^5$ and $R^6$ join each other to form a nonaromatic heterocyclic ring selected from a morpholine ring, a piperidine ring, a piperazine ring, a pyrrloline ring and a homopiperazine ring, the piperazine ring or the homopiperazine ring be substituted by lower alkyl, cycloalkyl, phenyl or $R^A$—CO—, the lower alkyl can be substituted by hydroxy, phenyl or $R^E$—OCO—, $R^A$ is lower alkyl, lower alkoxy or halogeno-lower alkyl, and $R^E$ is hydrogen or lower alkyl.

8. The compound or a salt thereof as claimed in claim 1, wherein $R^6$ is selected from lower alkyl and pyridyl, the lower alkyl can be substituted by a group selected from pyridyl, imidazolyl, phthalimido, piperidyl, piperazinyl, morpholinyl, $R^E$—OCO—, $R^F$—N($R^G$)—, $R^H$—N($R^J$)CO— and $R^K$—CONH—, $R^E$ is selected from hydrogen and lower alkyl, $R^F$ and $R^G$, being the same or different, are selected from hydrogen, lower alkyl, cycloalkyl and phenyl, $R^H$ and $R^J$, being the same or different, are selected from hydrogen and lower alkyl, $R^K$ is lower alkoxy, and the piperazinyl can be substituted by lower alkyl.

9. The compound of claim 6 which is 1-[(2S)-2-[3-[2-(Acetylthio)ethyl]-3-(2-cyclohexylethyl)ureido]propionyl]-4-methylpiperazine.

10. A pharmaceutical composition containing the compound or a salt thereof as claimed in claim 1 as an active ingredient, in a pharmaceutically acceptable carrier.

11. A pharmaceutical composition according to claim 10, wherein the compound of claim 1 is present in an amount effective as a TNF-α production inhibitor.

12. A pharmaceutical composition according to claim 10, wherein the compound or salt thereof of claim 1 is present in an amount effective as a therapeutic agent for autoimmune diseases.

13. A pharmaceutical composition of claim 10, wherein the compound or salt thereof of claim 1 is present in an amount effective as an antirheumatic.

* * * * *